(12) United States Patent
Eum et al.

(10) Patent No.: US 11,832,514 B2
(45) Date of Patent: *Nov. 28, 2023

(54) ORGANIC COMPOUND AND ORGANIC ELECTROLUMINESCENT ELEMENT COMPRISING SAME

(71) Applicant: SOLUS ADVANCED MATERIALS CO., LTD., Iksan-si (KR)

(72) Inventors: Min-Sik Eum, Seoul (KR); Hojun Son, Yongin-si (KR); Woo Jae Park, Seoul (KR); Tae Hyung Kim, Yongin-si (KR); Jiyi Kim, Yongin-si (KR); Youngmi Beak, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 378 days.

This patent is subject to a terminal disclaimer.

(21) Appl. No.: 16/795,230

(22) Filed: Feb. 19, 2020

(65) Prior Publication Data
US 2020/0185618 A1 Jun. 11, 2020

Related U.S. Application Data

(63) Continuation of application No. 15/539,223, filed as application No. PCT/KR2015/014222 on Dec. 24, 2015, now Pat. No. 10,916,709.

(30) Foreign Application Priority Data

| Dec. 24, 2014 | (KR) | 10-2014-0188953 |
|---|---|---|
| Dec. 3, 2015 | (KR) | 10-2015-0171639 |
| Dec. 3, 2015 | (KR) | 10-2015-0171678 |
| Dec. 15, 2015 | (KR) | 10-2015-0178926 |

(51) Int. Cl.

| H10K 85/60 | (2023.01) |
|---|---|
| C09K 11/06 | (2006.01) |
| C07D 239/26 | (2006.01) |
| C07D 251/24 | (2006.01) |
| C07D 213/16 | (2006.01) |
| H10K 50/11 | (2023.01) |
| H10K 85/30 | (2023.01) |
| C09K 11/02 | (2006.01) |
| H10K 50/16 | (2023.01) |
| H10K 50/80 | (2023.01) |
| H10K 50/17 | (2023.01) |
| H10K 101/40 | (2023.01) |
| H10K 101/10 | (2023.01) |
| H10K 101/30 | (2023.01) |

(52) U.S. Cl.
CPC ...... *H10K 85/654* (2023.02); *C07D 213/16* (2013.01); *C07D 239/26* (2013.01); *C07D 251/24* (2013.01); *C09K 11/025* (2013.01); *C09K 11/06* (2013.01); *H10K 50/11* (2023.02); *H10K 85/342* (2023.02); *H10K 85/615* (2023.02); *H10K 85/622* (2023.02); *H10K 85/623* (2023.02); *H10K 85/624* (2023.02); *H10K 85/631* (2023.02); *H10K 85/636* (2023.02); *H10K 85/6572* (2023.02); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/185* (2013.01); *H10K 50/16* (2023.02); *H10K 50/166* (2023.02); *H10K 50/171* (2023.02); *H10K 50/80* (2023.02); *H10K 2101/10* (2023.02); *H10K 2101/30* (2023.02); *H10K 2101/40* (2023.02)

(58) Field of Classification Search
None
See application file for complete search history.

(56) References Cited

U.S. PATENT DOCUMENTS

| 9,120,773 B2 | 9/2015 | Aihara et al. |
|---|---|---|
| 9,209,406 B2 | 12/2015 | Mizutani et al. |
| 9,266,851 B2 | 2/2016 | Yoshida et al. |
| 9,624,193 B2 | 4/2017 | Aihara et al. |
| 9,640,766 B2 | 5/2017 | Jang et al. |
| 9,960,363 B2 | 5/2018 | Eum et al. |
| 10,199,580 B2 | 2/2019 | Mizutani et al. |
| 10,916,709 B2 | 2/2021 | Eum et al. |
| 10,964,892 B2 * | 3/2021 | Huh ............... C07D 403/14 |
| 2007/0190355 A1 | 8/2007 | Ikeda et al. |
| 2010/0039026 A1 | 2/2010 | Yang et al. |
| 2012/0126217 A1 | 5/2012 | Yoshida et al. |
| 2012/0214993 A1 | 8/2012 | Aihara et al. |
| 2014/0001456 A1 | 1/2014 | Mizutani et al. |

(Continued)

FOREIGN PATENT DOCUMENTS

| CN | 1867646 A | 11/2006 |
|---|---|---|
| CN | 101381601 A | 3/2009 |

(Continued)

OTHER PUBLICATIONS

International Search Report of PCT/KR2015/014222, dated Aug. 12, 2016. [PCT/ISA/210].

(Continued)

*Primary Examiner* — Dawn L Garrett
(74) *Attorney, Agent, or Firm* — Sughrue Mion, PLLC

(57) ABSTRACT

Disclosed are a novel organic compound, and an organic electroluminescent element having improved characteristics, such as luminous efficiency, driving voltage, and lifespan, by containing the novel organic compound in one or more organic material layers.

8 Claims, No Drawings

(56) References Cited

U.S. PATENT DOCUMENTS

| | | |
|---|---|---|
| 2014/0054561 A1 | 2/2014 | Nam et al. |
| 2014/0073784 A1 | 3/2014 | Mizutani et al. |
| 2014/0100367 A1 | 4/2014 | Yoon et al. |
| 2014/0367654 A1 | 12/2014 | Kim et al. |
| 2015/0236273 A1 | 8/2015 | Jang et al. |
| 2015/0243897 A1 | 8/2015 | Montenegro et al. |
| 2015/0340622 A1 | 11/2015 | Inoue et al. |
| 2016/0028021 A1 | 1/2016 | Zeng et al. |
| 2016/0056388 A1 | 2/2016 | Oka et al. |
| 2016/0072073 A1 | 3/2016 | Lee et al. |
| 2016/0111655 A1 | 4/2016 | Mizutani et al. |
| 2016/0308147 A1 | 10/2016 | Parham et al. |
| 2017/0033294 A1 | 2/2017 | Jang et al. |
| 2017/0098777 A1 | 4/2017 | Huh et al. |
| 2017/0104163 A1 | 4/2017 | Lee et al. |
| 2017/0186965 A1 | 6/2017 | Parham et al. |
| 2018/0175302 A1 | 6/2018 | Jang et al. |

FOREIGN PATENT DOCUMENTS

| | | |
|---|---|---|
| CN | 102372665 A | 3/2012 |
| CN | 102574813 A | 7/2012 |
| CN | 103380508 A | 10/2013 |
| CN | 104073241 A | 10/2014 |
| CN | 106132937 A | 11/2016 |
| CN | 106471093 A | 3/2017 |
| EP | 2 752 902 A1 | 7/2014 |
| EP | 3 127 901 A1 | 2/2017 |
| EP | 3 127 988 A1 | 2/2017 |
| JP | 2004002297 A | 1/2004 |
| JP | 2008-110968 A | 5/2008 |
| JP | 2008-156316 A | 7/2008 |
| JP | 2009-170814 A | 7/2009 |
| JP | 2009-275030 A | 11/2009 |
| JP | 2012-62450 A | 3/2012 |
| JP | 2012522042 A | 9/2012 |
| JP | 2014514344 A | 6/2014 |
| JP | 2014-125449 A | 7/2014 |
| JP | 2014-183315 A | 9/2014 |
| JP | 2016-724 A | 1/2016 |
| JP | 2016019002 A | 2/2016 |
| JP | 2018506847 A | 3/2018 |
| JP | 2018-531883 A | 11/2018 |
| KR | 1020100112903 A | 10/2010 |
| KR | 10-2011-0008892 A | 1/2011 |
| KR | 1020110112186 A | 10/2011 |
| KR | 10-2012-0044523 A | 5/2012 |
| KR | 10-2012-0046778 A | 5/2012 |
| KR | 10-2012-0052231 A | 5/2012 |
| KR | 10-2012-0132815 A | 12/2012 |
| KR | 1020130094903 A | 8/2013 |
| KR | 10-2013-0135178 A | 12/2013 |
| KR | 10-2014-0014959 A | 2/2014 |
| KR | 10-2014-0030786 A | 3/2014 |
| KR | 1020140046541 A | 4/2014 |
| KR | 10-2014-0101661 A | 8/2014 |
| KR | 10-2015-0002072 | 1/2015 |
| KR | 10-2015-0041652 A | 4/2015 |
| KR | 10-1542714 B1 | 8/2015 |
| KR | 10-2015-0115622 A | 10/2015 |
| KR | 10-2015-0115648 A | 10/2015 |
| KR | 10-2015-0135097 A | 12/2015 |
| KR | 10-2016-0011036 A | 1/2016 |
| KR | 10-2016-0106217 A | 9/2016 |
| KR | 10-1737298 B1 | 5/2017 |
| KR | 10-1745799 B1 | 6/2017 |
| WO | 2004/039786 A1 | 5/2004 |
| WO | 2010/072300 A1 | 7/2010 |
| WO | 2011010843 A1 | 1/2011 |
| WO | 2011021689 A1 | 2/2011 |
| WO | 2011046182 A1 | 4/2011 |
| WO | 2012157537 A1 | 11/2012 |
| WO | 2013077352 A1 | 5/2013 |
| WO | 2013/122402 A1 | 8/2013 |
| WO | 2014023388 A1 | 2/2014 |
| WO | 2014/054912 A1 | 4/2014 |
| WO | 2014/171541 A1 | 10/2014 |
| WO | 2014185751 A1 | 11/2014 |
| WO | 2014200148 A1 | 12/2014 |
| WO | 2015005559 A1 | 1/2015 |
| WO | 2015041358 A1 | 3/2015 |
| WO | 2015090504 A2 | 6/2015 |
| WO | 2015/152634 A1 | 10/2015 |
| WO | 2015152633 A1 | 10/2015 |
| WO | 2015152650 A1 | 10/2015 |
| WO | 2015/169412 A1 | 11/2015 |
| WO | 2016076384 A1 | 5/2016 |
| WO | 2016111515 A1 | 7/2016 |

OTHER PUBLICATIONS

Korean Intellectual Property Office, Communication dated Jul. 31, 2017, issued in Korean Application No. 10-2017-0015045.
Korean Intellectual Property Office, Communication dated Nov. 21, 2016, issued in Korean Application No. 10-2015-0171639.
Japanese Patent Office; Communication dated Jul. 3, 2018 in counterpart application No. 2017-534340.
Japanese Patent Office; Communication dated Jul. 20, 2018 in counterpart application No. 2017-534328.
European Patent Office; Communication dated Sep. 4, 2018 in counterpart application No. 15873577.9.
Oyama, T., et al., "Electron-Transporting Materials Containing Pyridylphenyl groups and Their Application to Organic Light-Emitting Devices", Journal of Photopolymer Science and Technology, vol. 23, No. 3, 2010, pp. 2-9/E (8 pages).
Hongliang Zhong et al., "New Conjugated Triazine Based Molecular Materials for Application in Optoelectronic Devices: Design, Synthesis, and Properties", The Journal of Physical Chemistry, vol. 115, No. 5, pp. 2423-2427, 5 pages, Year: 2010.
Chris S. K. Mak et al., "Singlet and Triplet Emission from Polymers for OLED Applications", Proceedings of SPIE vol. 5519, 2004, pp. 24-33, 12 pages.
The State Intellectual Property Office of People's Republic of China; Communication dated Mar. 13, 2019 in Chinese Application No. 201580069761.5.
Japanese Patent Office; Communication dated Feb. 12, 2019 in counterpart application No. 2017-534340.
European Patent Office; Communication dated Mar. 28, 2019 in counterpart European Application No. 15873577.9.
Japanese Patent Office; Communication dated Mar. 12, 2019 in counterpart application No. 2017-534328.
Machine translation for KR 10-2015-0002072 (publication date: Jan. 2015). (Year: 2015).
Chen et al., "1,3,5-Triazine derivatives as new electron transport-type host materials for highly efficient green phosphorescent OLEDs", J. Mater. Chem., 2009, vol. 19, pp. 8112-8118 (7 pages total).

* cited by examiner

ORGANIC COMPOUND AND ORGANIC ELECTROLUMINESCENT ELEMENT COMPRISING SAME

CROSS REFERENCE TO RELATED APPLICATIONS

This application is a Continuation of U.S. application Ser. No. 15/539,223 filed Jun. 23, 2017, which is National Stage of International Application No. PCT/KR2015/014222 filed Dec. 24, 2015, claiming priorities based on Korean Patent Application Nos. 10-2014-0188953, filed Dec. 24, 2014, 10-2015-0171639, filed Dec. 3, 2015, 10-2015-0171678, filed Dec. 3, 2015, and 10-2015-0178926, filed Dec. 15, 2015, the contents of all of which are incorporated herein by reference in their entirety.

TECHNICAL FIELD

The present invention relates to an organic compound and an organic electroluminescent element comprising the same.

BACKGROUND ART

In an organic electroluminescent element, the application of a voltage across two opposite electrodes induces the injection of holes from the anode and electrons from the cathode into an organic layer. The injected holes and electrons recombine with each other to generate excitons which then return to the ground state, emitting light. The materials for use in the organic layer can be classified as luminescent materials, hole injection materials, hole transport materials, electron transport materials, and electron injection materials according to functions.

Widely known are NPB, BCP and $Alq_3$ as materials for hole injection, hole transport and electron transport, and anthracene derivatives and Ir-bearing metal complexes, such as Firpic, $Ir(ppy)_3$, $(acac)Ir(btp)_2$ etc., as luminescent materials.

However, not only are such materials poor in thermal stability due to their low glass transition temperatures, but also organic electroluminescent elements having the materials introduced into organic layers thereof exhibit only an unsatisfactory level of current efficiency and lifespan because the materials are of low triplet energy.

DISCLOSURE

Technical Problem

In order to solve the problems encountered in related art, the present invention provides an organic compound that can impart an organic electroluminescent element with an improvement in driving voltage, current efficiency, and lifespan.

Also, the present invention provides an organic electroluminescent element comprising the organic compound.

Technical Solution

In order to accomplish the above purposes thereof, the present invention provides a compound represented by the following Formula 1:

[Formula 1]

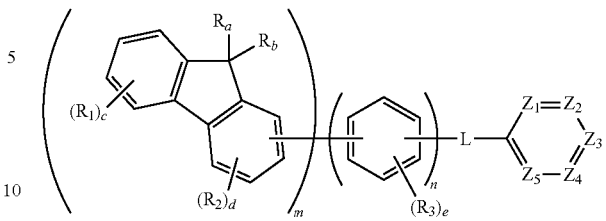

wherein, $R_a$ and $R_b$ may be the same or different from each other and are each independently a $C_1$-$C_{40}$ alkyl group or a $C_6$-$C_{60}$ aryl group, or combine with each other to form a fused ring, $R_1$ to $R_3$ may be the same or different from each other and are each independently selected from the group consisting of a hydrogen, a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, or provided that adjacent ones of $R_1$ to $R_3$ may combine with each other (in detail, combination between adjacent $R_1$'s, between adjacent $R_2$'s, between adjacent $R_3$'s, or between $R_1$ and $R_2$) to form a fused ring, L is selected from the group consisting of a single bond, a $C_6$-$C_{18}$ arylene group and a heteroarylene group having 5 to 18 nuclear atoms, $Z_1$ to $Z_5$ may be the same or different and are each independently N or $C(R_4)$, and provided that $Z_1$ to $Z_5$ include at least one N, and when $C(R_4)$ is present in a plural number, they are optionally the same as or different from each other, c and e are each an integer of 0 to 4, d is an integer of 0 to 3, m and n are each an integer of 1 to 3, $R_4$ is selected from the group consisting of a hydrogen, a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, or bonded to an adjacent substituent (in detail, adjacent $R_4$'s are bonded to each other) to form a fused ring, the alkyl and aryl groups of $R_a$ and $R_b$; the alkyl, alkenyl, alkynyl, cycloalkyl, heterocycloalkyl, aryl, heteroaryl, alkyloxy, aryloxy, alkylsilyl, arylsilyl, alkylboron, arylboron, phosphine, phosphine oxide, and arylamine groups of $R_1$ to $R_4$; and the arylene and heteroarylene groups of L may be optionally each independently unsubstituted or substituted with at least one selected from the group consisting of a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, and provided that when the substituent is present in a plural number, they are optionally the same or different from each other.

In addition, the present invention provides an organic electroluminescent element comprising an anode, a cathode, and at least one organic layer interposed therebetween, wherein at least one of the organic layer comprises the compound represented by Formula 1.

Advantageous Effects

Having excellent thermal stability and emitting properties, the compound, represented by Formula 1, of the present invention can be available for use in an organic layer of an organic electroluminescent element. Particularly when used as a material for a light-emitting layer or an auxiliary electron transport layer, the compound, represented by Formula 1, of the present invention can impart excellent emission performance, low driving voltage, high efficiency and long lifespan to the organic electroluminescent element, thereby allowing for the fabrication of a full-color display panel improved in performance and lifespan.

MODE FOR INVENTION

Below, a detailed description is given of the present invention.

1. Organic Compound

The organic compound of the present invention has a framework, represented by Formula 1, in which a fluorene moiety is bonded to a 6-membered heterocyclic ring through a linker (phenylene, biphenylene or terphenylene).

The fluorene moiety serves as an electron donor group (EDG) with high electron donating ability. When the fluorene moiety is connected via a linker to a 6-membered heterocyclic ring that serves as an electron withdrawing group (EWG) with high electron withdrawing ability (e.g., pyridine, pyrimidine, triazine, etc.), the overall molecule exhibits a bipolar property. Accordingly, the compound of the present invention can improve hole-electron recombination.

In addition, since the linker, e.g., phenylene, or biphenylene or terphenylene, functions to minimize interaction between the electron donor group and the electron withdrawing group, the compound of the present invention into which the linker is introduced has a wide bandgap and a high triplet energy. Hence, the compound of the present invention, if applied to an organic layer, minimizes the diffusion of excitons to adjacent other organic layers. An organic electroluminescent element comprising such an organic layer can be improved in light emission efficiency and lifespan, compared to that comprising an organic layer lacking the linker. Further, with the introduction of a linker thereto, the compound of the present invention has a higher molecular weight than those lacking the linker, thus improving in thermal stability.

Such effects may be more intensified when bonds between an electron donor group and a linker, between linkers, and between a linker and an electron drawing group are more twisted structure formed thereof.

The compound, represented by Formula 1, of the present invention may be embodied by one of the compounds represented by the following Formulas 2 to 4:

[Formula 2]

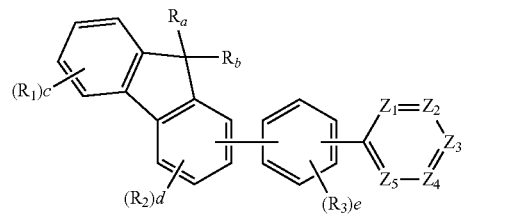

[Formula 3]

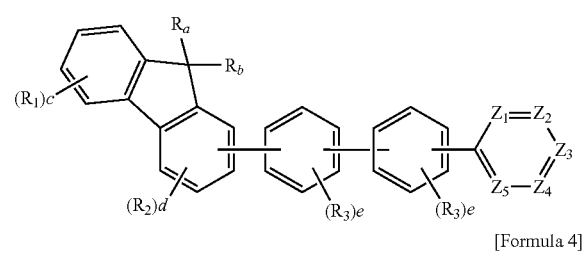

[Formula 4]

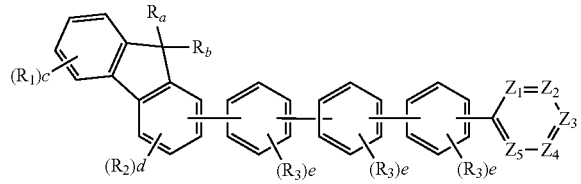

wherein, $R_a$, $R_b$, $R_1$ to $R_3$, $Z_1$ to $Z_5$, c, d, and e are the same as defined in Formula 1.

In the compound represented by Formula 1 of the present invention, the structure (substituent) represented by

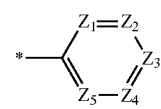

(* is a site where to bond with L) is particularly embodied by one of the structures (substituents) represented by the following C-1 to C-15.

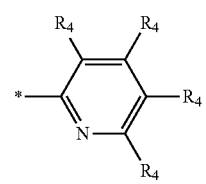

C-1

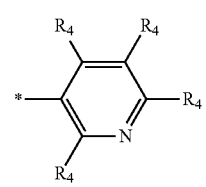

C-2

C-3 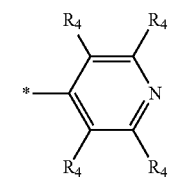

C-4 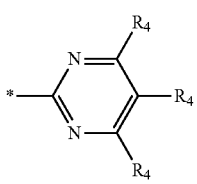

C-5 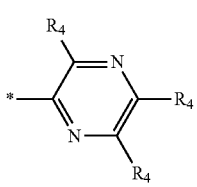

C-6 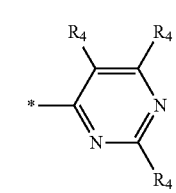

C-7 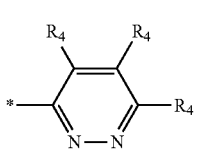

C-8 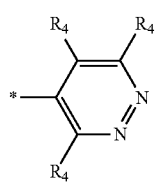

C-9 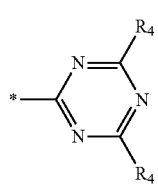

C-10 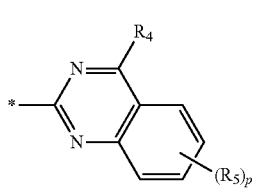

C-11 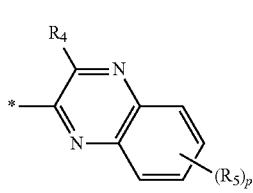

C-12 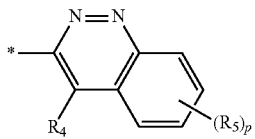

C-13 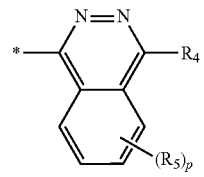

C-14 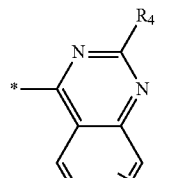

C-15 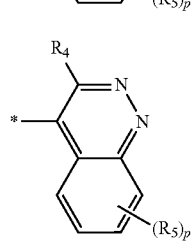

wherein, $R_4$ is the same as defined in Formula 1 and a plurality of $R_4$'s are the same or different, $R_5$ is selected from the group consisting of a hydrogen, a deuterium, a halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_6$-$C_{60}$ aryloxy group, a $C_1$-$C_{40}$ alkyloxy group, a $C_6$-$C_{60}$ arylamine group, a $C_1$-$C_{40}$ alkylsilyl group, a $C_1$-$C_{40}$ alkylboron group, a $C_6$-$C_{60}$ arylboron group, a $C_6$-$C_{60}$ arylphosphine group, a $C_6$-$C_{60}$ arylphosphine oxide group, and a $C_6$-$C_{60}$ arylsilyl group, or combines with an adjacent substituent (in detail, combination between adjacent R5's or between $R_4$ and $R_5$) to form a fused ring, p is an integer of 1 to 4, the alkyl, alkenyl, alkynyl, cycloalkyl, heterocycloalkyl, aryl, heteroaryl, aryloxy, alkyloxy, arylamine, alkylsilyl, alkylboron, arylboron, arylphosphine, arylphosphine oxide and arylsilyl groups of $R_5$ may be each independently unsubstituted or substituted with at least one selected from the group consisting of a deuterium, a halogen, a cyano group, a nitro group, a $C_1$-$C_{40}$ alkyl group, a $C_2$-$C_{40}$ alkenyl group, a $C_2$-$C_{40}$ alkynyl group, a $C_6$-$C_{60}$ aryl group, a heteroaryl group having 5 to 60 nuclear atoms, a $C_6$-$C_{60}$ aryloxy group, a $C_1$-$C_{40}$ alkyloxy group, a $C_6$-$C_{60}$ arylamine group, a $C_3$-$C_{40}$ cycloalkyl group, a heterocycloalkyl group having 3 to 40 nuclear atoms, a $C_1$-$C_{40}$ alkylsilyl group, a $C_1$-$C_{40}$ alkylboron group, a $C_6$-$C_{60}$ arylboron group, a $C_6$-$C_{60}$ arylphosphine group, a $C_6$-$C_{60}$ arylphosphine oxide group, and a $C_6$-$C_{60}$ arylsilyl group, and provided that when the substituent is present in a plural number, they are optionally the same or different from each other.

Here, the structure represented by

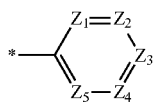

[Formula 5]

is more particularly the structure represented by C-4, C-6, or C-9. In greater detail, the compound, represented by Formula 1, of the present invention may be those represented by the following Formulas 5 to 7:

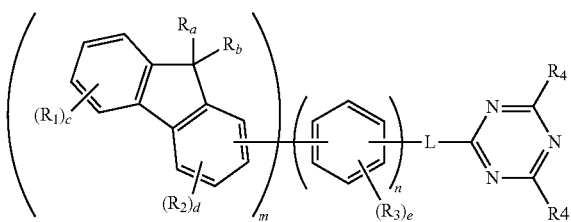

[Formula 5]

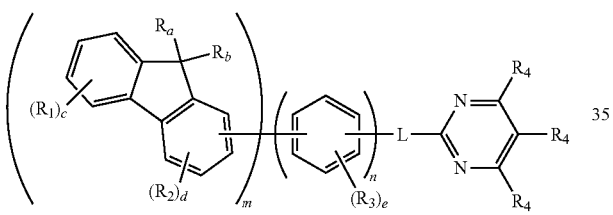

[Formula 6]

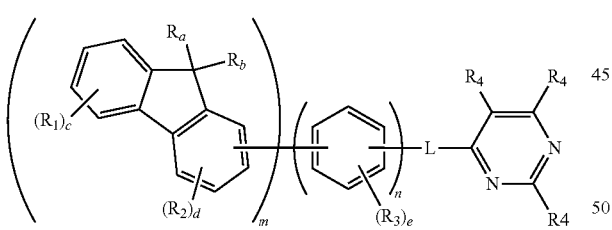

[Formula 7]

wherein, $R_a$, $R_b$, $R_1$ to $R_4$, L, c, d, e, m, and n are the same as defined in Formula 1, respectively. Here, considering properties of organic electroluminescent device, it is preferred that $R_4$'s in the compound represented by Formula 5 are the same. That is, identical $R_4$'s particularly give a symmetrical structure to the compound. In the compounds represented by Formulas 6 and 7, it is preferred that at least two of the plural $R_4$'s are different from each other.

When account is taken of properties of organic electroluminescent device, it is preferred that $R_a$ and $R_b$ in the compound represented Formula 1 of the present invention are each independently a methyl or a phenyl, or bond each other to form a fused ring represented by

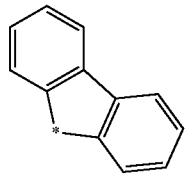 [SMILES: *1c2ccccc2c2ccccc12]

(* is a site where to bond).

In the compound represented by Formula 1, $R_1$ to $R_3$ are each independently selected from the group consisting of hydrogen, deuterium, a $C_1$-$C_{40}$ alkyl group, a $C_6$-$C_{60}$ aryl group, a heteroaryl group having 5 to 60 nuclear atoms, and a $C_6$-$C_{60}$ arylamine group. In addition, m and n are each an integer of 1 to 3, and preferably m is 1 and n is 1 or 2.

In the compound represented by Formula 1 of the present invention, L may be preferably a single bond, phenylene, or biphenylene. In detail, the linker L is preferably selected from the group consisting of the structures represented by the following L-1 to L-7 (* is a site where to bond), more preferably the structure represented by L-6.

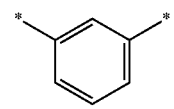

L-1

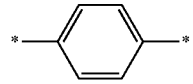

L-2

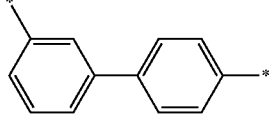

L-3

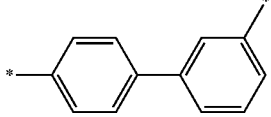

L-4

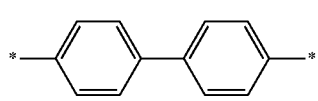

L-5

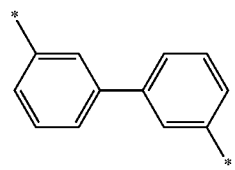

L-6

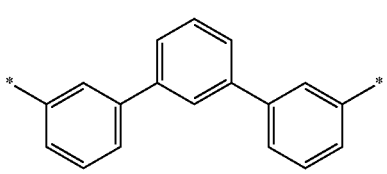

L-7

When the linker L is the structure represented by L-6, the compound, represented by Formula 1, of the present invention may be embodied by the compound represented by the following Formula 8:

[Formula 8]

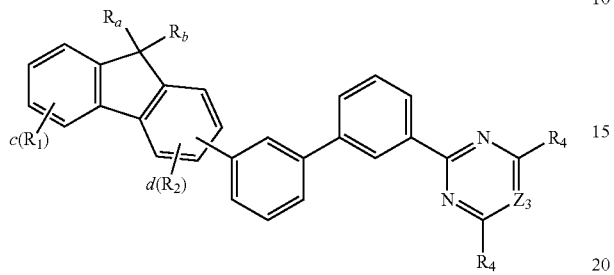

wherein, $R_a$, $R_b$, $R_1$, $R_2$, $R_4$, $Z_3$, c, and d are the same as defined in Formula 1, respectively.

In greater detail, the compound, represented by Formula 1, of the present invention may be further embodied by the compounds represented by the following Formulas 9 to 12:

[Formula 9]

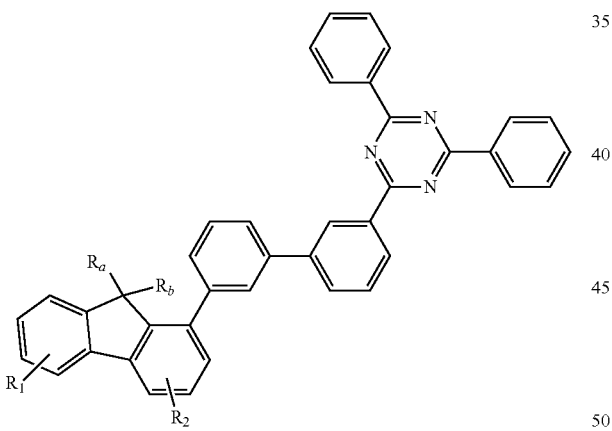

[Formula 10]

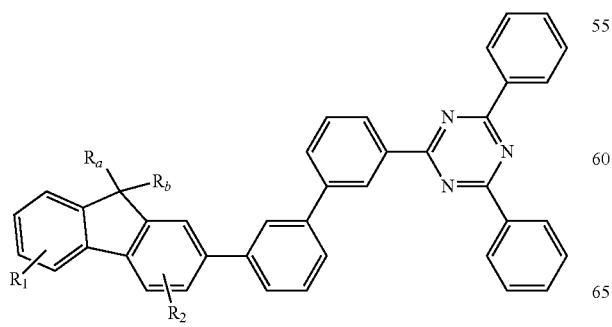

[Formula 11]

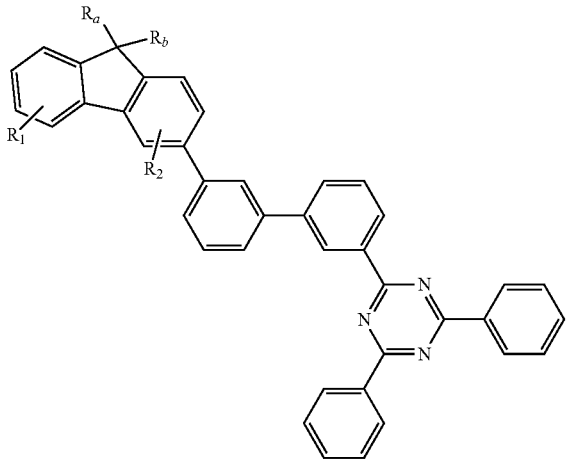

[Formula 12]

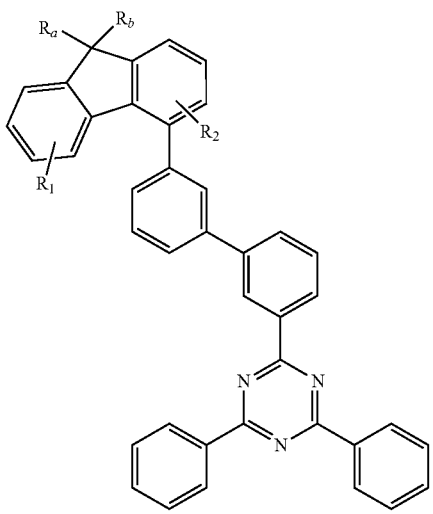

Concrete examples of the compound, represented by Formula 1, of the present invention include, but are not limited to, the following Compounds 1 to 366:

1

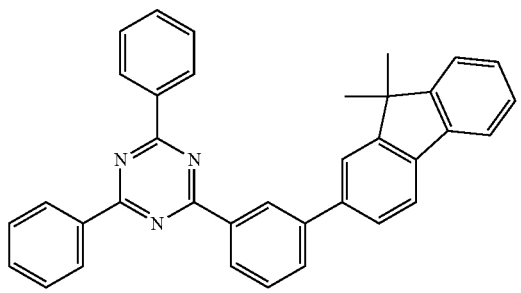

2
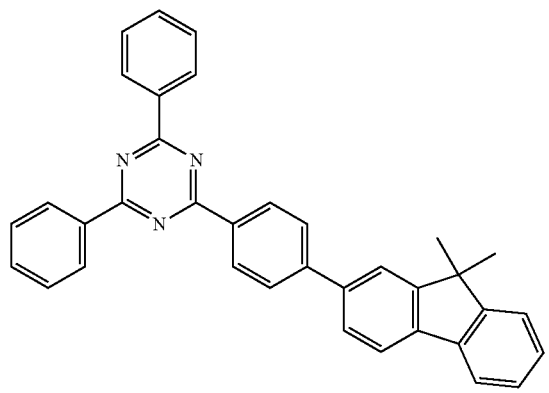
3
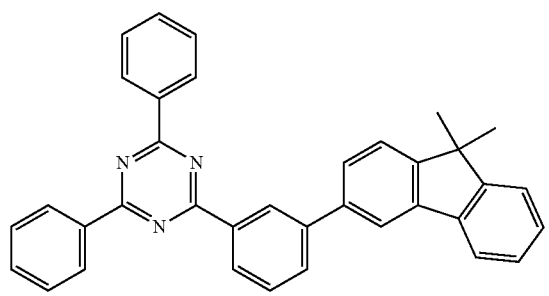
4
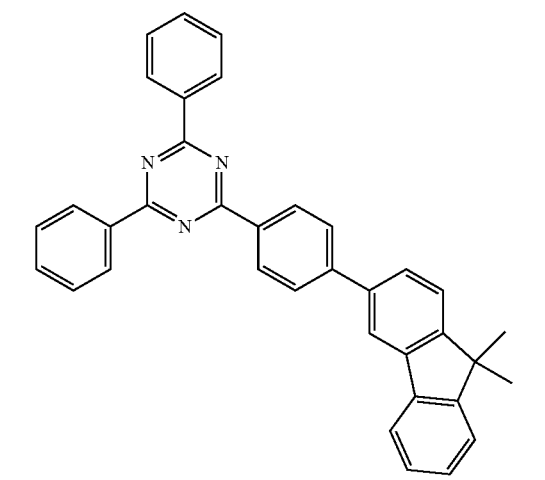
5
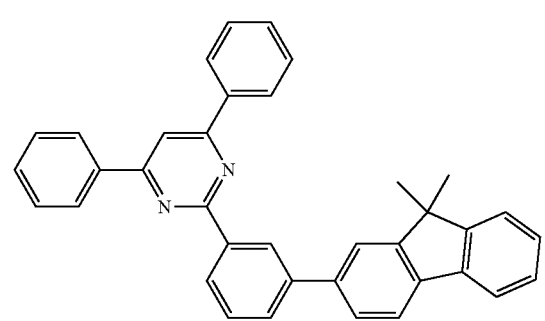
6
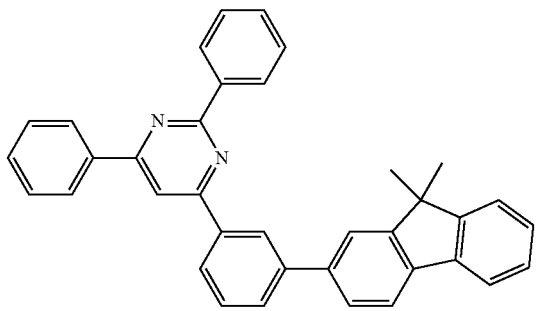
7
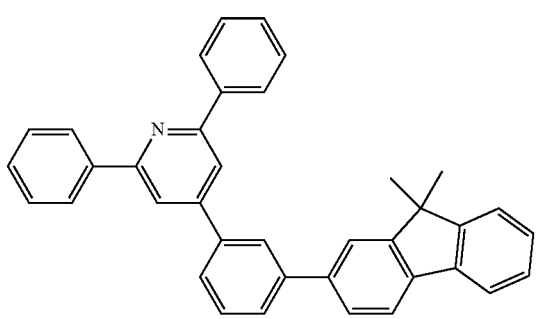
8
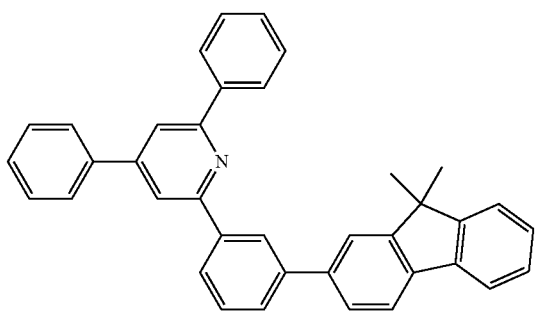
9
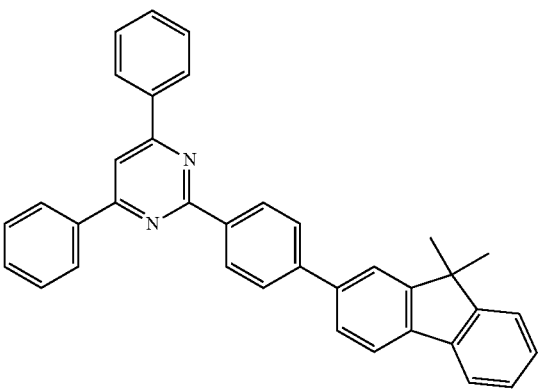

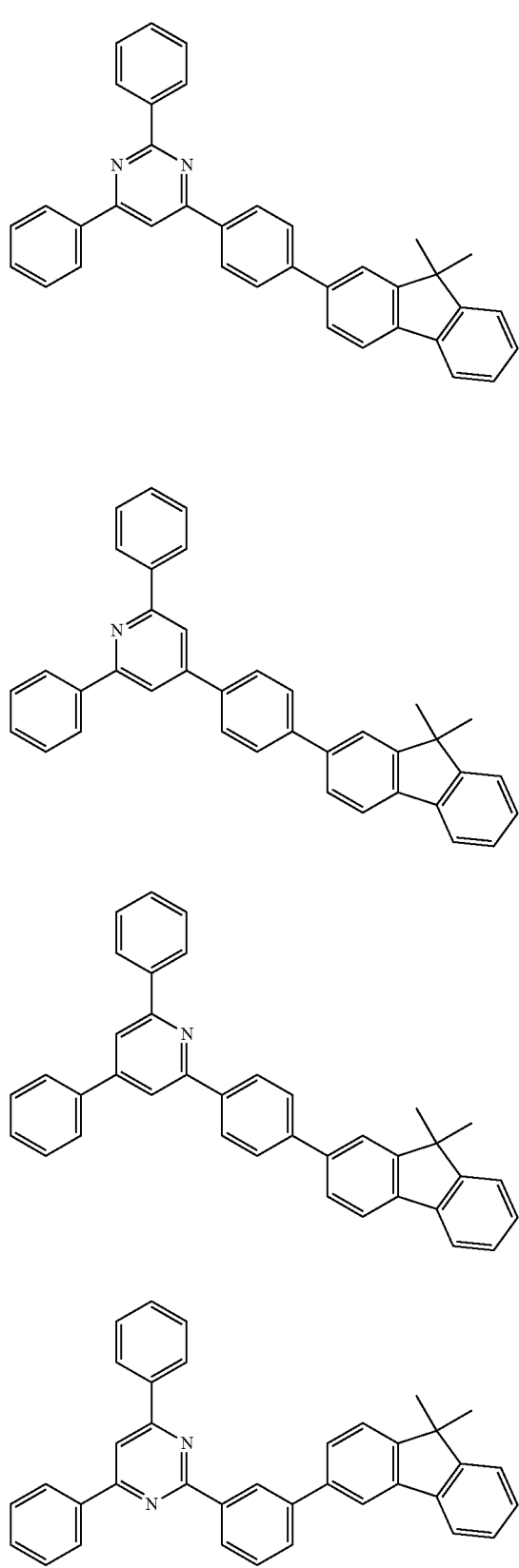
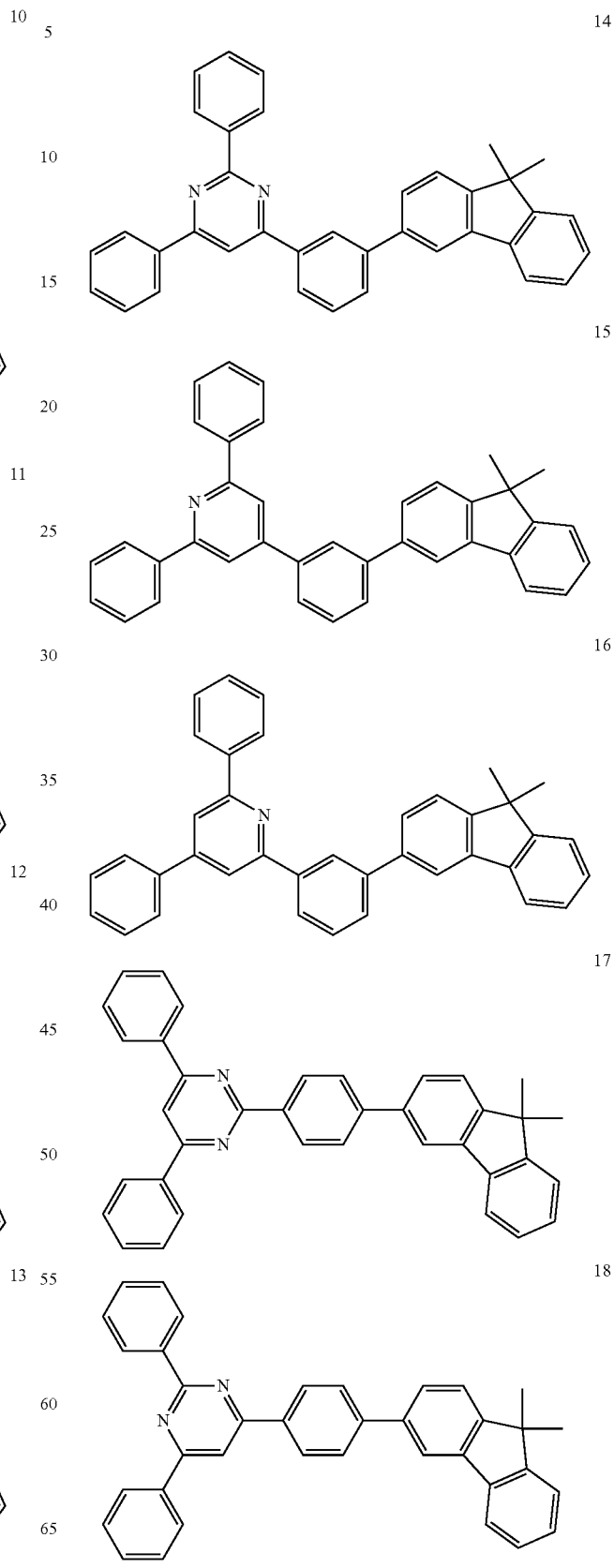

19
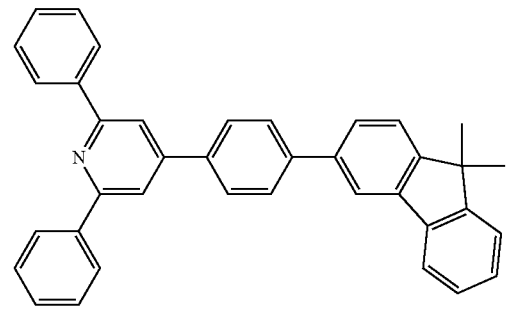
20
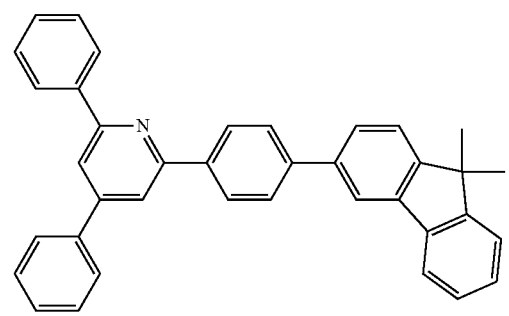
21
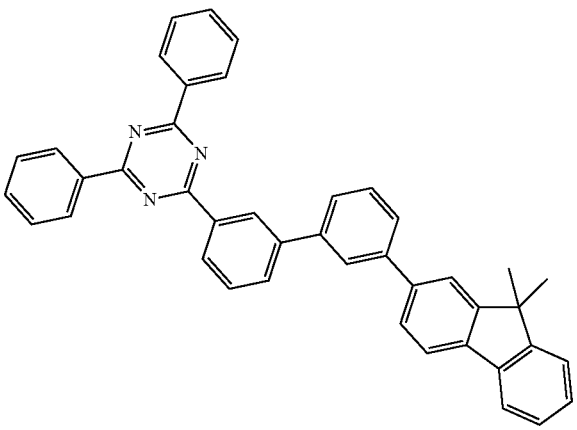
22
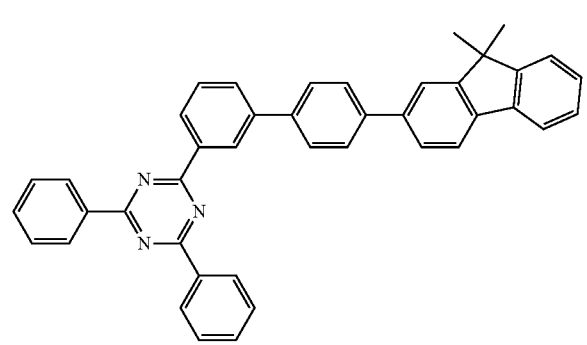
23
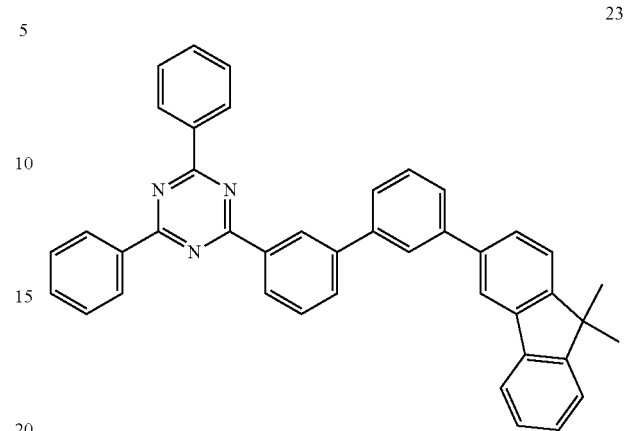
24
25
26
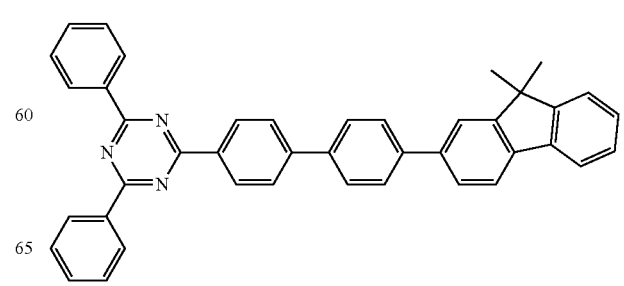

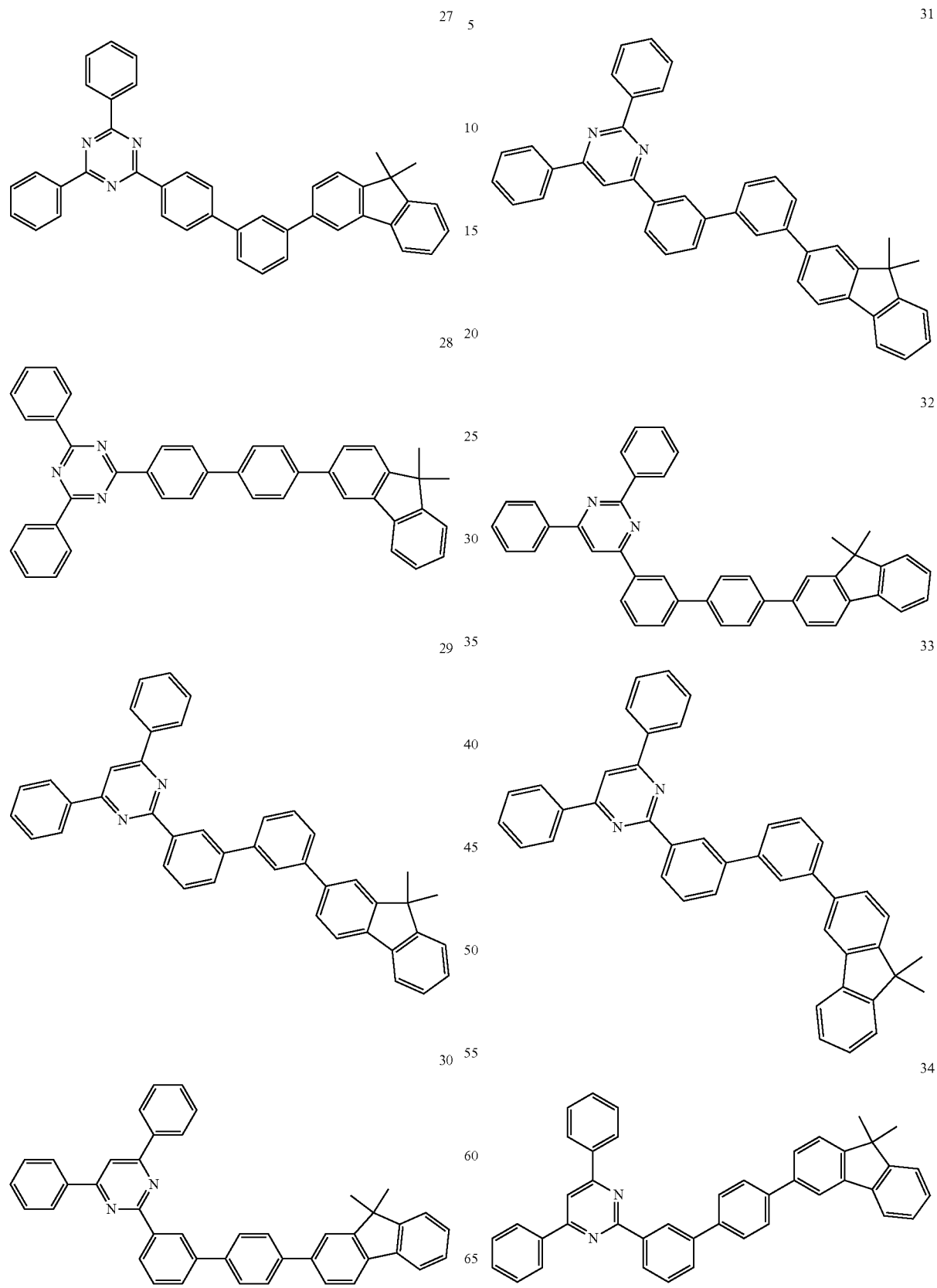

35
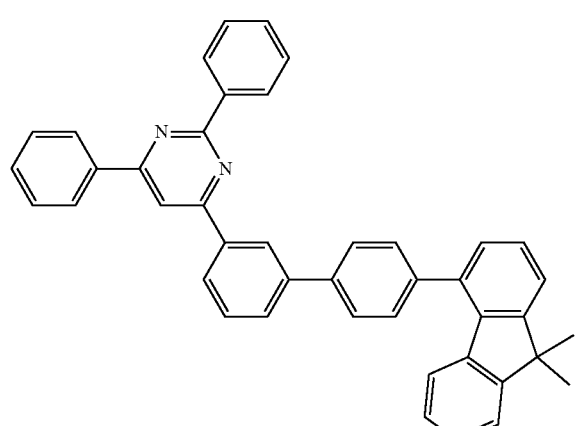
36
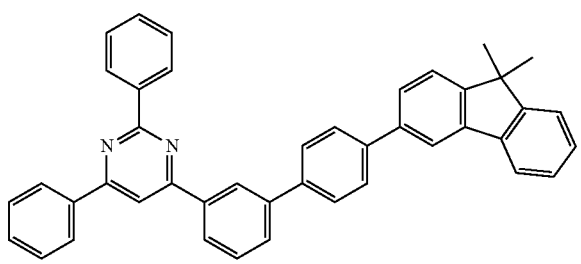
37
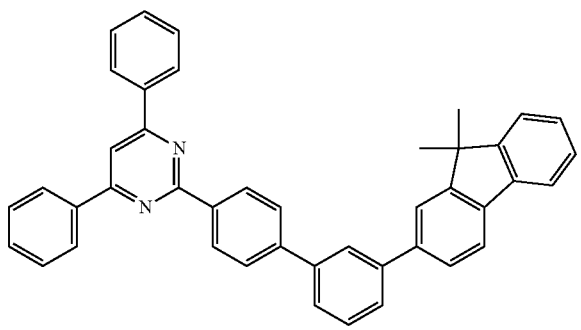
38
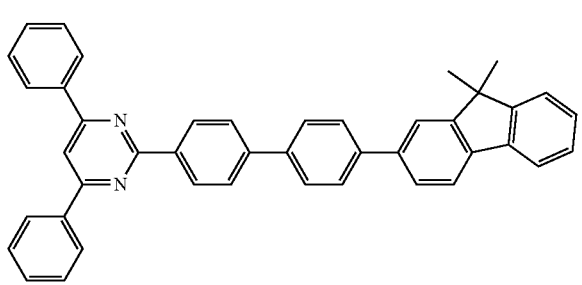
39
40
41
42
43
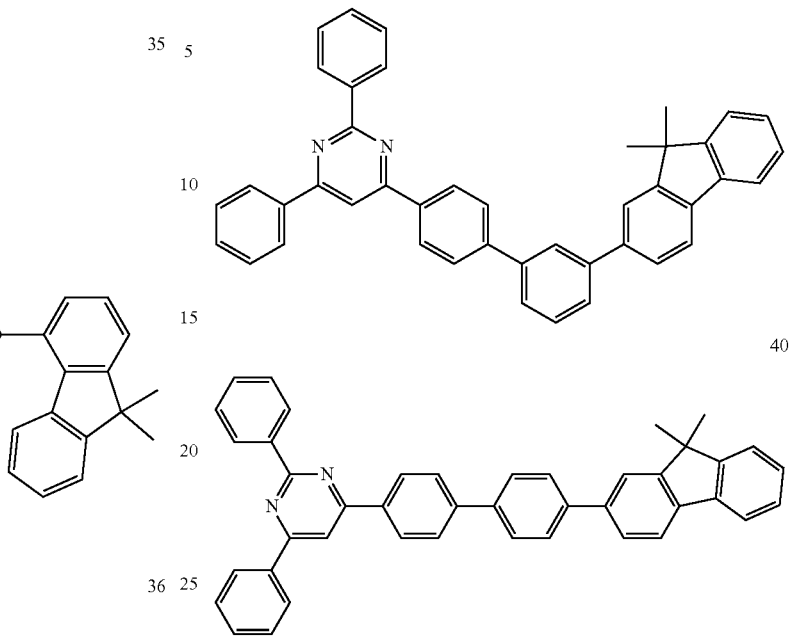
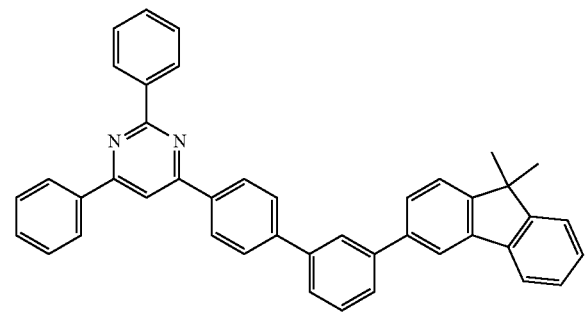

44
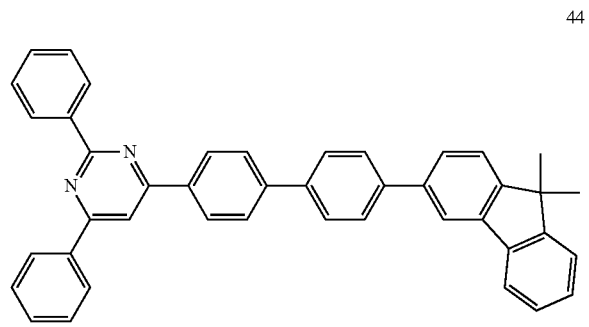
48
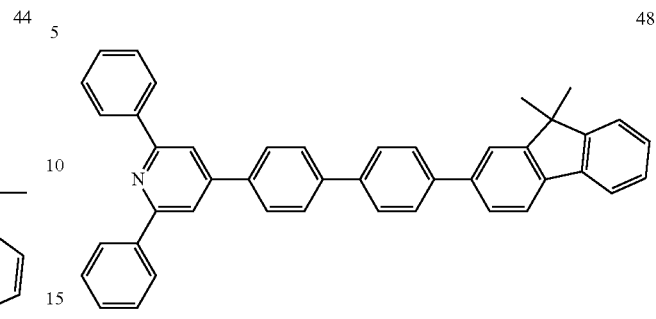
45
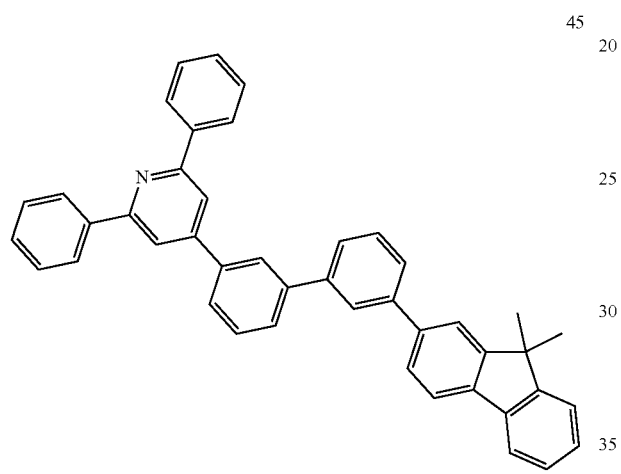
49
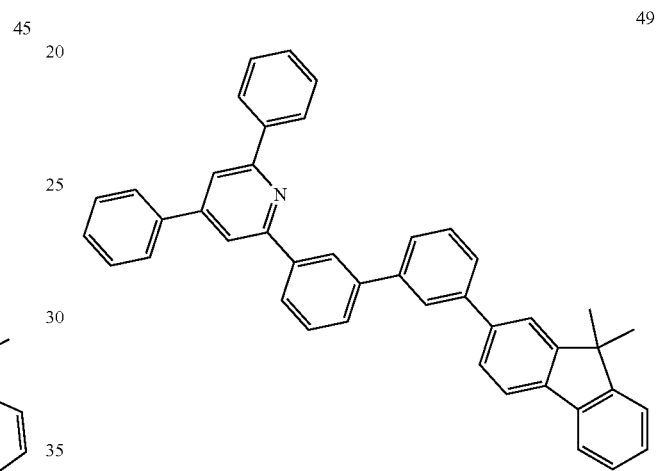
46
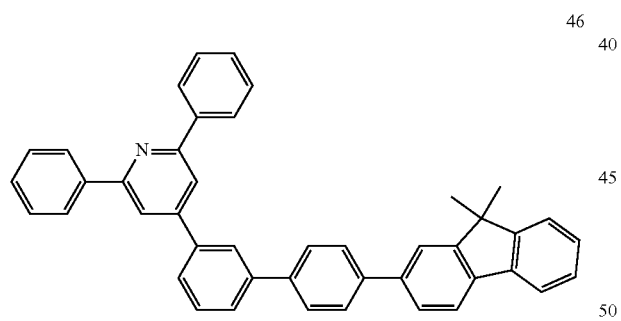
50
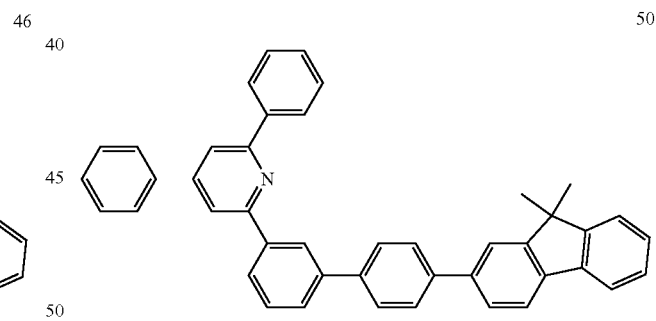
47
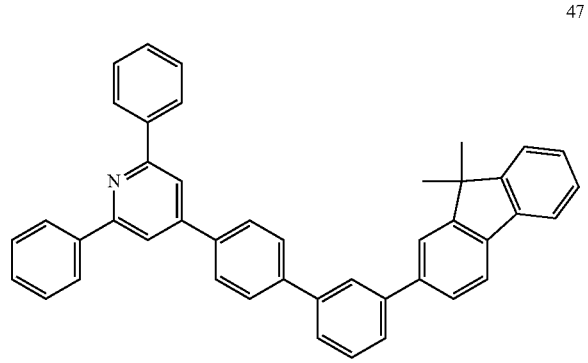
51
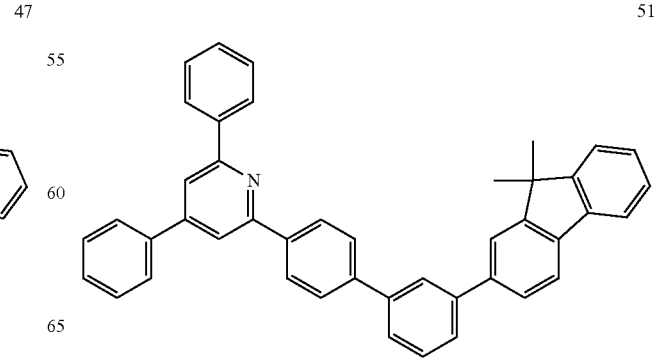

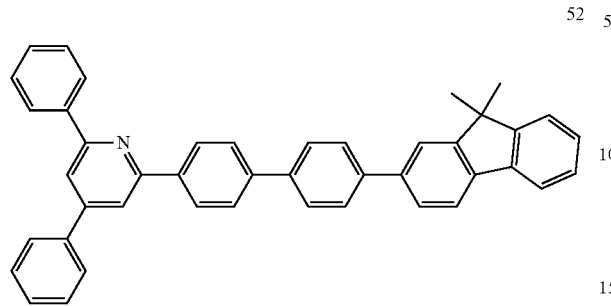
52
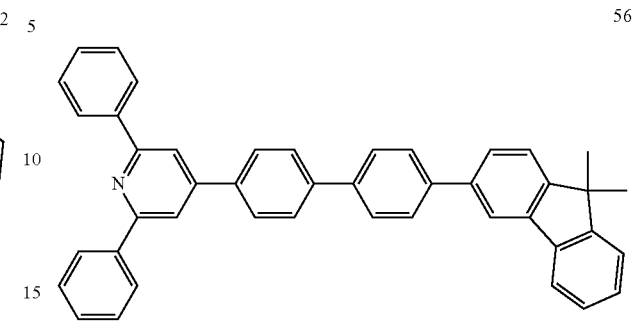
56
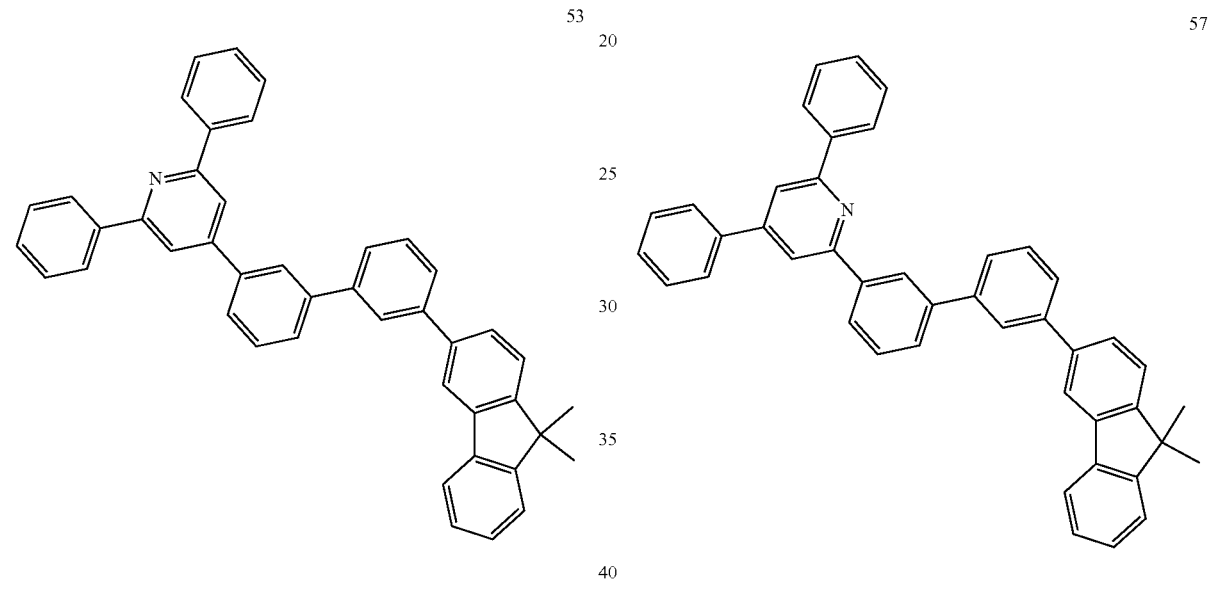
53
57
54
58
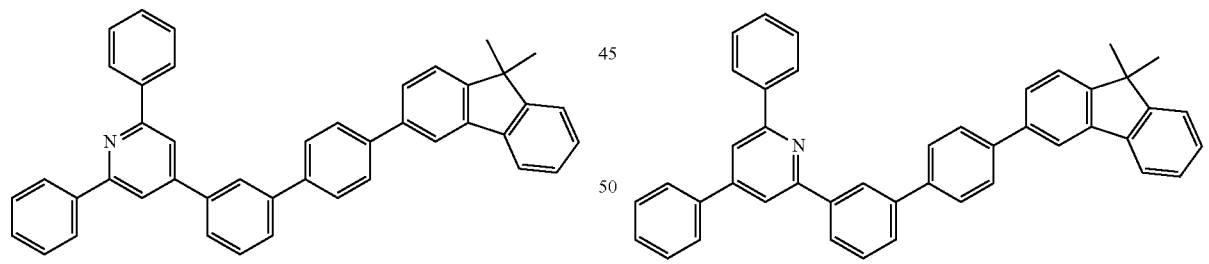
55
59
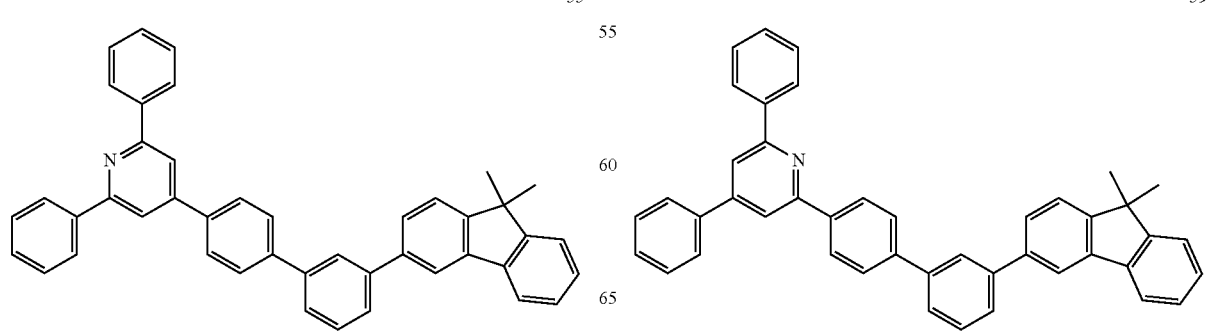

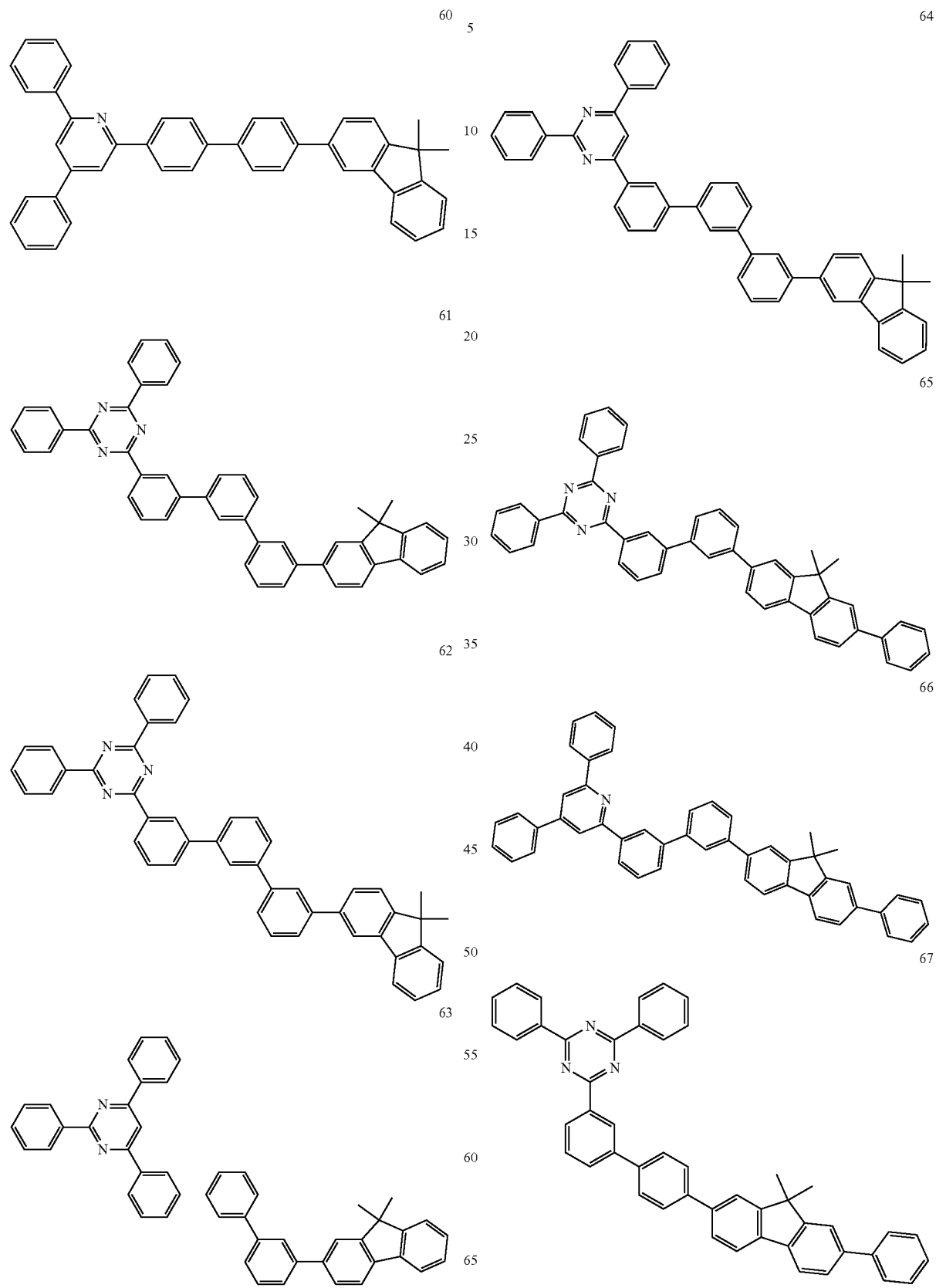

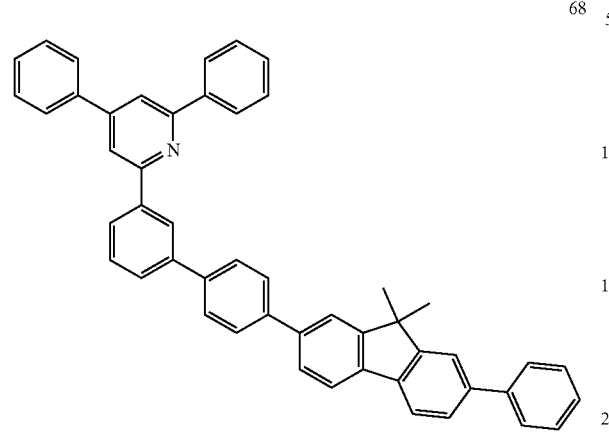
68
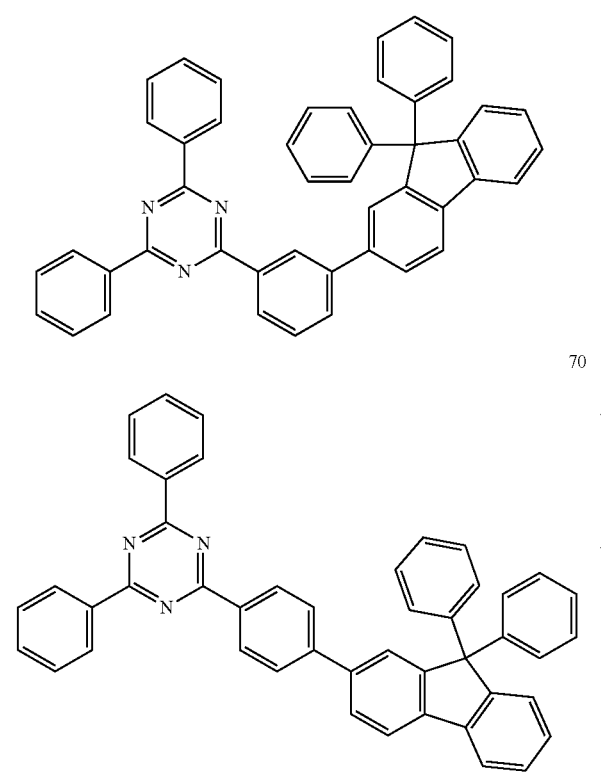
69
70
71
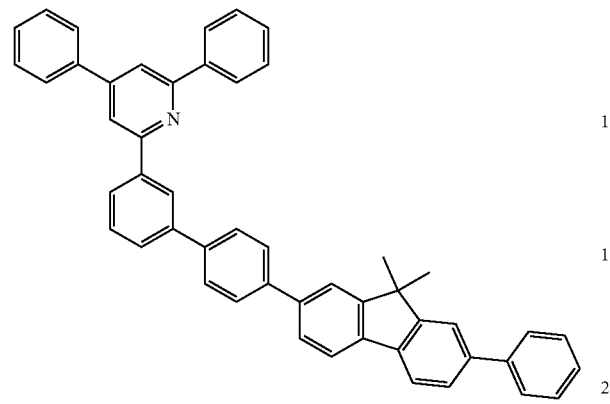
72
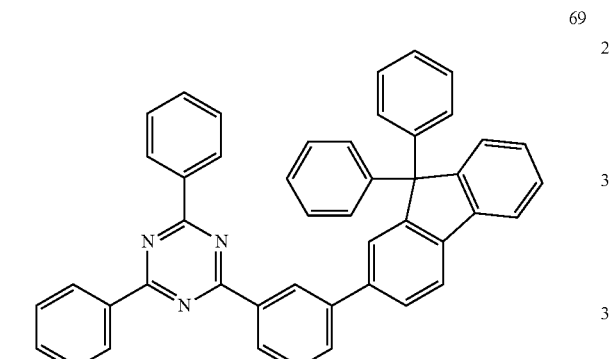
73
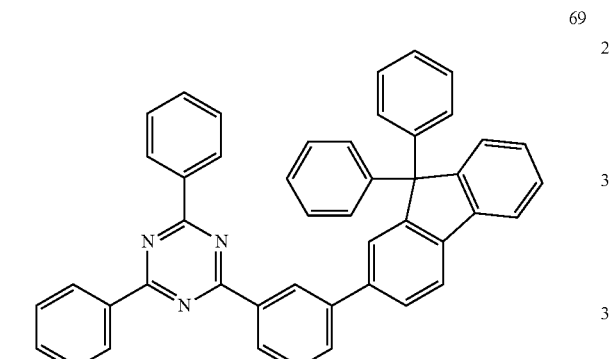
74
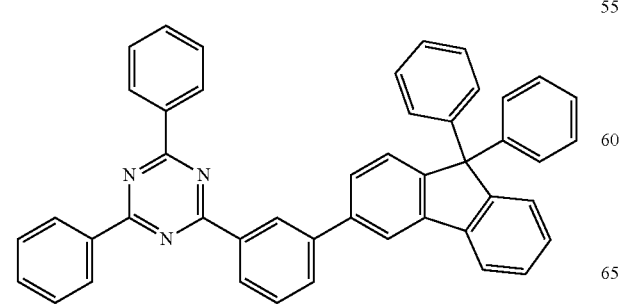
75

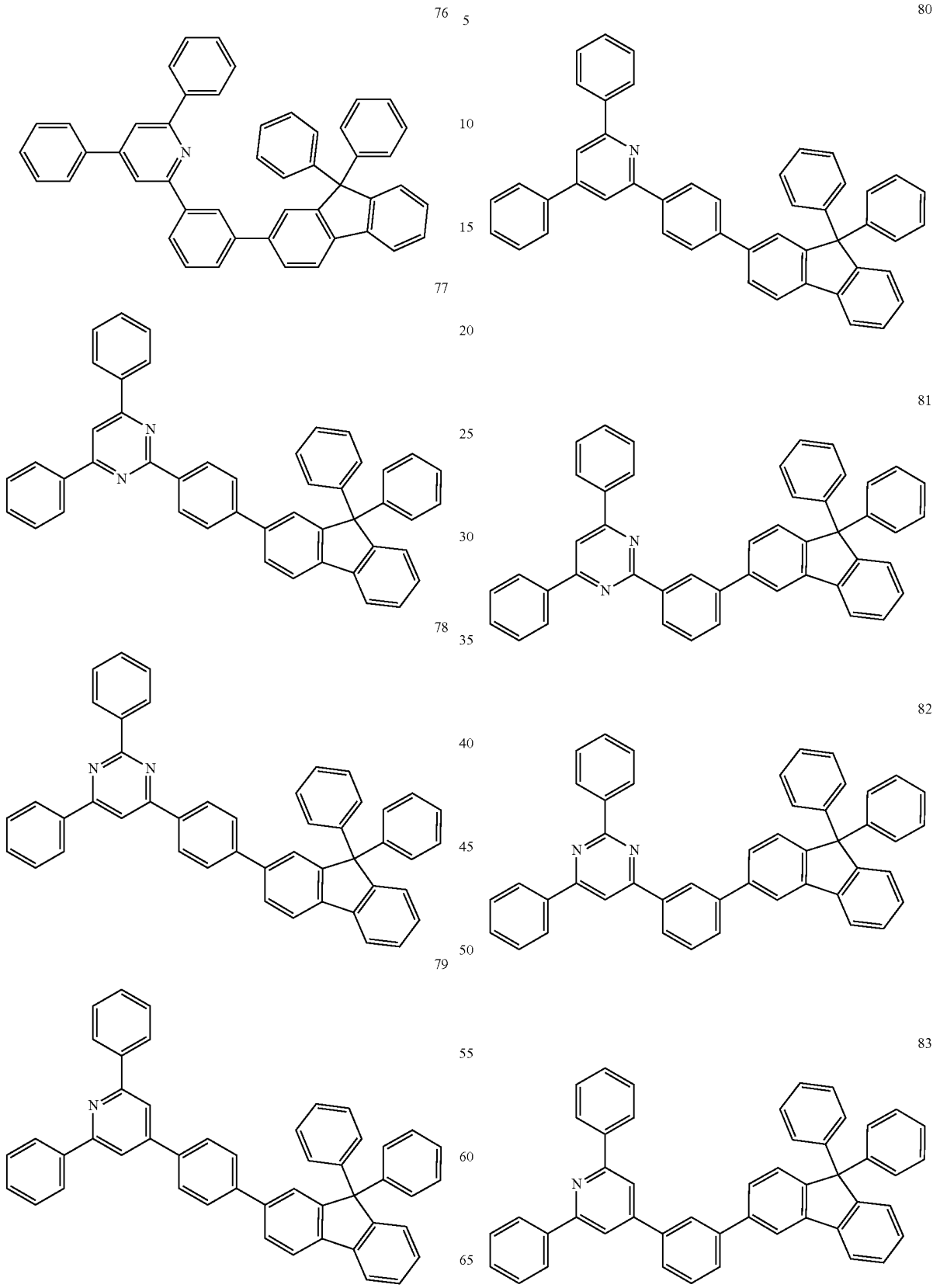

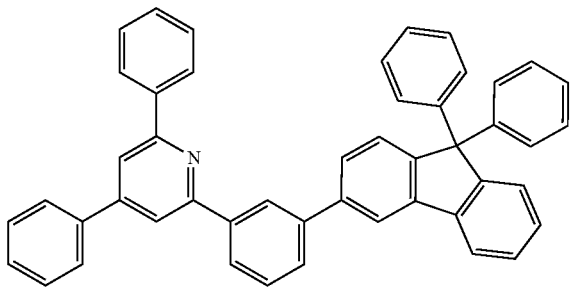
84
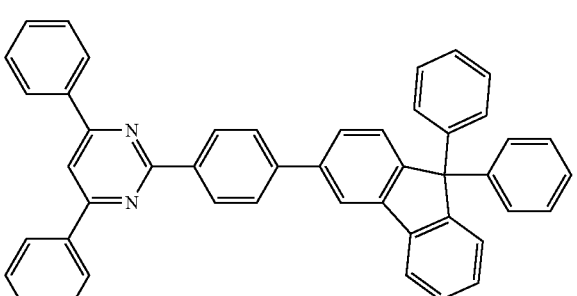
85
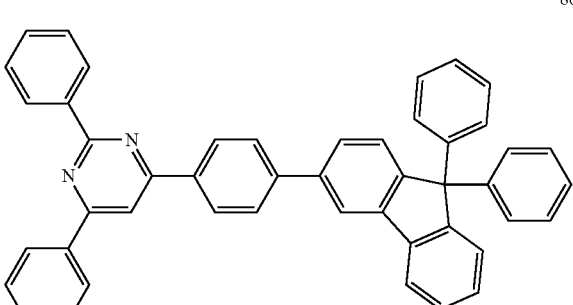
86
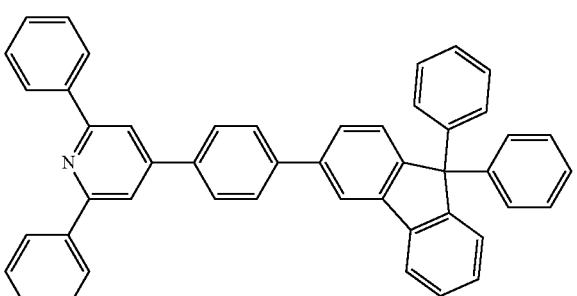
87
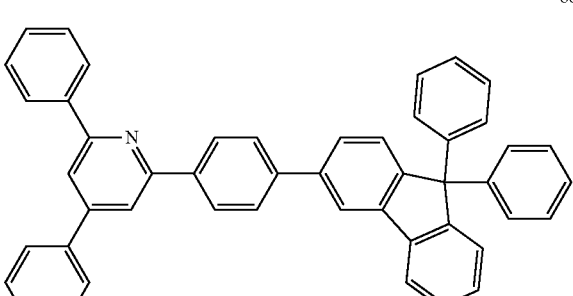
88
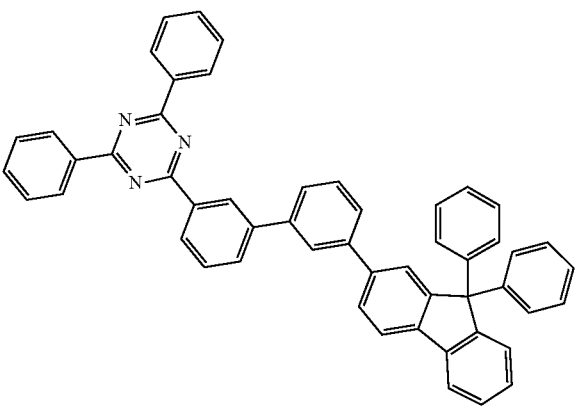
89
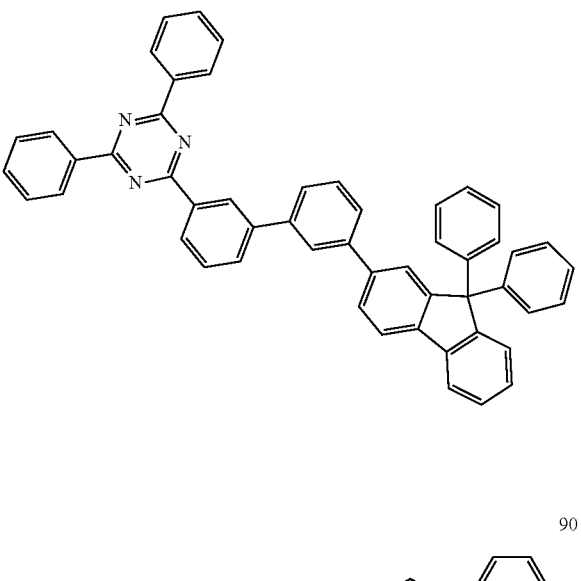
90
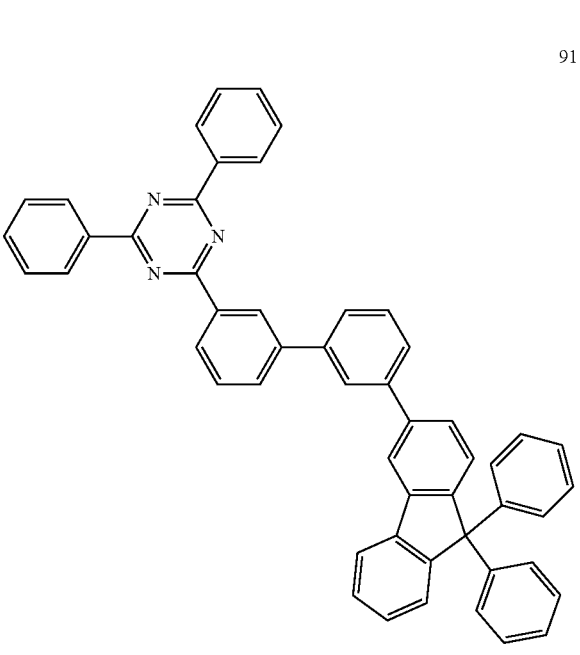
91

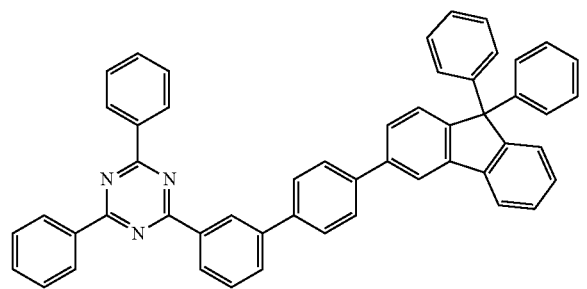
92
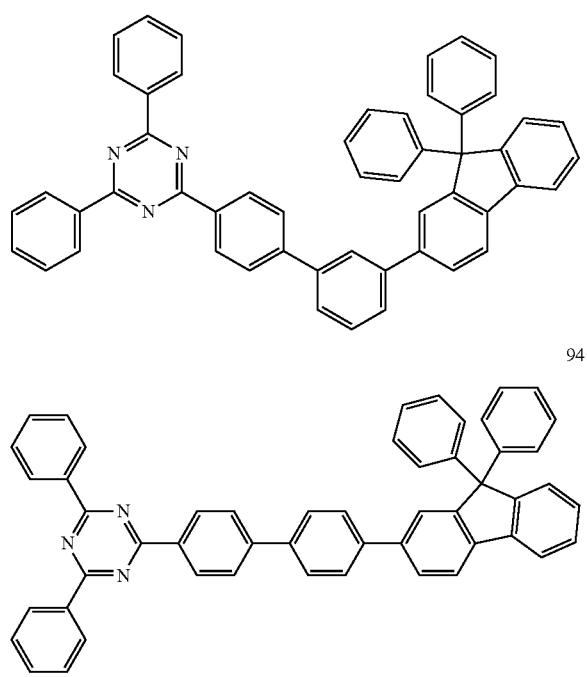
93
94
95
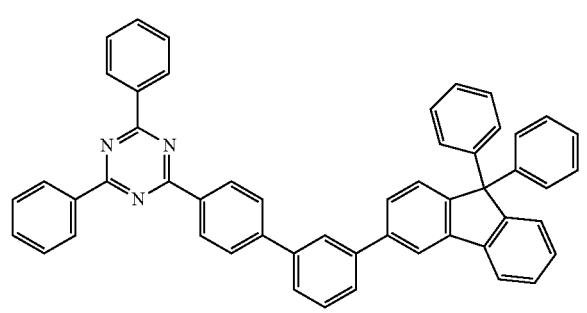
96
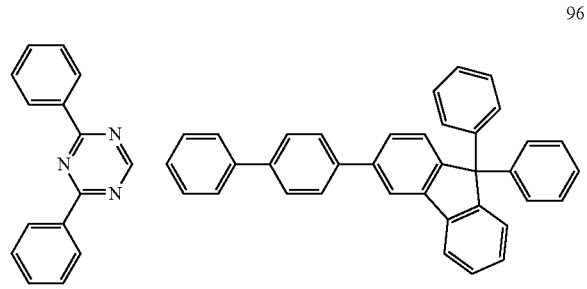
97
98
99
100

101
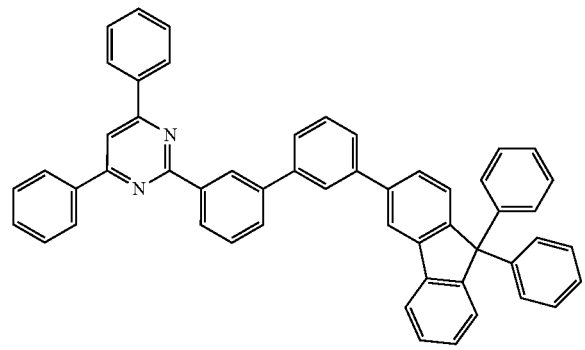
102
103
104
105
106
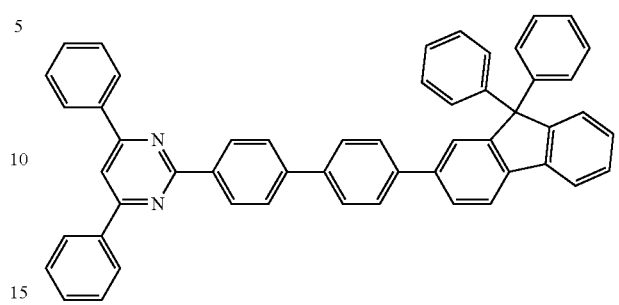
107
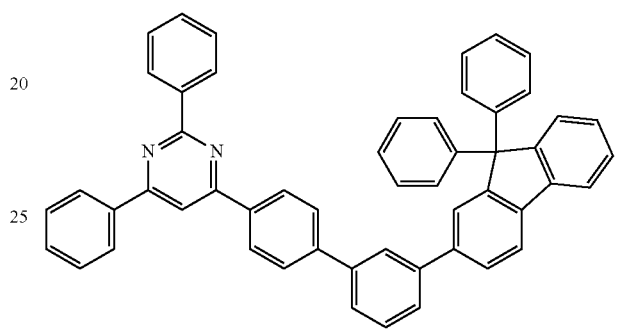
108
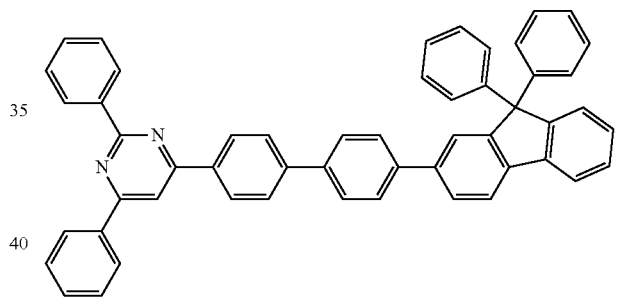
109
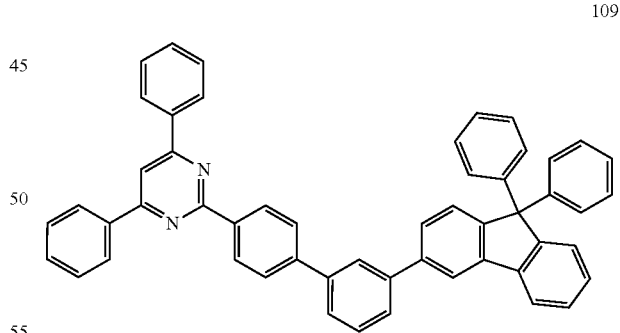
110
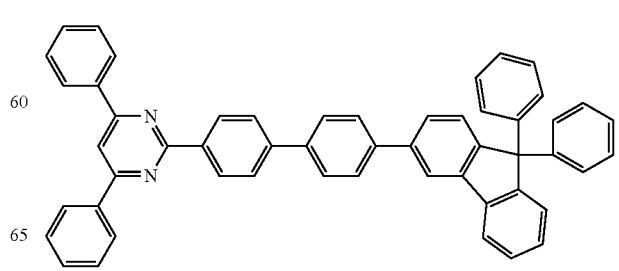

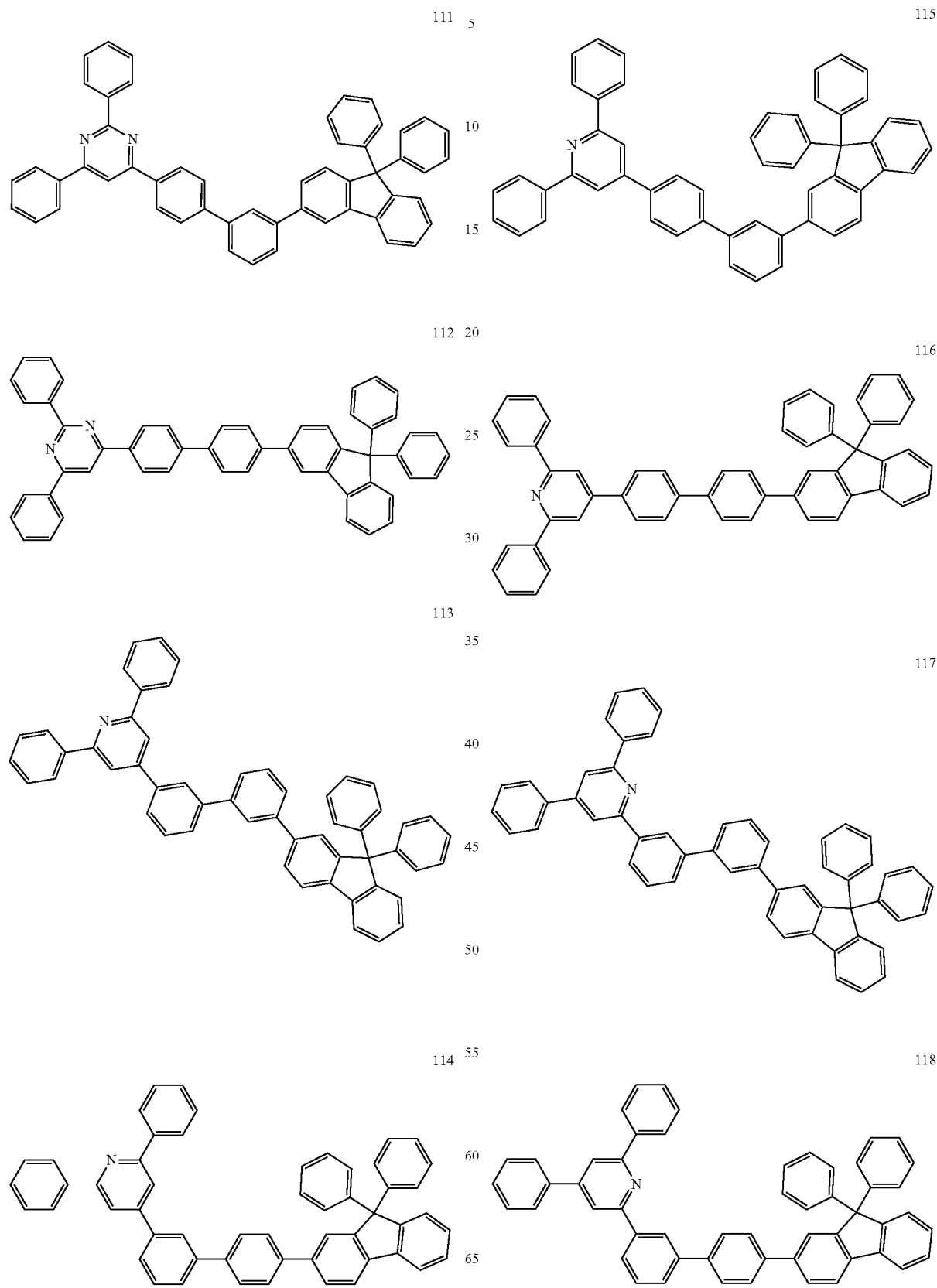

119
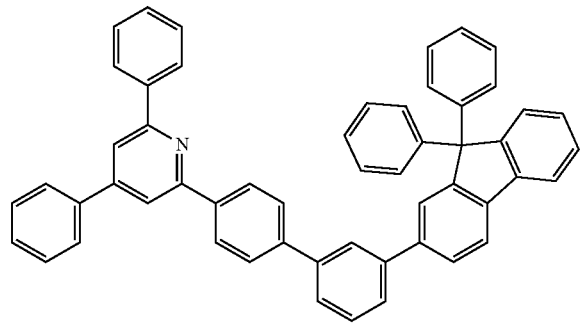
120
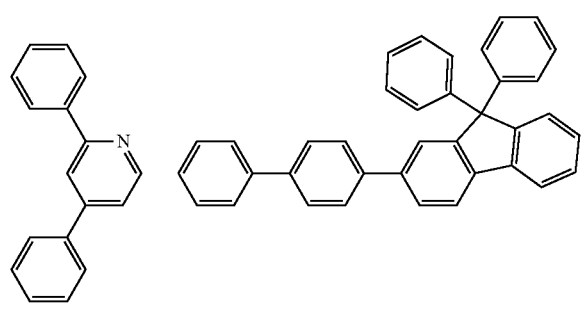
121
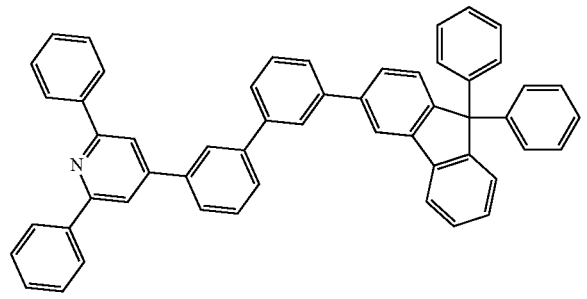
122
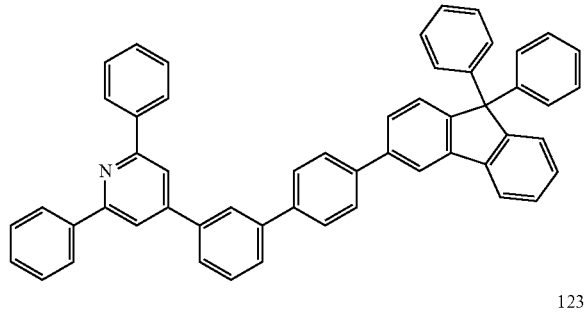
123
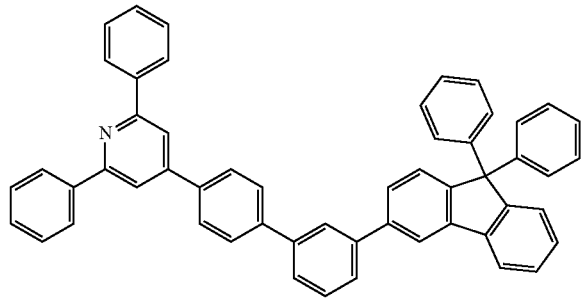
124
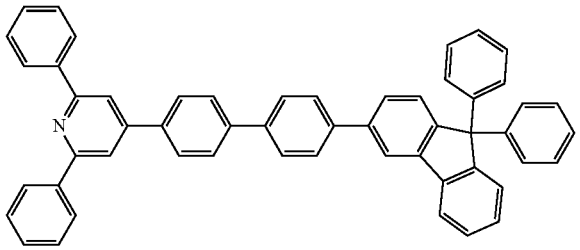
125
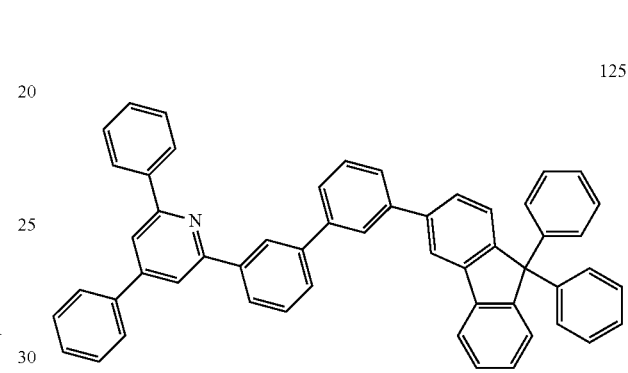
126
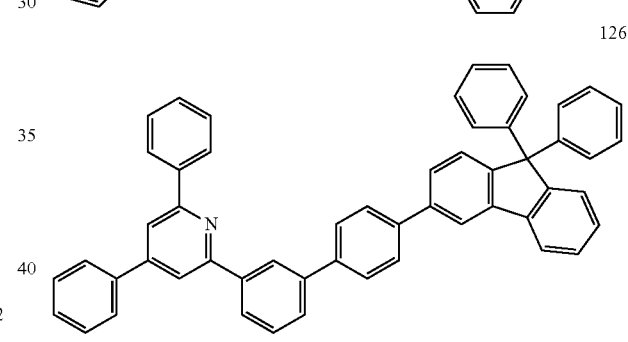
127
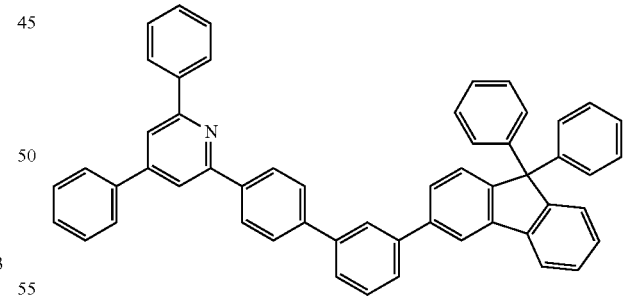
128
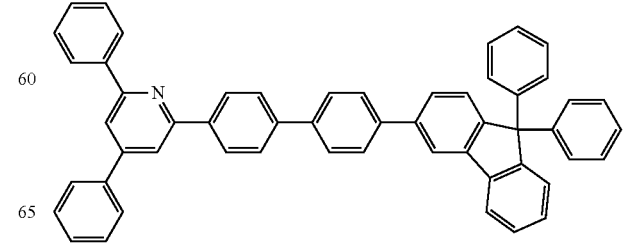

129
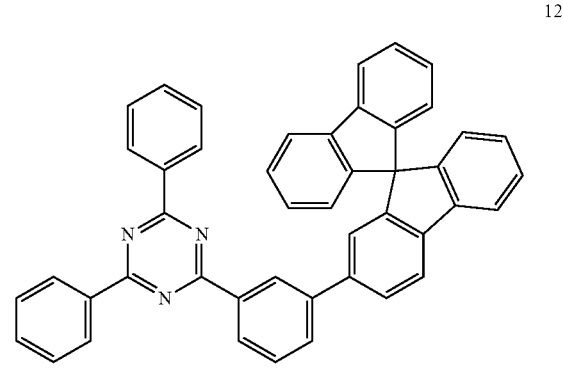
130
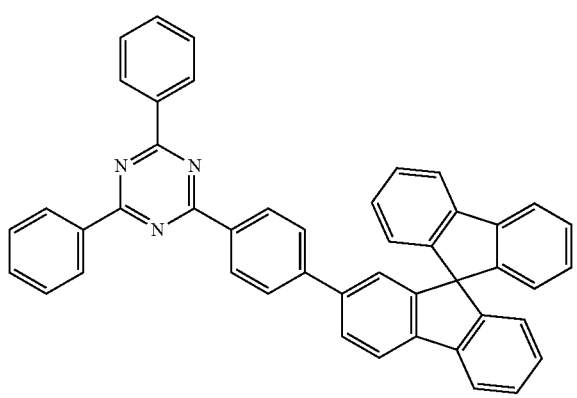
131
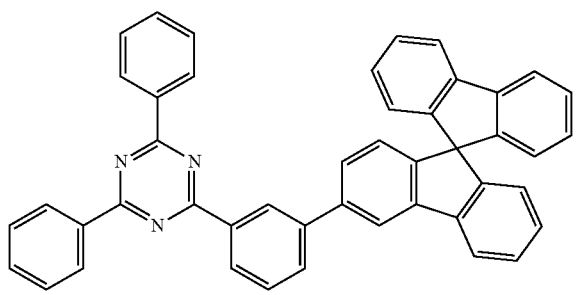
132
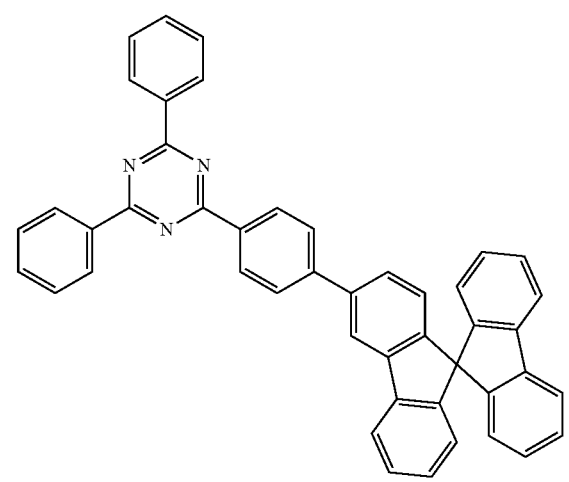
133
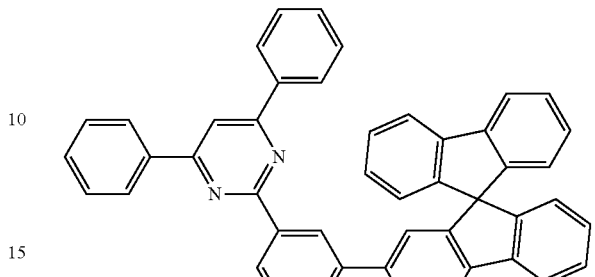
134
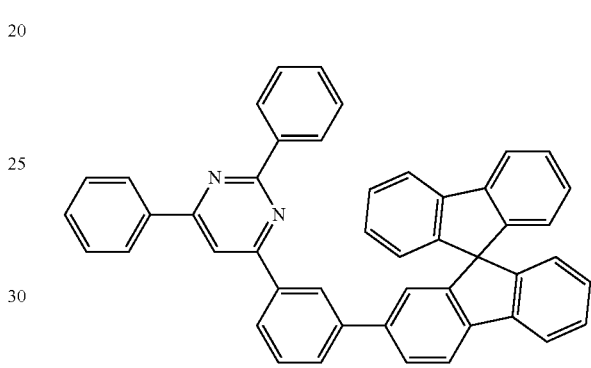
135
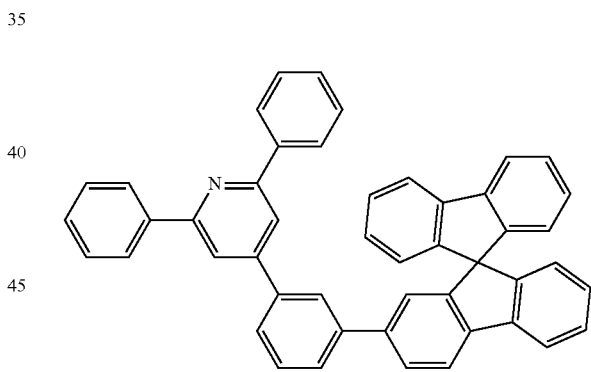
136
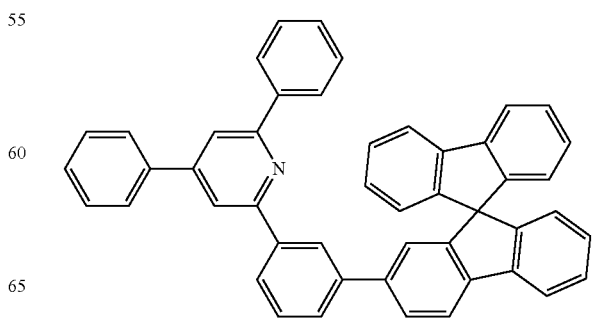

137
138
139
140
141
142
143
144
145

146
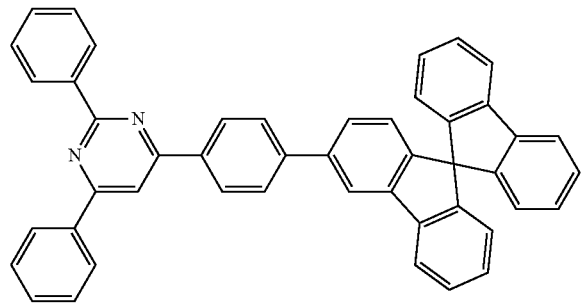
147
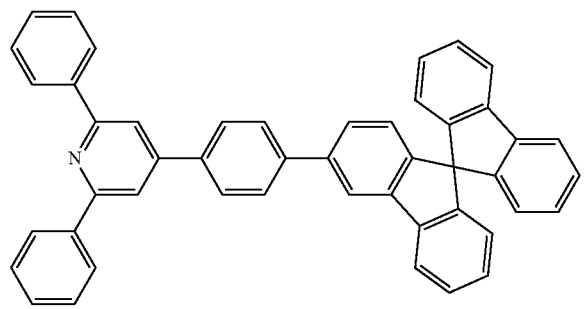
148
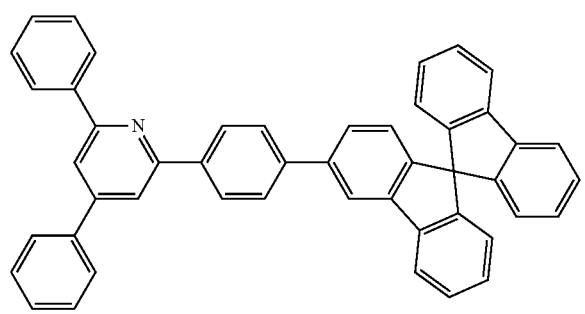
149
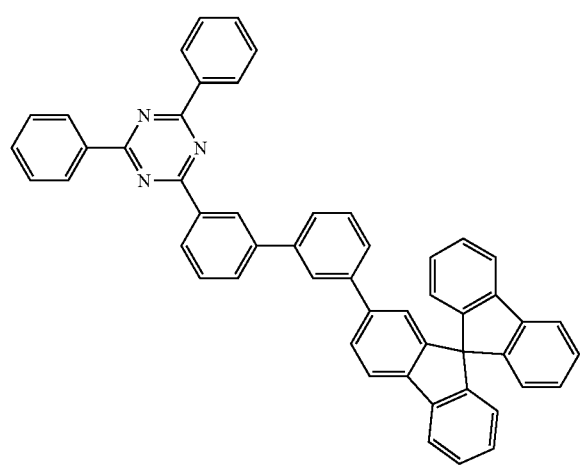
150
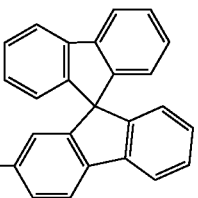
151
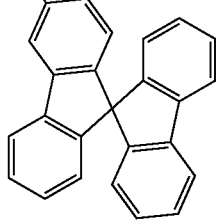
152
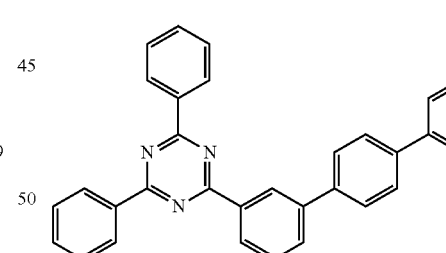
153
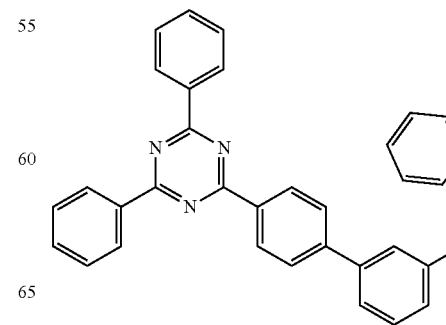

154
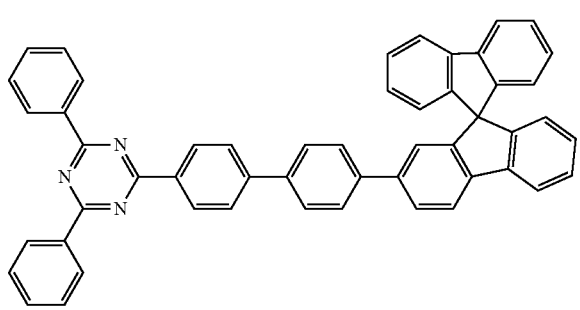
155
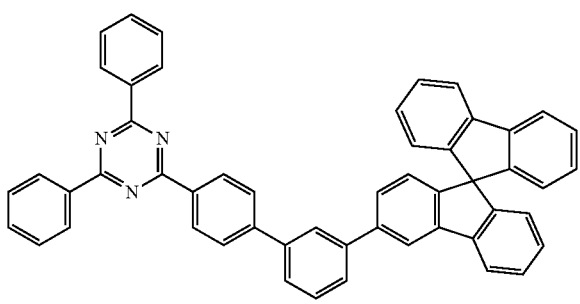
156
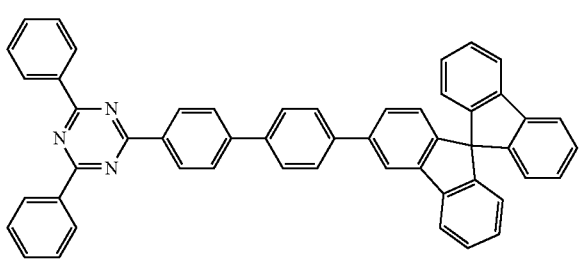
157
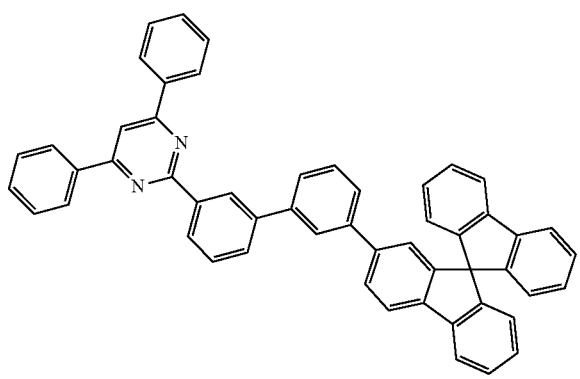
158
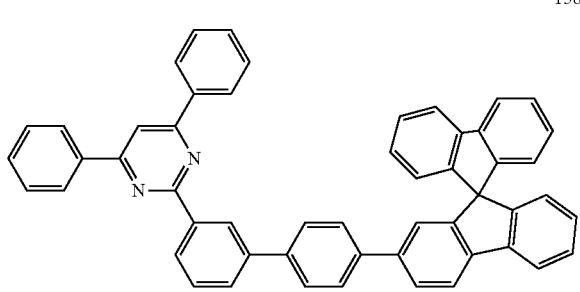
159
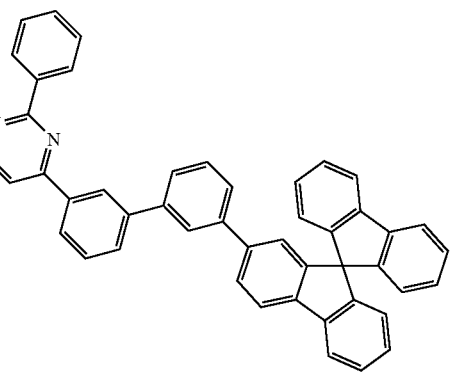
160
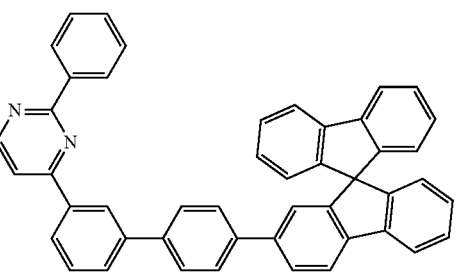
161
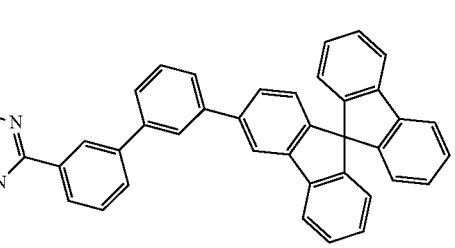
162
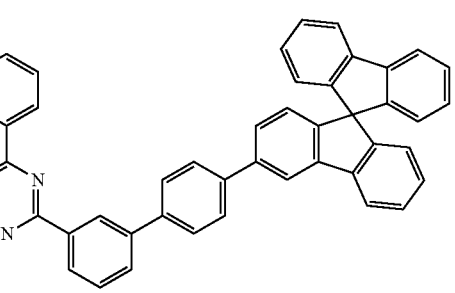
163
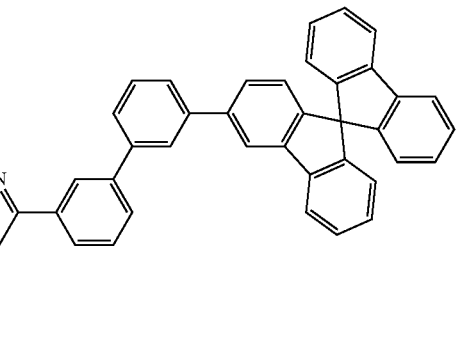

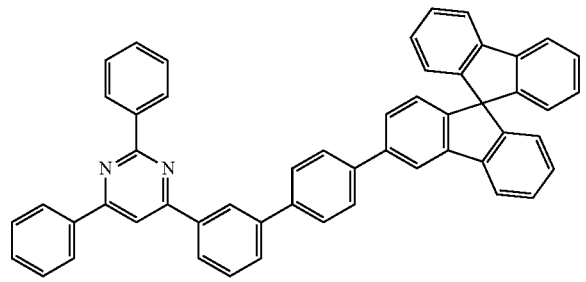
164
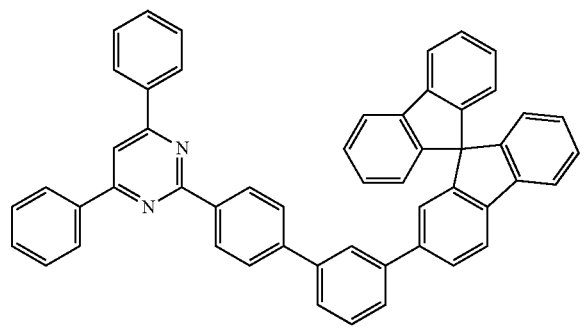
165
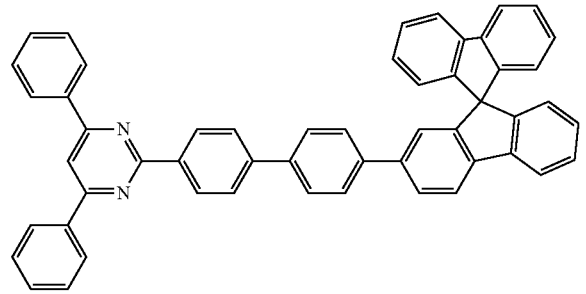
166
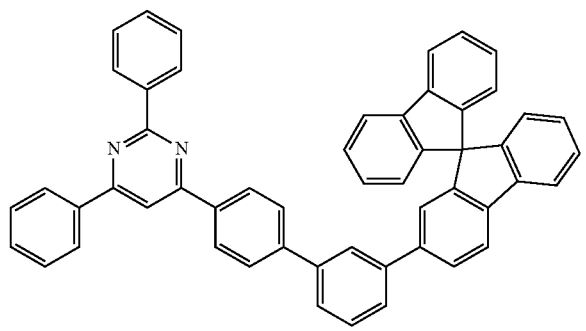
167
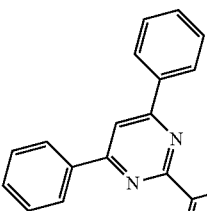
168
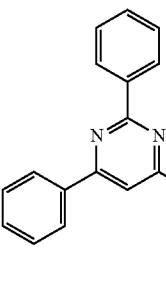
169
170
171
172
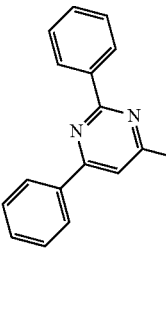

173
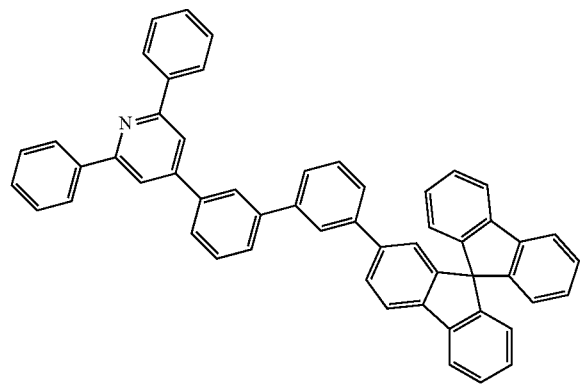
174
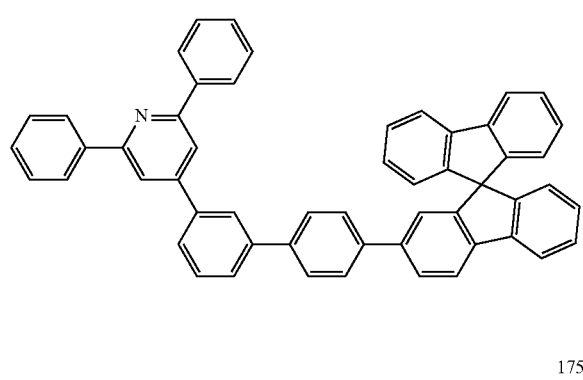
175
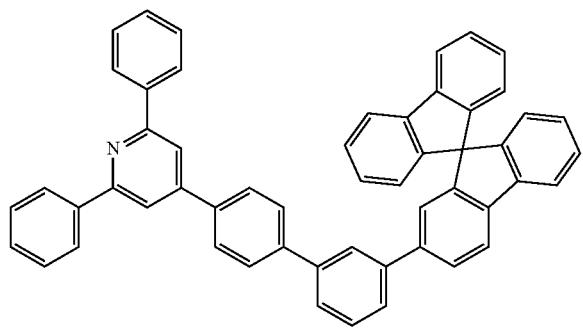
176
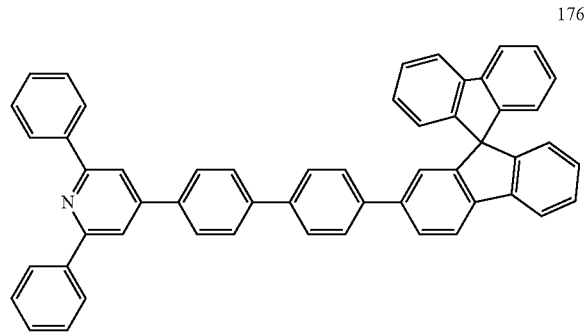
177
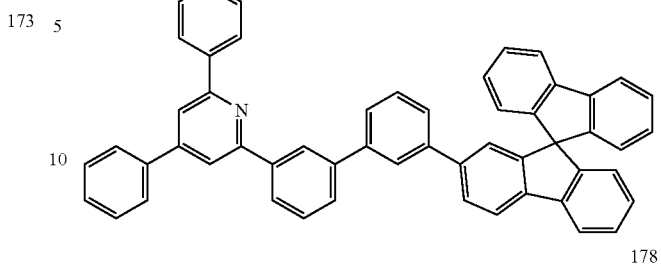
178
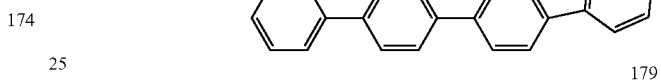
179
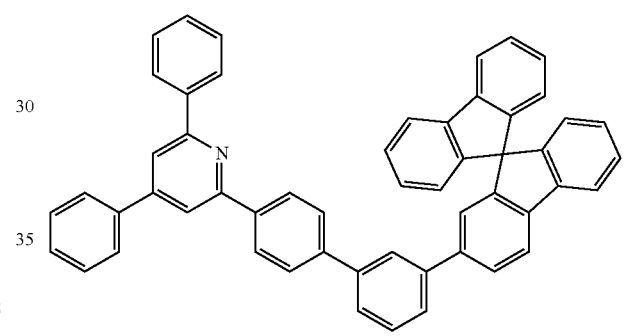
180
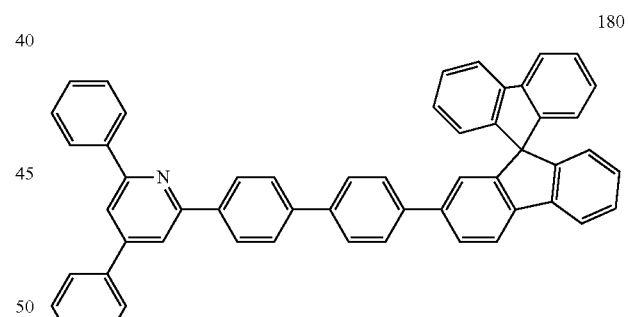
181
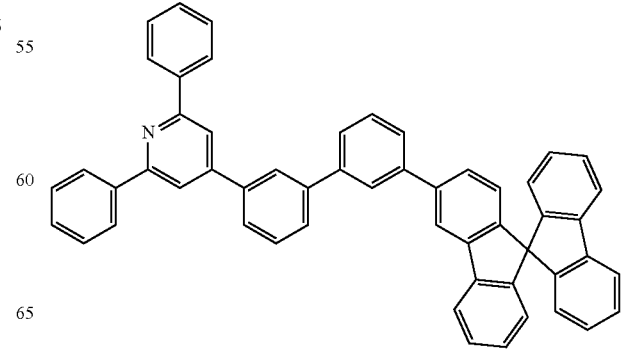

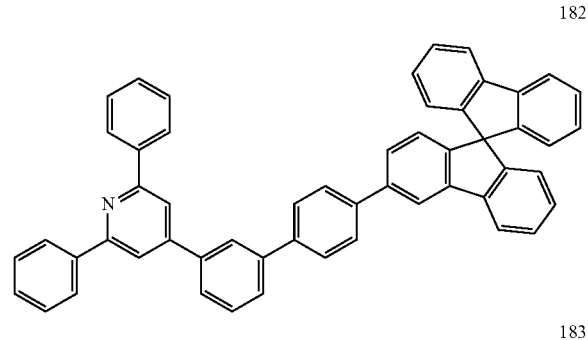
182
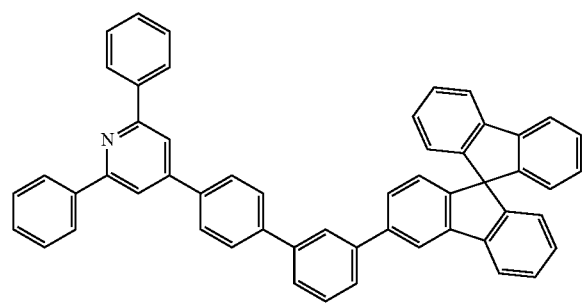
183
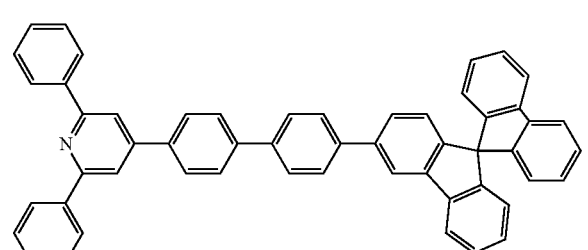
184
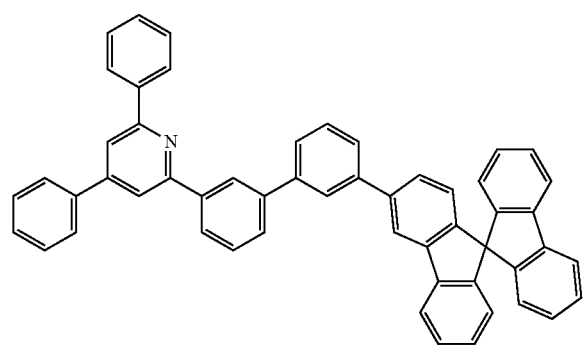
185
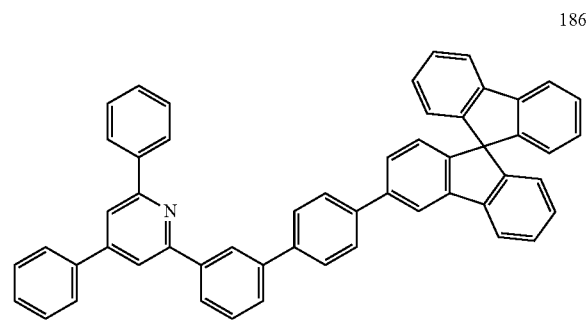
186
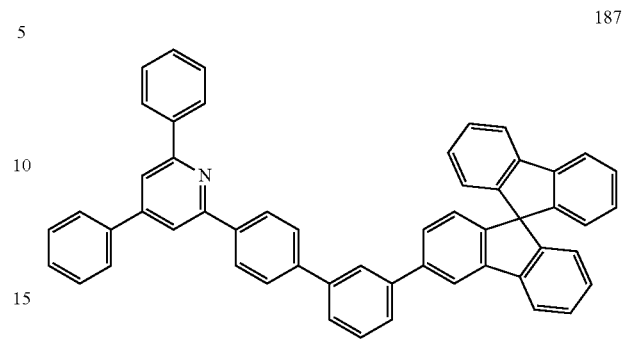
187
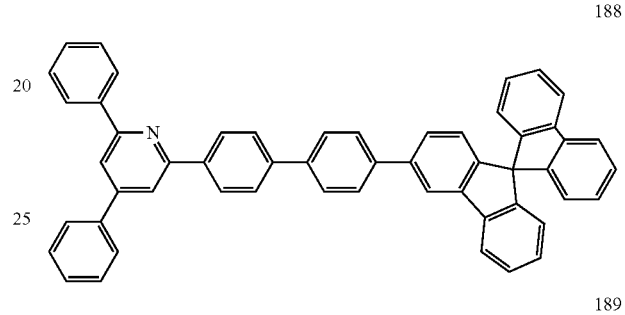
188
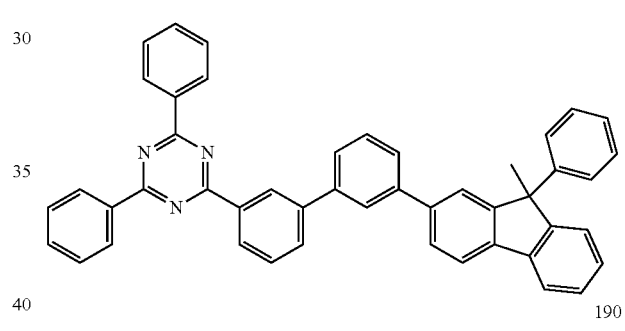
189
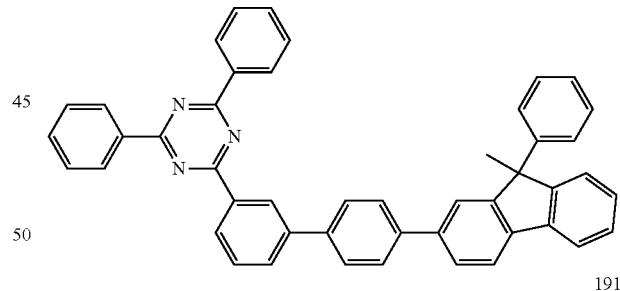
190
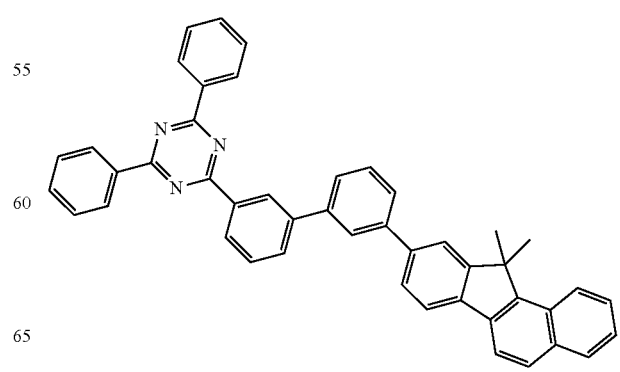
191

192
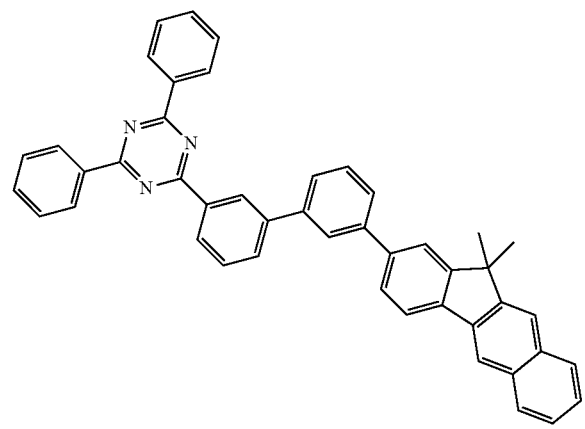
193
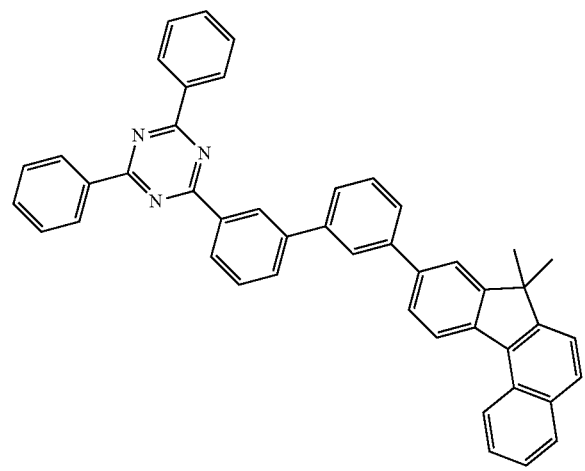
194
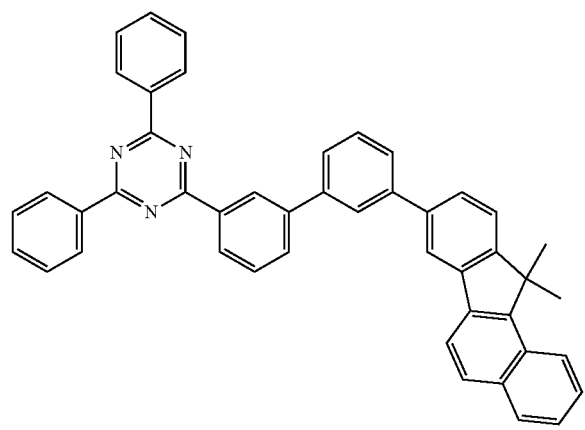
195
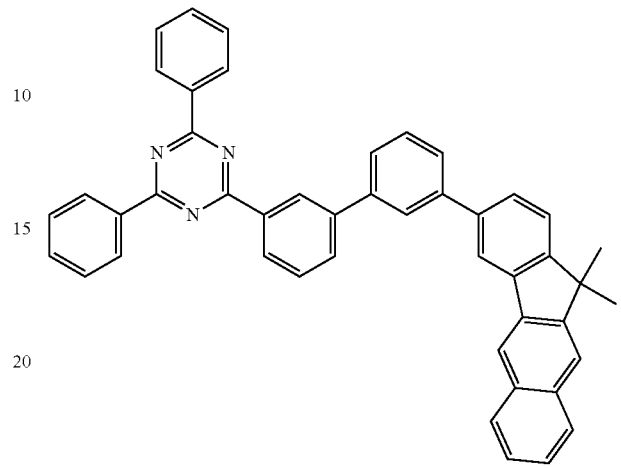
196
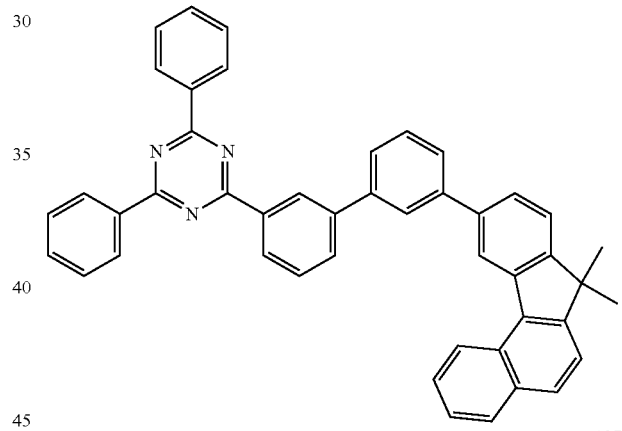
197
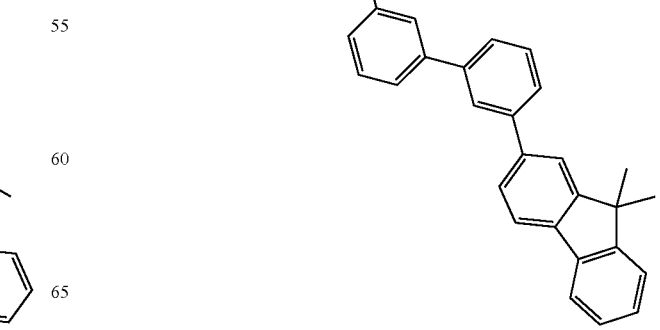

198
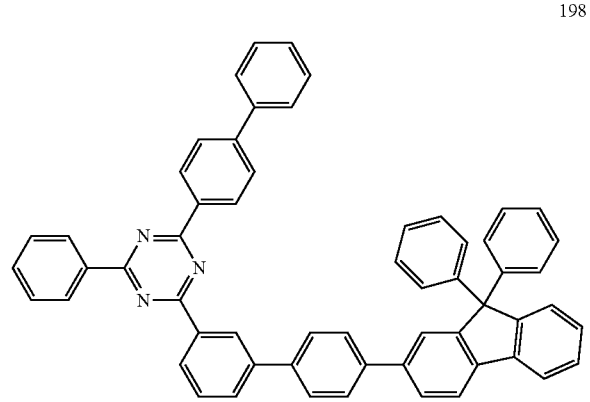
199
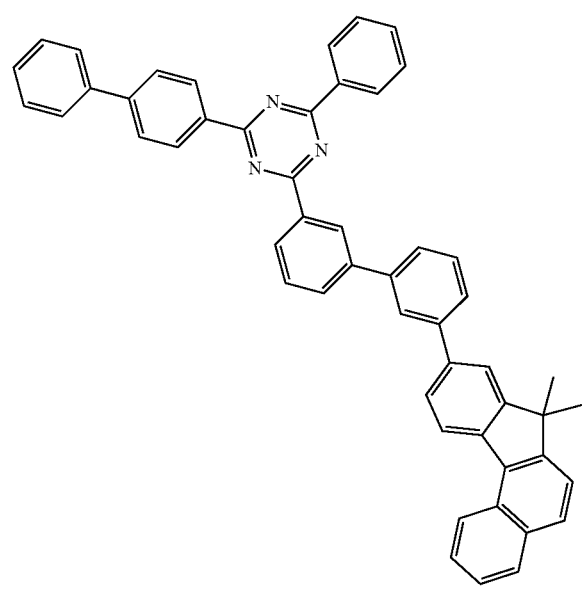
200
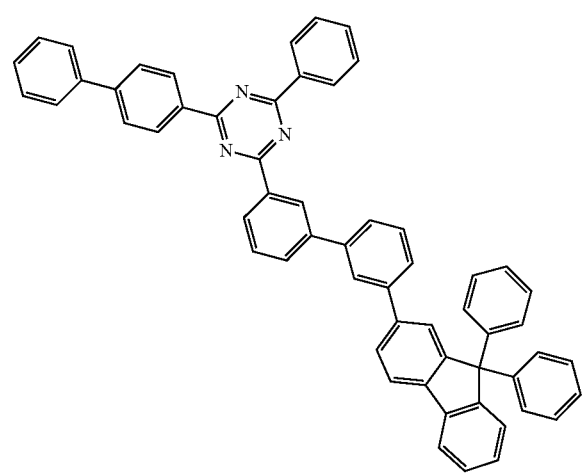
201
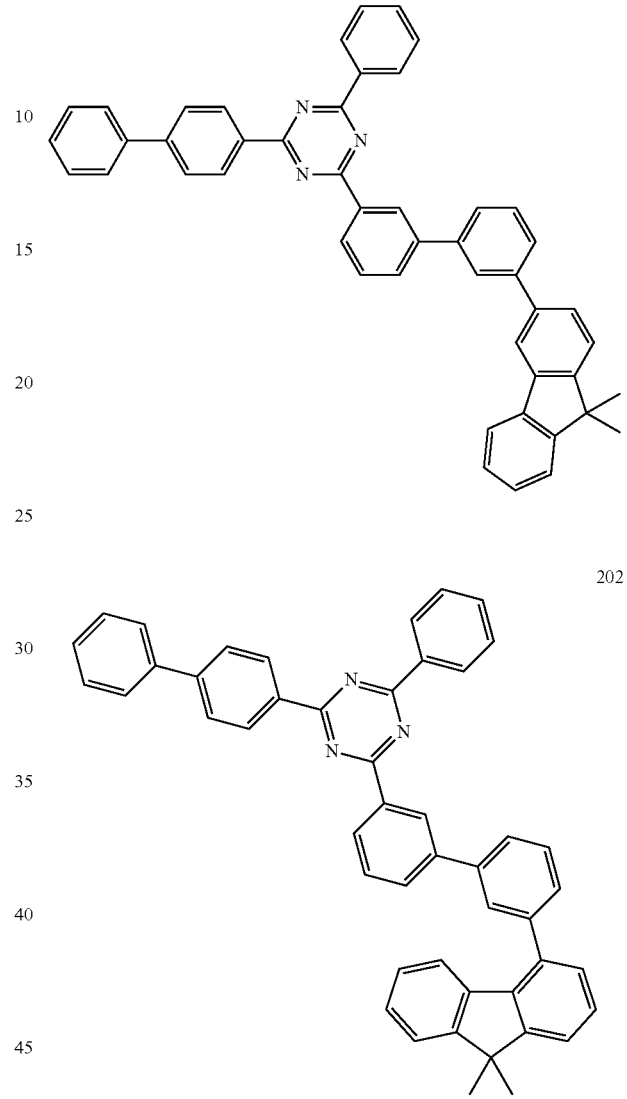
202
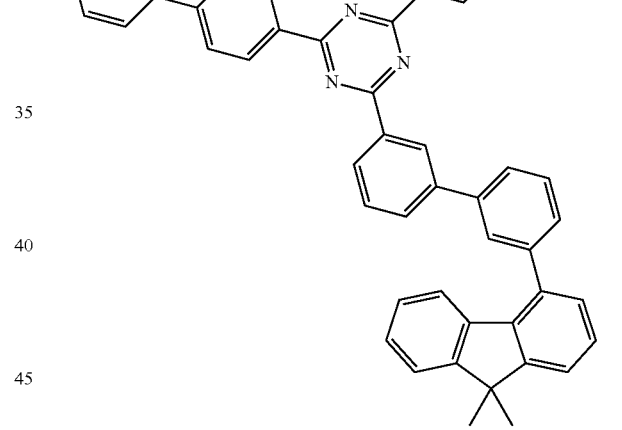
203
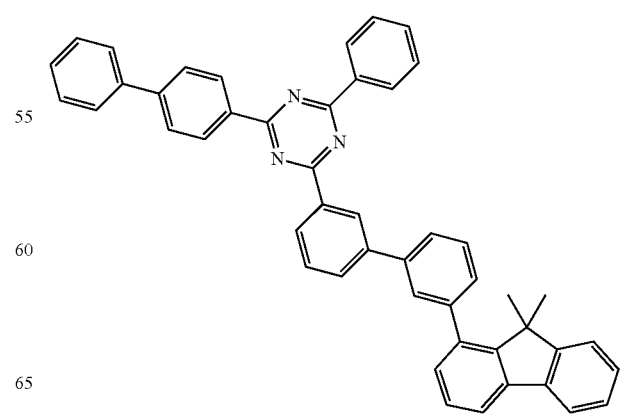

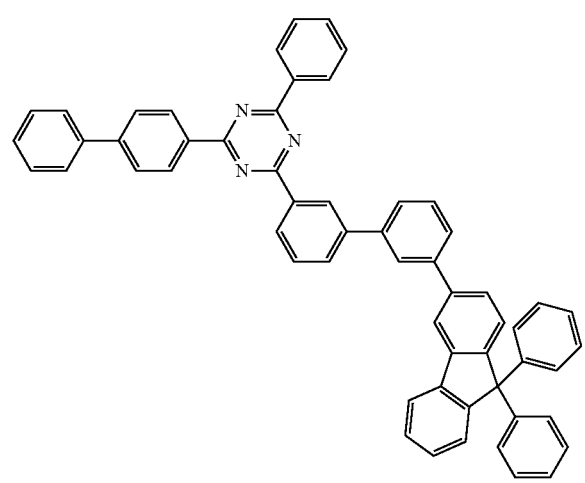
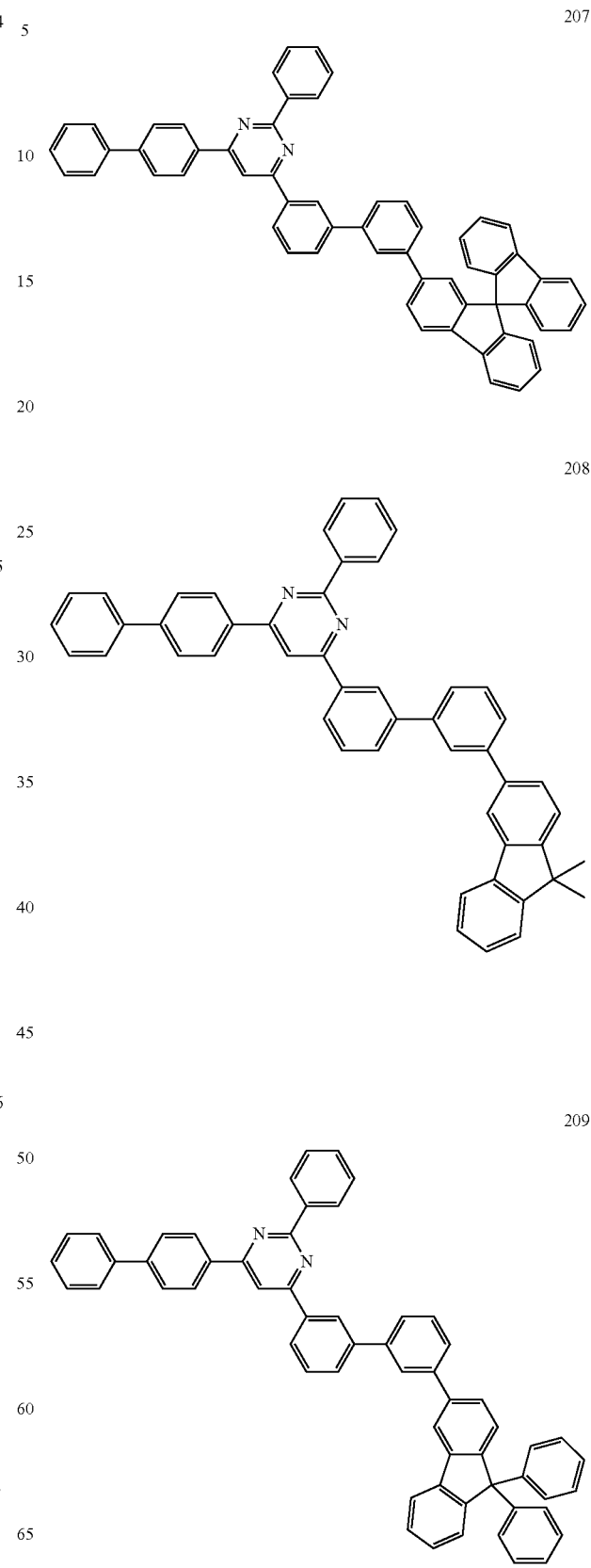

210
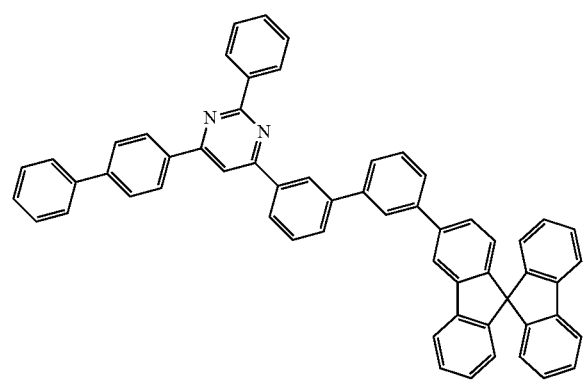
211
213
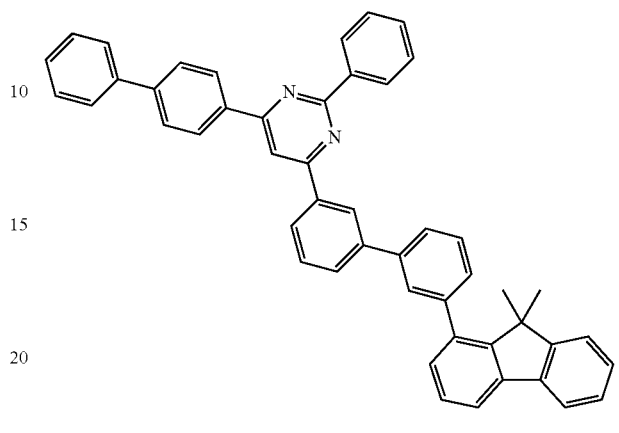
214
212
215
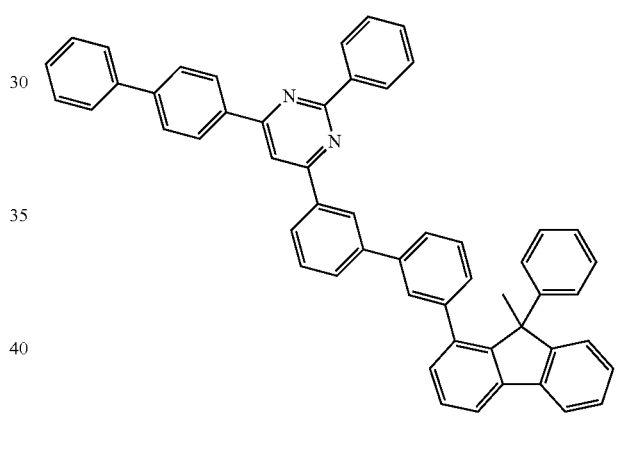
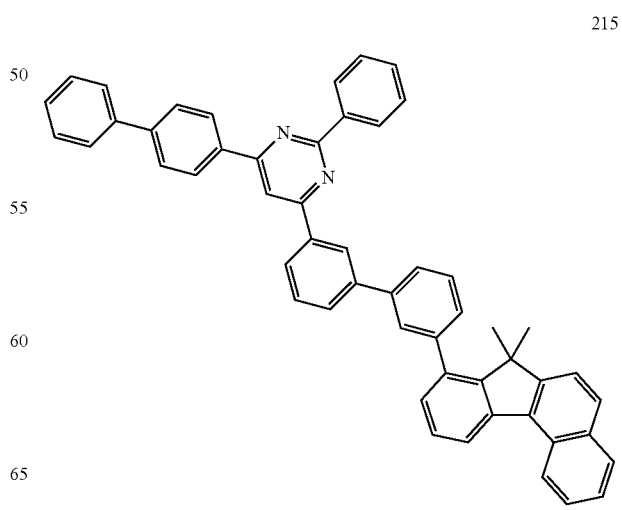

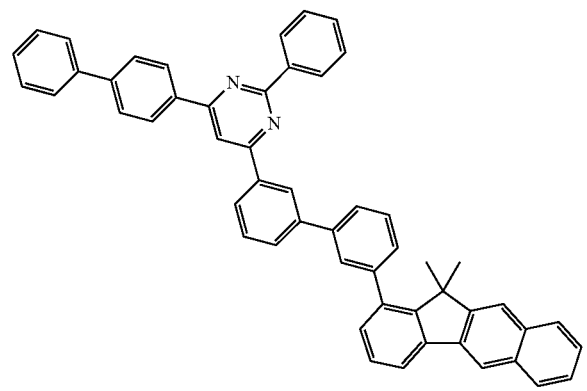
216
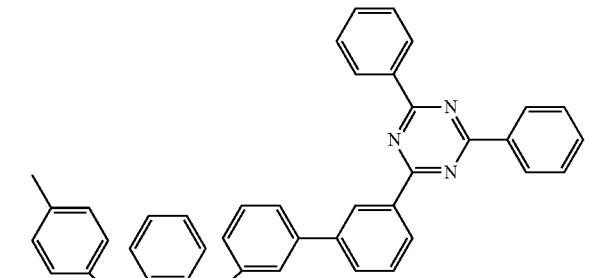
219
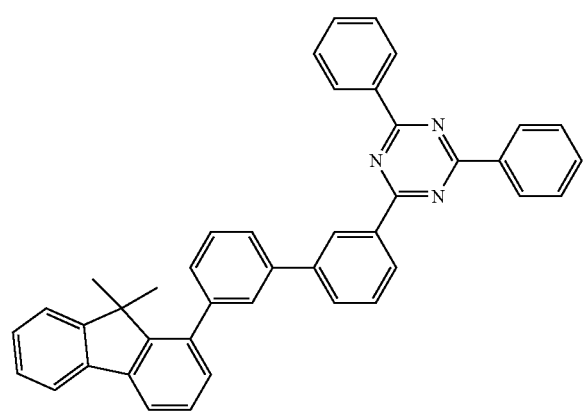
217
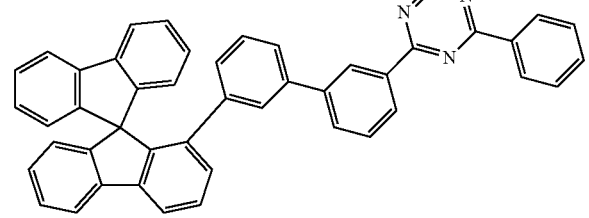
220
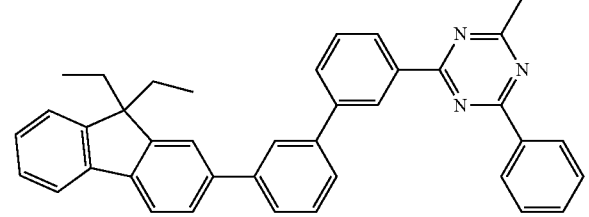
221
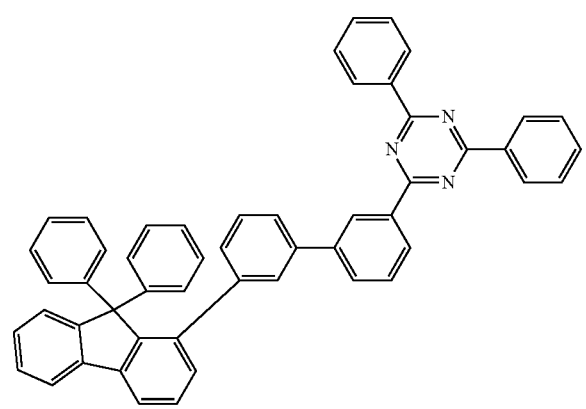
218
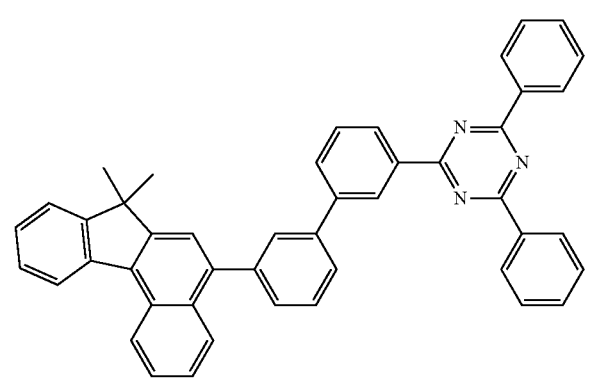
222

-continued
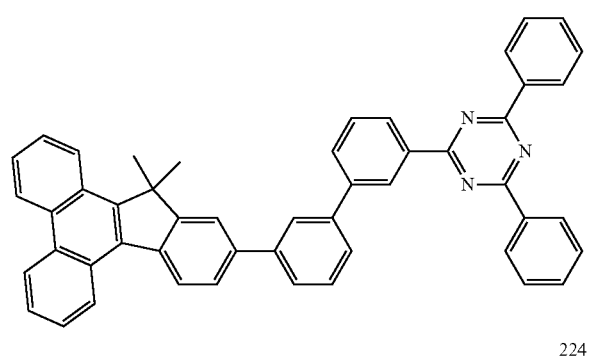
223
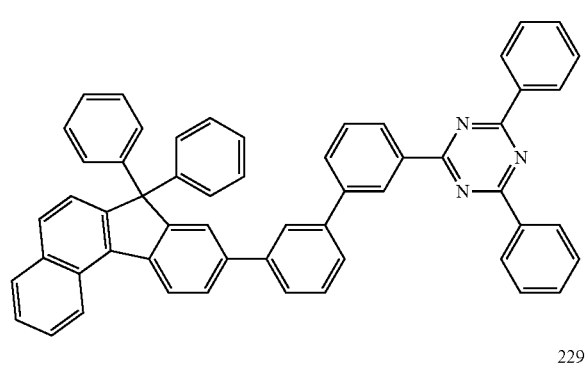
228
224
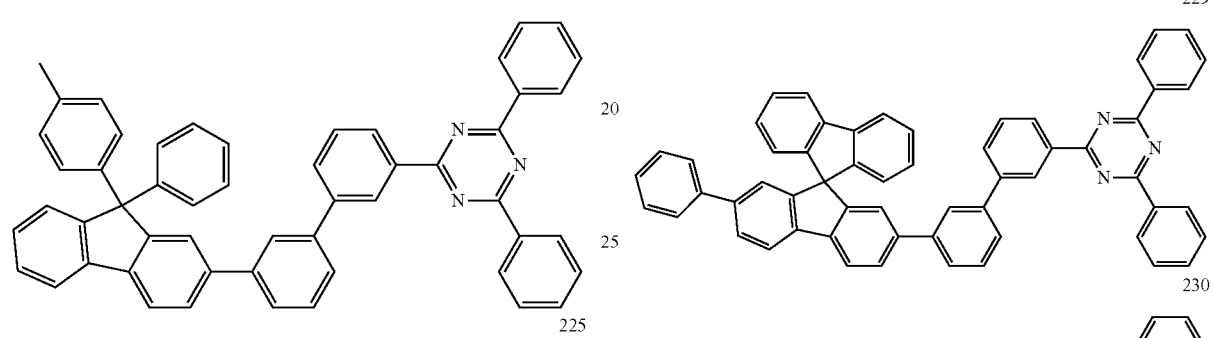
229
225
230
226
231
227
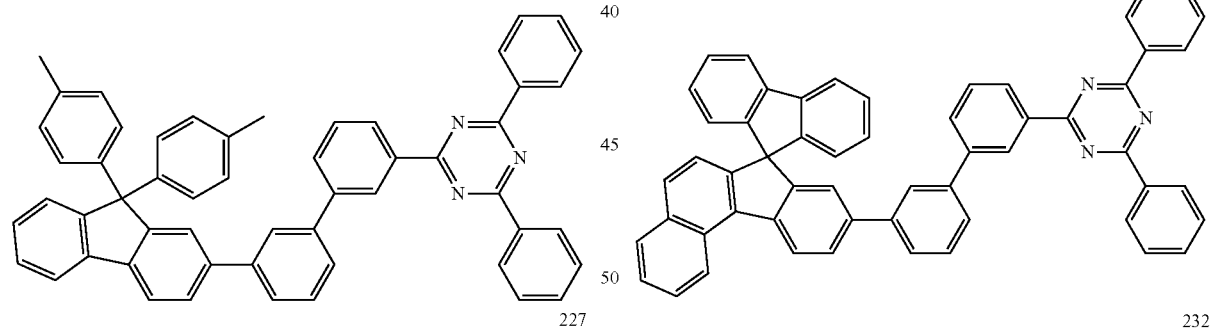
232
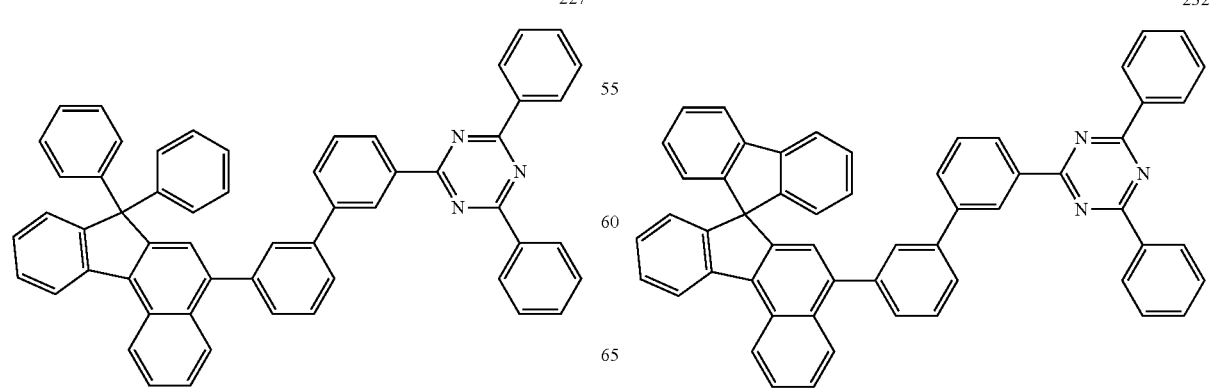

233
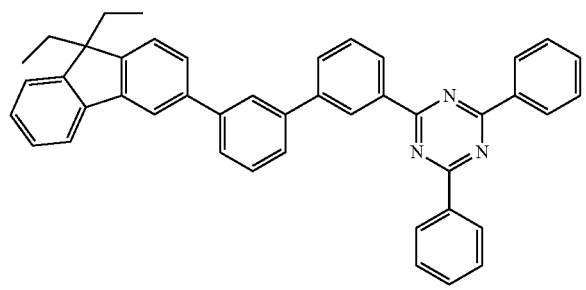
234
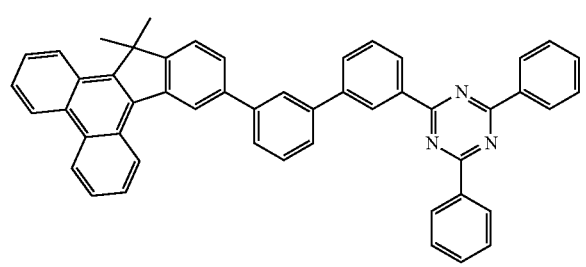
235
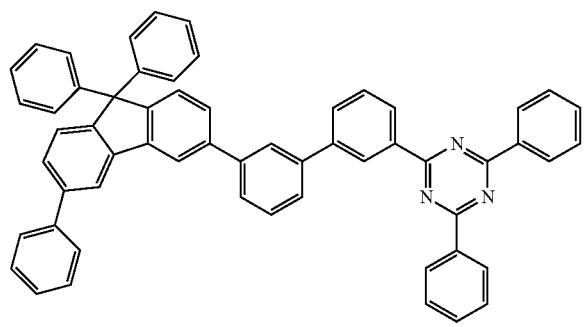
236
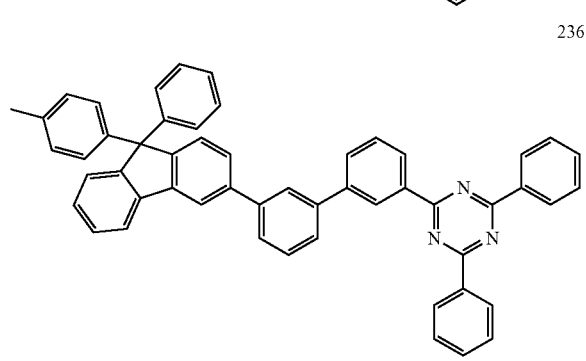
237
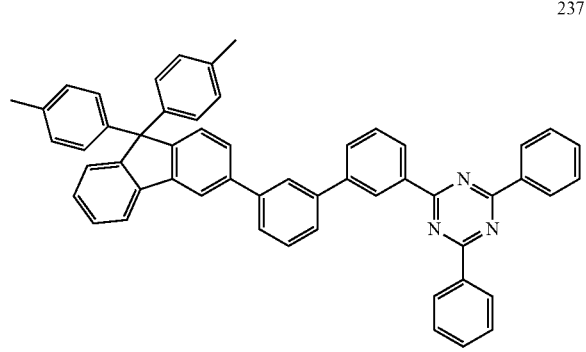
238
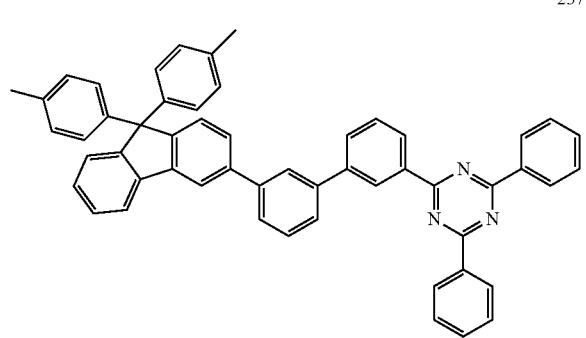
239
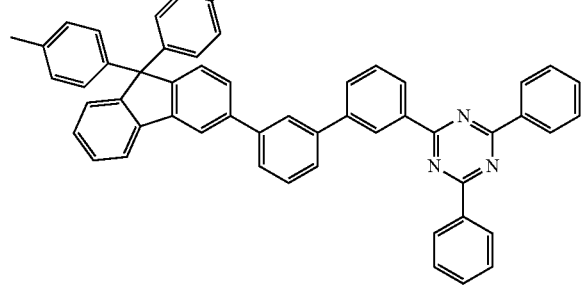
240
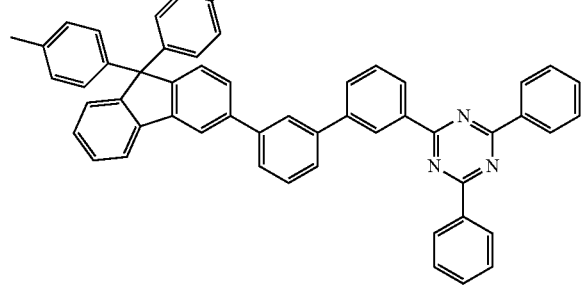
241
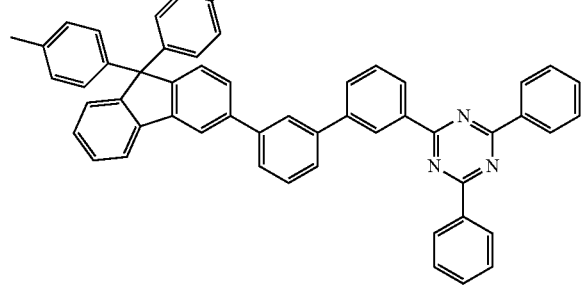

-continued
242
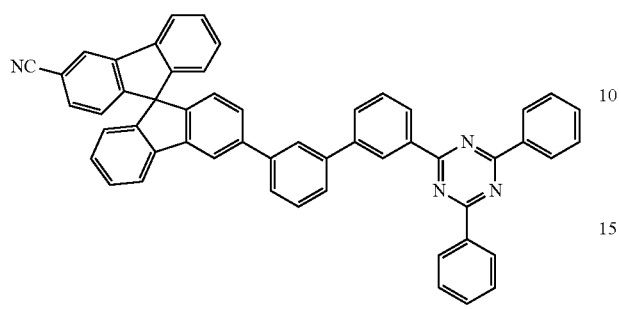
243
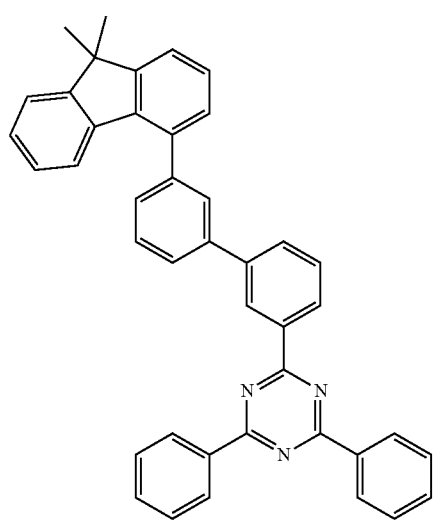
244
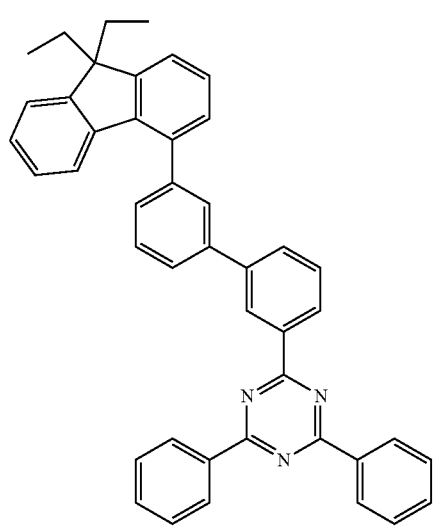
245
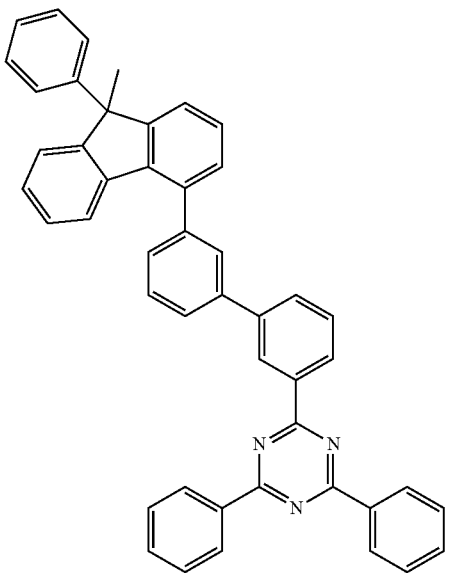
246
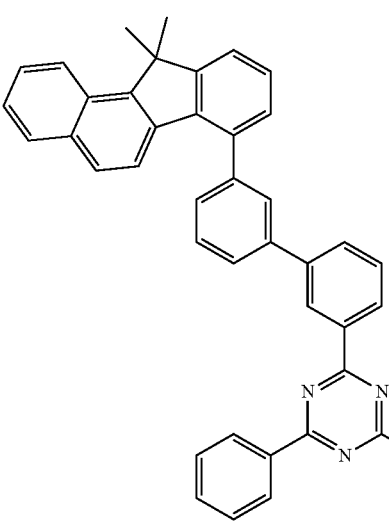
247
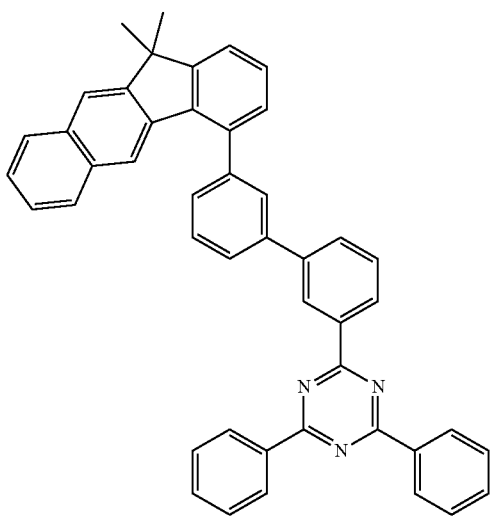

248
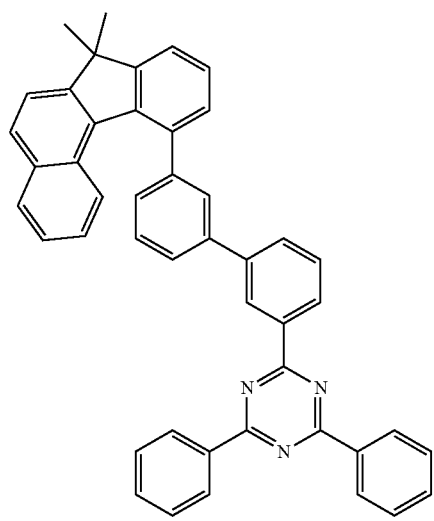
250
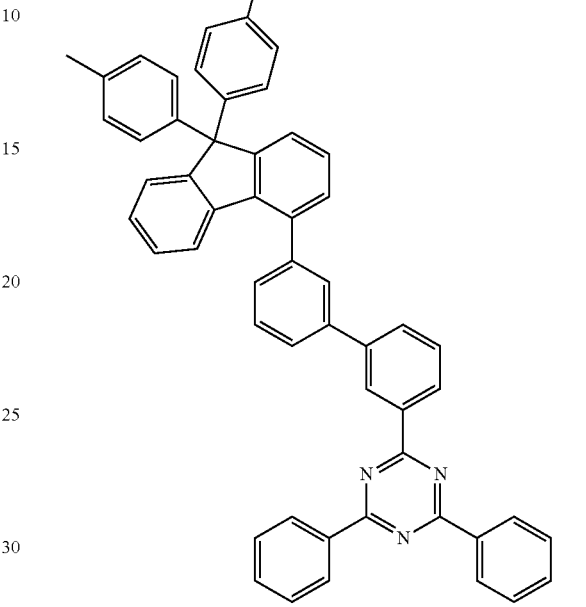
249
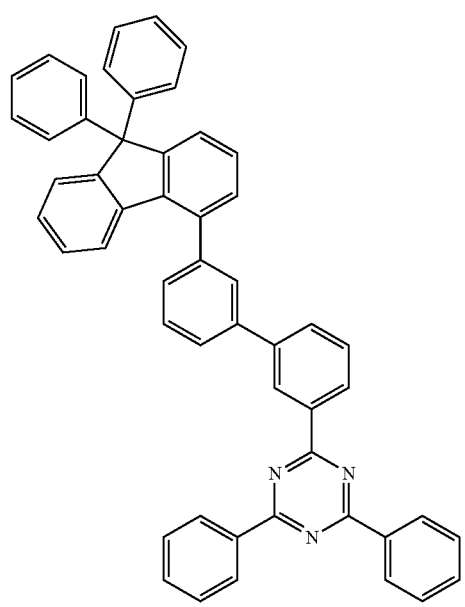
251
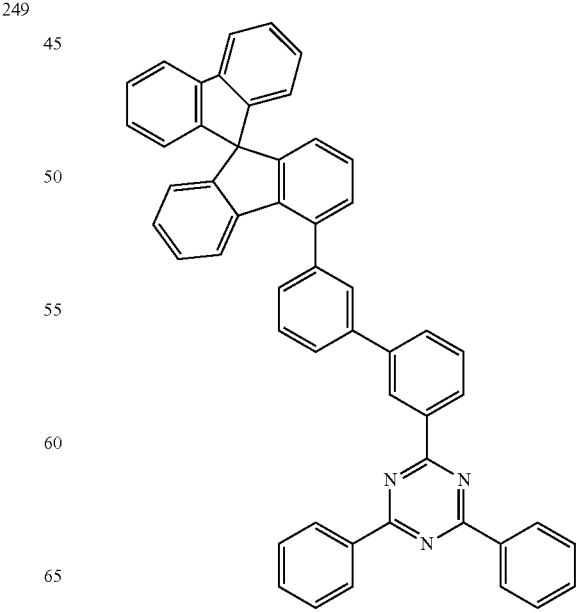

252
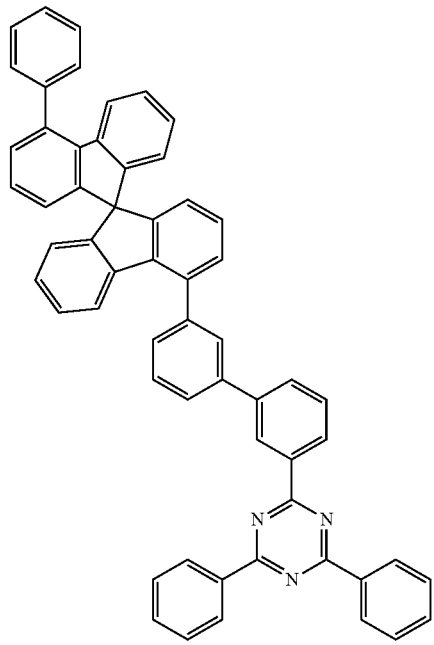
253
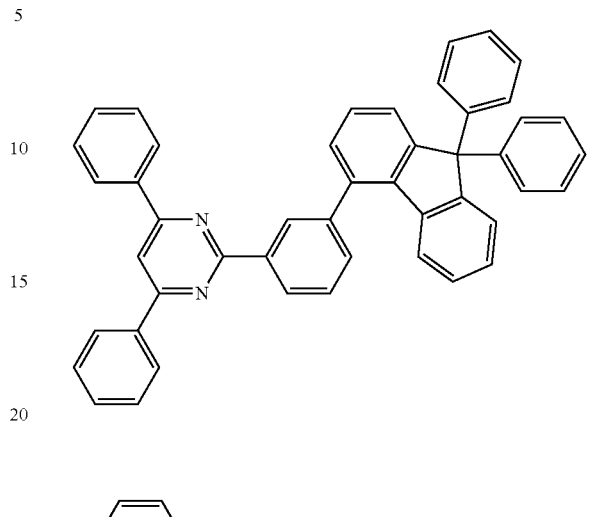
256
254
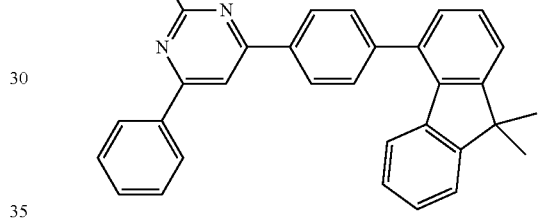
257
255
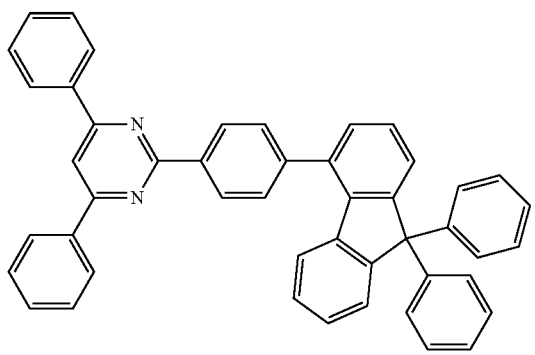
258
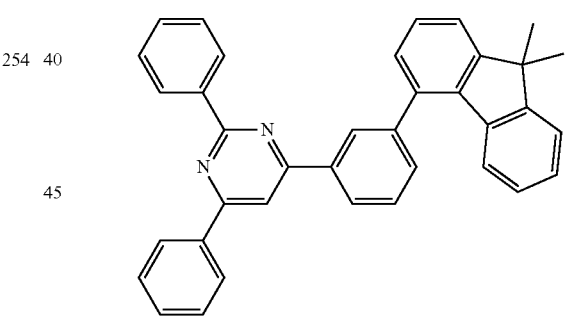
259
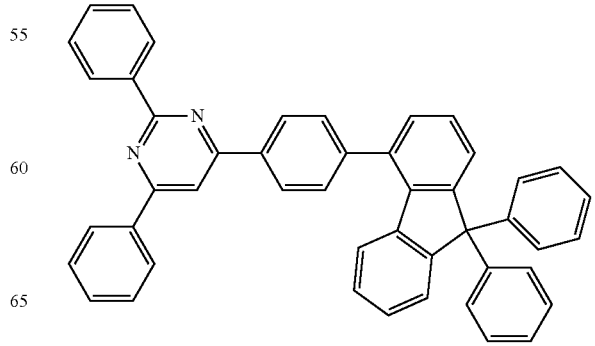

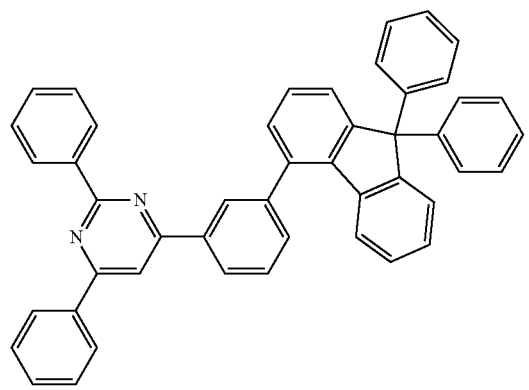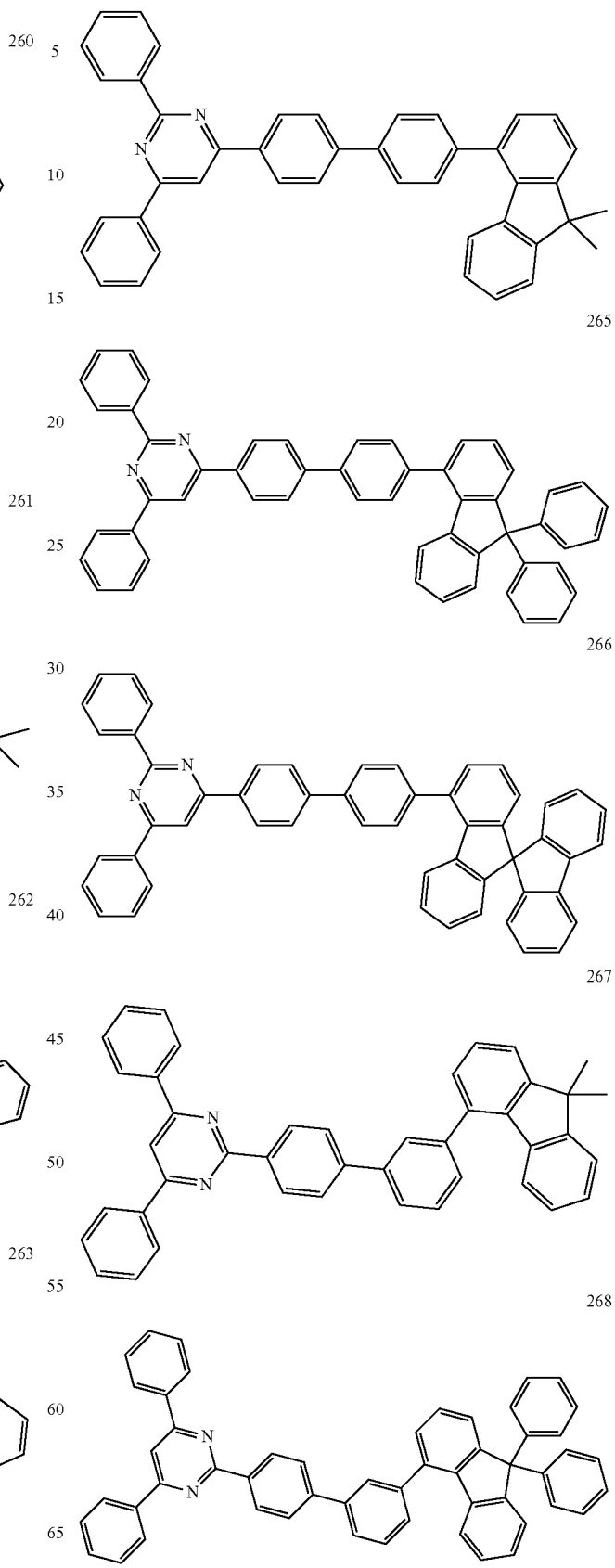

269
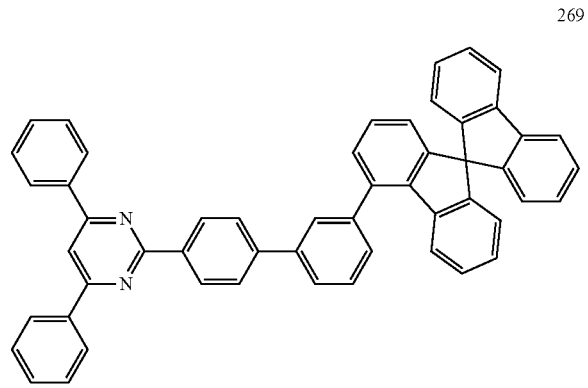
270
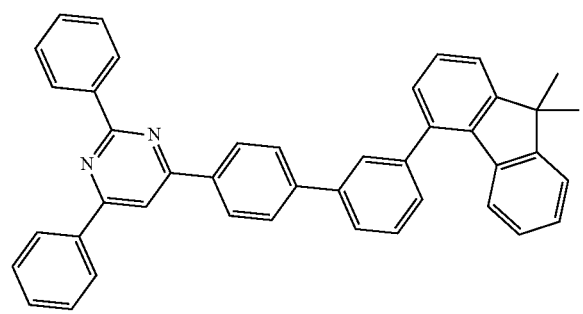
271
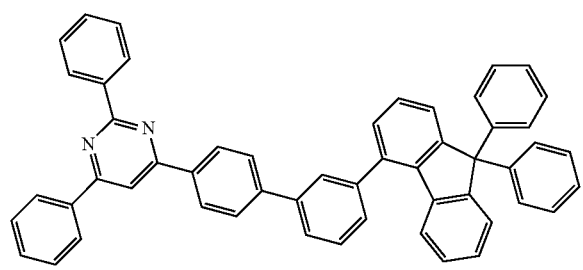
272
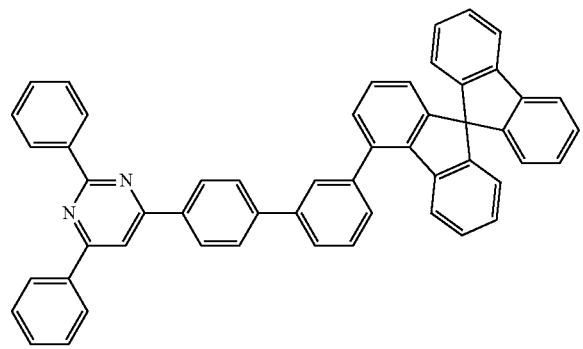
273
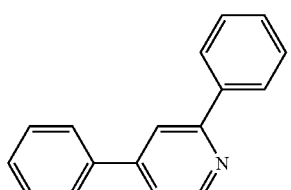
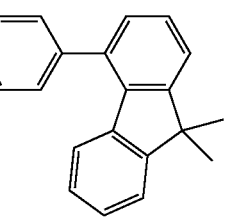
274
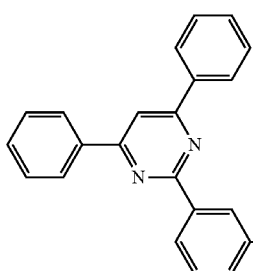
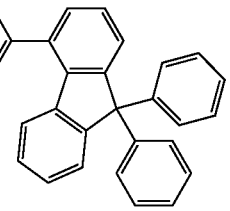
275
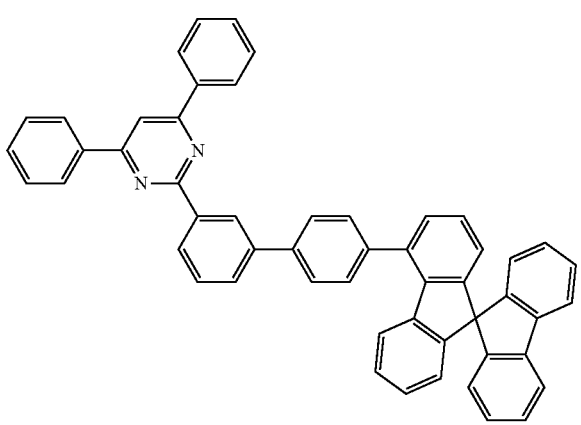

276 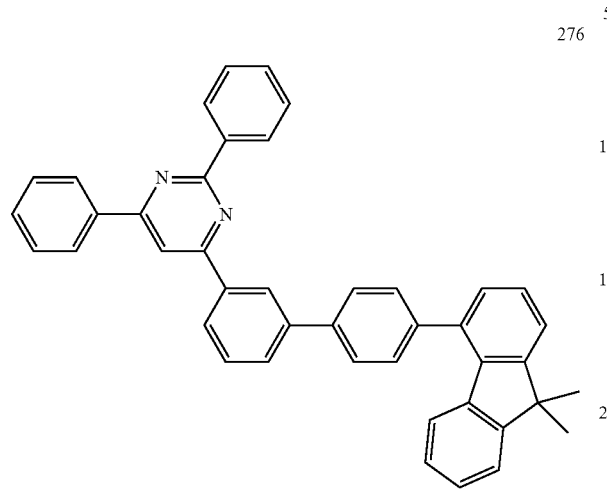
277 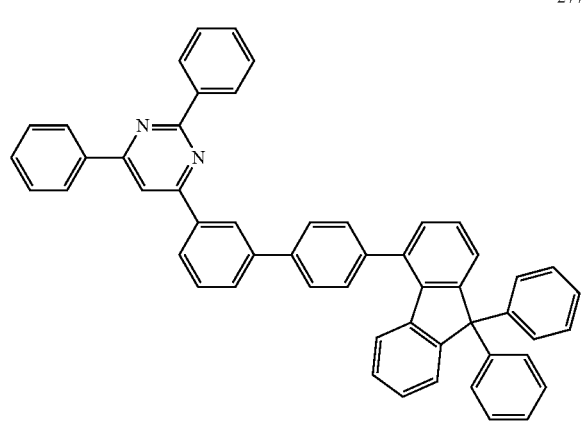
278 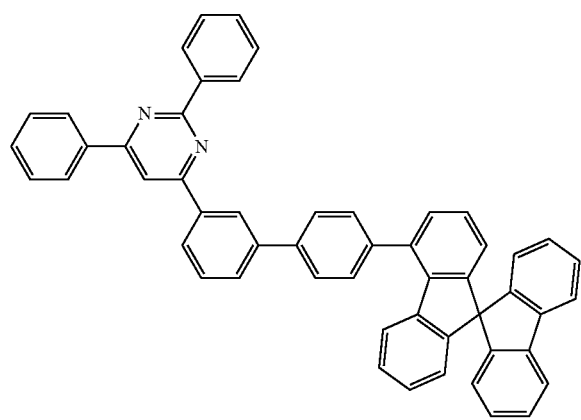
279 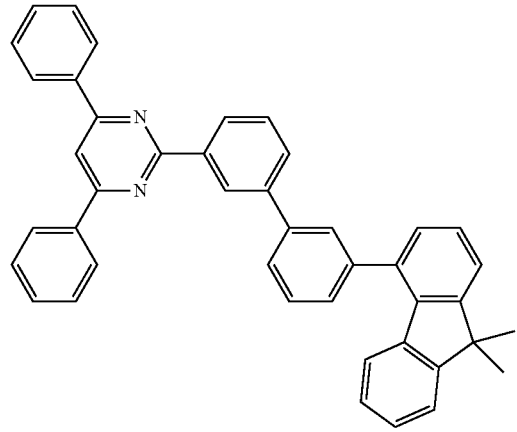
280 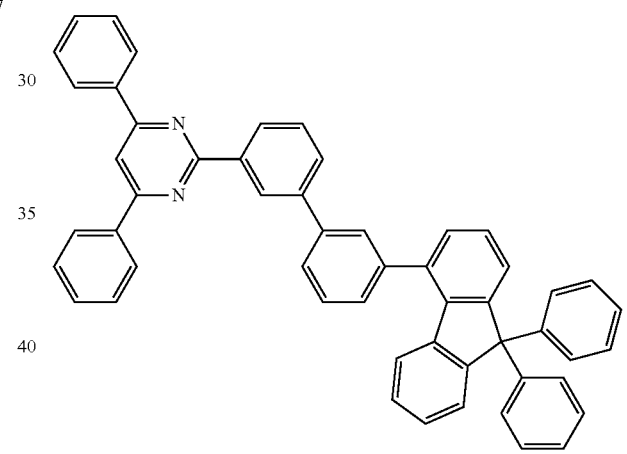
281 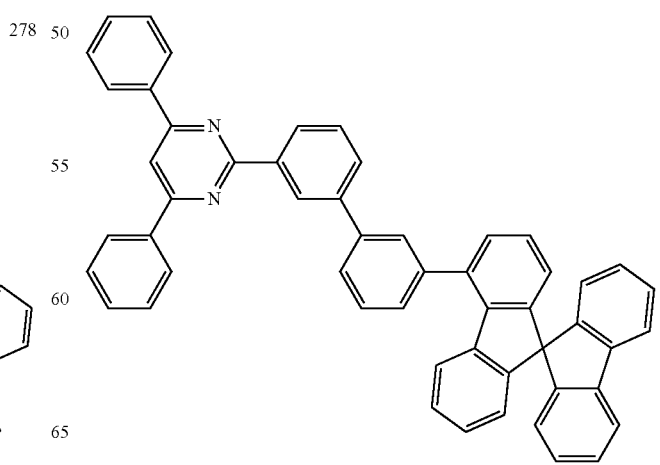

282
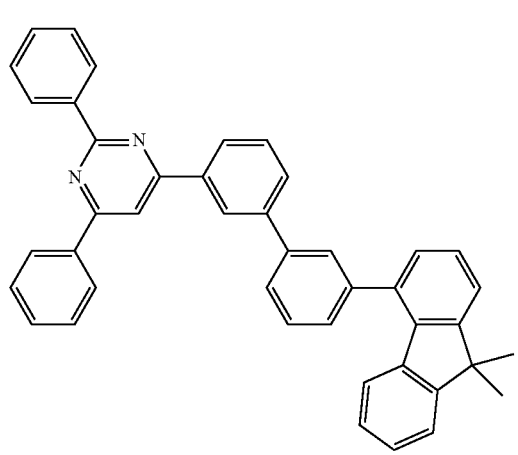
285
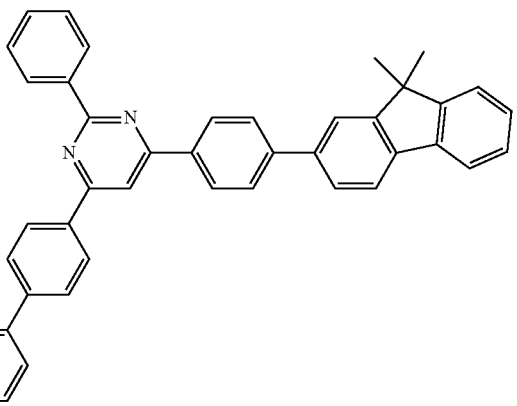
283
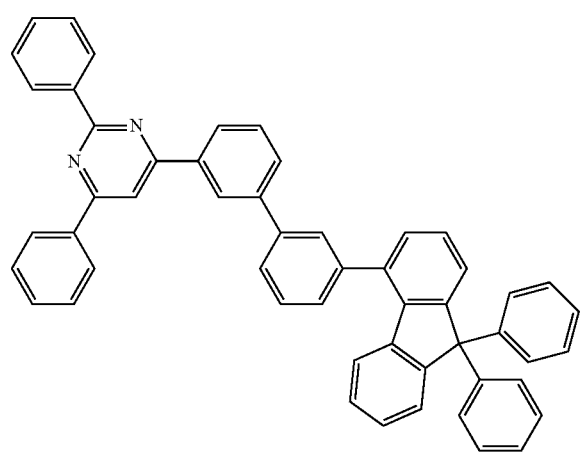
286
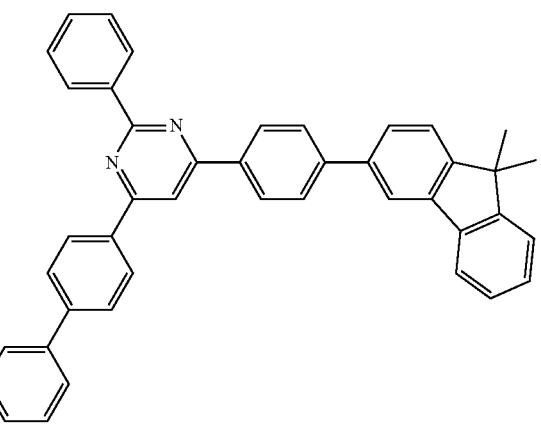
284
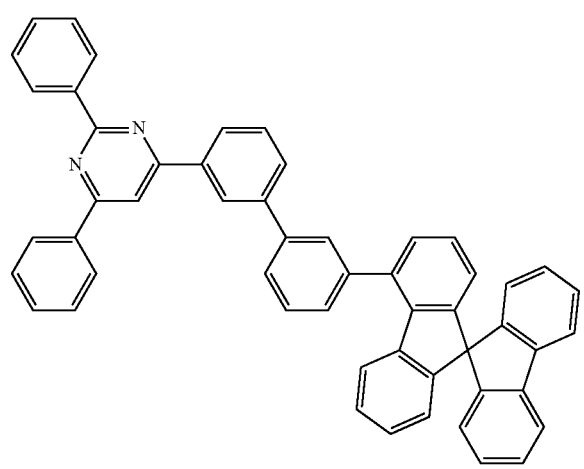
287
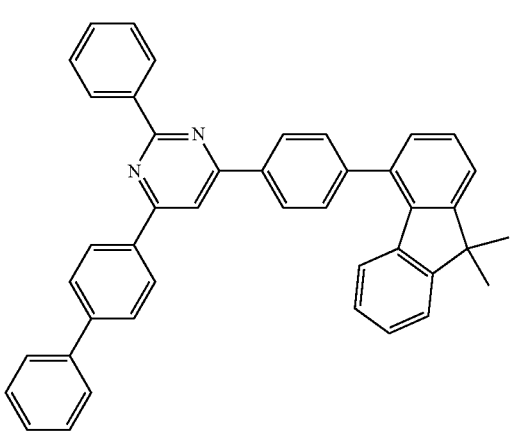

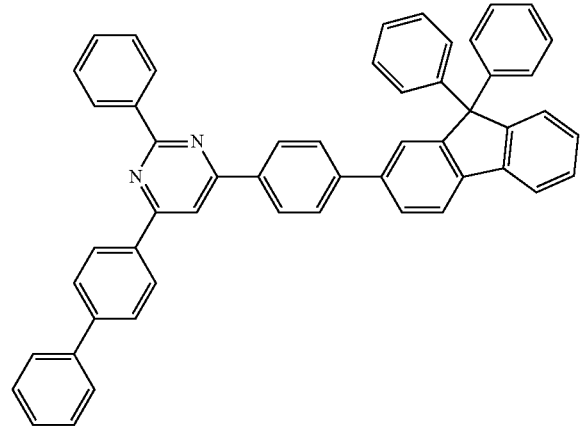
288
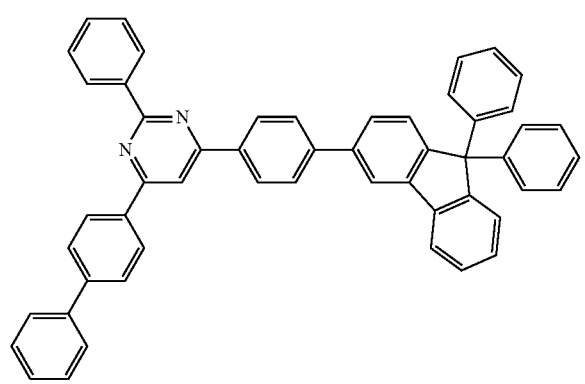
289
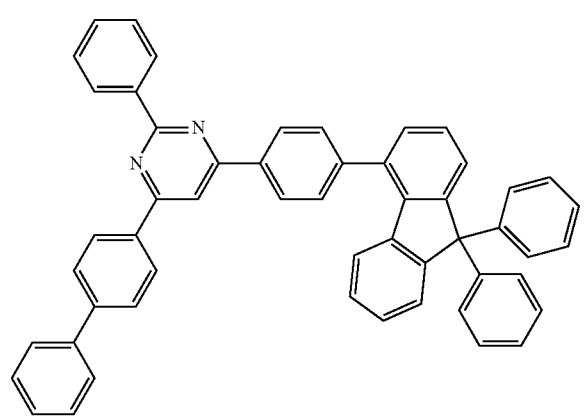
290
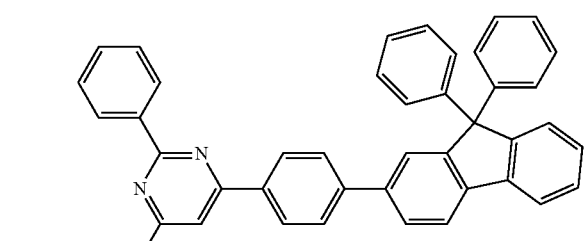
291
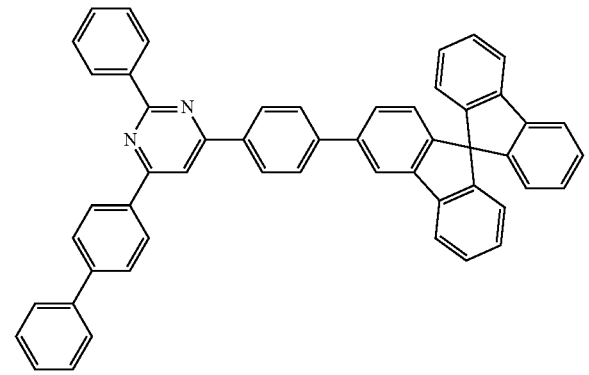
292
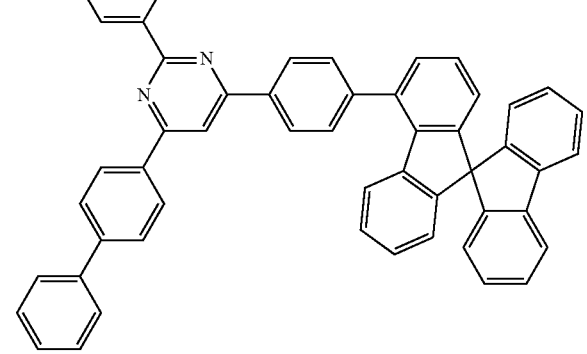
293
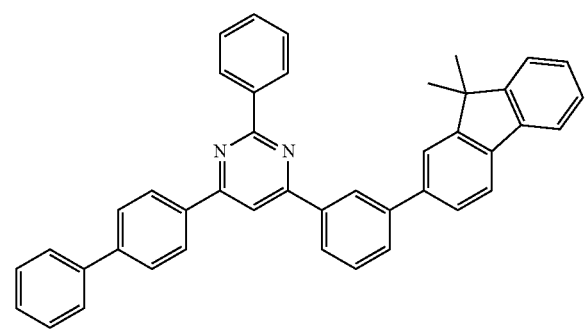
294

295
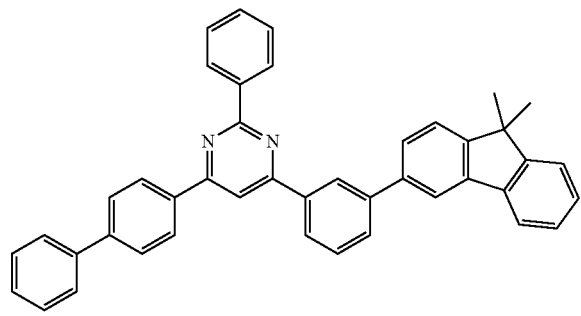
296
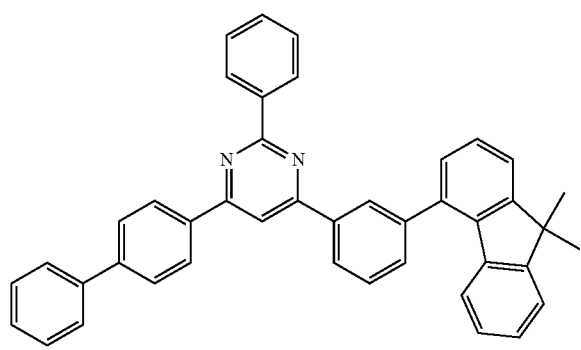
297
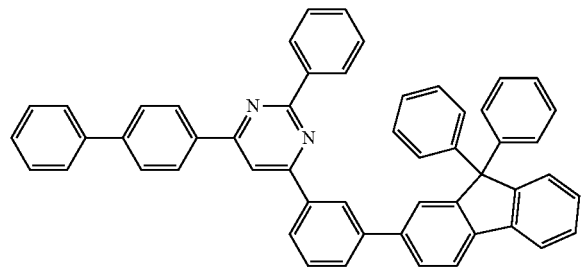
298
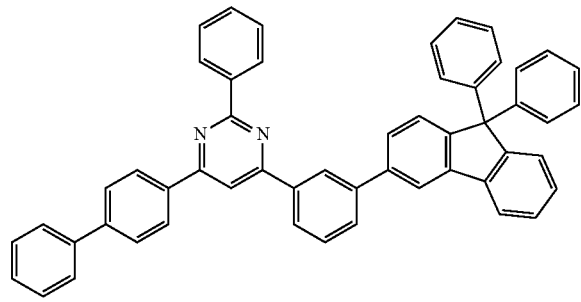
299
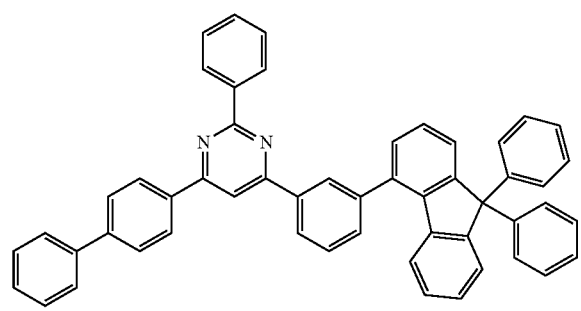
300
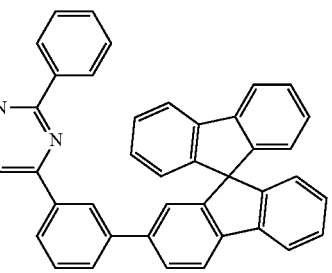
301
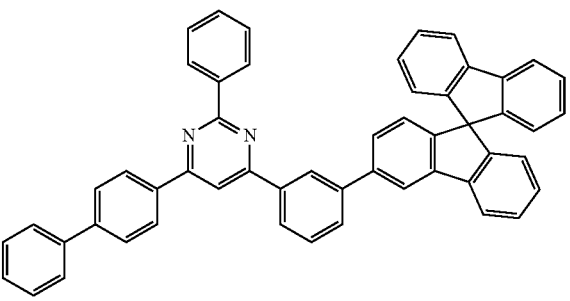
302
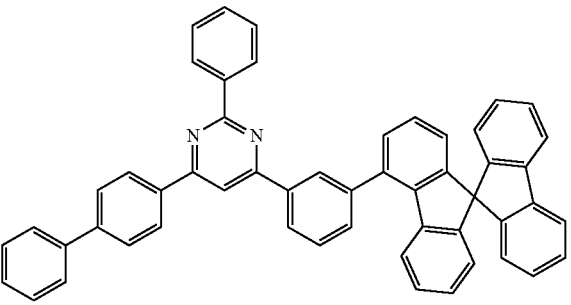
303
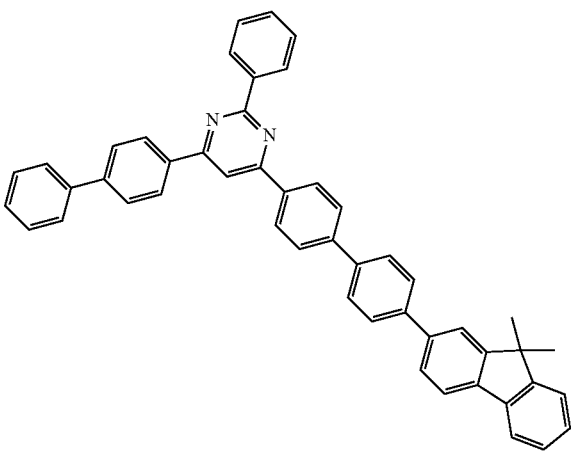

304
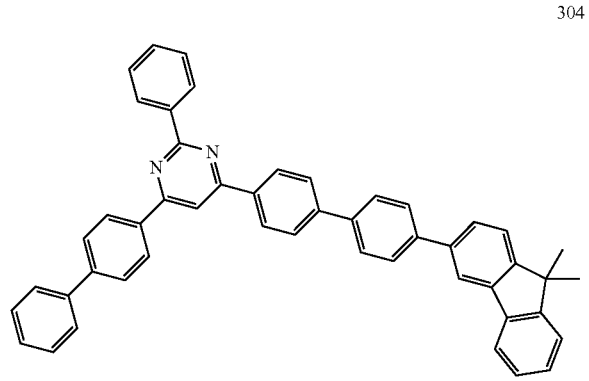
305
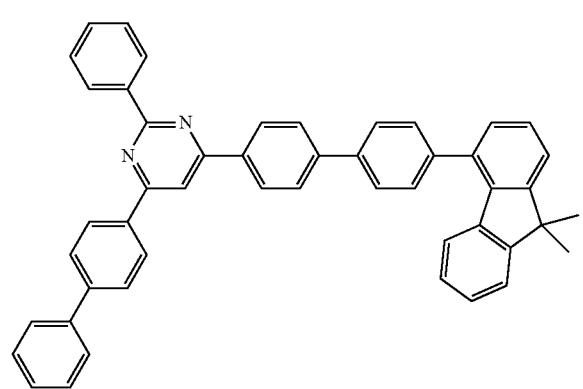
306
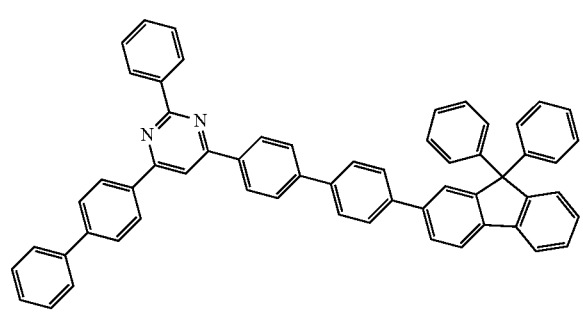
307
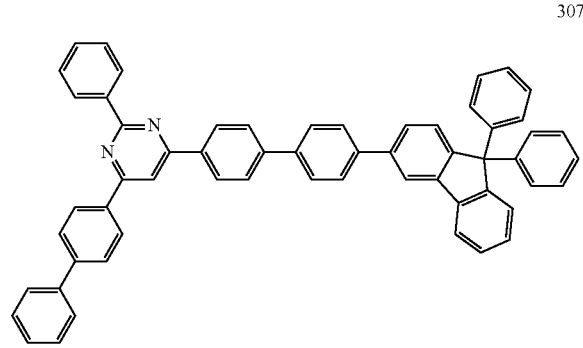
308
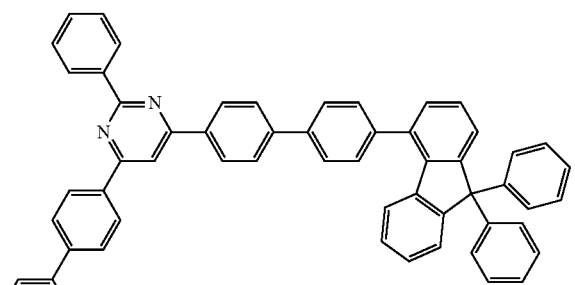
309
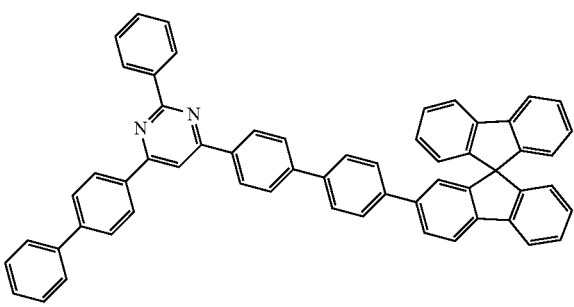
310
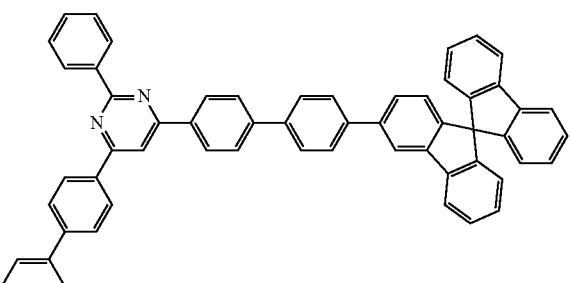
311
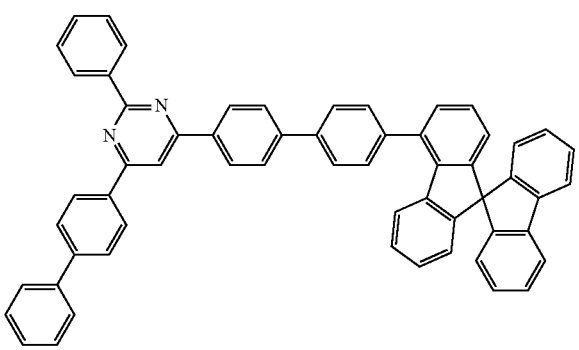

312
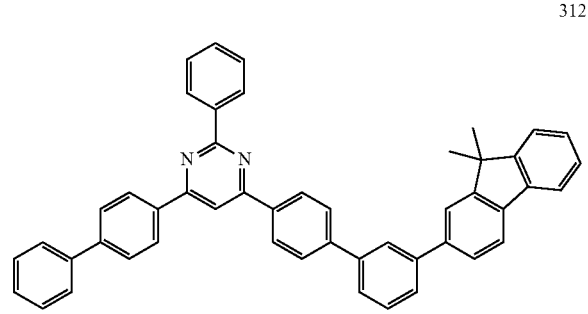
313
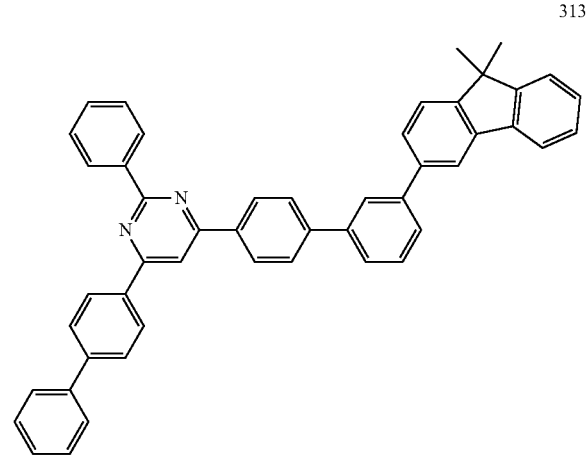
314
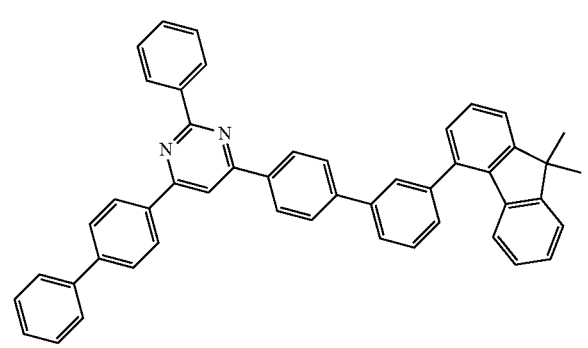
315
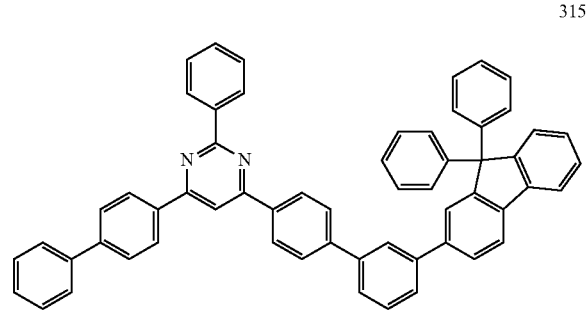
316
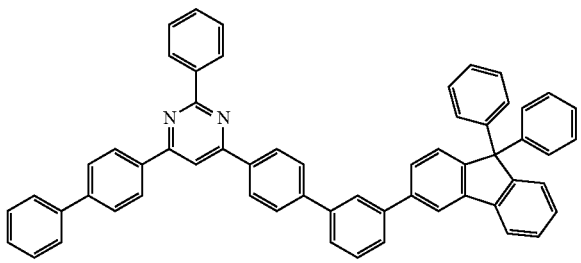
317
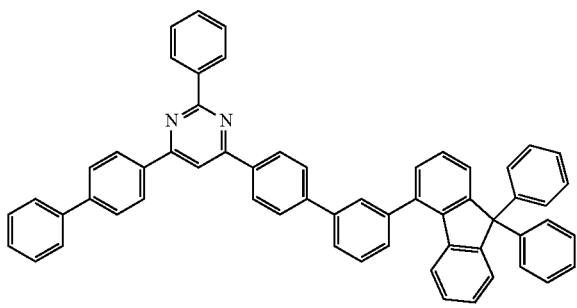
318
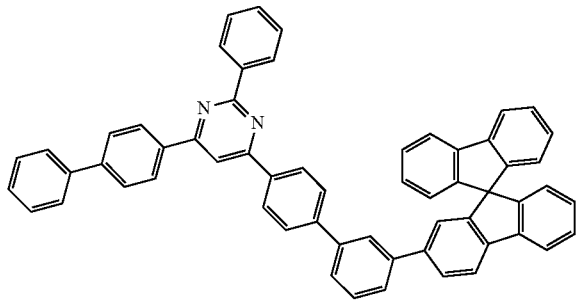
319
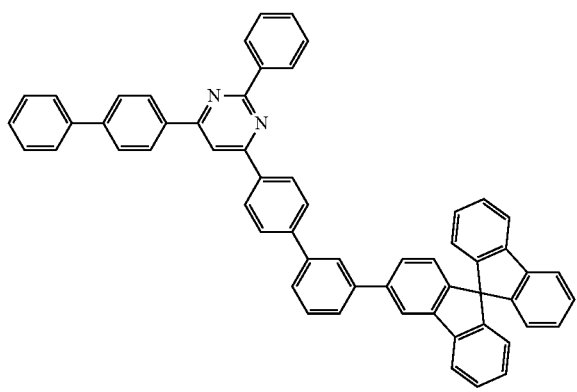

320
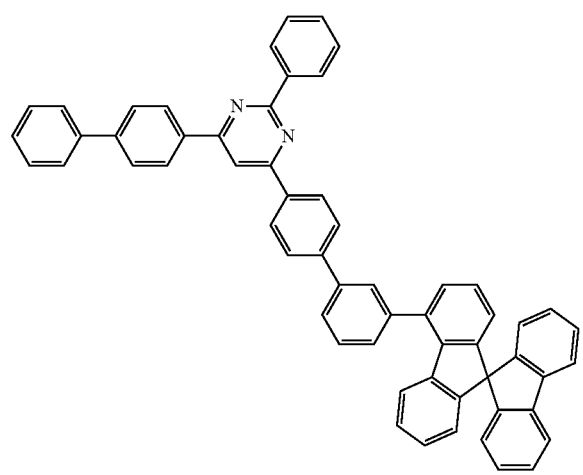
321
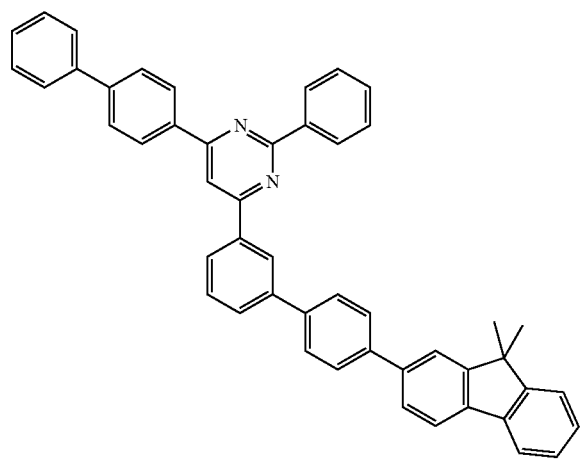
322
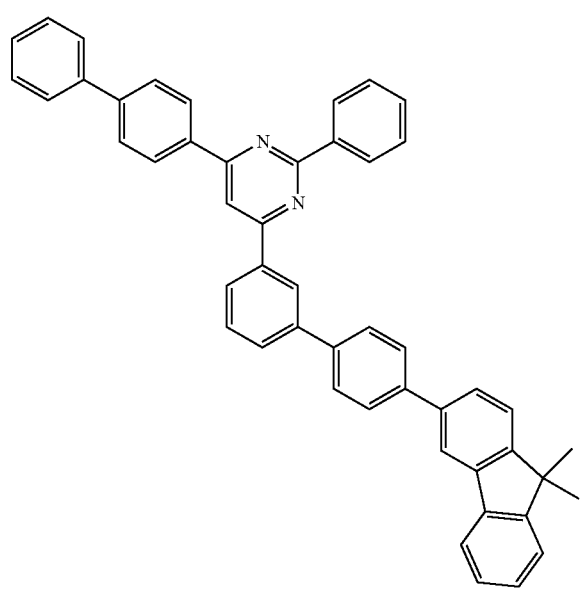
323
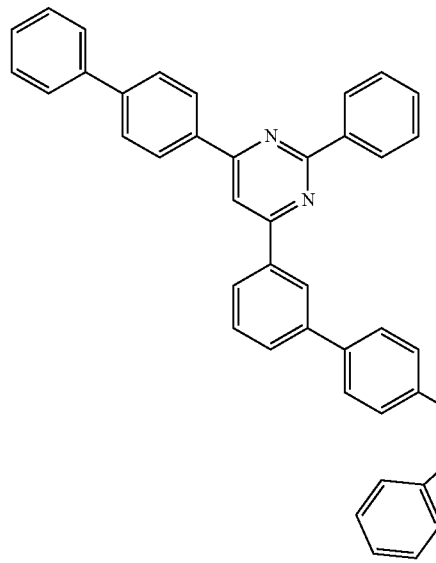
324
325
326
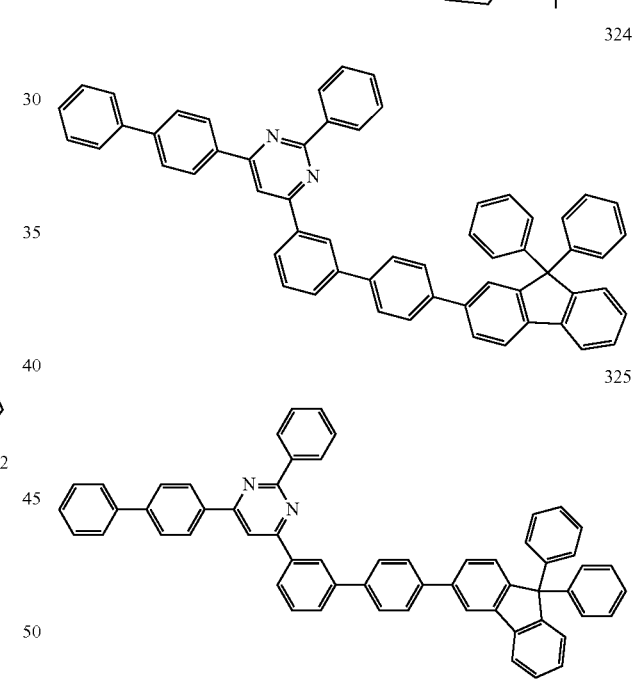

327
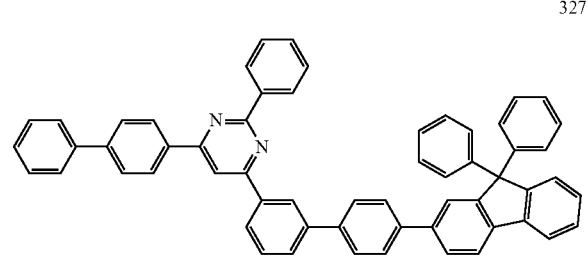
328
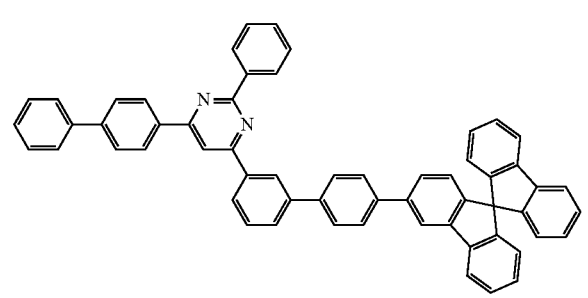
329
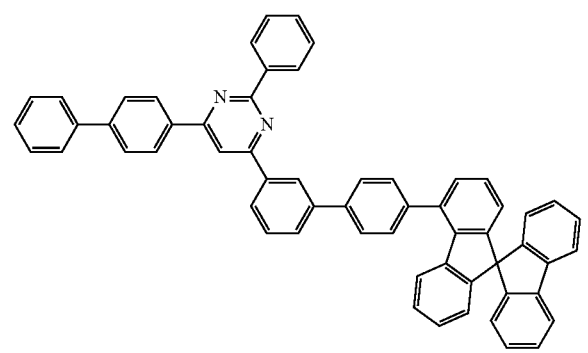
330
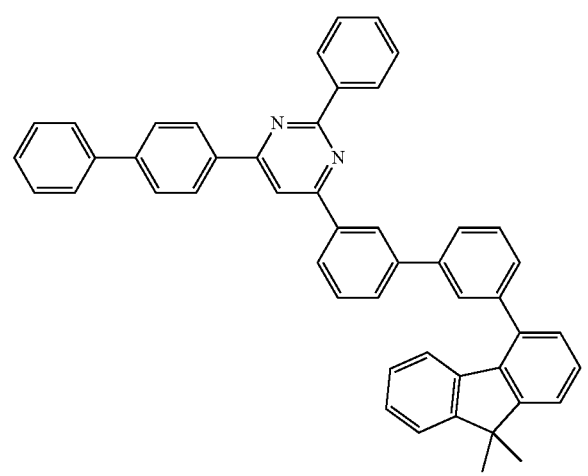
331
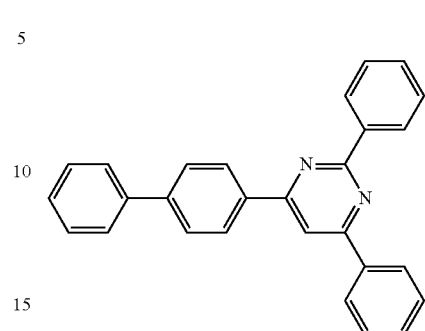
332
333
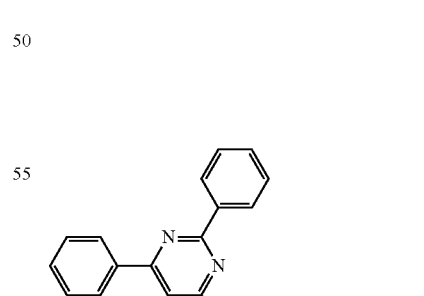

-continued
334
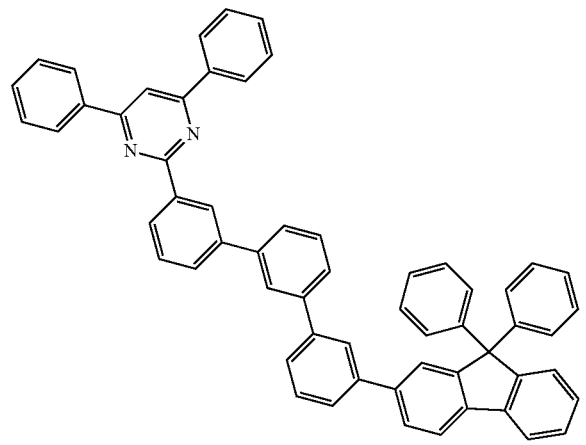
335
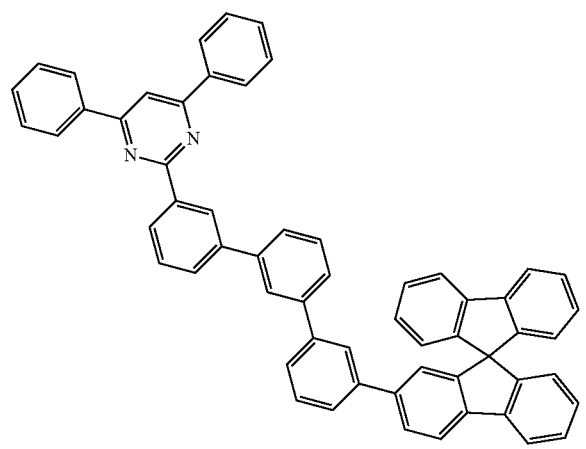
336
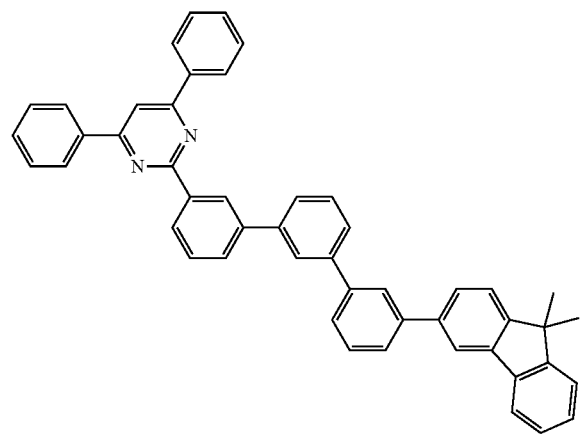
-continued
337
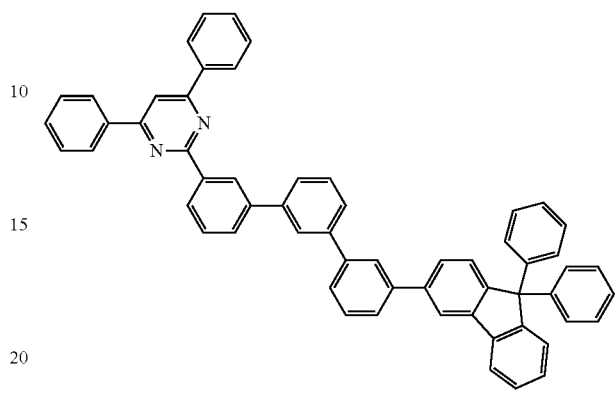
338
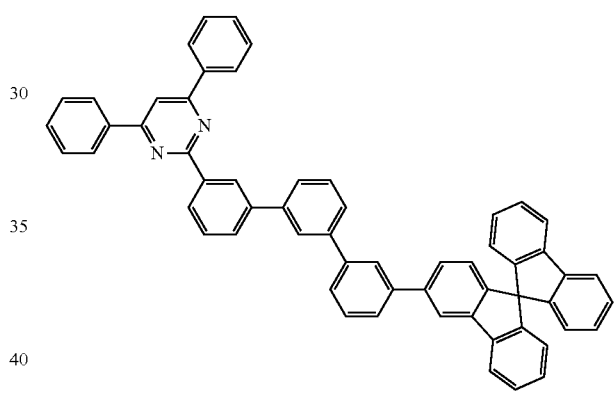
339
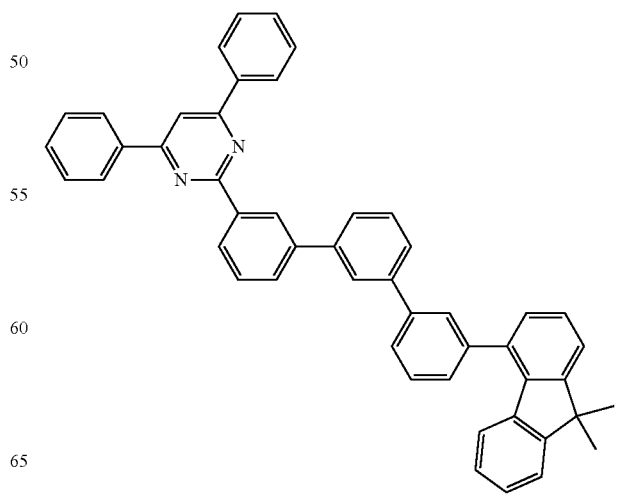

340
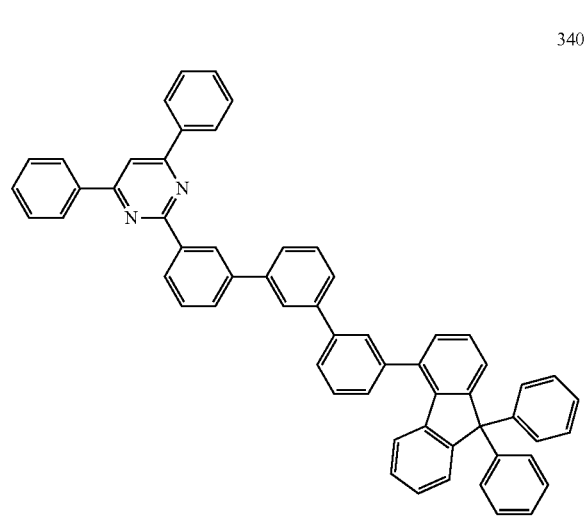
341
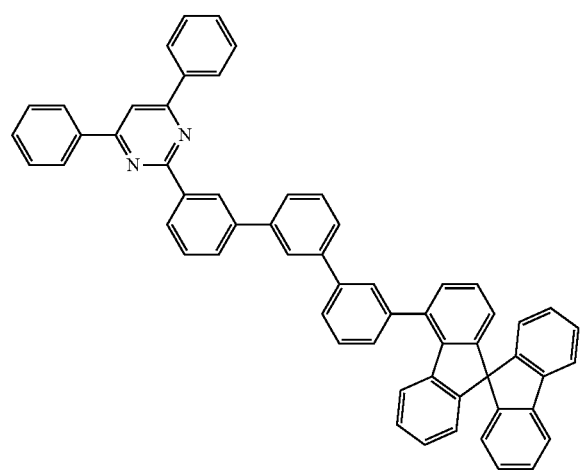
342
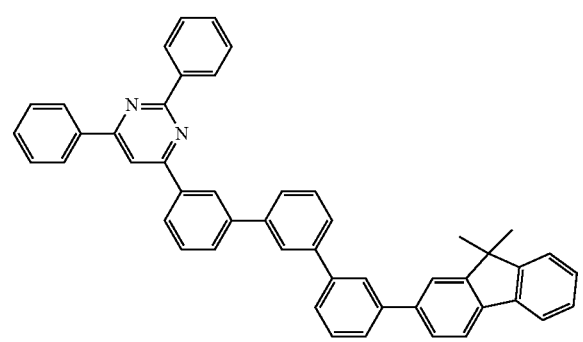
343
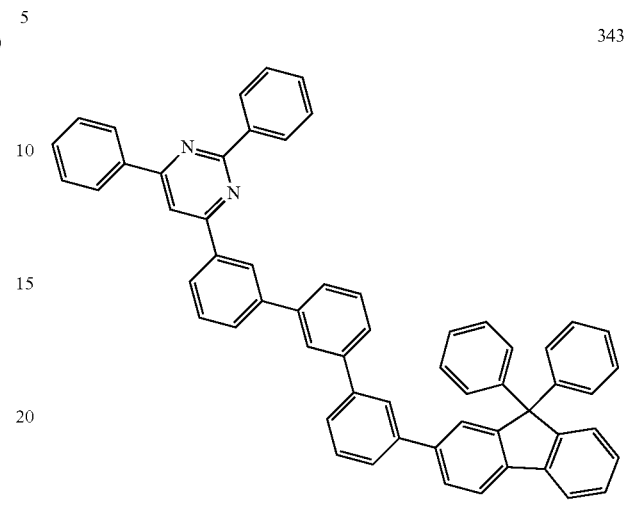
344
345

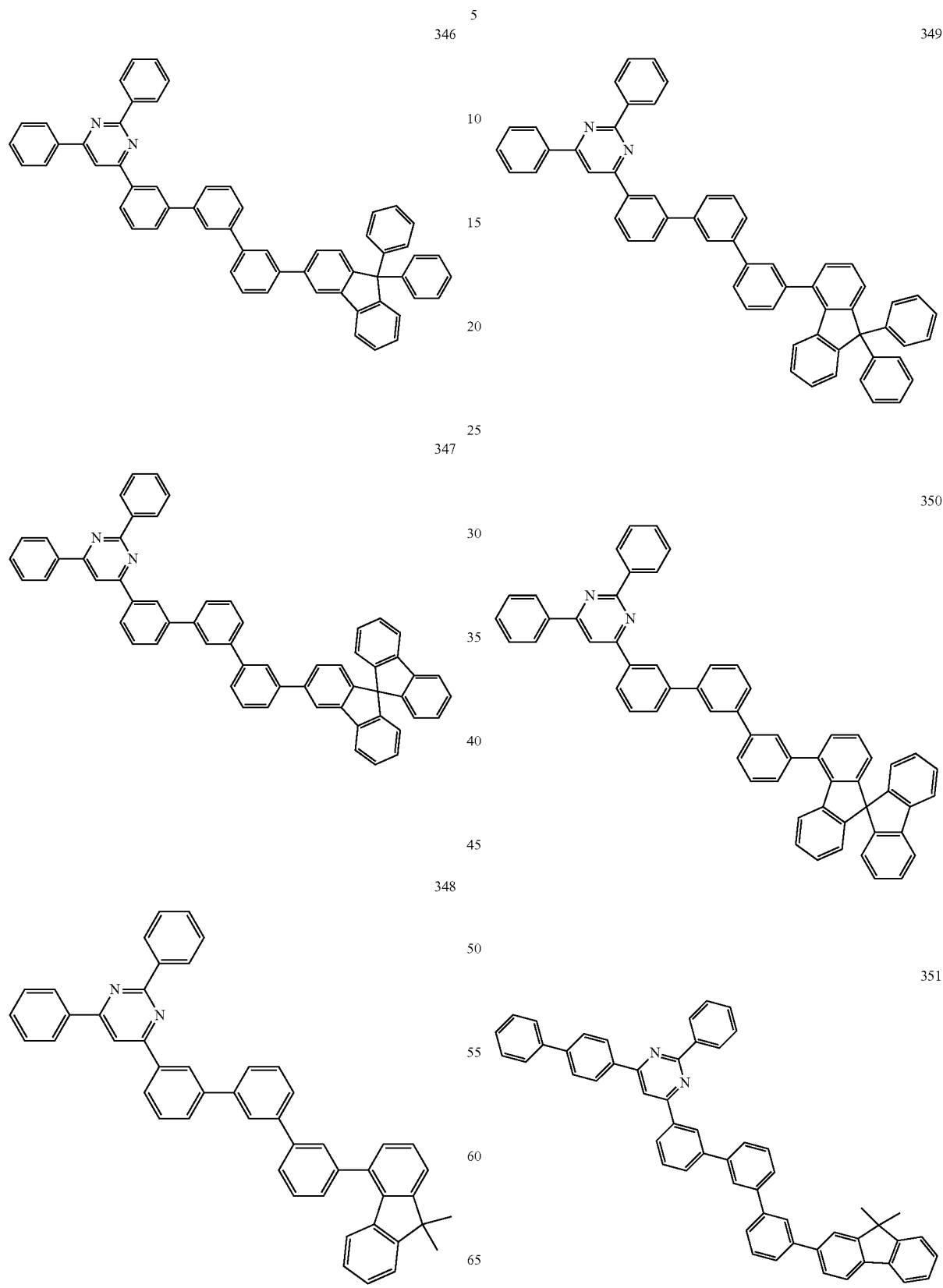

101
-continued
352
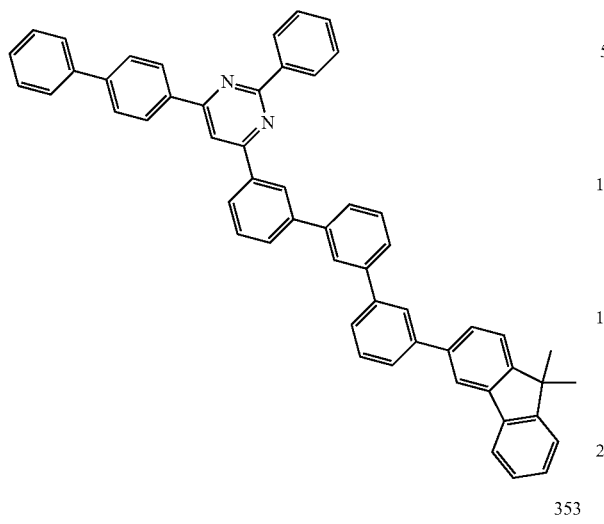
353
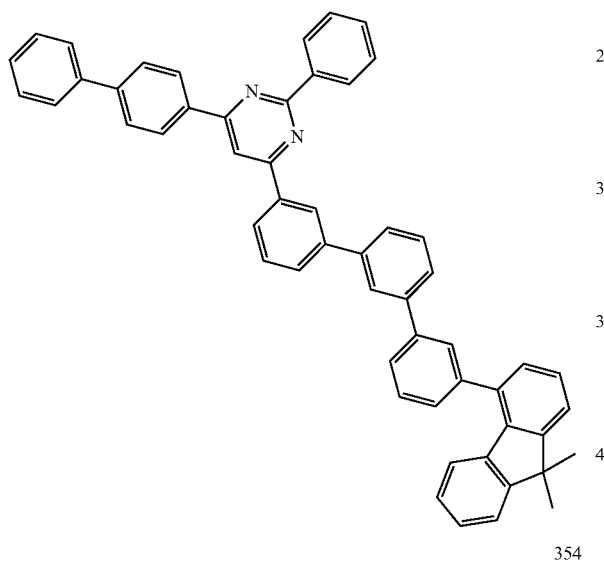
354
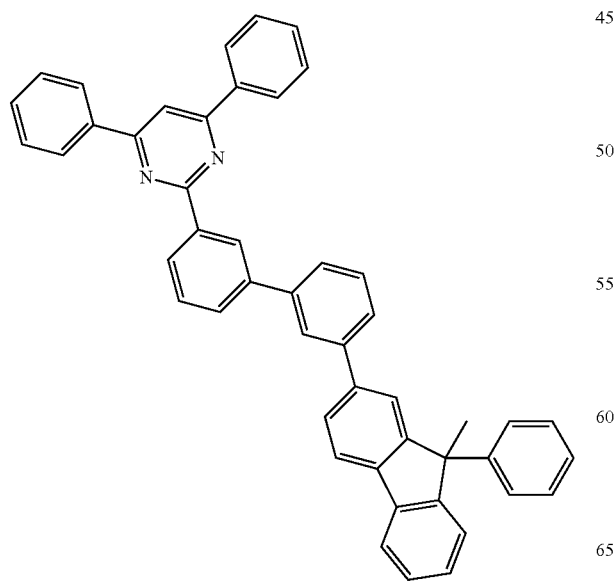
102
-continued
355
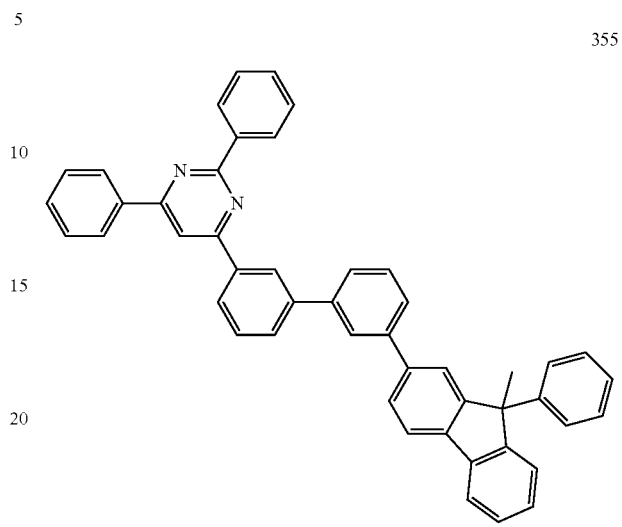
356
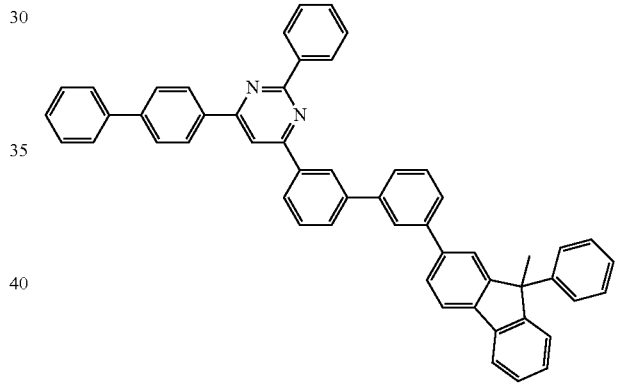
357

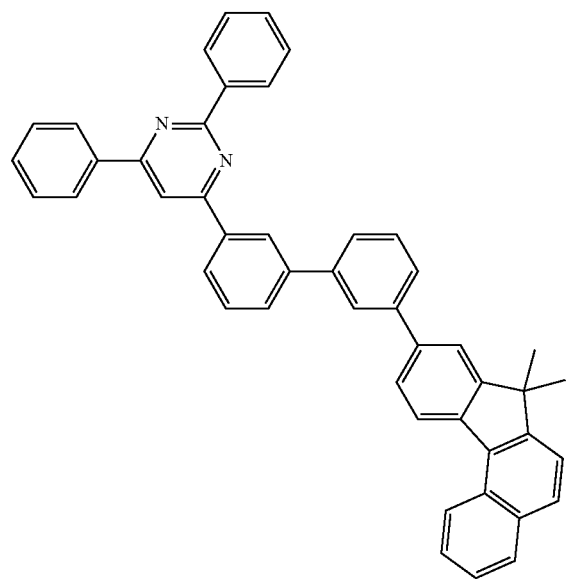
358
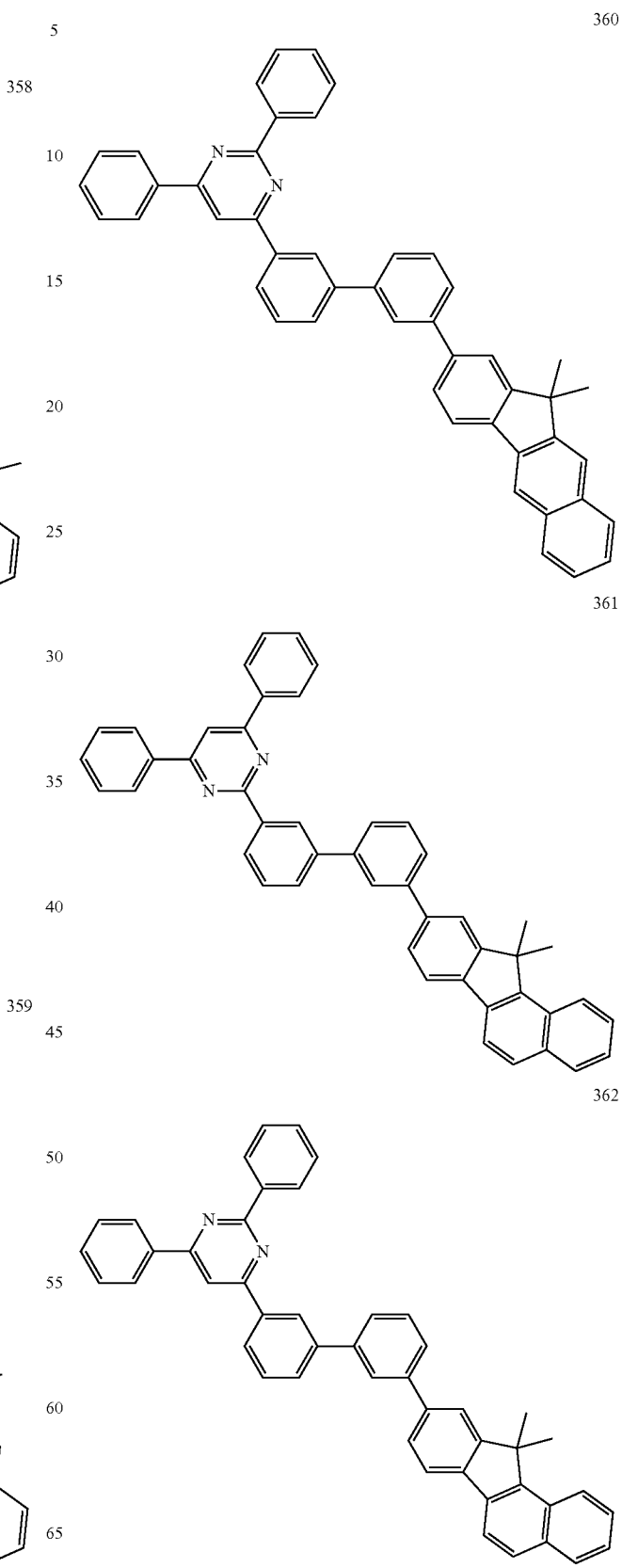
360
359
361
362

363

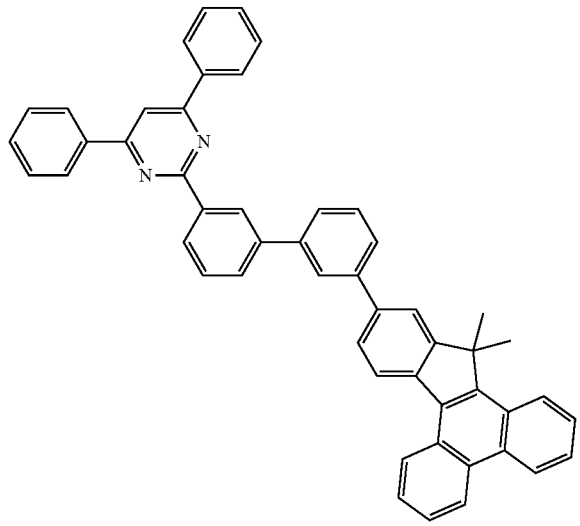

364

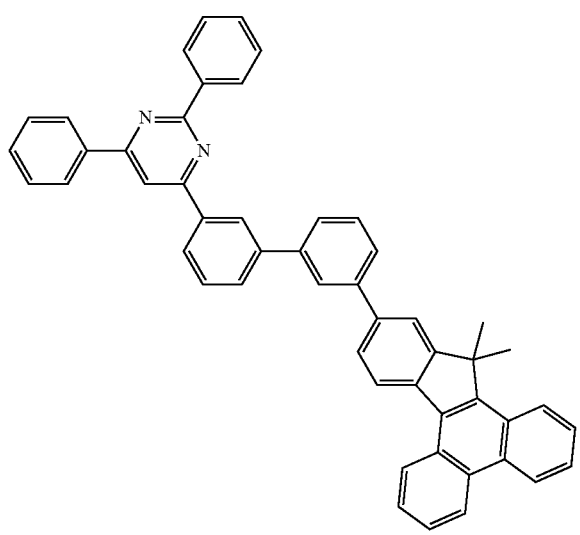

365

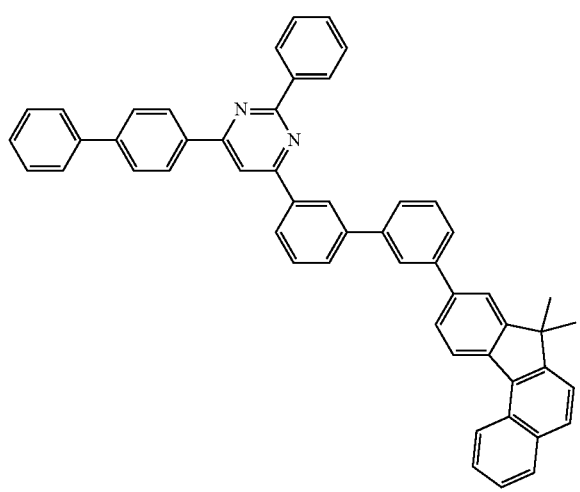

366

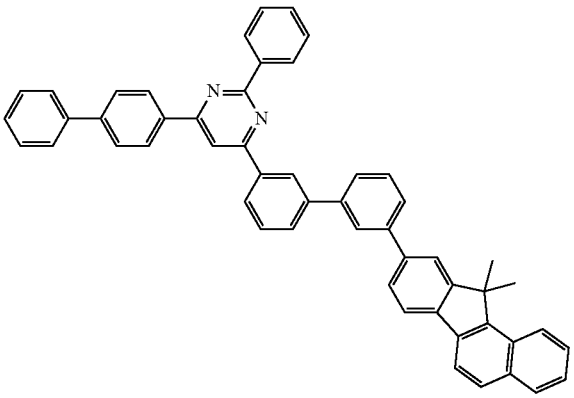

As used herein, the term "alkyl" refers to a monovalent substituent derived from linear or branched saturated hydrocarbon of 1 to 40 carbon atoms, including, for example, methyl, ethyl, propyl, isobutyl, sec-butyl, pentyl, iso-amyl, hexyl, and the like.

As used herein, the term "alkenyl" refers to a monovalent substituent derived from a linear or branched unsaturated hydrocarbon with one more carbon-carbon double bonds, as exemplified by vinyl, allyl, isopropenyl, 2-butenyl, and the like.

As used herein, the term "alkynyl" refers to a monovalent substituent derived from a linear or branched unsaturated hydrocarbon of 2 to 40 carbon atoms with at least one carbon-carbon triple bond, as exemplified by ethynyl, 2-propynyl, and the like.

As used herein, the term "aryl" denotes a monovalent substituent derived from an aromatic hydrocarbon of 6 to 60 carbon atoms with a single ring or a combination of two or more rings in which two or more rings may simply be pendant to each other or fused together, as exemplified by phenyl, naphthyl, phenantryl, anthryl, etc.

As used herein, the term "heteroaryl" denotes a monovalent substituent derived from a mono- or polyheterocyclic aromatic hydrocarbon of 5 to 60 nuclear atoms in which at least one, particularly one to three carbon atoms of the ring are substituted by a heteroatom such as N, O, S or Se. Two or more rings of the heteroaryl, if present, may simply be pendant to each other or fused together or to an aryl group. Examples include 6-membered monocyclic rings such as pyridyl, pyrazinyl, pyrimidinyl, pyridazinyl, and triazinyl, polycyclic rings such as phenoxathienyl, indolizinyl, indolyl, purinyl, quinolyl, benzothiazole, and carbazolyl, 2-furanyl, N-imidazolyl, 2-ixosazolyl, 2-pyridinyl, and 2-pyrimidinyl.

As used herein, the term "aryloxy" refers to a monovalent substituent represented by RO— wherein R denotes an aryl of 6 to 60 carbon atoms, as exemplified by phenyloxy, naphthyloxy, diphenyloxy, etc.

As used herein, the term "alkyloxy" refers to a monovalant substituent represented by R'O— wherein R' means an alkyl of 1 to 40 carbon atoms and is construed to include a linear, branched or cyclic structure and examples of which include methoxy, ethoxy, n-propoxy, 1-propoxy, t-butoxy, n-butoxy, pentoxy, etc.

As used herein, the term "arylamine" refers to an amine substituted with an aryl of 6 to 60 carbon atoms.

As used herein, the term "cycloalkyl" refers to a monovalent substituent derived from a mono- or polycyclic non-aromatic hydrocarbon of 3 to 40 carbon atoms, examples of which include cyclopropyl, cyclopentyl, cyclohexyl, norbornyl, and adamantine.

As used herein, the term "heterocycloalkyl" refers to a monovalent substituent derived from a non-aromatic hydrocarbon of 3 to 40 nuclear atoms in which at least one, particularly one to three carbon atoms of the ring are substituted by a heteroatom such as N, O, S or Se and examples of which include morpholinem, piperazine, and the like.

As used herein, the term "alkylsilyl" refers to a silyl substituent substituted with an alkyl of 1 to 40 carbon atoms, and the term "arylsilyl" refers to a silyl group substituted with an aryl of 6 to 60 carbon atoms.

As used herein, the term "fused ring" refers to a fused aliphatic ring, a fused aromatic ring, a fused heteroaliphatic ring, a heteroaromatic ring, or a combination thereof.

2. Organic Electroluminescent Element

The present invention provides an organic electroluminescent element comprising the compound represented by Formula 1.

In detail, the organic electroluminescent element of the present invention comprises an anode, a cathode, and at least one organic layer interposed therebetween wherein the at least one organic layer comprises the compound represented by Formula 1. Here, the compound may be a single kind or a combination of two or more different kinds.

The at least one organic layer may be selected from among a hole injection layer, a hole transport layer, an auxiliary light-emitting layer, an electron transport layer, an electron injection layer, and a combination thereof, and may comprise the compound represented by Formula 1. In detail, the organic layer comprising the compound represented by Formula 1 is particularly a light-emitting layer or an auxiliary electron transport layer (interposed between a light-emitting layer and an electron transport layer).

Meanwhile, the light-emitting layer may comprise a host. Here, the host may be the compound represented by Formula 1, alone or in combination with other compounds. In addition, the light-emitting layer may comprise a dopant based on a metal complex compound, together with the host.

No particular limitations are imparted to the structure of the organic electroluminescent element of the present invention. For example, the organic electroluminescent element may have a structure in which a substrate, an anode, a hole injection layer, a hole transport layer, an auxiliary light-emitting layer, a light-emitting layer, an auxiliary electron transport layer, an electron transport layer, and a cathode are sequentially deposited. Here, an electron injection layer may be further deposited on the electron transport layer. Moreover, an insulation layer or an adhesive layer may be introduced into the interface between the electrode (cathode or anode) and the organic layer.

The organic electroluminescent element of the present invention can be fabricated using materials and methods known in the art, with the exception that at least one of the organic layers comprises the compound represented by Formula 1.

The organic layer may be formed using a vacuum deposition method or a solution coating method. Examples of the solution coating method include spin coating, dip coating, doctor blade coating, inkjet printing and a thermal transfer method, but are not limited thereto.

The substrate used for the fabrication of the organic electroluminescent element of the present invention is not particularly limited, and may be a silicon wafer, quartz, a glass plate, a metal plate, or a plastic film.

As for the anode, its material is not particularly limited, but may be a metal such as vanadium, chromium, copper, zinc, gold, etc., or an alloy thereof; a metal oxide such as zinc oxide, indium oxide, indium tin oxide(ITO), and indium zinc oxide(IZO); a combination of metal and oxide such as ZnO:Al or SnO2:Sb; a conductive polymer such as polythiophene, poly(3-methylthiophene), poly[3,4-(ethylene-1,2-dioxy)thiophene] (PEDT), polypyrrole or polyaniline; and carbon black.

Although no particular limitations are imparted thereto, a material available for the cathode may be a metal such as magnesium, calcium, sodium, potassium, titanium, indium, yttrium, lithium, gadolinium, aluminum, silver, tin and lead, or an alloy thereof; or a multilayer material such as LiF/Al or LiO2/A·l.

In addition, the hole injection layer, the hole transport layer, the electron injection layer and the electron transport layer are not particularly limited, and may be made of conventional materials known in the art.

The present invention will be in greater detail described through the following examples that are set forth to illustrate, but are not to be construed as limiting the present invention.

Synthesis Example 1: Synthesis of Compound 1 (2-(3-(9,9-dimethyl-9H-fluoren-2-yl)phenyl)-4,6-diphenyl-1,3,5-triazine)

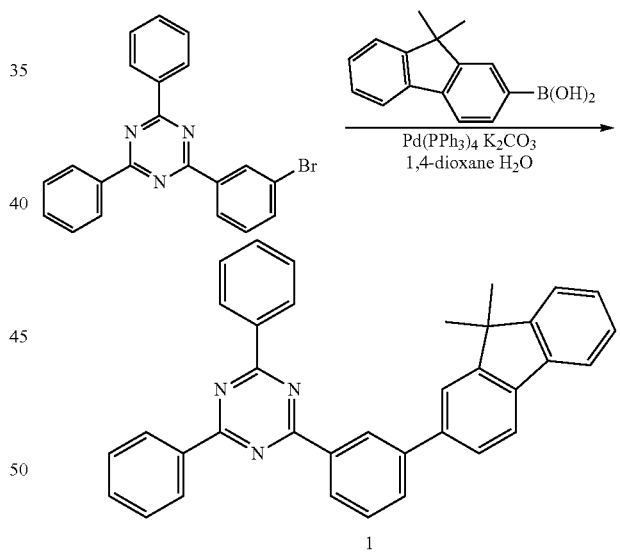

Under a nitrogen stream, 2-(3-bromophenyl)-4,6-diphenyl-[1,3,5]triazine (10.0 g, 0.026 mol), 9,9-dimethyl-9H-fluoren-2-yl-boronic acid (7.9 g, 0.033 mol), Pd(PPh$_3$)$_4$ (0.95 g, 0.001 mol), and potassium carbonate (7.65 g, 0.078 mol) were mixed and then stirred under reflux with 1,4-dioxane (80 ml) and H$_2$O (20 ml). After completion of the reaction, an organic layer was separated with methylene chloride, and dried over MgSO$_4$. The solvent was removed from the dehydrated organic layer, followed by purification through column chromatography [hexane:MC=5:1 (v/v)] to afford Compound 1 (8.2 g, yield 63%).

HRMS [M]+: 501.62

Synthesis Example 2: Synthesis of Compound 3
(2-[3-(9,9-Dimethyl-9H-fluoren-3-yl)-phenyl]-4,6-diphenyl-[1,3,5]triazine)

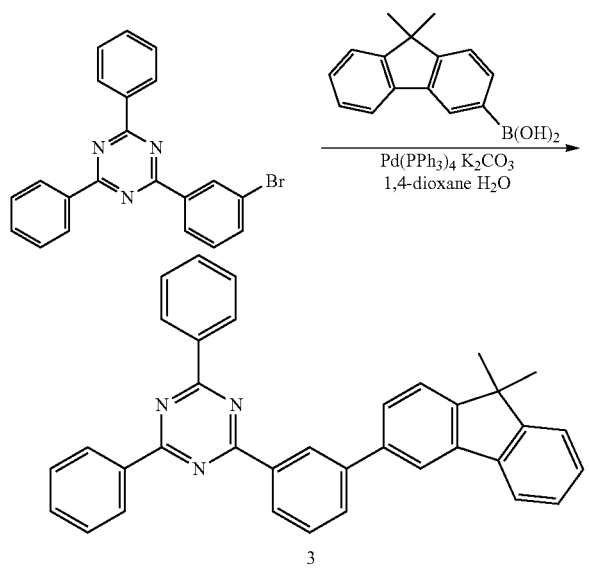

3

The same procedure was conducted as in Synthesis Example 1, with the exception of using 9,9-dimethyl-9H-fluoren-3-yl-boronic acid (7.9 g, 0.033 mol) instead of 9,9-dimethyl-9H-fluoren-2-yl-boronic acid, to afford Compound 3.

HRMS [M]+: 501.62

Synthesis Example 3: Synthesis of Compound 69
(2-[3-(9,9-Diphenyl-9H-fluoren-2-yl)-phenyl]-4,6-diphenyl-[1,3,5]triazine)

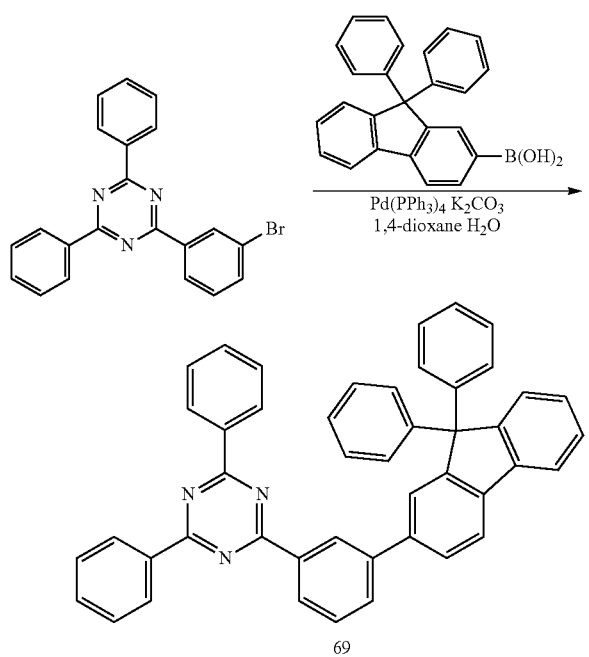

69

The same procedure was conducted as in Synthesis Example 1, with the exception of using (9,9-diphenyl-9H-fluoren-2-yl)-boronic acid (11.9 g, 0.033 mol) instead of 9,9-dimethyl-9H-fluoren-2-yl-boronic acid, to afford Compound 69.

HRMS [M]+: 625.76

Synthesis Example 4: Synthesis of Compound 129
(2-[3-(9,9-Spirobi[9H-fluorene]-2-yl)-phenyl]-4,6-diphenyl-[1,3,5]triazine)

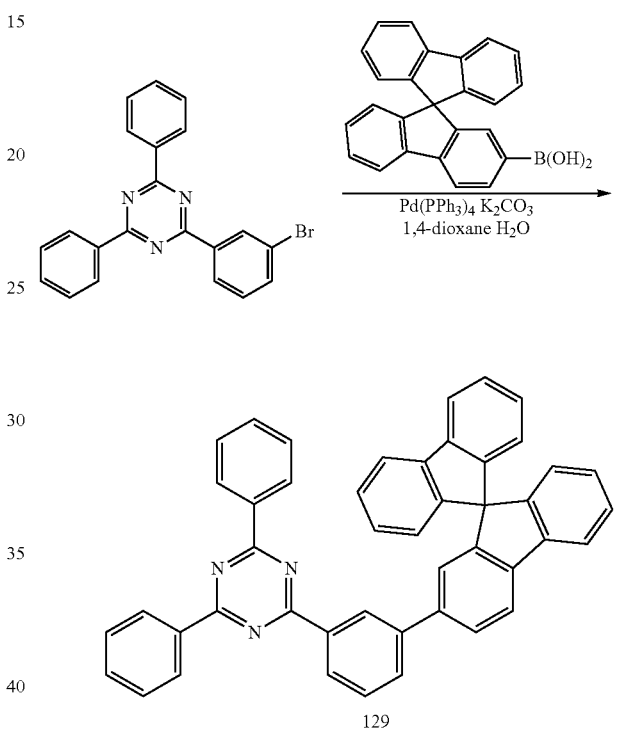

129

The same procedure was conducted as in Synthesis Example 1, with the exception of using 9,9'-spirobi[9H-fluorene]-2-yl-boronic acid (11.88 g, 0.033 mol) instead of 9,9-dimethyl-9H-fluoren-2-yl-boronic acid, to afford Compound 129.

HRMS [M]+: 623.74

Synthesis Example 5: Synthesis of Compound 6
(4-[3-(9,9-Dimethyl-9H-fluoren-2-yl)-phenyl]-2,6-diphenyl-pyrimidine

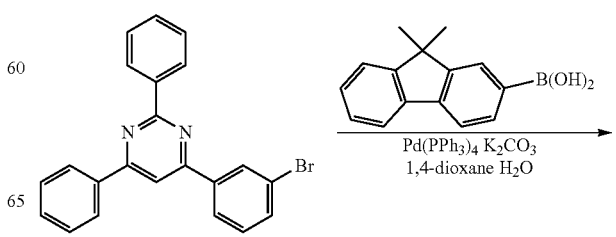

-continued

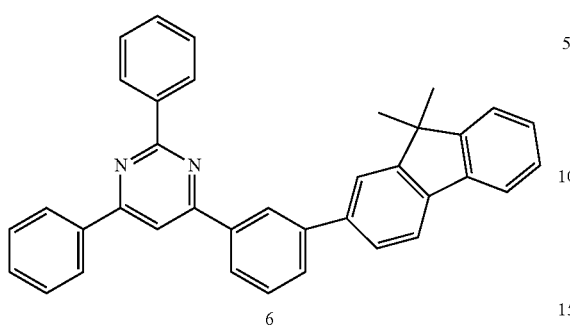

6

The same procedure was conducted as in Synthesis Example 1, with the exception of using 4-(3-bromophenyl)-2,6-diphenyl-pyrimidine (10.0 g, 0.026 mol) instead of 2-(3-bromophenyl)-4,6-diphenyl-[1,3,5]triazine, to afford Compound 6.

HRMS [M]+: 500.63

Synthesis Example 6: Synthesis of Compound 74 (4-[3-(9, 9-Diphenyl-9H-fluoren-2-yl)-phenyl]-2,6-diphenyl-pyrimidine)

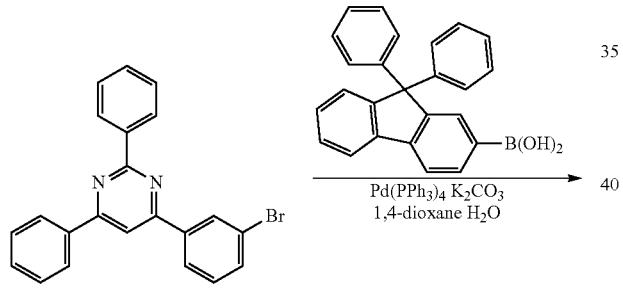

74

The same procedure was conducted as in Synthesis Example 5, with the exception of using (9,9-diphenyl-9H-fluoren-2-yl)-boronic acid (11.9 g, 0.033 mol) instead of 9,9-dimethyl-9H-fluoren-2-yl-boronic acid, to afford Compound 74.

HRMS [M]+: 624.77

Synthesis Example 7: Synthesis of Compound 134 (4-[3-(9,9-Spirobi[9H-fluorene]-2-yl)-phenyl]-2,6-diphenyl-pyrimidine

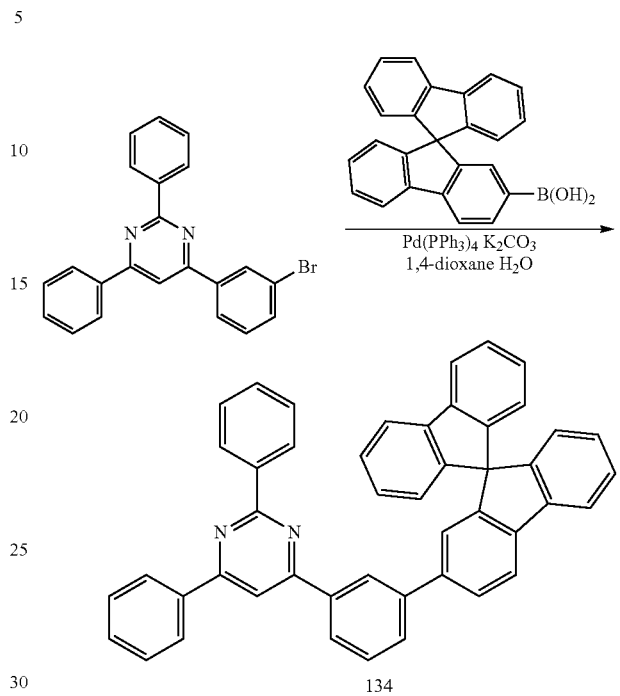

134

The same procedure was conducted as in Synthesis Example 5, with the exception of using 9,9'-spirobi[9H-fluorene]-2-yl-boronic acid (12.77 g, 0.033 mol) instead of 9,9-dimethyl-9H-fluoren-2-yl-boronic acid, to afford Compound 134.

HRMS [M]+: 622.75

Synthesis Example 8: Synthesis of Compound 7 (4-[3-(9,9-Dimethyl-9H-fluoren-2-yl)-phenyl]-2,6-diphenyl-pyridine)

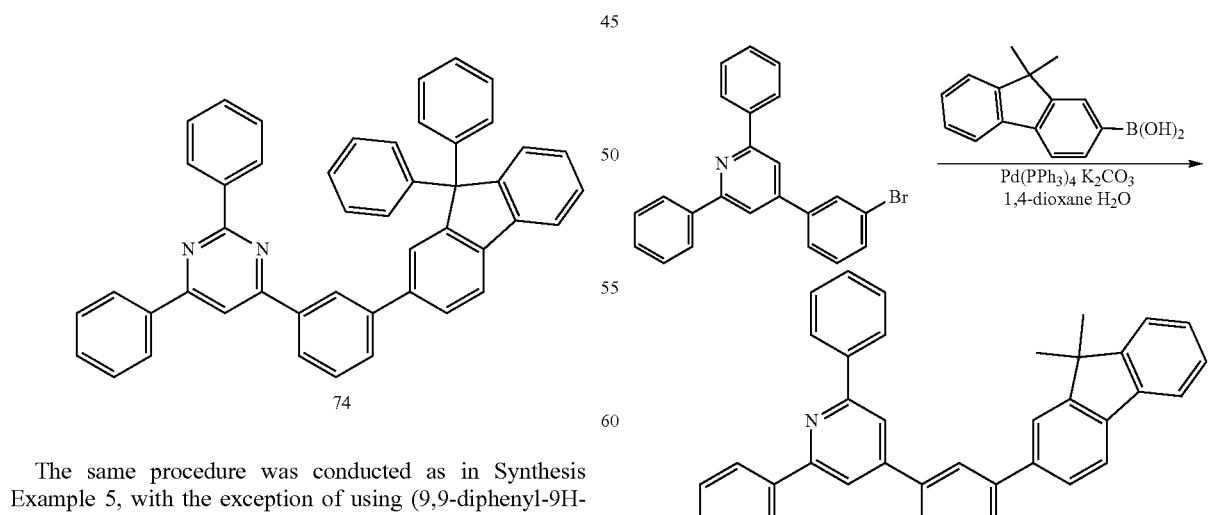

7

The same procedure was conducted as in Synthesis Example 1, with the exception of using 4-(3-bromophenyl)-2,6-diphenyl-pyridine (10.0 g, 0.026 mol) instead of 2-(3-bromophenyl)-4,6-diphenyl-[1,3,5]triazine, to afford Compound 7.

HRMS [M]+: 499.64

Synthesis Example 9: Synthesis of Compound 75 (4-[3-(9,9-Diphenyl-9H-fluoren-2-yl)-phenyl]-2,6-diphenyl-pyridine

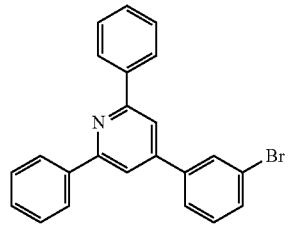
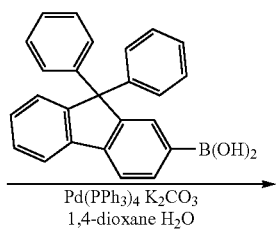

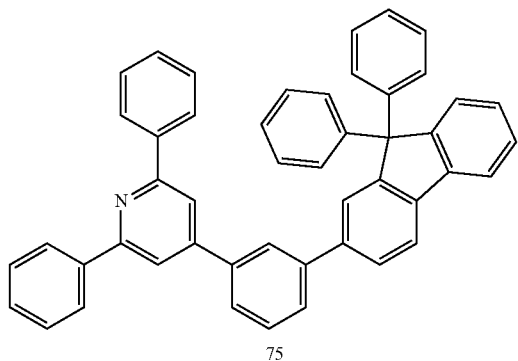

75

The same procedure was conducted as in Synthesis Example 8, with the exception of using (9,9-diphenyl-9H-fluoren-2-yl)-boronic acid (11.9 g, 0.033 mol) instead of 9,9-dimethyl-9H-fluoren-2-yl-boronic acid, to afford Compound 75.

HRMS [M]+: 623.78

Synthesis Example 10: Synthesis of Compound 135 (4-[3-(9,9-Spirobi[9H-fluorene]-2-yl)-phenyl]-2,6-diphenyl-pyridine

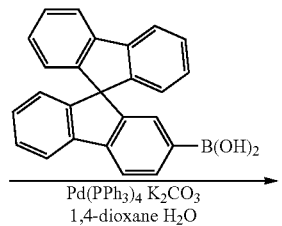

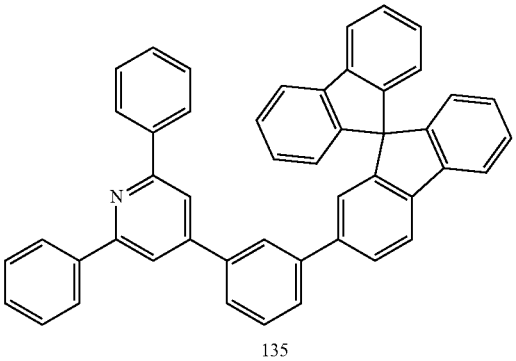

135

The same procedure was conducted as in Synthesis Example 8, with the exception of using 9,9'-spirobi[9H-fluorene]-2-yl-boronic acid (12.77 g, 0.033 mol) instead of 9,9-dimethyl-9H-fluoren-2-yl-boronic acid, to afford Compound 135.

HRMS [M]+: 622.71

Synthesis Example 11: Synthesis of Compound 21 (2-(3'-(9,9-dimethyl-9H-fluoren-2-yl) biphenyl-3-yl)-4,6-diphenyl-1,3,5-triazine)

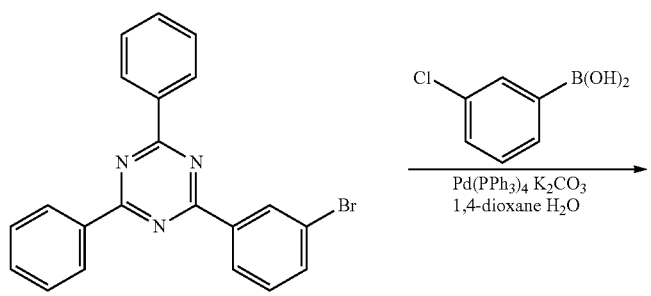

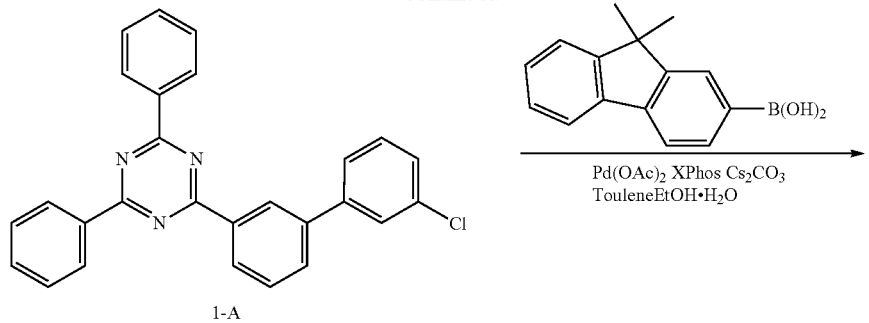

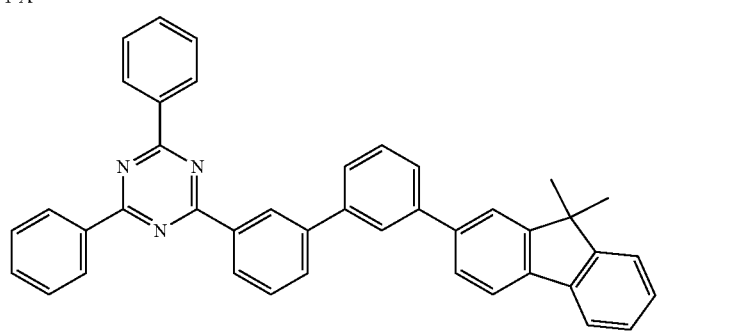

<Step 1> Synthesis of Intermediate 1-A (2-(3'-chloro-biphenyl-3-yl)-4,6-diphenyl-1,3,5-triazine)

Under a nitrogen stream, 2-(3-bromophenyl)-4,6-diphenyl-[1,3,5]triazine (12.0 g, 0.031 mol), 3-chlorophenylboronic acid (6.3 g, 0.040 mol), Pd(PPh$_3$)$_4$ (1.15 g, 0.001 mol), and potassium carbonate (12.85 g, 0.093 mol) were mixed and then stirred under reflux with 1,4-dioxane (100 ml) and H$_2$O (25 ml).

After completion of the reaction, an organic layer was separated with methylene chloride and dried over MgSO$_4$. The solvent was removed from the dehydrated organic layer, followed by purification through column chromatography [hexane:MC=5:1 (v/v)] to afford Intermediate 1-A (11.0 g, yield 83%).

<Step 2> Synthesis of Compound 21 (2-(3'-(9,9-dimethyl-9H-fluoren-2-yl)biphenyl-3-yl)-4,6-diphenyl-1,3,5-triazine)

Under a nitrogen stream, Intermediate 1-A (11.0 g, 0.026 mol) obtained in Step 1, 9,9-dimethyl-9H-fluoren-2-yl-boronic acid (7.9 g, 0.033 mol), Pd (OAc)$_2$ (0.29 g, 0.001 mol), cesium carbonate (25.4 g, 0.078 mol), and Xphos (1.23 g, 0.003 mol) were mixed and then stirred under reflux with toluene (100 ml)/ethanol (20 ml)/H$_2$O (20 ml).

After completion of the reaction, an organic layer was separated with methylene chloride and dried over MgSO$_4$. The solvent was removed from the dehydrated organic layer, followed by purification through column chromatography [hexane:MC=5:1 (v/v)] to afford Compound 21 (8.2 g, yield 63%).

HRMS [M]+: 577.72

Synthesis Example 12: Synthesis of Compound 23 (2-[3'-(9,9-Dimethyl-9H-fluoren-3-yl)-biphenyl-3-yl]-4,6-diphenyl-[1,3,5]triazine

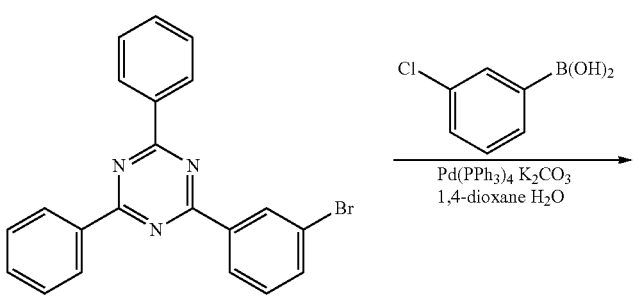

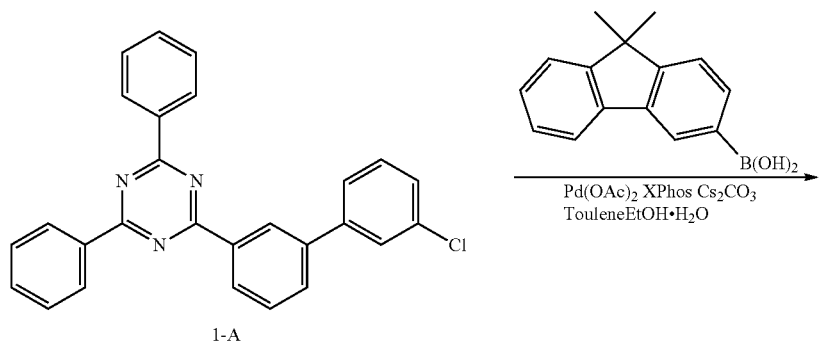
1-A
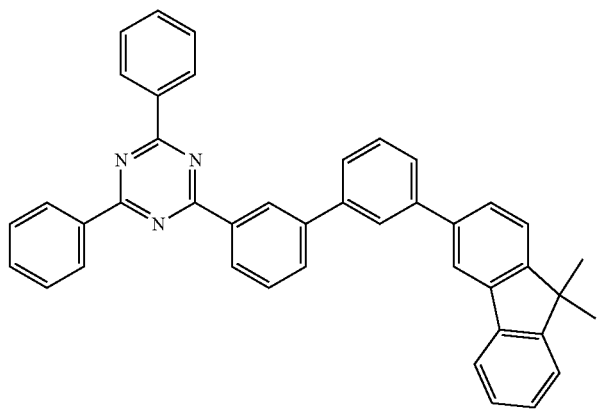
23
The same procedure was conducted as in Synthesis Example 11, with the exception of using 9,9-dimethyl-9H-fluoren-3-yl-boronic acid (7.9 g, 0.033 mol) instead of 9,9-dimethyl-9H-fluoren-2-yl-boronic acid used in Step 2 of Synthesis Example 11, to afford Compound 23.
HRMS [M]+: 577.72
Synthesis Example 13: Synthesis of Compound 89 (2-[3'-(9,9-Diphenyl-9H-fluoren-2-yl)-biphenyl-3-yl]-4,6-diphenyl-[1,3,5]triazine
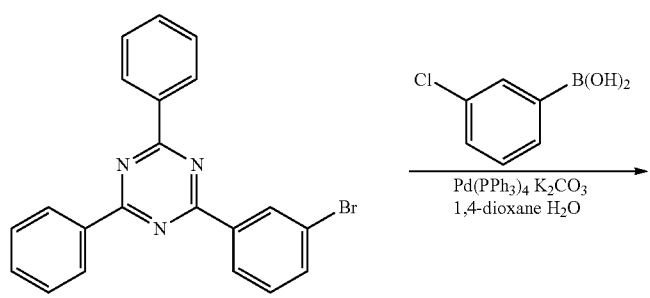

-continued
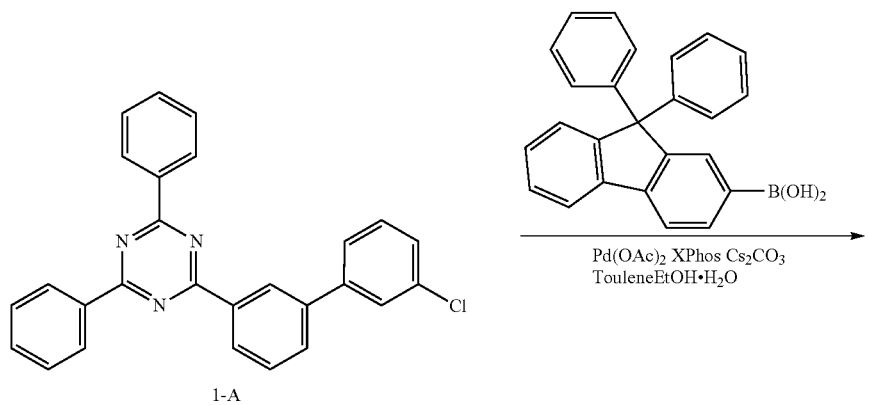
1-A
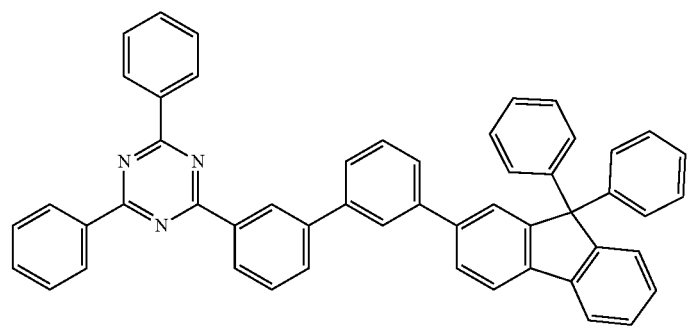
89
The same procedure was conducted as in Synthesis Example 11, with the exception of using (9,9-diphenyl-9H-fluoren-2-yl)-boronic acid (7.9 g, 0.033 mol) instead of 9,9-Dimethyl-9H-fluoren-2-yl-boronic acid used in Step 2 of Synthesis Example 11.
HRMS [M]+: 701.85
Synthesis Example 14: Synthesis of Compound 91 (2-(3'-(9,9-diphenyl-9H-fluoren-3-yl)-[1,1'-biphenyl]-3-yl)-4,6-diphenyl-1,3,5-triazine
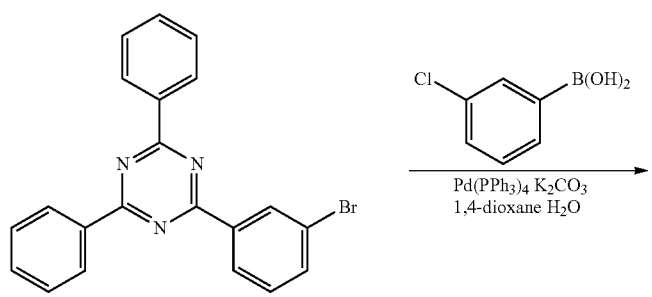

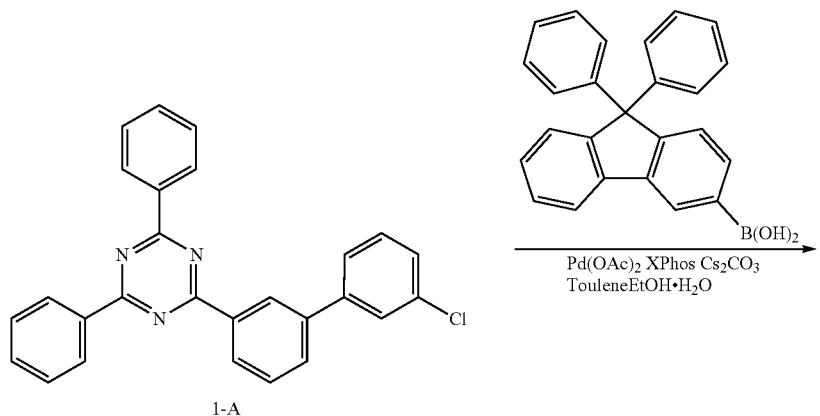
1-A
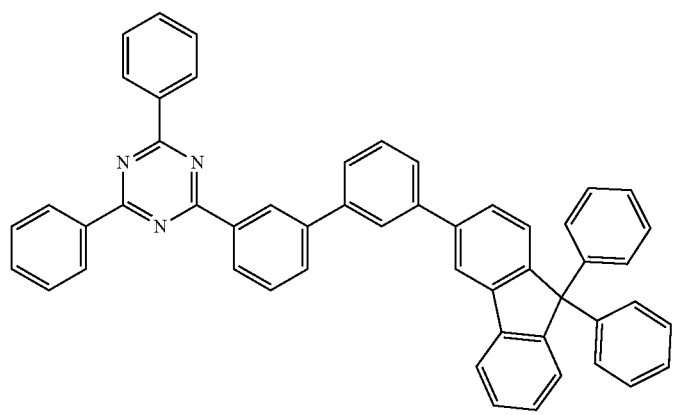
91
The same procedure was conducted as in Synthesis Example 11, with the exception of using (9,9-diphenyl-9H-fluoren-3-yl)boronic acid (7.9 g, 0.033 mol) instead of (9,9-dimethyl-9H-fluoren-2-yl)boronic acid used in Step 2 of Synthesis Example 11, to afford Compound 91.
HRMS [M]+: 701.85
Synthesis Example 15: Synthesis of Compound 149 (2-[3'-(9,9-Spirobi[9H-fluorene]-2-yl)-biphenyl-3-yl]-4,6-diphenyl-[1,3,5]triazine
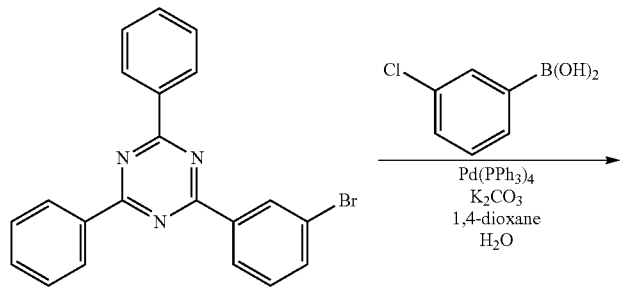

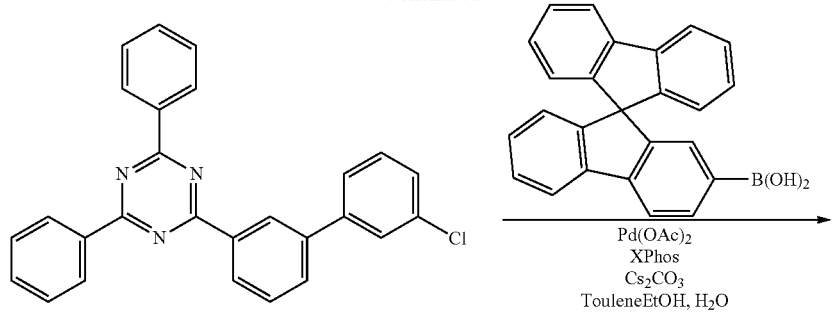
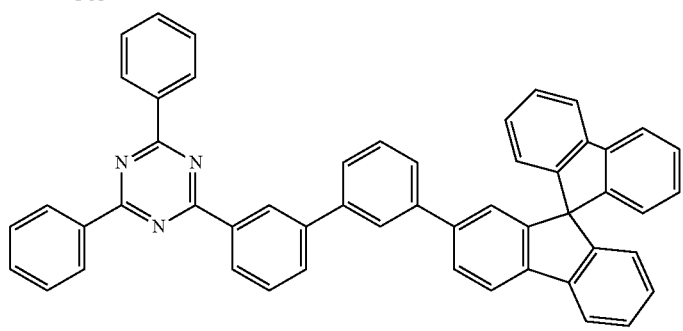
The same procedure was conducted as in Synthesis Example 11, with the exception of using 9,9'-Spirobi[9H-fluorene]-2-yl-boronic acid (12.77 g, 0.033 mol) instead of 9,9-dimethyl-9H-fluoren-2-yl-boronic acid used in Step 2 of Synthesis Example 11, to afford Compound 149.
HRMS [M]+: 699.84
Synthesis Example 16: Synthesis of Compound 151 (2-(3'-(9,9'-spirobi[fluoren]-3-yl)-[1,1'-biphenyl]-3-yl)-4,6-diphenyl-1,3,5-triazine
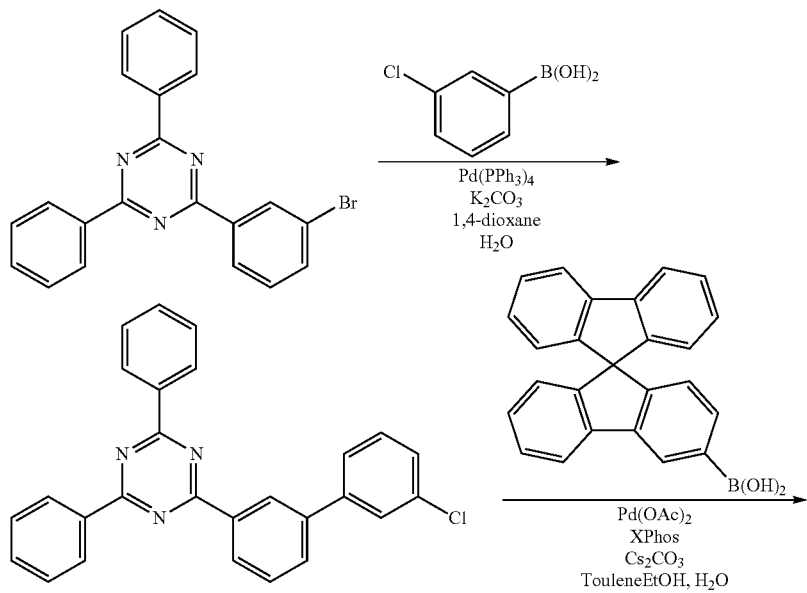

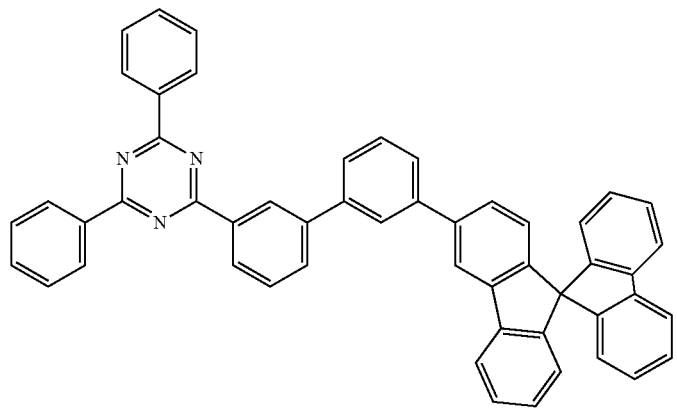
151
The same procedure was conducted as in Synthesis Example 11, with the exception of using 9,9'-spirobi[fluoren]-3-yl-boronic acid (12.77 g, 0.033 mol) instead of 9,9-dimethyl-9H-fluoren-2-yl-boronic acid used in Step 2 of Synthesis Example 11, to afford Compound 151.
HRMS [M]+: 699.84
Synthesis Example 17: Synthesis of Compound 31 (4-[3'-(9,9-Dimethyl-9H-fluoren-2-yl)-biphenyl-3-yl]-2,6-diphenyl-pyrimidine
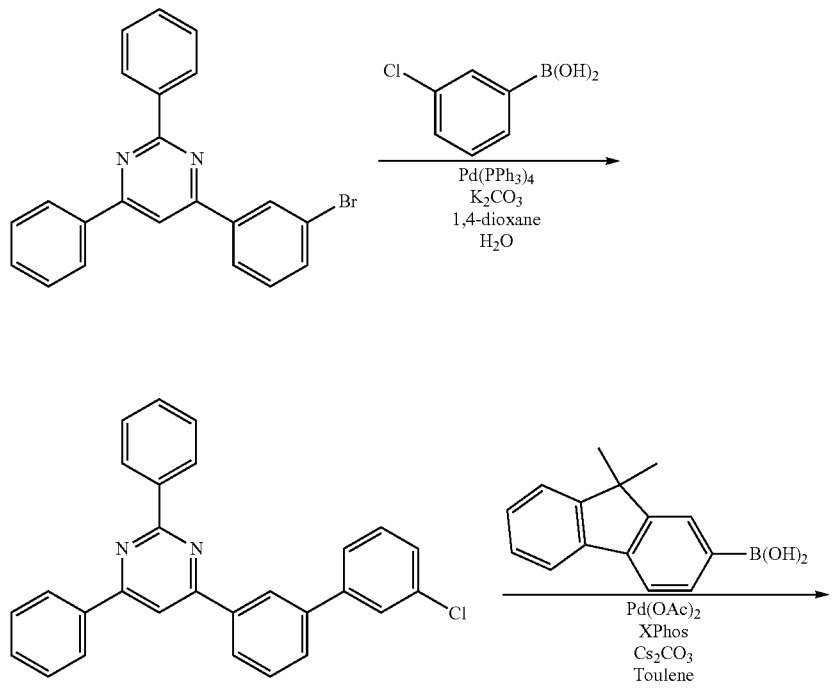
2-A

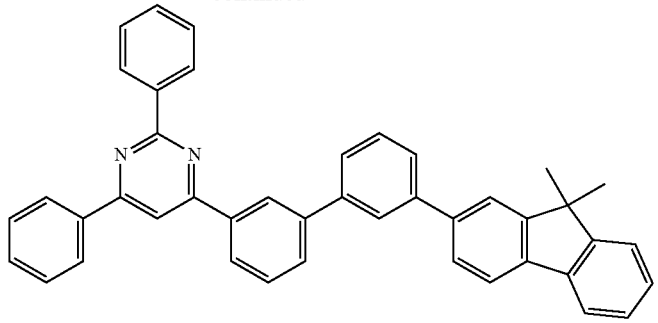

31

<Step 1> Synthesis of Intermediate 2-A (4-(3'-Chloro-biphenyl-3-yl)-2,6-diphenyl-pyrimidine The same procedure was conducted as in Step 1 of Synthesis Example 11, with the exception of using 4-(3-bromophenyl)-2,6-diphenyl-pyrimidine (12.0 g, 0.031 mol) instead of 2-(3-bromophenyl)-4,6-diphenyl-[1,3,5]triazine used in Step 1 of Synthesis Example 11, to afford Intermediate 2-A.

<Step 2> Synthesis of Compound 31 4-[3'-(9,9-Dimethyl-9H-fluoren-2-yl)-biphenyl-3-yl]-2,6-diphenyl-pyrimidine The same procedure was conducted as in Step 2 of Synthesis Example 11, with the exception of using Intermediate 2-A (11.0 g, 0.026 mol) synthesized in Step 1 instead of Intermediate 1-A used in Step 2 of Synthesis Example 11, to afford Compound 31.

HRMS [M]+: 576.73

Synthesis Example 18: Synthesis of Compound 35 (4-[3'-(9,9-Dimethyl-9H-fluoren-3-yl)-biphenyl-3-yl]-2,6-diphenyl-pyrimidine

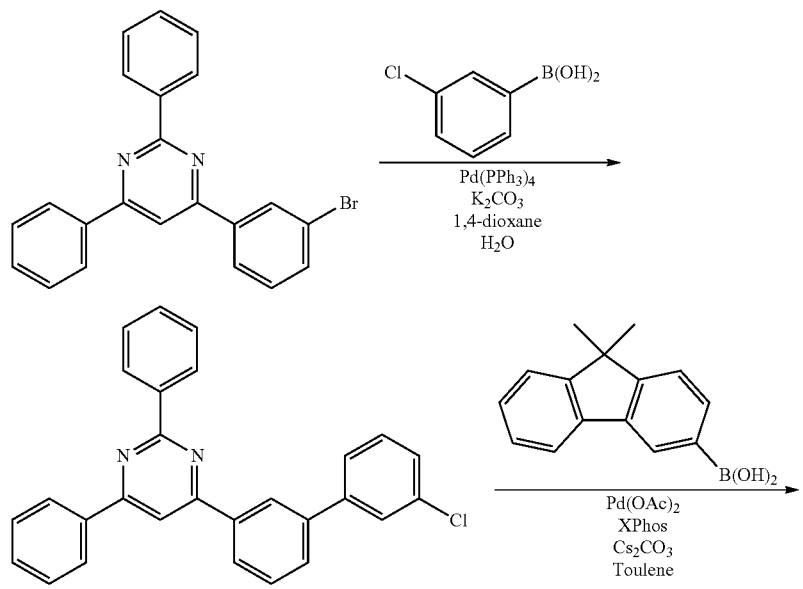

2-A

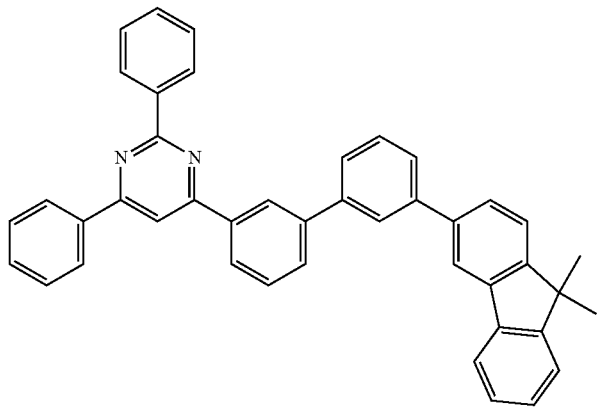
35
The same procedure was conducted as in Synthesis Example 17, with the exception of using 9,9-dimethyl-9H-fluoren-3-yl-boronic acid (7.9 g, 0.033 mol) instead of 9,9-dimethyl-9H-fluoren-2-yl-boronic acid used in Step 2 of Synthesis Example 17, to afford Compound 35.
HRMS [M]+: 576.73
Synthesis Example 19: Synthesis of Compound 99 (4-[3'-(9,9-Diphenyl-9H-fluoren-2-yl)-biphenyl-3-yl]-2,6-diphenyl-pyrimidine
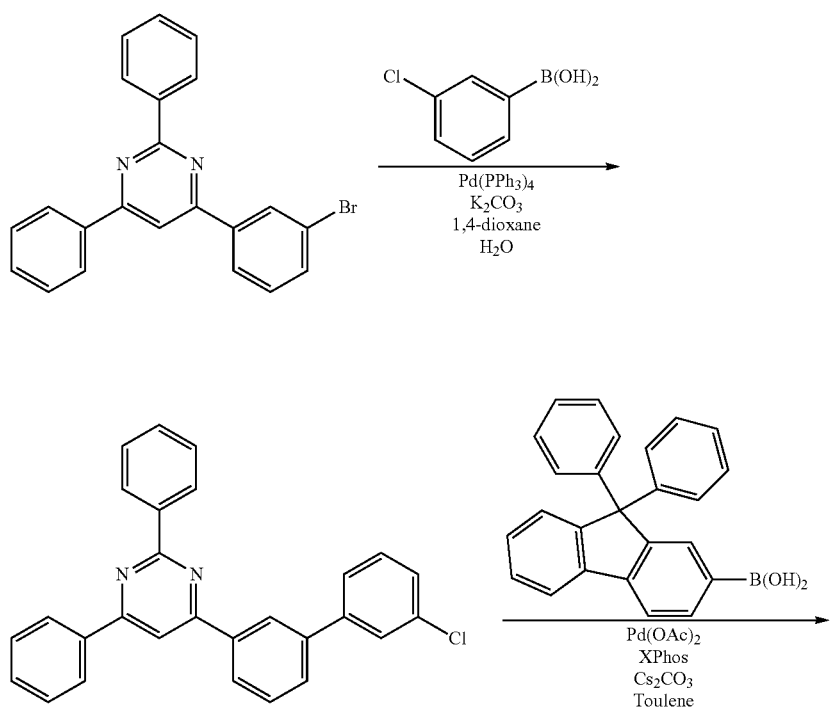
2-A

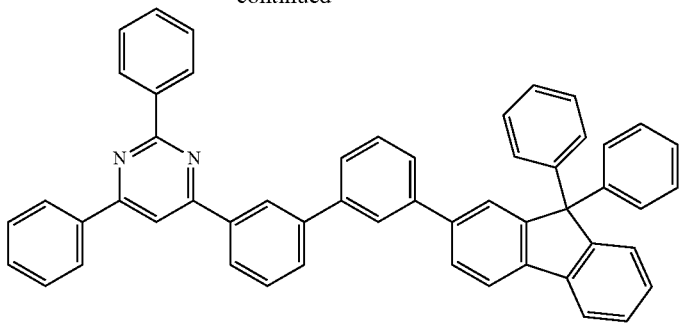
99
The same procedure was conducted as in Synthesis Example 17, with the exception of using (9,9-diphenyl-9H-fluoren-2-yl)-boronic acid (11.9 g, 0.033 mol) instead of 9,9-dimethyl-9H-fluoren-2-yl-boronic acid used in Step 2 of Synthesis Example 17, to afford Compound 99.
HRMS [M]+: 687.85
Synthesis Example 20: Synthesis of Compound 159 (4-[3'-(9,9-Spirobi[9H-fluorene]-2-yl)-biphenyl-3-yl]-2,6-diphenyl-pyrimidine
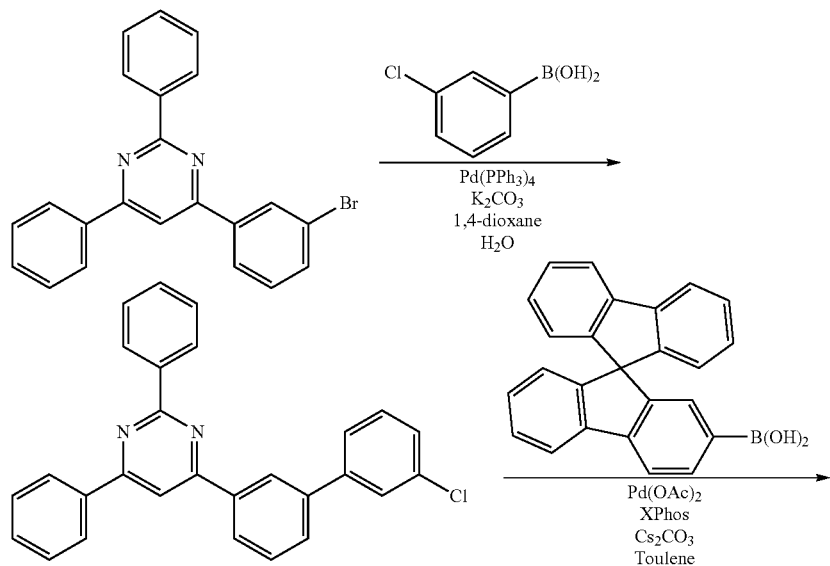
2-A
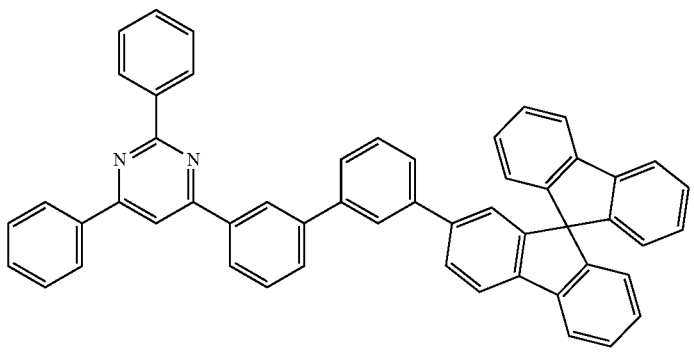
159

The same procedure was conducted as in Synthesis Example 17, with the exception of using 9,9'-spirobi[9H-fluorene]-2-yl-boronic acid (11.88 g, 0.033 mol) instead of 9,9-dimethyl-9H-fluoren-2-yl-boronic acid used in Step 2 of Synthesis Example 17, to afford Compound 159.

HRMS [M]+: 698.85

Synthesis Example 21: Synthesis of Compound 45 (4-[3'-(9,9-Dimethyl-9H-fluoren-2-yl)-biphenyl-3-yl]-2,6-diphenyl-pyridine

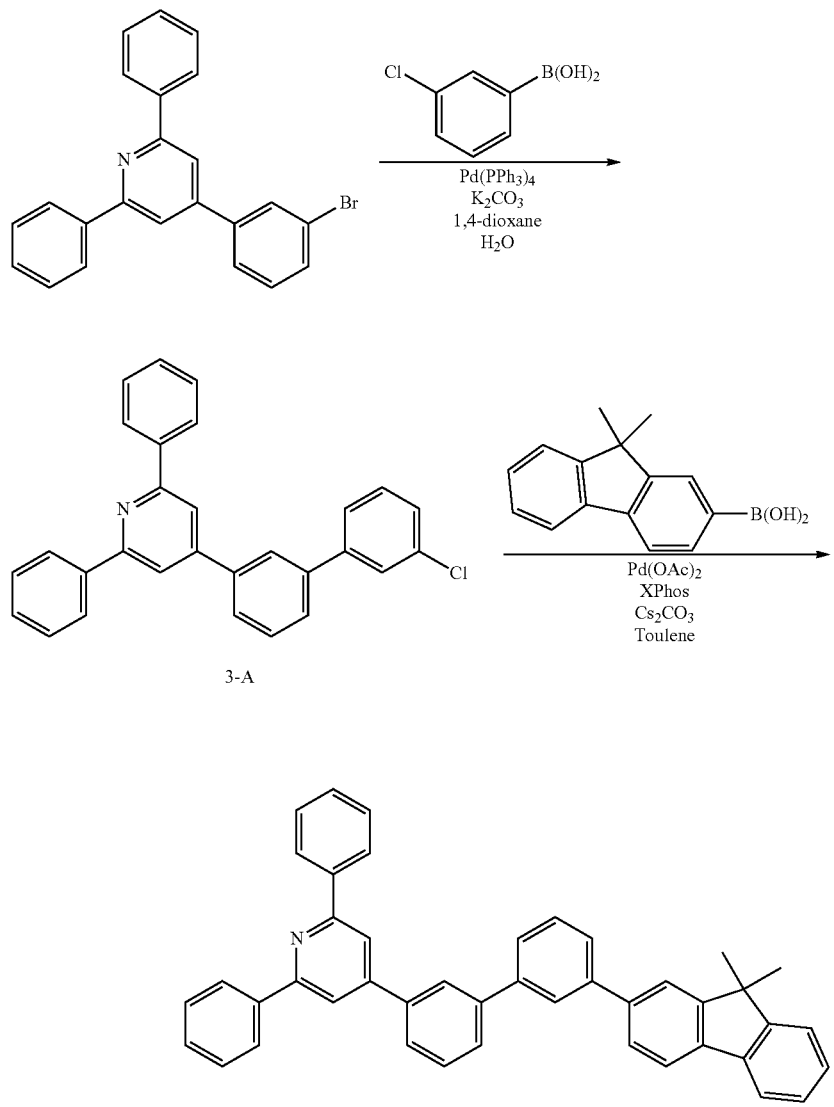

<Step 1> Synthesis of Intermediate 3-A (4-(3'-Chloro-biphenyl-3-yl)-2,6-diphenyl-pyridine The same procedure was conducted as in Step 1 of Synthesis Example 11, with the exception of using 4-(3-bromophenyl)-2,6-diphenyl-pyridine (12.0 g, 0.031 mol) instead of 2-(3-bromophenyl)-4,6-diphenyl-[1,3,5]triazine used in Step 1 of Synthesis Example 11, to afford Intermediate 3-A.

<Step 2> Synthesis of Compound 45 (4-[3'-(9,9-Dimethyl-9H-fluoren-2-yl)-biphenyl-3-yl]-2,6-diphenyl-pyridine The same procedure was conducted as in Step 2 of Synthesis Example 11, with the exception of using Intermediate 3-A (11.0 g, 0.026 mol) synthesized in Step 1 instead of Intermediate 1-A used in Step 2 of Synthesis Example 11, to afford Compound 45.

Synthesis Example 22: Synthesis of Compound 53 (4-[3'-(9,9-Dimethyl-9H-fluoren-3-yl)-biphenyl-3-yl]-2,6-diphenyl-pyridine

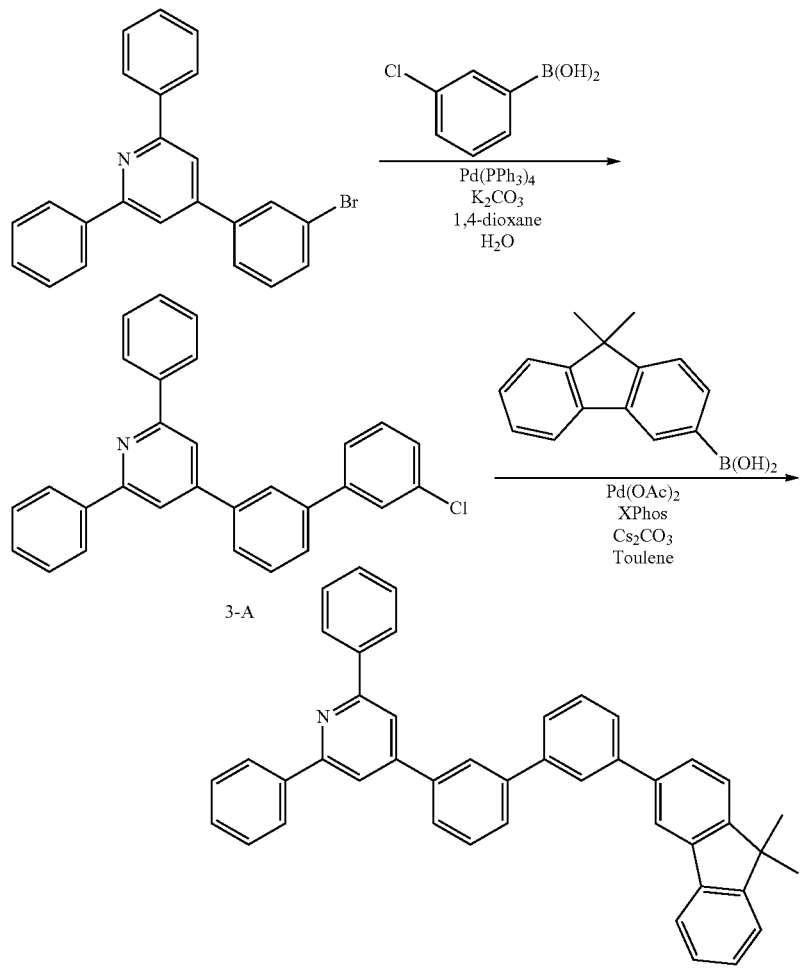

53

The same procedure was conducted as in Synthesis Example 21, with the exception of using 9,9-dimethyl-9H-fluoren-3-yl-boronic acid (7.9 g, 0.033 mol) instead of 9,9-dimethyl-9H-fluoren-2-yl-boronic acid used in Step 2 of Synthesis Example 21, to afford Compound 53.

HRMS [M]+: 501.62

Synthesis Example 23: Synthesis of Compound 113 (4-[3'-(9,9-Diphenyl-9H-fluoren-2-yl)-biphenyl-3-yl]-2,6-diphenyl-pyridine

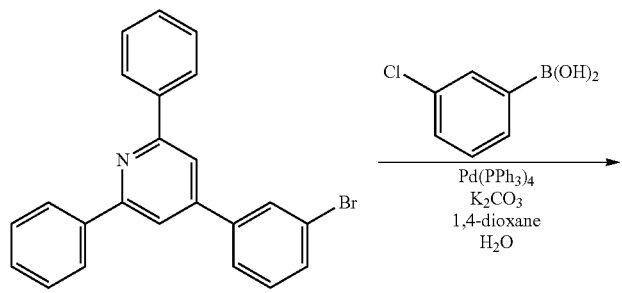

-continued
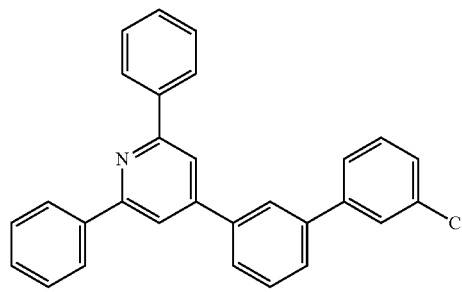 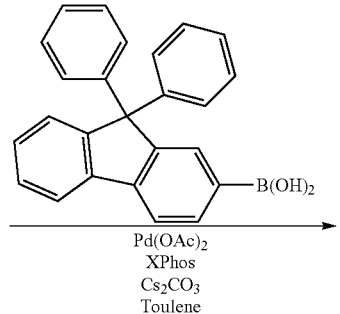
3-A
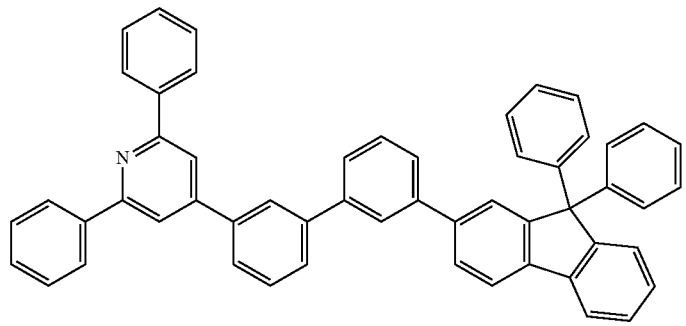
113
The same procedure was conducted as in Synthesis Example 21, with the exception of using (9,9-diphenyl-9H-fluoren-2-yl)-boronic acid (11.9 g, 0.033 mol) instead of 9,9-Dimethyl-9H-fluoren-2-yl-boronic acid used in Step 2 of Synthesis Example 21, to afford Compound 113.
HRMS [M]+: 699.88
Synthesis Example 24: Synthesis of Compound 173 (4-[3'-(9,9-Spirobi[9H-fluorene]-2-yl)-biphenyl-3-yl]-2,6-diphenyl-pyridine
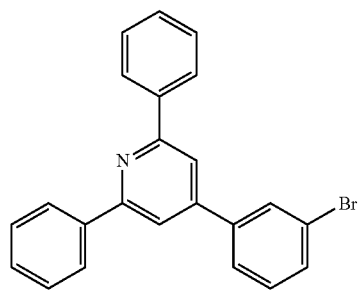 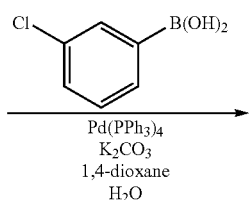
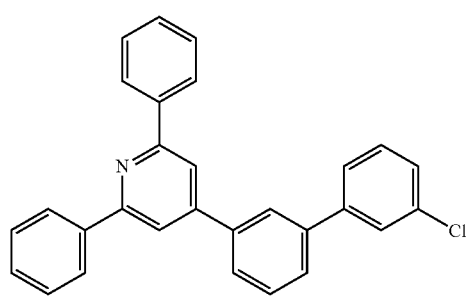 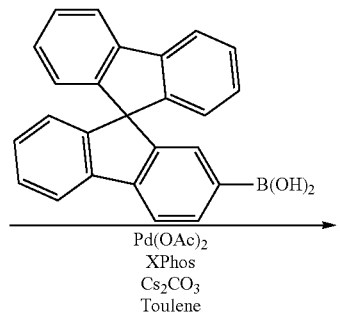
3-A

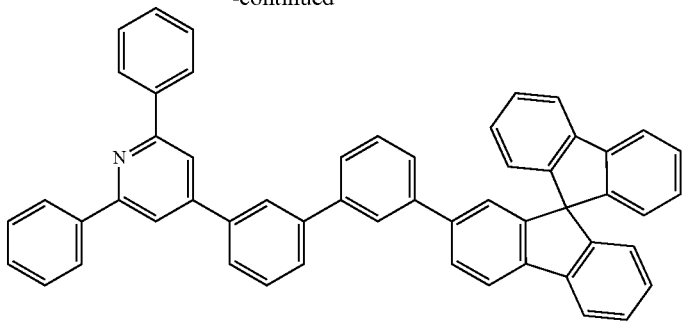
173
The same procedure was conducted as in Synthesis Example 21, with the exception of using 9,9'-spirobi[9H-fluorene]-2-yl-boronic acid (11.88 g, 0.033 mol) instead of 9,9-dimethyl-9H-fluoren-2-yl-boronic acid used in Step 2 of Synthesis Example 21, to afford Compound 173.
HRMS [M]+: 697.86
Synthesis Example 25: Synthesis of Compound 61 (2-(3"-(9,9-dimethyl-9H-fluoren-2-yl)-[1,1':3',1"-terphenyl]-3-yl)-4,6-diphenyl-1,3,5-triazine)
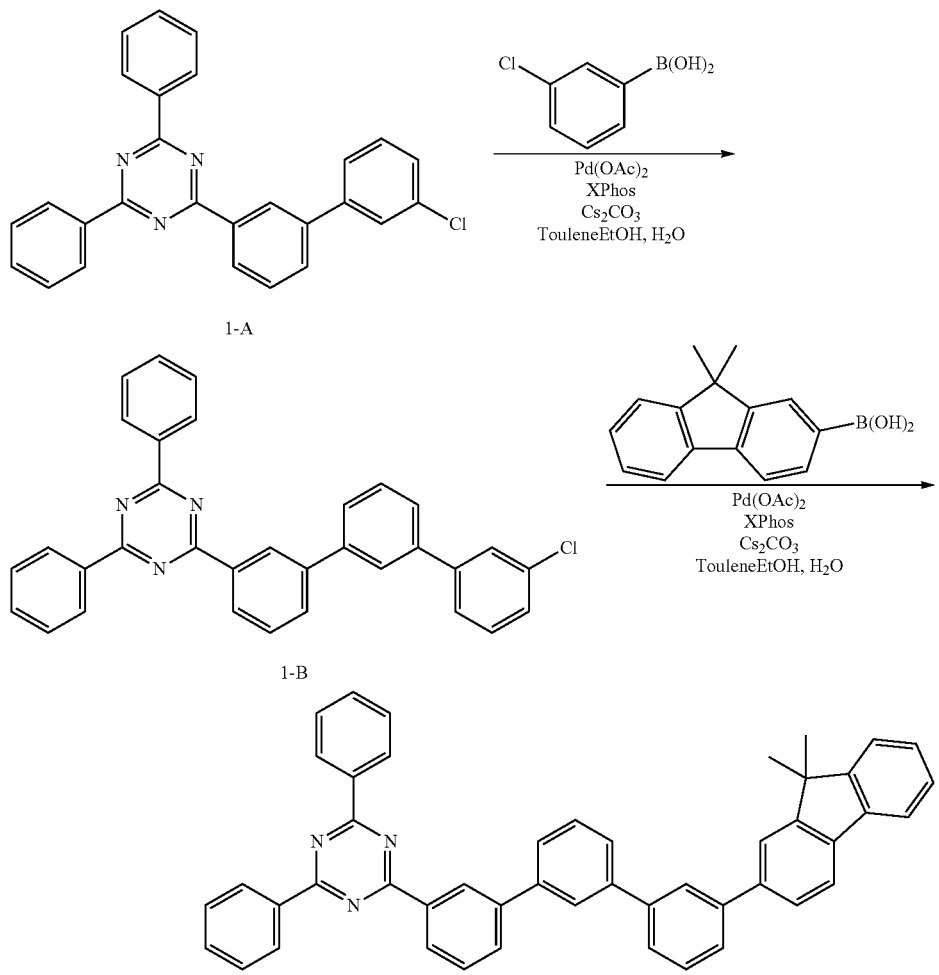

<Step 1> Synthesis of Intermediate 1-B (2-(3"-chloro-[1,1':3',1"-terphenyl]-3-yl)-4,6-diphenyl-1,3,5-triazine)

Under a nitrogen stream, Intermediate 1-A (11.0 g, 0.026 mol), 3-Chlorophenylboronic acid (4.8 g, 0.031 mol), Pd(OAc)$_2$ (0.29 g, 0.001 mol), Cesium carbonate (25.4 g, 0.078 mol), and Xphos (0.3 g, 0.003 mol) were mixed and then stirred under reflux with toluene (100 ml)/ethanol (20 ml)/H$_2$O (20 ml).
After completion of the reaction, an organic layer was separated with methylene chloride and dried over MgSO$_4$. The solvent was removed from the dehydrated organic layer, followed by purification through column chromatography [hexane:MC=5:1 (v/v)] to afford Intermediate 1-B (7.5 g, yield 58%).

<Step 2> Synthesis of Compound 61 (2-(3"-(9,9-dimethyl-9H-fluoren-2-yl)-[1,1':3',1"-terphenyl]-3-yl)-4,6-diphenyl-1,3,5-triazine)

Under a nitrogen stream, Intermediate 1-B (7.5 g, 0.015 mol) obtained in Step 1, 9,9-dimethyl-9H-fluoren-2-yl-boronic acid (4.3 g, 0.018 mol), Pd(OAc)$_2$ (0.17 g, 0.75 mmol), cesium carbonate (14.6 g, 0.045 mol), and Xphos (0.7 g, 1.5 mmol) were mixed and stirred under reflux with toluene (60 ml)/ethanol (15 ml)/H$_2$O (15 ml).

After completion of the reaction, an organic layer was separated with methylene chloride and dried over MgSO$_4$. The solvent was removed from the dehydrated organic layer, followed by purification through column chromatography [hexane:MC=4:1 (v/v)] to afford Compound 61 (8.1 g, yield 83%).

HRMS [M]+: 653.83

Synthesis Example 26: Synthesis of Compound 62 (2-(3"-(9,9-dimethyl-9H-fluoren-3-yl)-[1,1':3',1"-terphenyl]-3-yl)-4,6-diphenyl-1,3,5-triazine

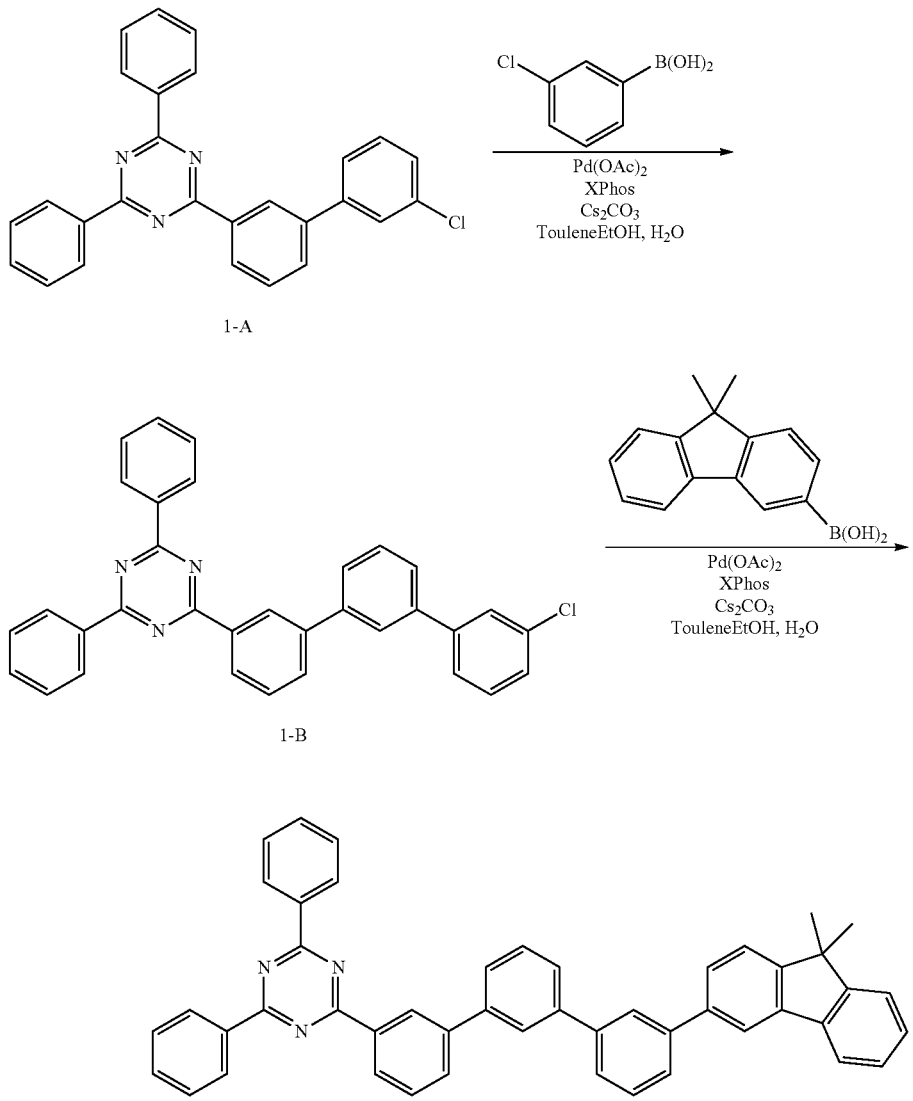

The same procedure was conducted as in Synthesis Example 25, with the exception of using (9,9-dimethyl-9H-fluoren-3-yl)boronic acid (4.3 g, 0.018 mol) instead of 9,9-dimethyl-9H-fluoren-2-yl-boronic acid used in Step 2 of Synthesis Example 25, to afford Compound 62.

HRMS [M]+: 653.83

Synthesis Example 27: Synthesis of Compound 63 (4-(3''-(9,9-dimethyl-9H-fluoren-2-yl)-[1,1':3',1''-terphenyl]-3-yl)-2,6-diphenylpyrimidine

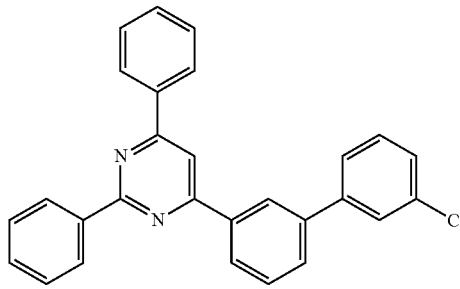 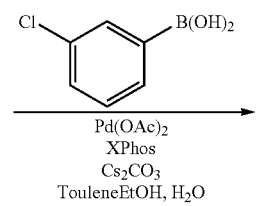

2-A

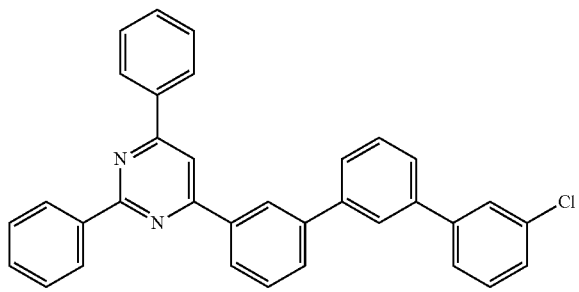 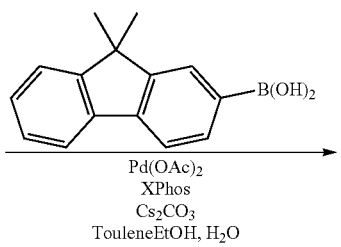

2-B

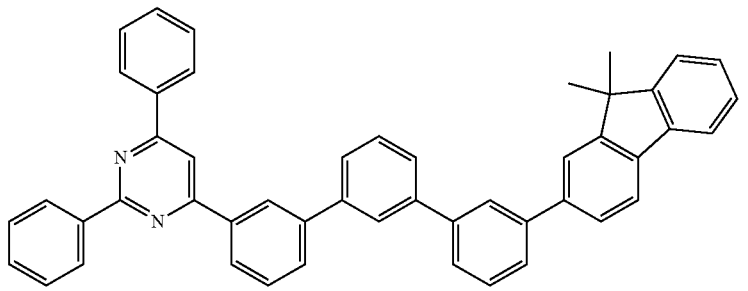

63

<Step 1> Synthesis of Intermediate 2-B (4-(3''-chloro-[1,1':3',1''-terphenyl]-3-yl)-2,6-diphenylpyrimidine Under a nitrogen stream, Intermediate 2-A (11.0 g, 0.026 mol), 3-chlorophenylboronic acid (4.8 g, 0.031 mol), Pd(OAc)₂ (0.29 g, 0.001 mol), Cesium carbonate (25.4 g, 0.078 mol), and Xphos (0.3 g, 0.003 mol) were mixed and then stirred under reflux with toluene (100 ml)/ethanol (20 ml)/H₂O (20 ml).

After completion of the reaction, an organic layer was separated with methylene chloride and then dried over MgSO₄. The solvent was removed from the dehydrated organic layer, followed by purification through column chromatography [hexane:MC=5:1 (v/v)] to afford Intermediate 2-B (7.5 g, yield 58%).

<Step 2> Synthesis of Compound 63 (4-(3''-(9,9-dimethyl-9H-fluoren-2-yl)-[1,1':3',1''-terphenyl]-3-yl)-2,6-diphenylpyrimidine Under a nitrogen stream, Intermediate 2-B (7.5 g, 0.015 mol), 9,9-dimethyl-9H-fluoren-2-yl-boronic acid (4.3 g, 0.018 mol) obtained in Step 1, Pd(OAc)₂ (0.17 g, 0.75 mmol), cesium carbonate (14.6 g, 0.045 mol), and Xphos (0.7 g, 1.5 mmol) were mixed and then mixed and then stirred under reflux with toluene (60 ml)/Ethanol (15 ml)/H₂O (15 ml).

After completion of the reaction, an organic layer was separated with methylene chloride and then dried over MgSO₄. The solvent was removed from the dehydrated organic layer, followed by purification through column chromatography [hexane:MC=4:1 (v/v)] to afford Compound 63 (8.1 g, yield 83%).

HRMS [M]+: 652.84

Synthesis Example 28: Synthesis of Compound 64 (4-(3"-(9,9-dimethyl-9H-fluoren-3-yl)-[1,1':3',1"-terphenyl]-3-yl)-2,6-diphenylpyrimidine
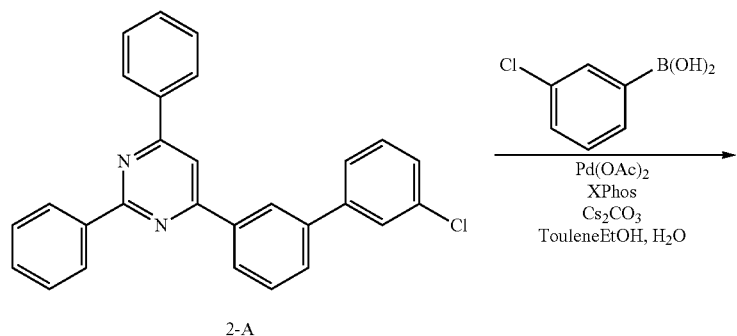
2-A
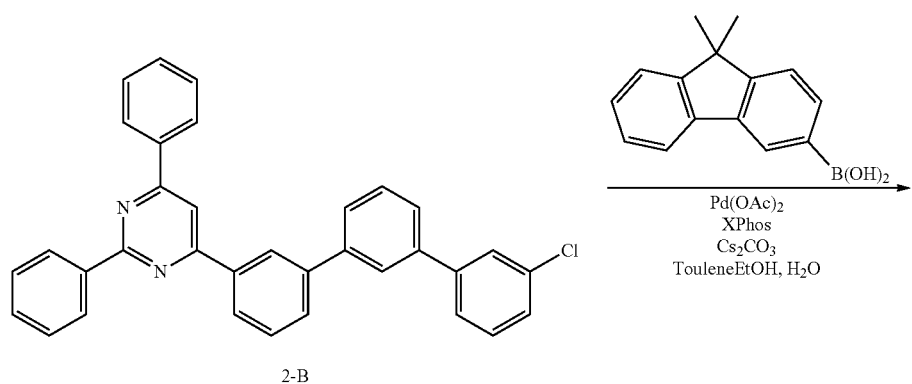
2-B
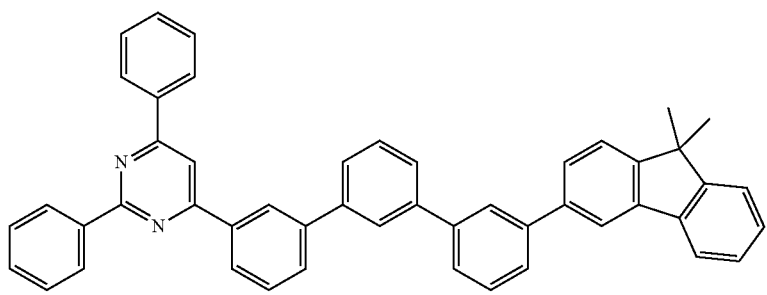
64
The same procedure was conducted as in Synthesis Example 27, with the exception of using (9,9-dimethyl-9H-fluoren-3-yl)boronic acid (4.3 g, 0.018 mol) instead of 9,9-dimethyl-9H-fluoren-2-yl-boronic acid used in Step 2 of Synthesis Example 27, to afford Compound 64.
HRMS [M]+: 652.84

Synthesis Example 29: Synthesis of Compound 200 (2 2-([1,1'-biphenyl]-4-yl)-4-(3'-(9,9-diphenyl-9H-fluoren-2-yl)-[1,1'-biphenyl]-3-yl)-6-phenyl-1,3,5-triazine
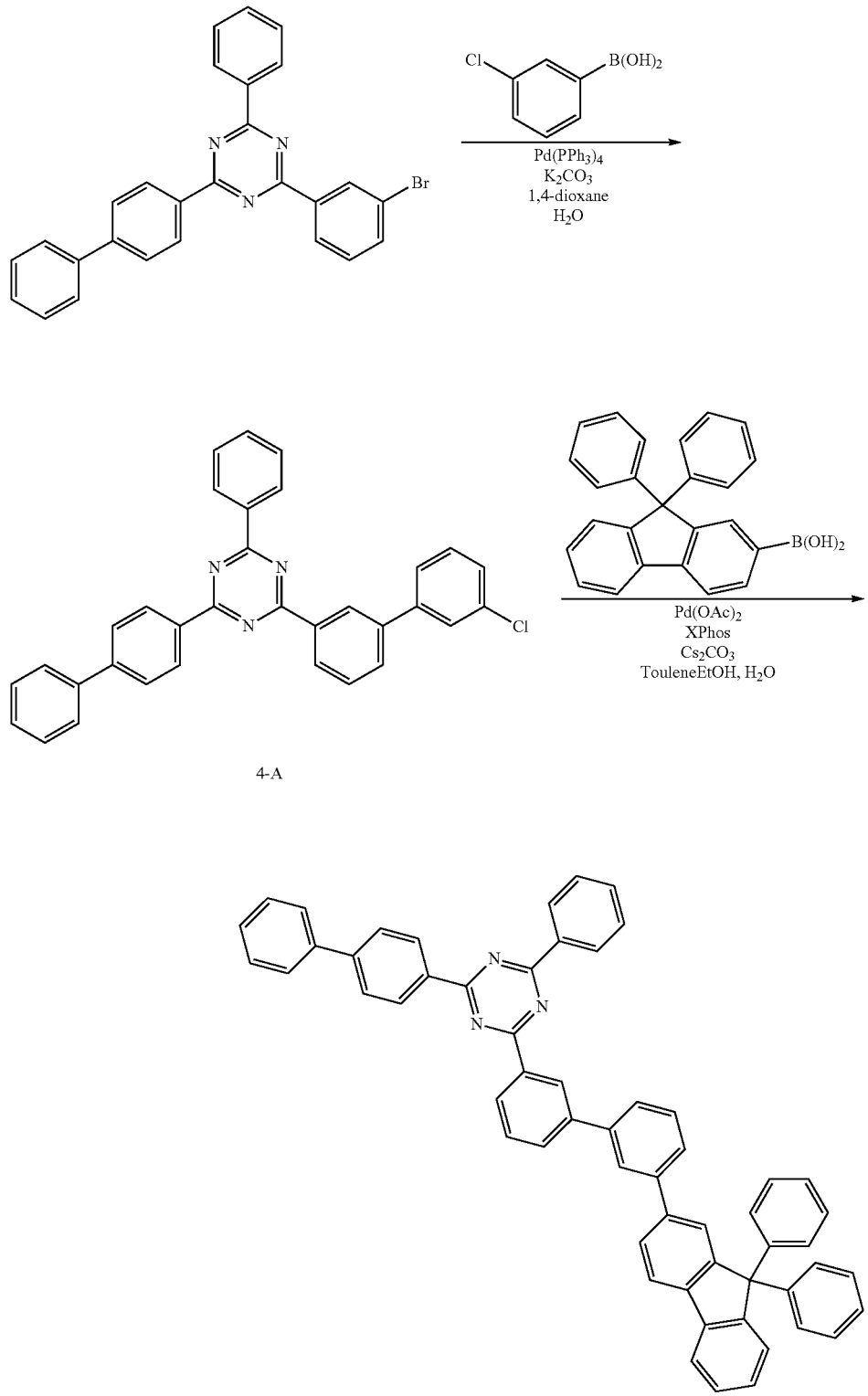
4-A
200

<Step 1> Synthesis of Intermediate 4-A

The same procedure was conducted as in Step 1 of Synthesis Example 11, with the exception of using 2-([1,1'-biphenyl]-4-yl)-4-(3-bromophenyl)-6-phenyl-1,3,5-triazine (14.4 g, 0.031 mol) instead of 2-(3-bromophenyl)-4,6-diphenyl-1,3,5-triazine used in Step 1 of Synthesis Example 11, to afford Intermediate 4-A.

<Step 2> Synthesis of Compound 200 (2 2-([1,1'-biphenyl]-4-yl)-4-(3'-(9,9-diphenyl-9H-fluoren-2-yl)-[1,1'-biphenyl]-3-yl)-6-phenyl-1,3,5-triazine The same procedure was conducted as in Step 2 of Synthesis Example 11, with the exception of using (9,9-diphenyl-9H-fluoren-2-yl)-boronic acid (11.9 g, 0.033 mol) instead of 9,9-dimethyl-9H-fluoren-2-yl-boronic acid used in Step 2 of Synthesis Example 11, to afford Compound 200.

HRMS [M]+: 777.97

Synthesis Example 30: Synthesis of Compound 206 (4-([1,1'-biphenyl]-4-yl)-6-(3'-(9,9-diphenyl-9H-fluoren-2-yl)-[1,1'-biphenyl]-3-yl)-2-phenylpyrimidine

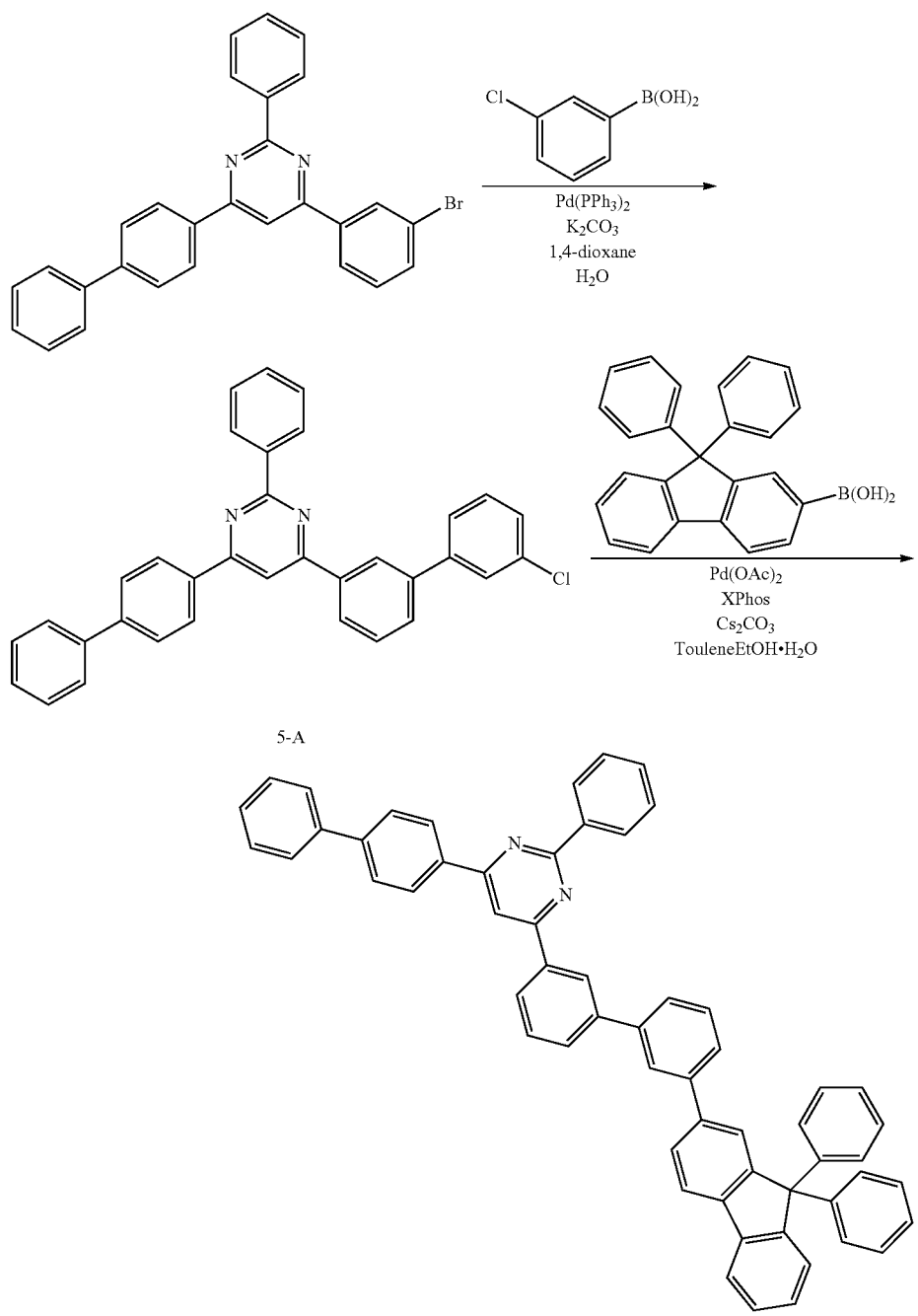

<Step 1> Synthesis of Intermediate 5-A

The same procedure was conducted as in Step 1 of Synthesis Example 11, with the exception of using 4-([1,1'-biphenyl]-4-yl)-6-(3-bromophenyl)-2-phenylpyrimidine (14.3 g, 0.031 mol) instead of 2-(3-bromophenyl)-4,6-diphenyl-1,3,5-triazine used in Step 1 of Synthesis Example 11, to afford Intermediate 5-A.

<Step 2> Synthesis of Compound 206 (4-([1,1'-biphenyl]-4-yl)-6-(3'-(9,9-diphenyl-9H-fluoren-2-yl)-[1,1'-biphenyl]-3-yl)-2-phenylpyrimidine The same procedure was conducted as in Step 2 of Synthesis Example 11, with the exception of using (9,9-diphenyl-9H-fluoren-2-yl)-boronic acid (11.9 g, 0.033 mol) instead of 9,9-dimethyl-9H-fluoren-2-yl-boronic acid used in Step 2 of Synthesis Example 11, to afford Compound 206.

HRMS [M]+: 776.98

Synthesis Example 31: Synthesis of Compound 217 (2-(3'-(9,9-dimethyl-9H-fluoren-1-yl)-[1,1'-biphenyl]-3-yl)-4,6-diphenyl-1,3,5-triazine

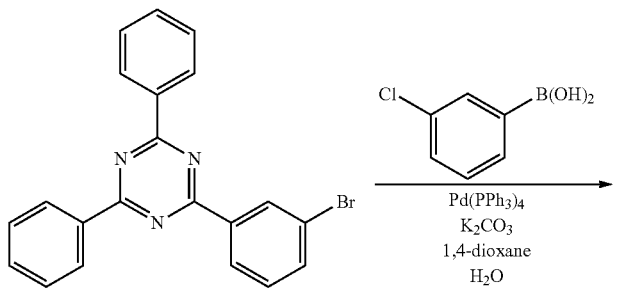

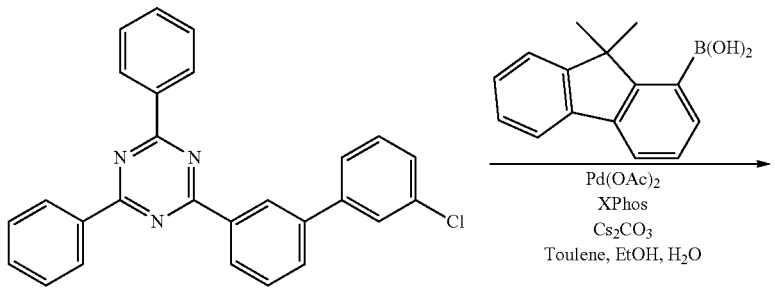

I-1

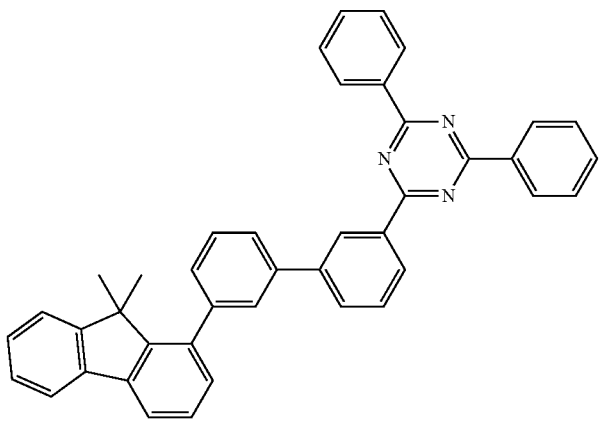

217

<Step 1> Intermediate I-1 (2-(3'-chloro-biphenyl-3-yl)-4,6-diphenyl-1,3,5-triazine Under a nitrogen stream, 2-(3-Bromo-phenyl)-4,6-diphenyl-[1,3,5]triazine (12.0 g, 0.031 mol), 3-Chlorophenylboronic acid (6.3 g, 0.040 mol), Pd(PPh$_3$)$_4$ (1.15 g, 0.001 mol) and potassium carbonate (12.85 g, 0.093 mol) were mixed and then stirred under reflux with, 1,4-dioxane (100 ml) and H$_2$O (25 ml).

After completion of the reaction, an organic layer was separated with methylene chloride and then dried over MgSO$_4$. The solvent was removed from the dehydrated organic layer, followed by purification through column chromatography [hexane:MC=5:1 (v/v)] to afford Intermediate I-1 (11.0 g, yield 83%).

<Step 2> Synthesis of Compound 217 (2-(3'-(9,9-dimethyl-9H-fluoren-1-yl)-[1,1'-biphenyl]-3-yl)-4,6-diphenyl-1,3,5-triazine Under a nitrogen stream, Intermediate I-1 (11.0 g, 0.026 mol) obtained in Step 1, (9,9-dimethyl-9H-fluoren-1-yl) boronic acid (7.9 g, 0.033 mol), Pd(OAc)$_2$ (0.29 g, 0.001 mol), Cesium carbonate (25.4 g, 0.078 mol), and Xphos (1.23 g, 0.003 mol) were mixed and then stirred under reflux with toluene (100 ml), ethanol (20 ml) and H$_2$O (20 ml).

After completion of the reaction, an organic layer was separated with methylene chloride and then dried over MgSO$_4$. The solvent was removed from the dehydrated organic layer, followed by purification through column chromatography [hexane:MC=5:1 (v/v)] to afford Compound 217 (8.2 g, yield 63%).

HRMS [M]+: 577.25

Synthesis Example 32: Synthesis of Compound 218 (2-(3'-(9,9-diphenyl-9H-fluoren-1-yl)-[1,1'-biphenyl]-3-yl)-4,6-diphenyl-1,3,5-triazine

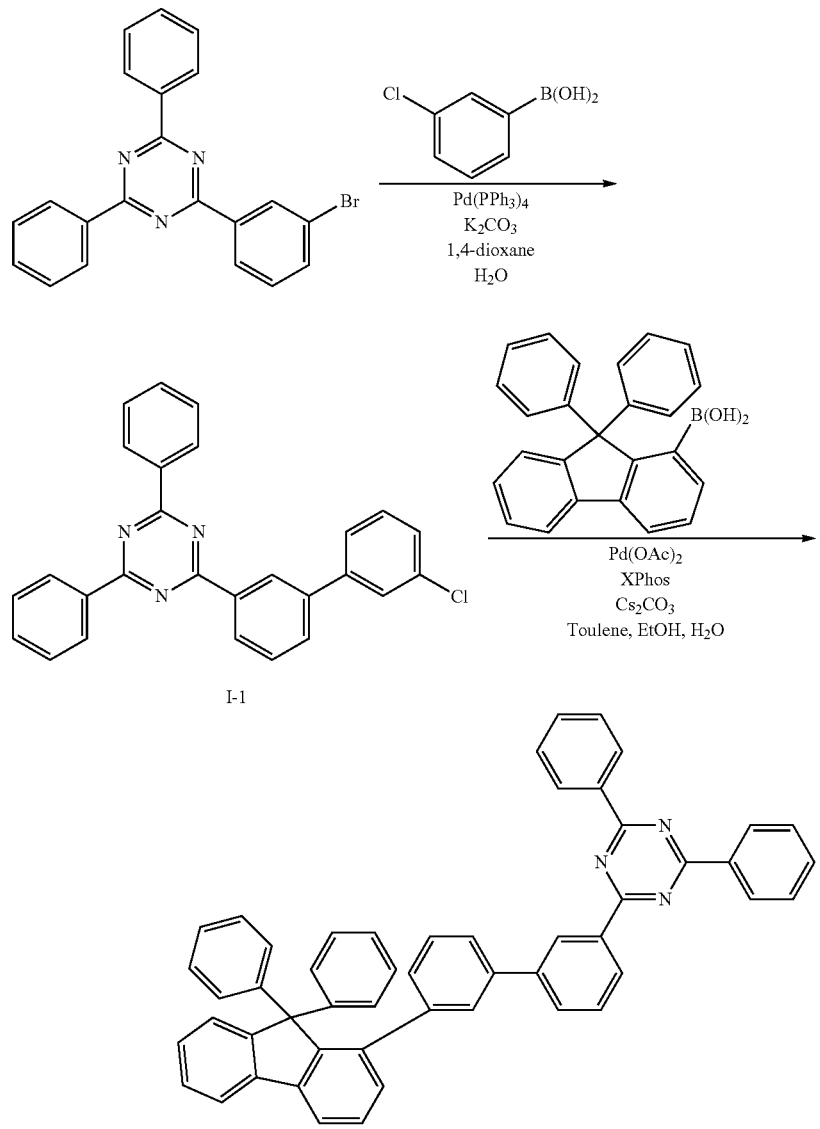

I-1

218

The same procedure was conducted as in Synthesis Example 31, with the exception of using (9,9-diphenyl-9H-fluoren-1-yl)boronic acid (12.0 g, 0.033 mol) instead of (9,9-dimethyl-9H-fluoren-1-yl)boronic acid used in Step 2 of Synthesis Example 31, to afford Compound 218.

HRMS [M]+: 701.28

Synthesis Example 33: Synthesis of Compound 220 (2-(3'-(9,9'-spirobi[fluoren]-1-yl)-[1,1'-biphenyl]-3-yl)-4,6-diphenyl-1,3,5-triazine

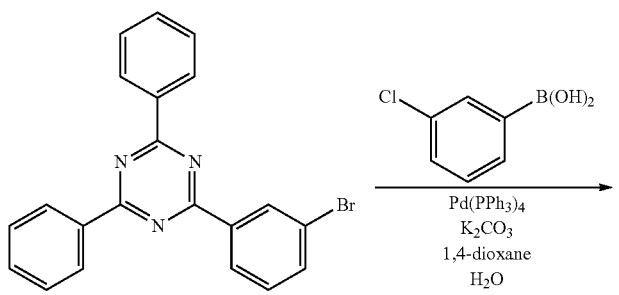

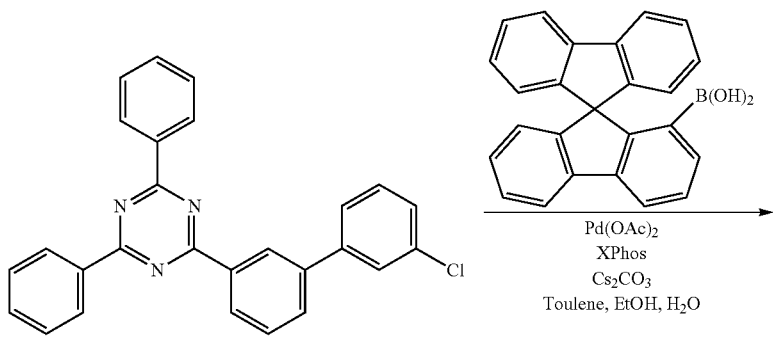

I-1

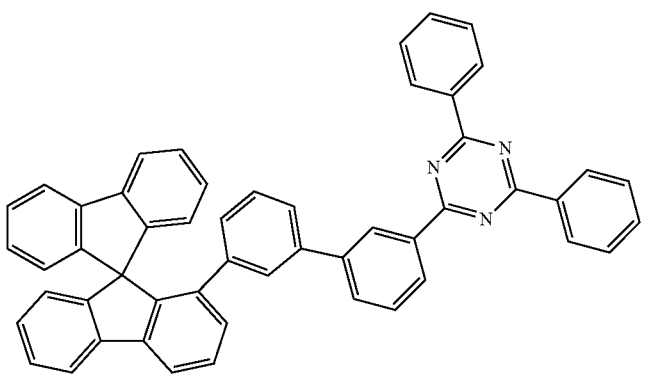

220

The same procedure was conducted as in Synthesis Example 31, with the exception of using (9,9'-spirobi[fluoren]-1-yl)boronic acid (11.9 g, 0.033 mol) instead of (9,9-dimethyl-9H-fluoren-1-yl)boronic acid used in Step 2 of Synthesis Example 31, to afford Compound 220.

HRMS [M]+: 699.27

Synthesis Example 34: Synthesis of Compound 21 (2-(3'-(9,9-dimethyl-9H-fluoren-2-yl)-[1,1'-biphenyl]-3-yl)-4,6-diphenyl-1,3,5-triazine

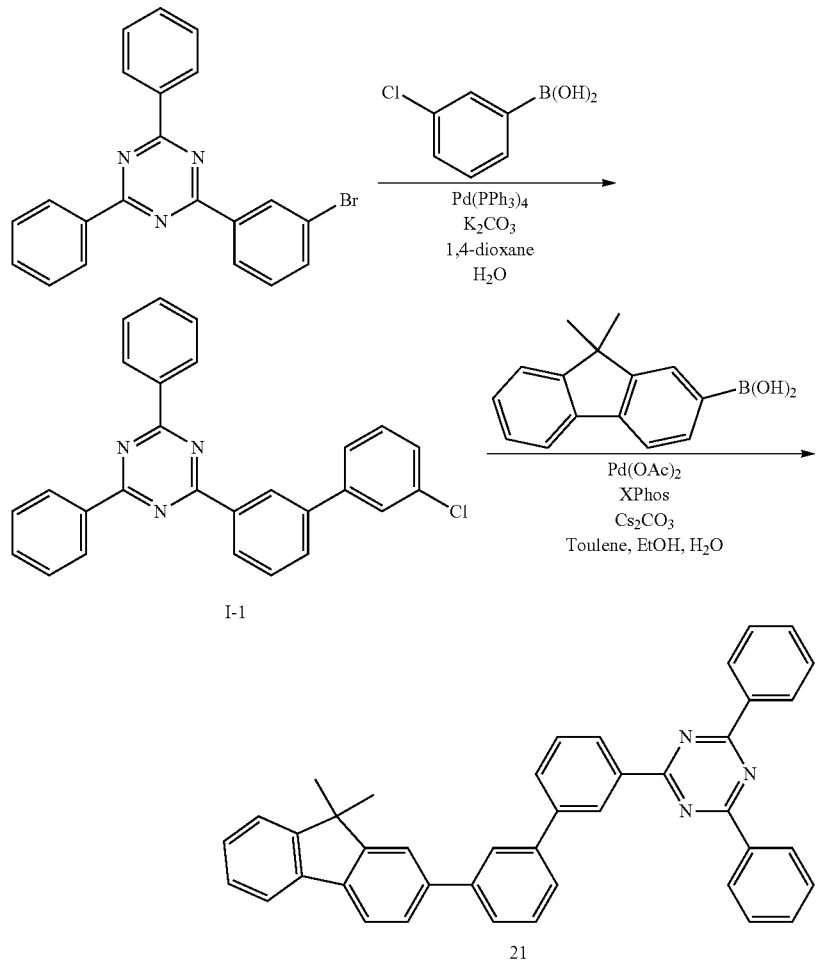

The same procedure was conducted as in Synthesis Example 31, with the exception of using (9,9-dimethyl-9H-fluoren-2-yl)boronic acid (7.9, 0.033 mol) instead of (9,9-dimethyl-9H-fluoren-1-yl)boronic acid used in Step 2 of Synthesis Example 31, to afford Compound 21.

HRMS [M]+: 577.25

Synthesis Example 35: Synthesis of Compound 189 (2-(3'-(9-methyl-9-phenyl-9H-fluoren-2-yl)-[1,1'-biphenyl]-3-yl)-4,6-diphenyl-1,3,5-triazine

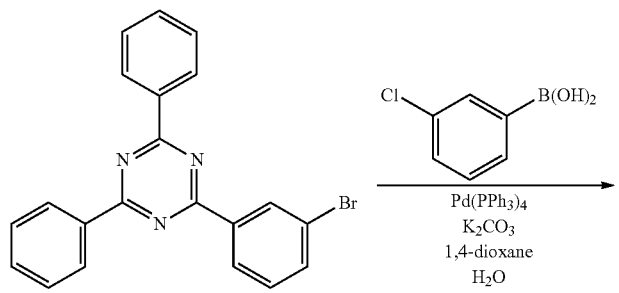

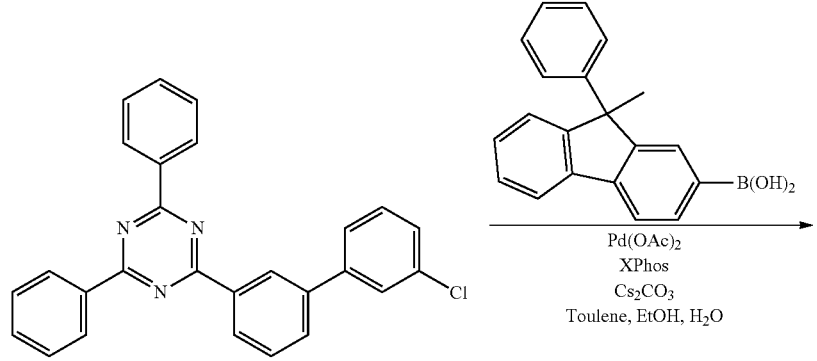
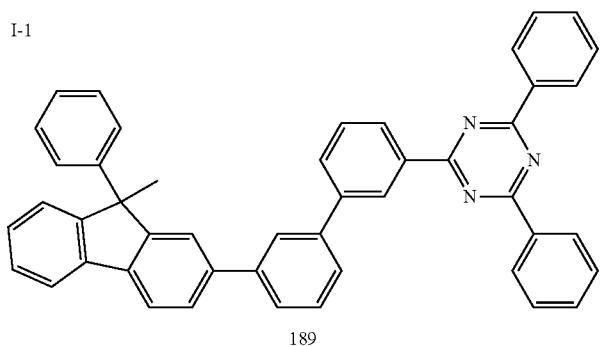
The same procedure was conducted as in Synthesis Example 31, with the exception of using (9-methyl-9-phenyl-9H-fluoren-2-yl)boronic acid (9.9, 0.033 mol) instead of (9,9-dimethyl-9H-fluoren-1-yl)boronic acid used in Step 2 of Synthesis Example 31, to afford Compound 189.
HRMS [M]+: 639.27
Synthesis Example 36: Synthesis of Compound 193 (2-(3'-(7,7-dimethyl-7H-benzo[c]fluoren-9-yl)-[1,1'-biphenyl]-3-yl)-4,6-diphenyl-1,3,5-triazine
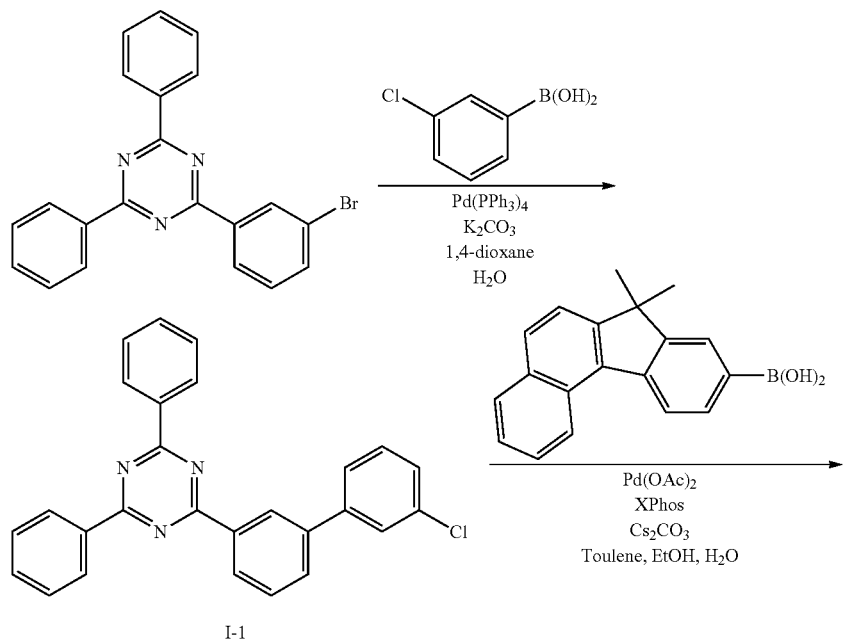

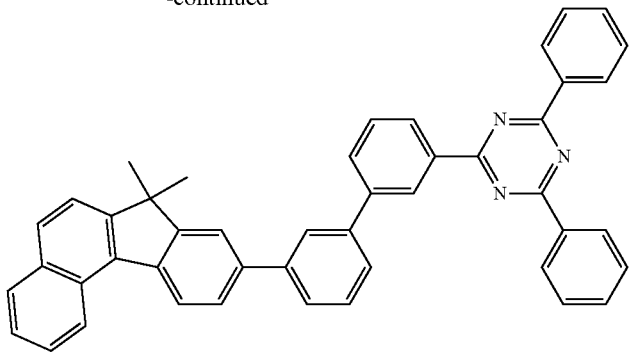
193
The same procedure was conducted as in Synthesis Example 31, with the exception of using (7,7-dimethyl-7H-benzo[c]fluoren-9-yl)boronic acid (9.5, 0.033 mol) instead of (9,9-dimethyl-9H-fluoren-1-yl)boronic acid used in Step 2 of Synthesis Example 31, to afford Compound 193.
HRMS [M]+: 627.27
Synthesis Example 37: Synthesis of Compound 65 (2-(3'-(9,9-dimethyl-7-phenyl-9H-fluoren-2-yl)-[1,1'-biphenyl]-3-yl)-4,6-diphenyl-1,3,5-triazine
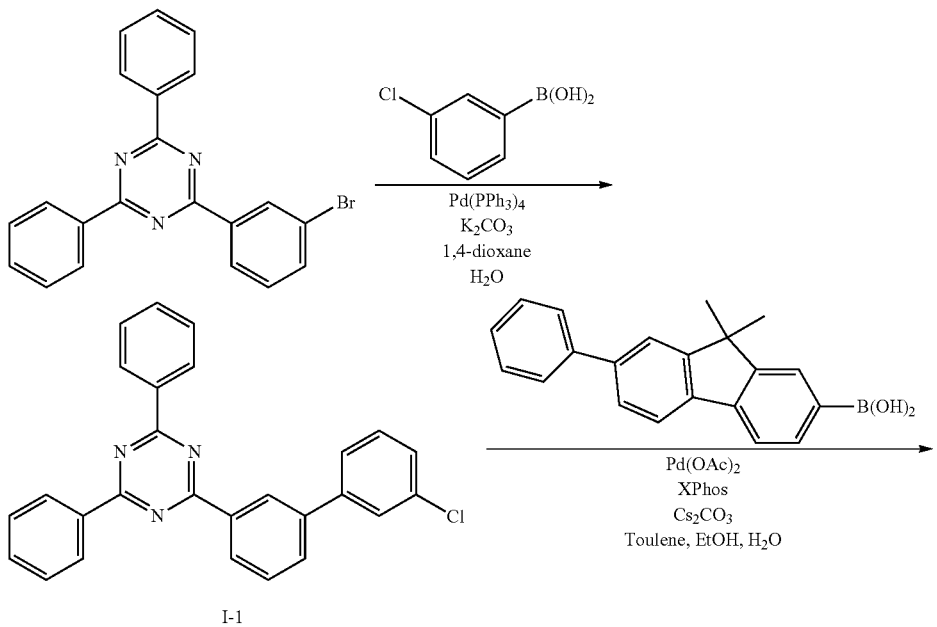
I-1
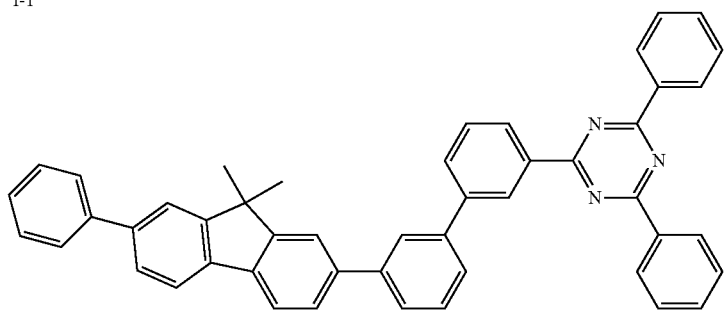
65

The same procedure was conducted as in Synthesis Example 31, with the exception of using (9,9-dimethyl-7-phenyl-9H-fluoren-2-yl)boronic acid (10.4 g, 0.033 mol) instead of (9,9-dimethyl-9H-fluoren-1-yl)boronic acid used in Step 2 of Synthesis Example 31, to afford Compound 65.
HRMS [M]+: 653.28

Synthesis Example 38: Synthesis of Compound 231 (2,4-diphenyl-6-(3'-(spiro[benzo[c]fluorene-7,9'-fluoren]-9-yl)-[1,1'-biphenyl]-3-yl)-1,3,5-triazine

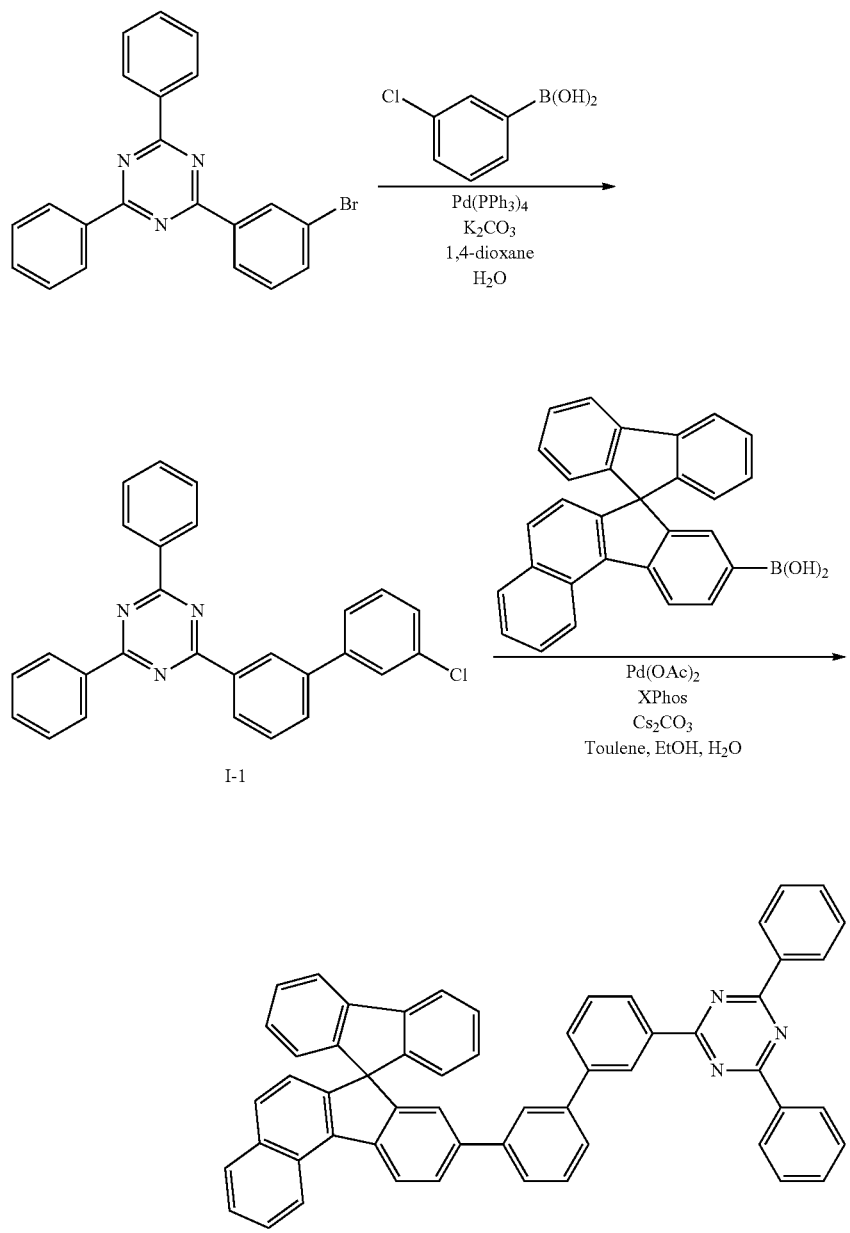

The same procedure was conducted as in Synthesis Example 31, with the exception of using (spiro[benzo[c]fluorene-7,9'-fluoren]-9-yl)boronic acid (13.5 g, 0.033 mol) instead of (9,9-dimethyl-9H-fluoren-1-yl)boronic acid used in Step 2 of Synthesis Example 31, to afford Compound 231.
HRMS [M]+: 749.28

Synthesis Example 39: Synthesis of Compound 234 (2-(3'-(13,13-dimethyl-13H-indeno[1,2-1]phenanthren-10-yl)-[1,1'-biphenyl]-3-yl)-4,6-diphenyl-1,3,5-triazine

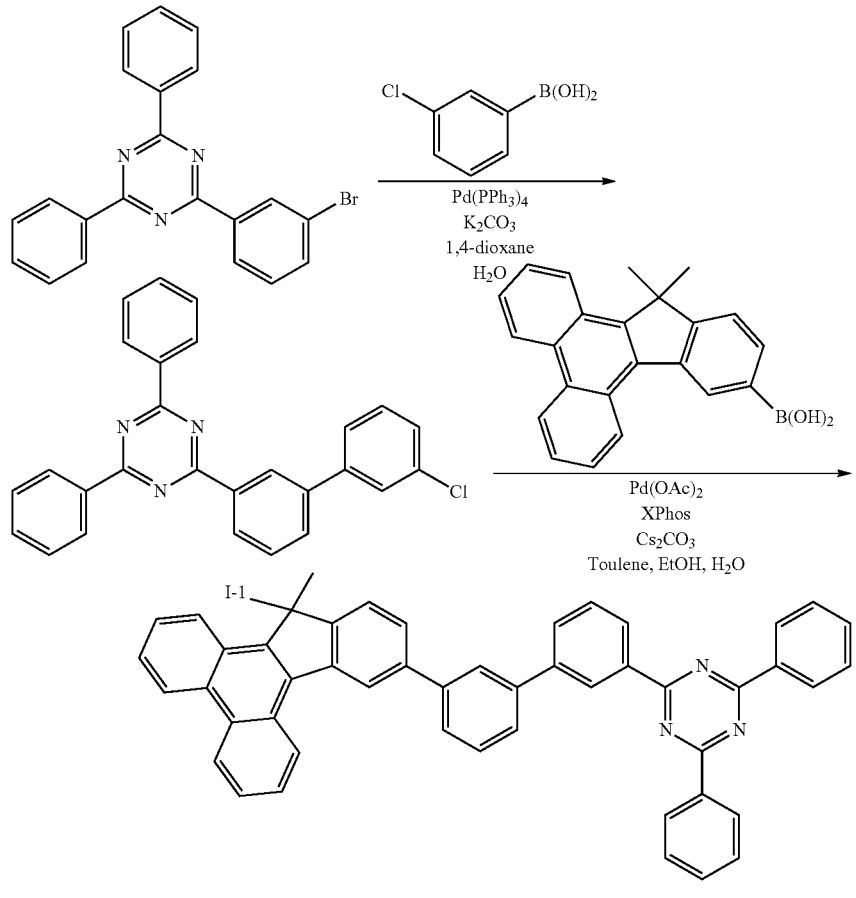

234

The same procedure was conducted as in Synthesis Example 31, with the exception of using (13,13-dimethyl-13H-indeno[1,2-1]phenanthren-11-yl)boronic acid (11.2 g, 0.033 mol) instead of (9,9-dimethyl-9H-fluoren-1-yl)boronic acid used in Step 2 of Synthesis Example 31, to afford Compound 234.

HRMS [M]+: 677.28

Synthesis Example 40: Synthesis of Compound 250 (2-(3'-(9,9-di-p-tolyl-9H-fluoren-4-yl)-[1,1'-biphenyl]-3-yl)-4,6-diphenyl-1,3,5-triazine

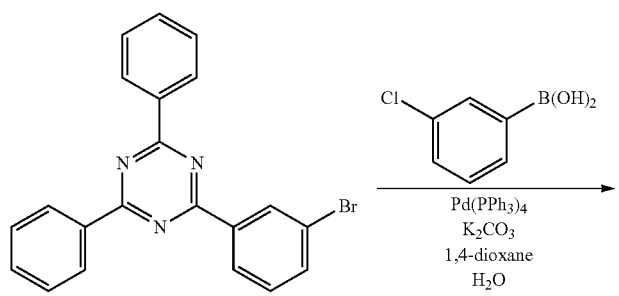

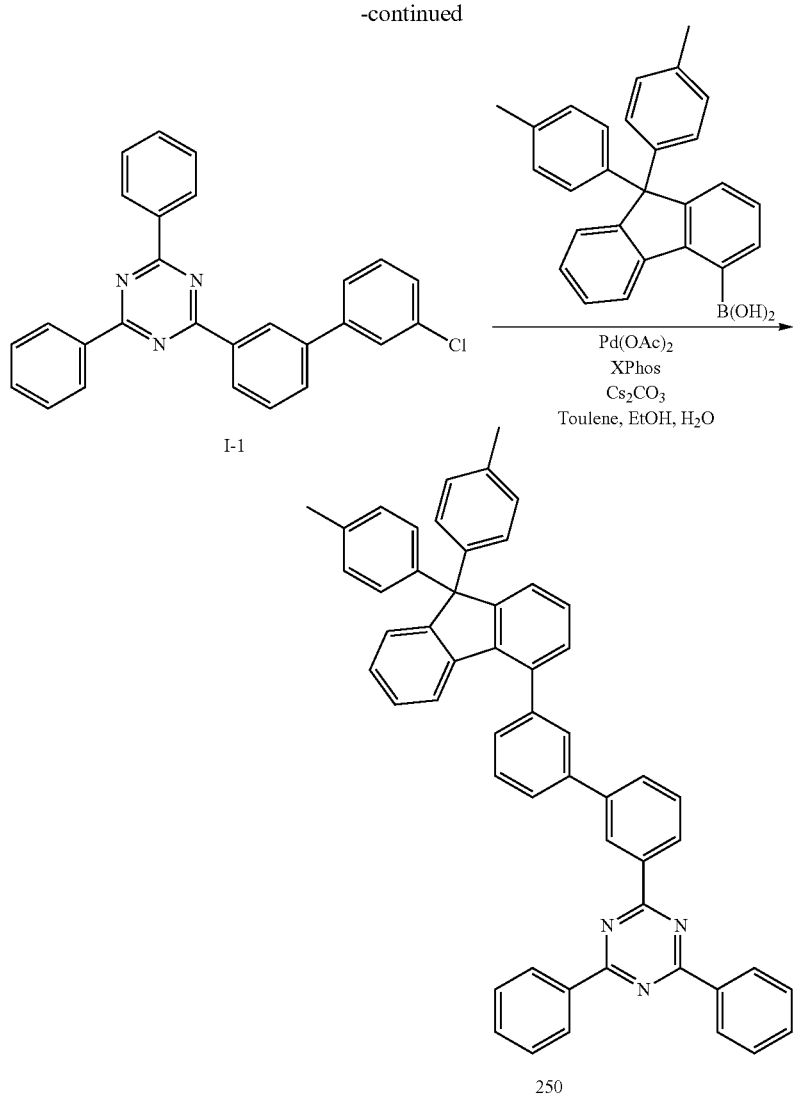
The same procedure was conducted as in Synthesis Example 31, with the exception of using (9,9-di-p-tolyl-9H-fluoren-4-yl)boronic acid (12.9 g, 0.033 mol) instead of (9,9-dimethyl-9H-fluoren-1-yl)boronic acid used in Step 2 of Synthesis Example 31, to afford Compound 250.
HRMS [GP-72, C]+: 729.31
Synthesis Example 41: Synthesis of Compound 252 (2,4-diphenyl-6-(3'-(4'-phenyl-9,9'-spirobi[fluoren]-4-yl)-[1,1'-biphenyl]-3-yl)-1,3,5-triazine
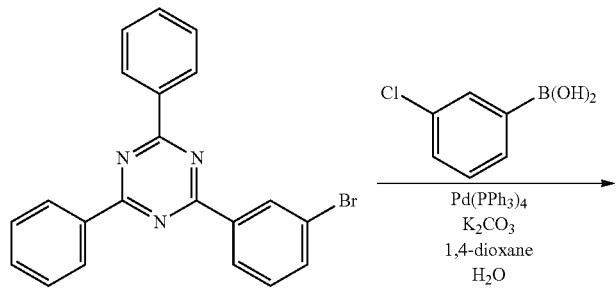

-continued
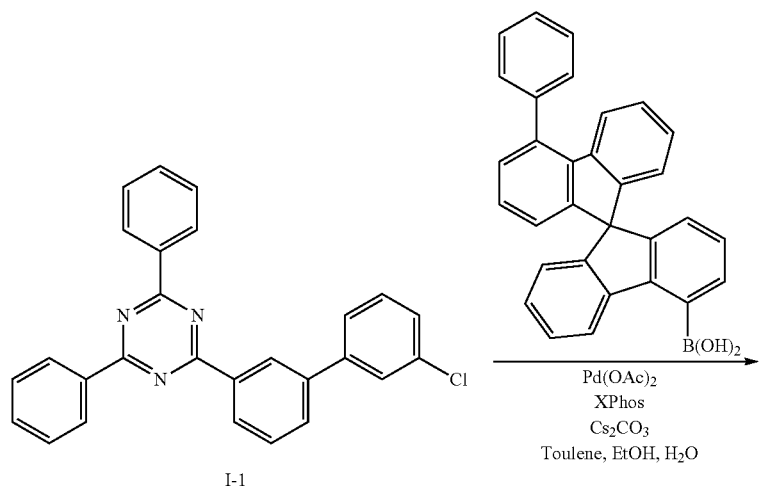
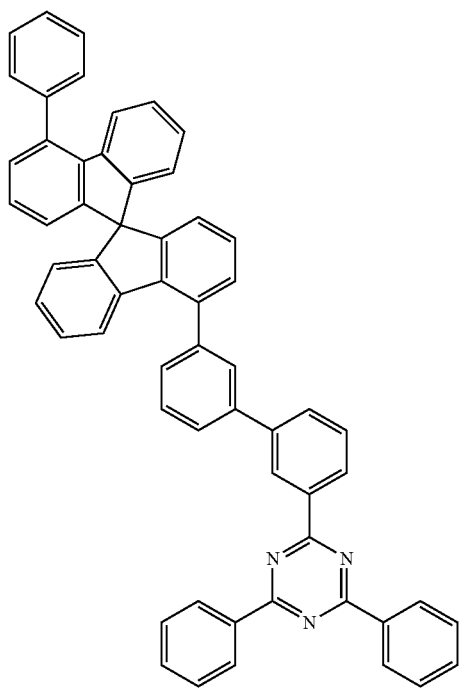
252
The same procedure was conducted as in Synthesis Example 31, with the exception of using (4'-phenyl-9,9'-spirobi[fluoren]-4-yl)boronic acid (14.4 g, 0.033 mol) instead of (9,9-dimethyl-9H-fluoren-1-yl)boronic acid used in Step 2 of Synthesis Example 31, to afford Compound 252.
HRMS [M]+: 775.30

Synthesis Example 42: Synthesis of Compound 5 (2-(3-(9,9-dimethyl-9H-fluoren-2-yl)phenyl)-4,6-diphenylpyrimidine

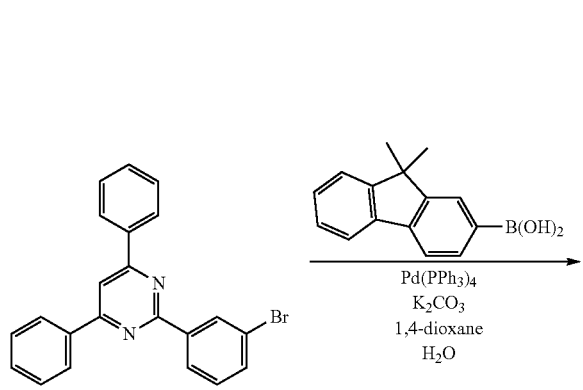

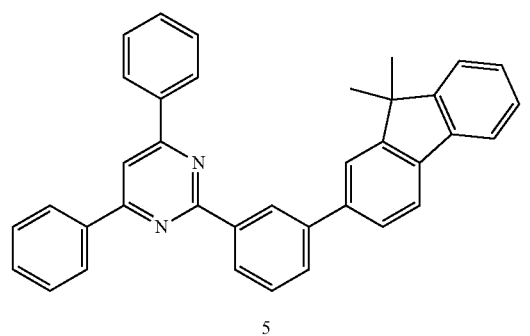

Under a nitrogen stream, 2-(3-bromophenyl)-4,6-diphenylpyrimidine (10.0 g, 0.026 mol), 9,9-dimethyl-9H-fluoren-2-yl-boronic acid (7.9 g, 0.033 mol), Pd(PPh$_3$)$_4$ (0.95 g, 0.001 mol), and potassium carbonate (7.65 g, 0.078 mol) were mixed and then stirred under reflux with 1,4-dioxane (80 ml) and H$_2$O (20 ml). After completion of the reaction, an organic layer was separated with methylene chloride and then dried over MgSO$_4$. The solvent was removed from the dehydrated organic layer, followed by purification through column chromatography [hexane:MC=5:1 (v/v)] to afford Compound 5 (8.5 g, yield 66%).

HRMS [M]+: 500.23

Synthesis Example 43: Synthesis of Compound 13 (2-(3-(9,9-dimethyl-9H-fluoren-3-yl)phenyl)-4,6-diphenylpyrimidine

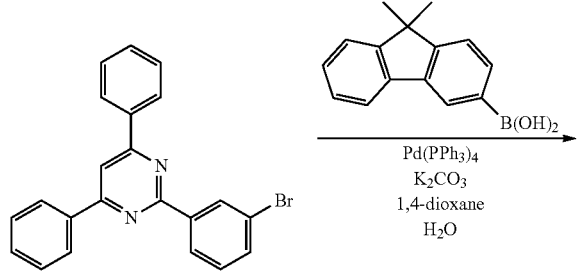

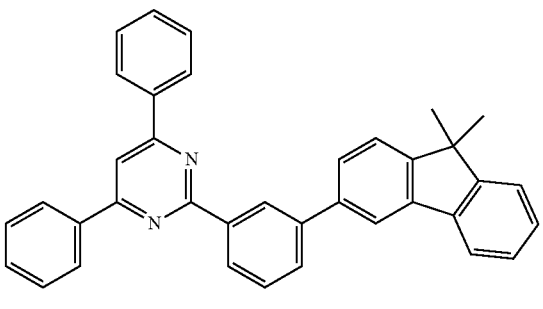

The same procedure was conducted as in Synthesis Example 42, with the exception of using 9,9-dimethyl-9H-fluoren-3-yl-boronic acid (7.9 g, 0.033 mol) instead of 9,9-dimethyl-9H-fluoren-2-yl-boronic acid, to afford Compound 13.

HRMS [M]+: 500.23

Synthesis Example 44: Synthesis of Compound 73 (2-(3-(9,9-diphenyl-9H-fluoren-2-yl)phenyl)-4,6-diphenylpyrimidine

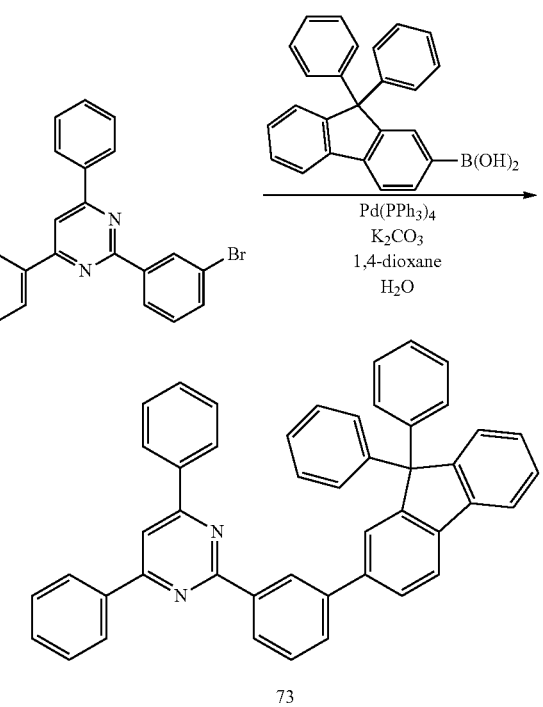

The same procedure was conducted as in Synthesis Example 42, with the exception of using (9,9-diphenyl-9H-fluoren-2-yl)-boronic acid (11.9 g, 0.033 mol) instead of 9,9-dimethyl-9H-fluoren-2-yl-boronic acid to afford Compound 73.

HRMS [M]+: 624.26

Synthesis Example 45: Synthesis of Compound 133 (2-(3-(9,9'-spirobi[fluoren]-2-yl)phenyl)-4,6-diphenylpyrimidine

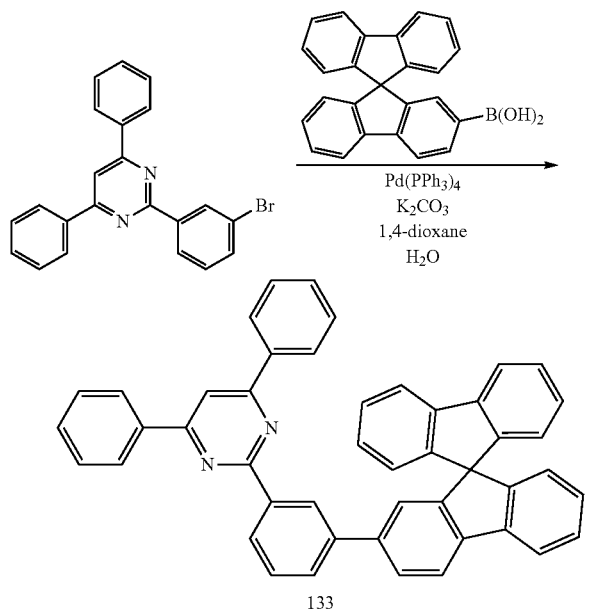

The same procedure was conducted as in Synthesis Example 42, with the exception of using 9,9'-Spirobi[9H-fluorene]-2-yl-boronic acid (11.88 g, 0.033 mol) instead of 9,9-dimethyl-9H-fluoren-2-yl-boronic acid to afford Compound 133.

HRMS [M]+: 622.24

Synthesis Example 46: Synthesis of Compound 134 (4-[3-(9,9-Spirobi[9H-fluorene]-2-yl)-phenyl]-2,6-diphenyl-pyrimidine

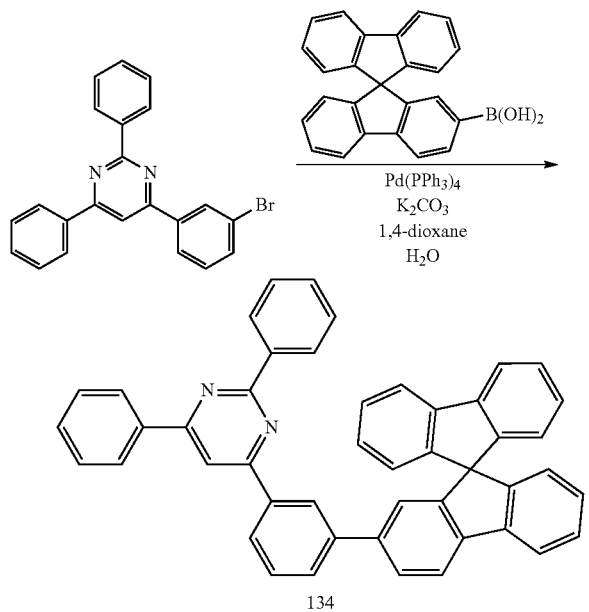

The same procedure was conducted as in Synthesis Example 42, with the exception of using 4-(3-bromophenyl)-2,6-diphenylpyrimidine (10.0 g, 0.026 mol) and 9,9'-Spirobi[9H-fluorene]-2-yl-boronic acid (12.77 g, 0.033 mol) instead of 2-(3-bromophenyl)-4,6-diphenylpyrimidine and 9,9-dimethyl-9H-fluoren-2-yl-boronic acid, respectively, to afford Compound 134.

HRMS [M]+: 622.24

Synthesis Example 47: Synthesis of Compound 29 (2-(3'-(9,9-dimethyl-9H-fluoren-2-yl)-[1,1'-biphenyl]-3-yl)-4,6-diphenylpyrimidine

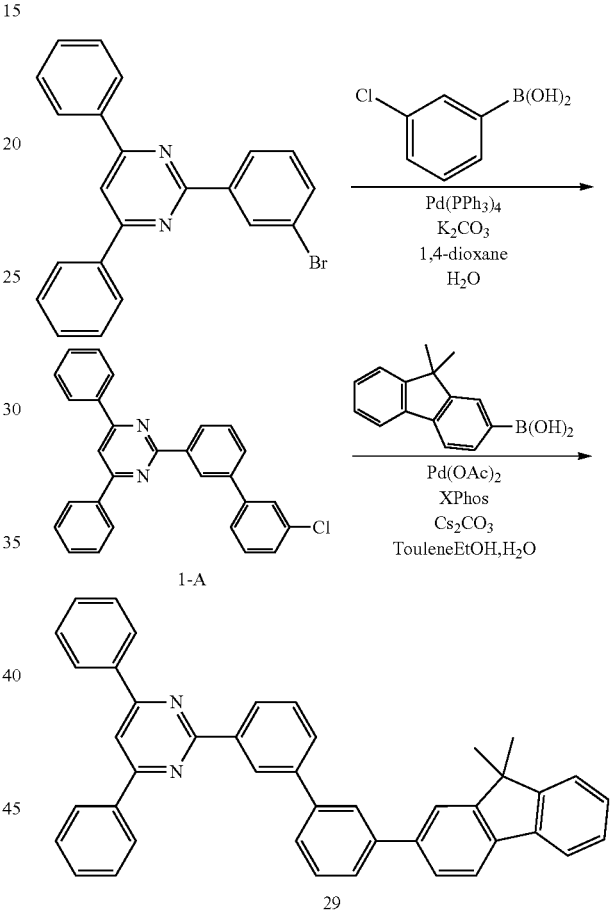

<Step 1> Synthesis of Intermediate 1-A (2-(3'-chloro-[1,1'-biphenyl]-3-yl)-4,6-diphenylpyrimidine Under a nitrogen stream, 2-(3-bromophenyl)-4,6-diphenylpyrimidine (12.0 g, 0.031 mol), 3-chlorophenylboronic acid (6.3 g, 0.040 ol), Pd(PPh₃)₄ (1.15 g, 0.001 mol), and potassium carbonate (12.85 g, 0.093 mol) were mixed and then stirred under reflux with 1,4-dioxane (100 ml) and H₂O (25 ml).

After completion of the reaction, an organic layer was separated with methylene chloride and then dried over MgSO₄. The solvent was removed from the dehydrated organic layer, followed by purification through column chromatography [hexane:MC=5:1 (v/v)] to afford Intermediate 1-A (11.0 g, yield 83%).

<Step 2> Synthesis of Compound 29 (2-(3'-(9,9-dimethyl-9H-fluoren-2-yl)-[1,1'-biphenyl]-3-yl)-4,6-diphenylpyrimidine Under a nitrogen stream, Intermediate 1-A (11.0 g, 0.026 mol) obtained in Step 1, 9,9-dimethyl-9H-fluoren-2-yl-boronic acid (7.9 g, 0.033 mol), Pd(OAc)₂ (0.29 g, 0.001 mol), Cesium carbonate (25.4 g, 0.078 mol), and Xphos (1.23 g, 0.003 mol) were mixed and then stirred under reflux with toluene (100 ml), ethanol (20 ml), and H₂O (20 ml).

After completion of the reaction, an organic layer was separated with methylene chloride and then dried over MgSO₄. The solvent was removed from the dehydrated organic layer, followed by purification through column chromatography [hexane:MC=5:1 (v/v)] to afford Compound 29 (11.2 g, yield 74%).

HRMS [M]+: 576.26

Synthesis Example 48: Synthesis of Compound 33 (2-(3'-(9,9-dimethyl-9H-fluoren-3-yl)-[1,1'-biphenyl]-3-yl)-4,6-diphenylpyrimidine

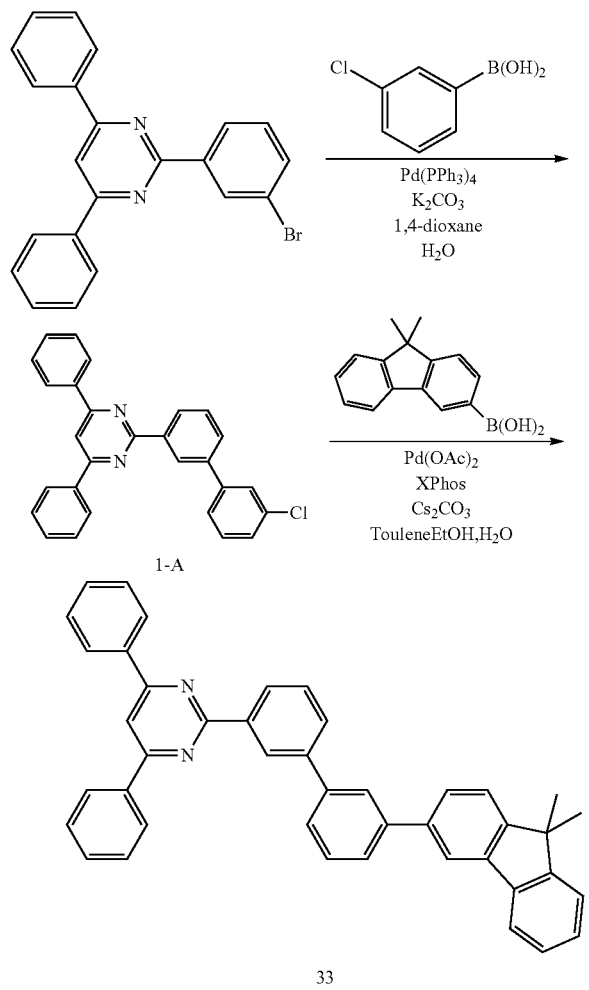

The same procedure was conducted as in Synthesis Example 47, with the exception of using 9,9-dimethyl-9H-fluoren-3-yl-boronic acid (7.9 g, 0.033 mol) instead of 9,9-dimethyl-9H-fluoren-2-yl-boronic acid used in Step 2 of Synthesis Example 47 to afford Compound 33.

HRMS [M]+: 576.26

Synthesis Example 49: Synthesis of Compound 97 (2-(3'-(9,9-diphenyl-9H-fluoren-2-yl)-[1,1'-biphenyl]-3-yl)-4,6-diphenylpyrimidine

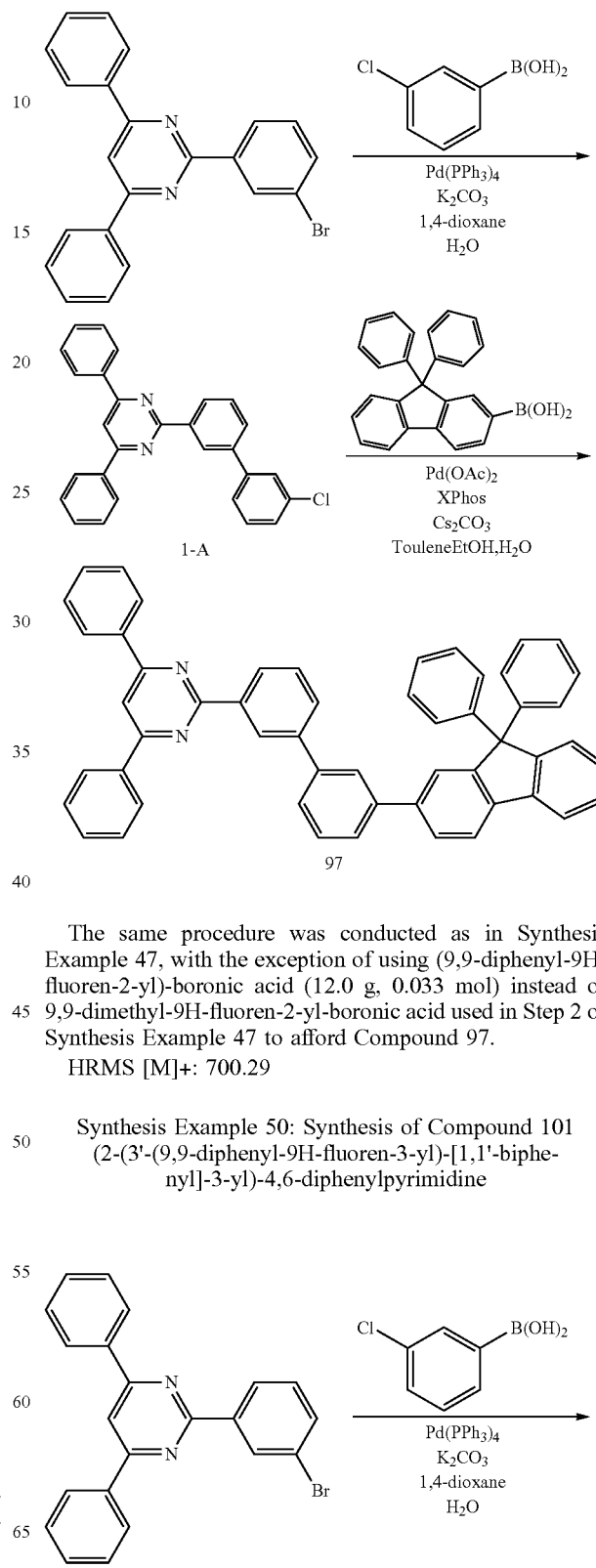

The same procedure was conducted as in Synthesis Example 47, with the exception of using (9,9-diphenyl-9H-fluoren-2-yl)-boronic acid (12.0 g, 0.033 mol) instead of 9,9-dimethyl-9H-fluoren-2-yl-boronic acid used in Step 2 of Synthesis Example 47 to afford Compound 97.

HRMS [M]+: 700.29

Synthesis Example 50: Synthesis of Compound 101 (2-(3'-(9,9-diphenyl-9H-fluoren-3-yl)-[1,1'-biphenyl]-3-yl)-4,6-diphenylpyrimidine

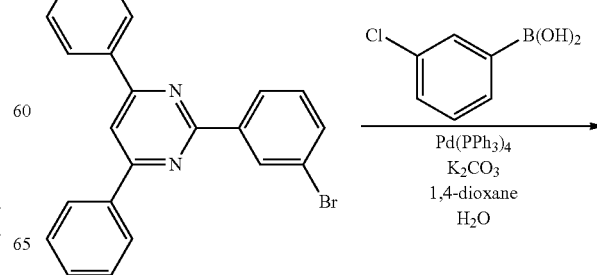

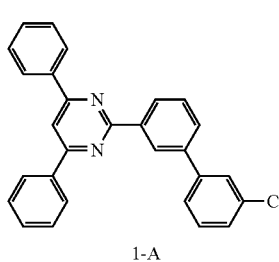

1-A

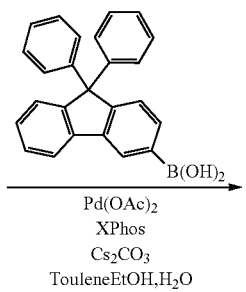

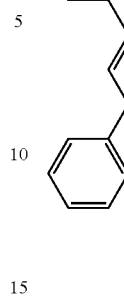

Pd(OAc)₂
XPhos
Cs₂CO₃
TouleneEtOH,H₂O

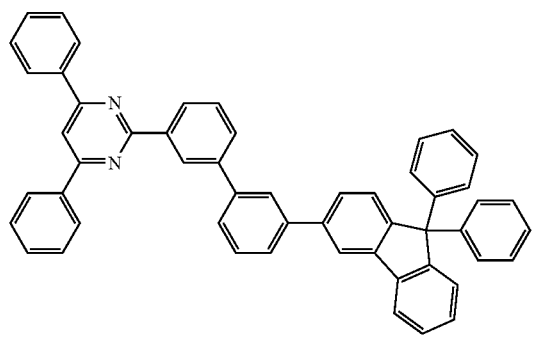

101

The same procedure was conducted as in Synthesis Example 47, with the exception of using (9,9-diphenyl-9H-fluoren-3-yl)boronic acid (12.0 g, 0.033 mol) instead of (9,9-dimethyl-9H-fluoren-2-yl)boronic acid used in Step 2 of Synthesis Example 47 to afford Compound 101.

HRMS [M]+: 700.29

Synthesis Example 51: Synthesis of Compound 157 (2-(3'-(9,9'-spirobi[fluoren]-2-yl)-[1,1'-biphenyl]-3-yl)-4,6-diphenylpyrimidine

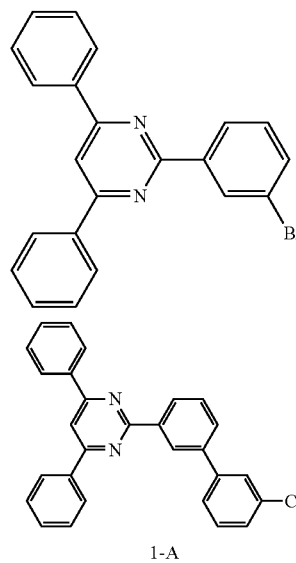

1-A

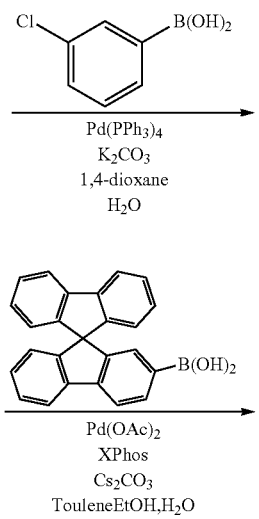

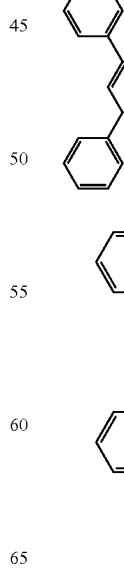

Pd(OAc)₂
XPhos
Cs₂CO₃
TouleneEtOH,H₂O

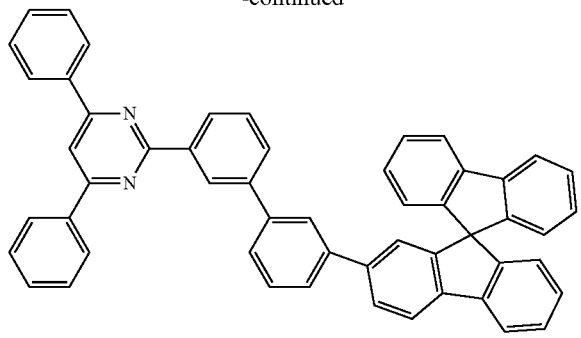

157

The same procedure was conducted as in Synthesis Example 47, with the exception of using 9,9'-Spirobi[9H-fluorene]-2-yl-boronic acid (11.9 g, 0.033 mol) instead of 9,9-dimethyl-9H-fluoren-2-yl-boronic acid used in Step 2 of Synthesis Example 47 to afford Compound 157.

HRMS [M]+: 698.27

Synthesis Example 52: Synthesis of Compound 161 (2-(3'-(9,9'-spirobi[fluoren]-3-yl)-[1,1'-biphenyl]-3-yl)-4,6-diphenylpyrimidine

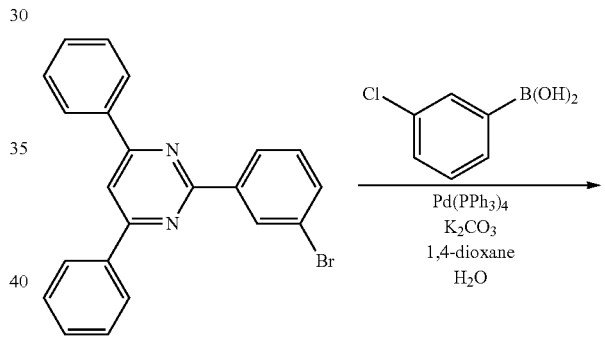

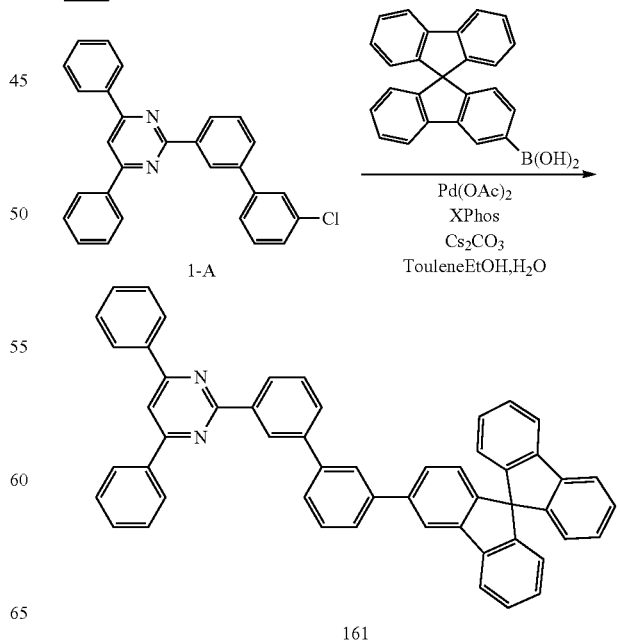

161

The same procedure was conducted as in Synthesis Example 47, with the exception of using 9,9'-spirobi[fluoren]-3-yl-boronic acid (11.9 g, 0.033 mol) instead of 9,9-dimethyl-9H-fluoren-2-yl-boronic acid used in Step 2 of Synthesis Example 47 to afford Compound 161.

HRMS [M]+: 698.27

Synthesis Example 53: Synthesis of Compound 282 (4-(3'-(9,9-dimethyl-9H-fluoren-4-yl)-[1,1'-biphenyl]-3-yl)-2,6-diphenylpyrimidine <Step 1> Synthesis of Intermediate 2-A (4-(3'-chloro-[1,1'-biphenyl]-3-yl)-2,6-diphenylpyrimidine The same procedure was conducted as in Step 1 of Synthesis Example 47, with the exception of using 4-(3-bromophenyl)-2,6-diphenylpyrimidine (12.0 g, 0.031 mol) instead of 2-(3-bromophenyl)-4,6-diphenylpyrimidine used in Step 1 of Synthesis Example 47 to afford Intermediate 2-A.

<Step 2> Synthesis of Compound 282 (4-(3'-(9,9-dimethyl-9H-fluoren-4-yl)-[1,1'-biphenyl]-3-yl)-2,6-diphenylpyrimidine The same procedure was conducted as in Step 2 of Synthesis Example 47, with the exception of using Intermediate 2-A (11.0 g, 0.026 mol) synthesized in Step 1 and (9,9-dimethyl-9H-fluoren-4-yl)boronic acid (7.9 g, 0.033 mol) instead of Intermediate 1-A used in Step 2 of Synthesis Example 47 and 9,9-dimethyl-9H-fluoren-2-yl-boronic acid, respectively, to afford Compound 282.

HRMS [M]+: 576.26

Synthesis Example 54: Synthesis of Compound 159 (4-(3'-(9,9'-spirobi[fluoren]-2-yl)-[1,1'-biphenyl]-3-yl)-2,6-diphenylpyrimidine

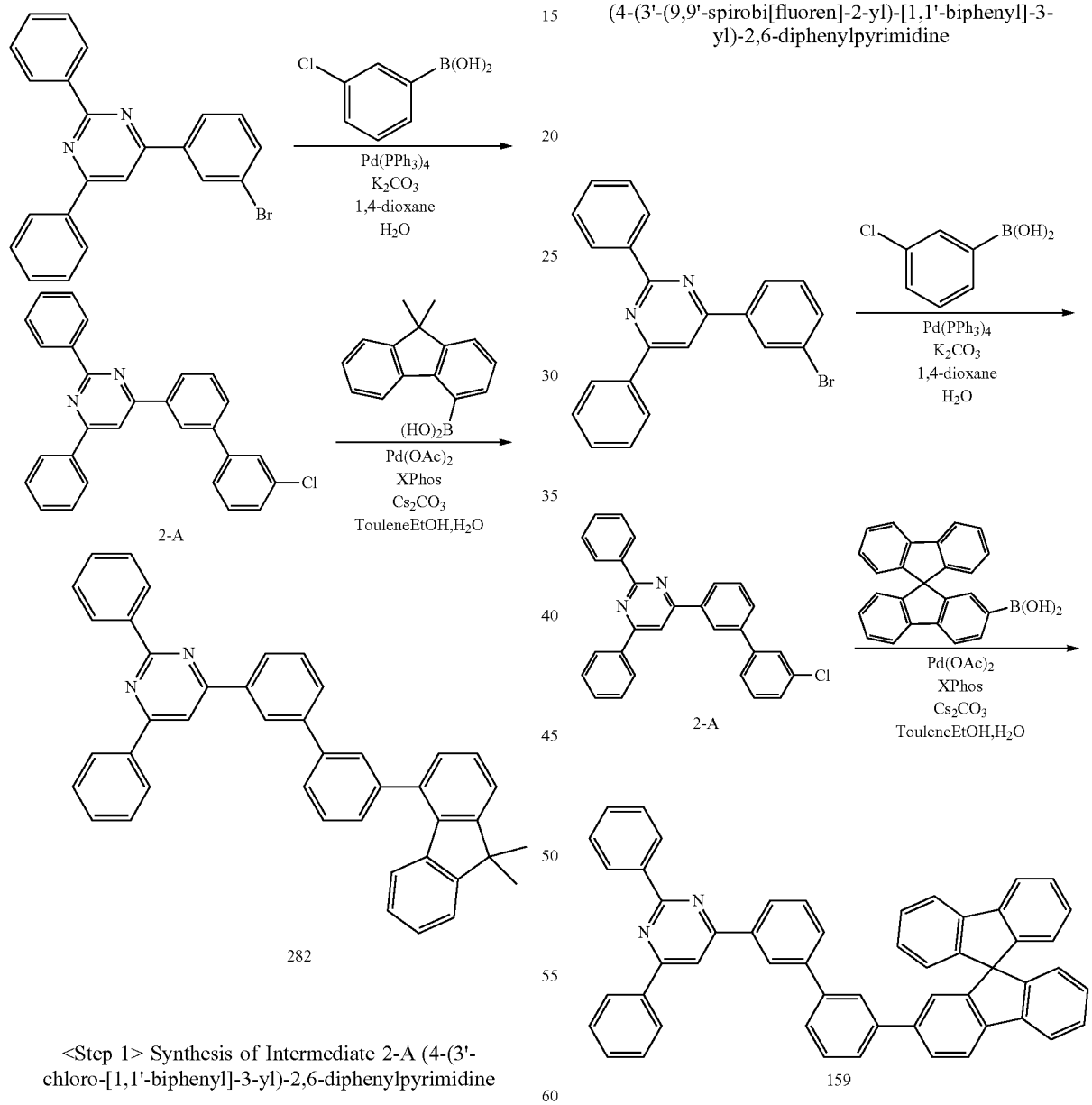

The same procedure was conducted as in Synthesis Example 53, with the exception of using 9,9'-spirobi[9H-fluorene]-2-yl-boronic acid (11.9 g, 0.033 mol) instead of (9,9-dimethyl-9H-fluoren-4-yl)boronic acid used in Step 2 of Synthesis Example 53 to afford Compound 159.

HRMS [M]+: 698.27

Synthesis Example 55: Synthesis of Compound 205 (4-([1,1'-biphenyl]-4-yl)-6-(3'-(9,9-dimethyl-9H-fluoren-2-yl)-[1,1'-biphenyl]-3-yl)-2-phenylpyrimidine

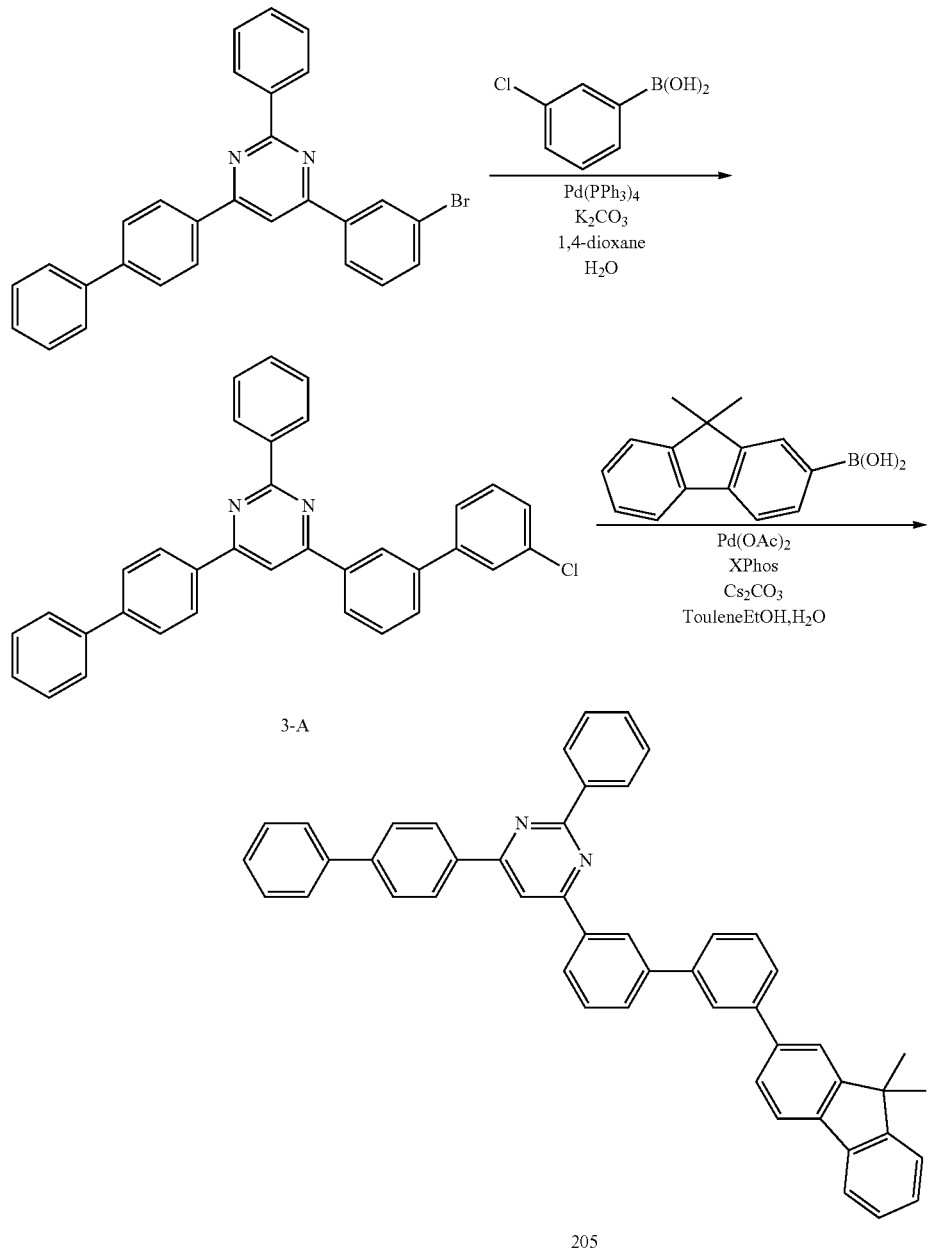

<Step 1> Synthesis of Intermediate 3-A (4-([1,1'-biphenyl]-4-yl)-6-(3'-chloro-[1,1'-biphenyl]-3-yl)-2-phenylpyrimidine The same procedure was conducted as in Step 1 of Synthesis Example 53, with the exception of using 4-([1,1'-biphenyl]-4-yl)-6-(3-bromophenyl)-2-phenyl-pyrimidine (14.4 g, 0.031 mol) instead of 4-(3-bromo-phenyl)-2,6-diphenyl-pyrimidine used in Step 1 of Synthesis Example 53 to afford Intermediate 3-A.

<Step 2> Synthesis of Compound 205 (4-([1,1'-biphenyl]-4-yl)-6-(3'-(9,9-dimethyl-9H-fluoren-2-yl)-[1,1'-biphenyl]-3-yl)-2-phenylpyrimidine The same procedure was conducted as in Step 2 of Synthesis Example 53, with the exception of using Intermediate 3-A (12.9 g, 0.026 mol) synthesized in Step 1 and (9,9-dimethyl-9H-fluoren-2-yl)boronic acid instead of Intermediate 2-A used in Step 2 of Synthesis Example 53 and (9,9-dimethyl-9H-fluoren-4-yl)boronic acid, respectively, to afford Compound 205.

HRMS [M]+: 652.29

Synthesis Example 56: Synthesis of Compound 206 (4-([1,1'-biphenyl]-4-yl)-6-(3'-(9,9-dimethyl-9H-fluoren-2-yl)-[1,1'-biphenyl]-3-yl)-2-phenylpyrimidine
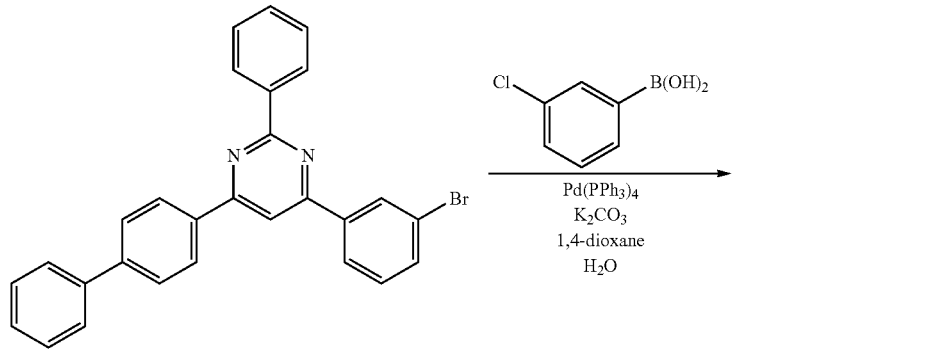
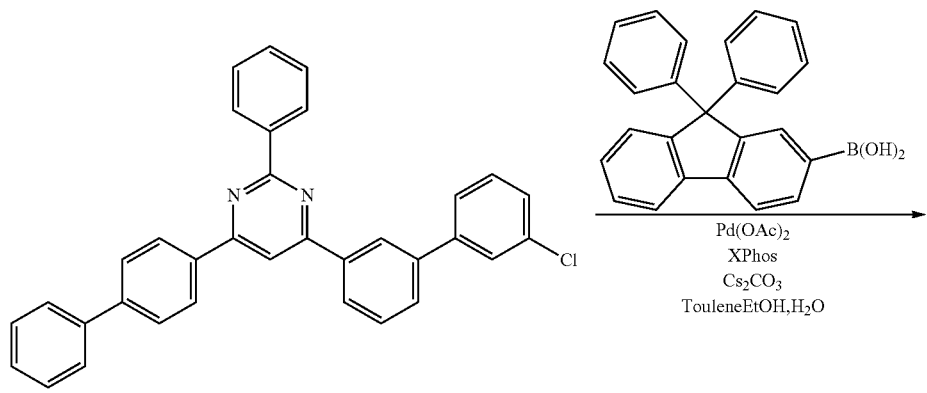
3-A
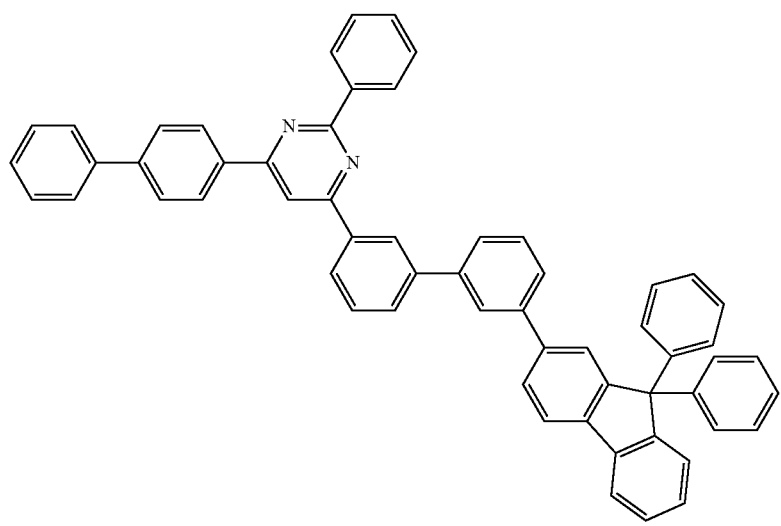
206
The same procedure was conducted as in Synthesis Example 55, with the exception of using (9,9-diphenyl-9H-fluoren-2-yl)-boronic acid (11.9 g, 0.033 mol) instead of 9,9-dimethyl-9H-fluoren-2-yl-boronic acid used in Step 2 of Synthesis Example 55, to afford Compound 206.
HRMS [M]+: 776.32

Synthesis Example 57: Synthesis of Compound 336 (2-(3"-(9,9-dimethyl-9H-fluoren-3-yl)-[1,1':3',1"-terphenyl]-3-yl)-4,6-diphenylpyrimidine

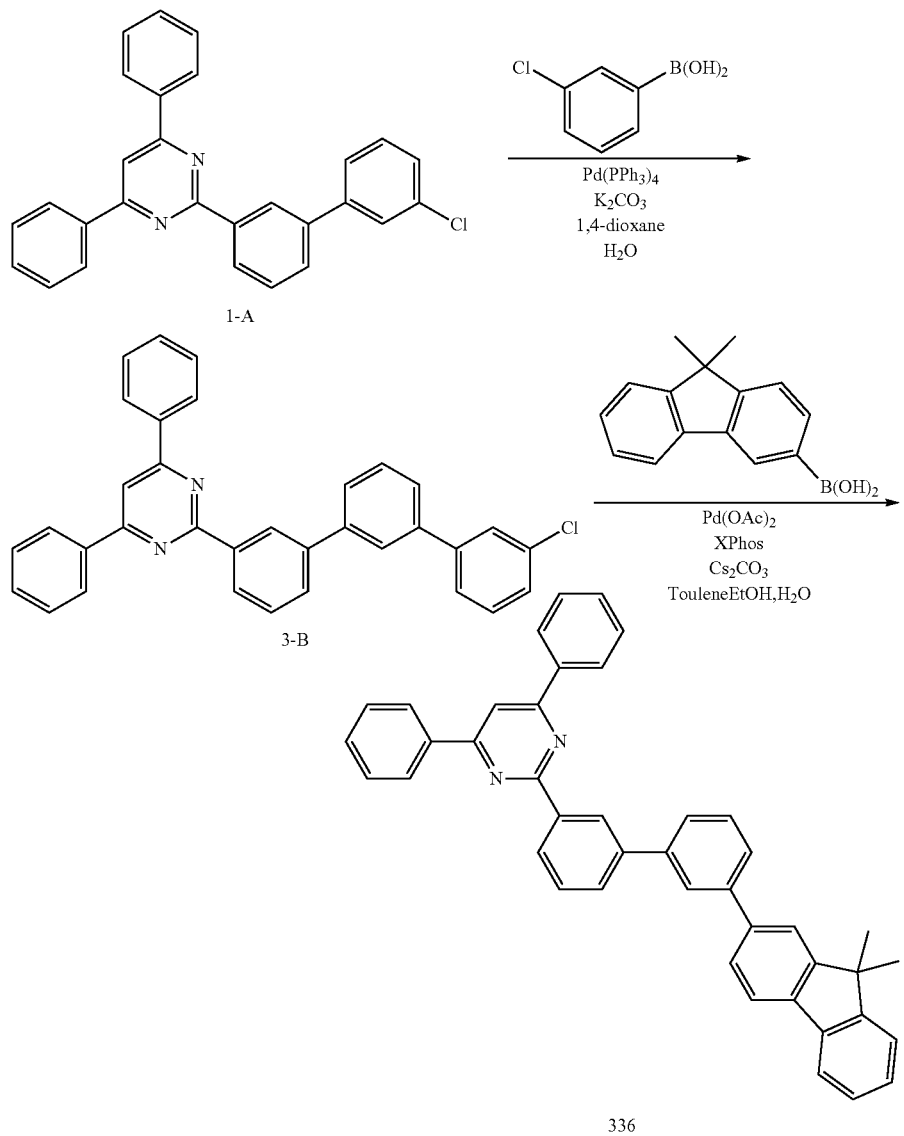

<Step 1> Intermediate 1-B (2-(3"-chloro-[1,1':3',1"-terphenyl]-3-yl)-4,6-diphenylpyrimidine Under a nitrogen stream, Intermediate 1-A (11.0 g, 0.026 mol), 3-chlorophenylboronic acid (4.8 g, 0.031 mol), Pd(OAc)$_2$ (0.29 g, 0.001 mol), Cesium carbonate (25.4 g, 0.078 mol), and Xphos (0.3 g, 0.003 mol) were mixed and then stirred under reflux with toluene (100 ml), ethanol (20 ml) and H$_2$O (20 ml).

After completion of the reaction, an organic layer was separated with methylene chloride and then dried over MgSO$_4$. The solvent was removed from the dehydrated organic layer, followed by purification through column chromatography [hexane:MC=5:1 (v/v)] to afford Intermediate 1-B (7.5 g, yield 58%).

<Step 2> Synthesis of Compound 336 (2-(3"-(9,9-dimethyl-9H-fluoren-3-yl)-[1,1':3',1"-terphenyl]-3-yl)-4,6-diphenylpyrimidine Under a nitrogen stream, Intermediate 1-B (7.5 g, 0.015 mol) synthesized in Step 1, 9,9-dimethyl-9H-fluoren-3-yl-boronic acid (4.3 g, 0.018 mol), Pd(OAc)$_2$ (0.17 g, 0.75 mmol), Cesium carbonate (14.6 g, 0.045 mol), and Xphos (0.7 g, 1.5 mmol) were mixed and then stirred under reflux with toluene (60 ml), ethanol (15 ml) and H$_2$O (15 ml).

After completion of the reaction, an organic layer was separated with methylene chloride and then dried over MgSO$_4$. The solvent was removed from the dehydrated organic layer, followed by purification through column chromatography [hexane:MC=4:1 (v/v)] to afford Compound 336 (8.1 g, yield 83%).

HRMS [M]+: 652.29

Examples 1 TO 41: Fabrication of Green Organic Electroluminescent Element

The compounds synthesized in the Synthesis Examples were purified by sublimation to a high degree of purity using a conventional method known in the art before being applied to the fabrication of green organic electroluminescent elements as follows.

First, a glass substrate coated with an ITO (indium tin oxide) thin film 1500 Å thick was cleansed by ultrasonication in distilled water and then in a solvent such as isopropyl alcohol, acetone, methanol, etc. and then dried. The glass substrate was transferred to a UV OZONE cleaner (Power sonic 405, Hwashin Tech) and cleaned for 5 min using UV, and transferred to a vacuum evaporator.

On the transparent ITO substrate (electrode) thus obtained, m-MTDATA (60 nm)/TCTA (80 nm)/90% of each of the compounds synthesized in Synthesis Examples 1 to 41+10% of Ir(ppy)$_3$ (30 nm)/BCP (10 nm)/Alq$_3$ (30 nm)/LiF (1 nm)/Al (200 nm) were deposited in that order to fabricate organic electroluminescent elements.

Structures of m-MTDATA, TCTA, Ir(ppy)$_3$ and BCP are as follows.

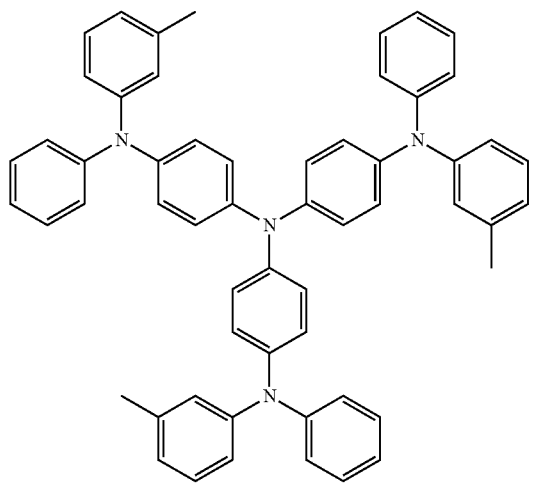

m-MTDATA

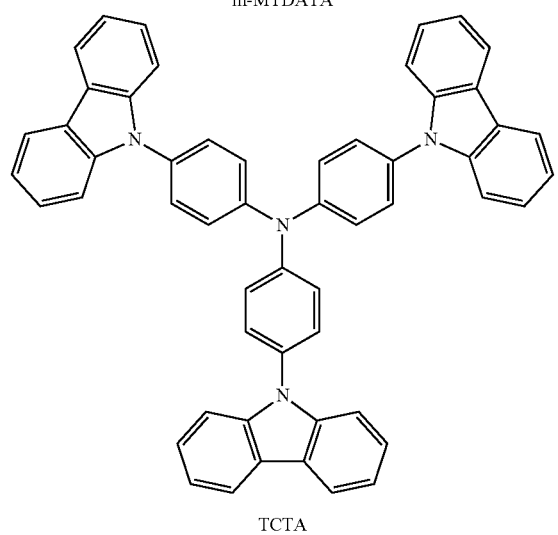

TCTA

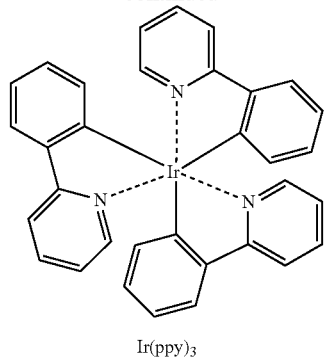

Ir(ppy)$_3$

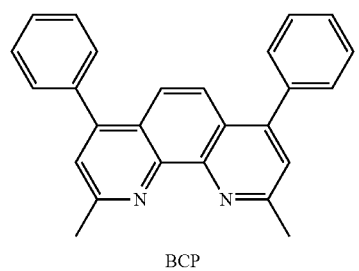

BCP

Comparative Example 1: Fabrication of Green Organic Electroluminescent Element A green organic electroluminescent element was fabricated in the same manner as in Example 1, with the exception of using the following CBP instead of Compound 1 synthesized in Synthesis Example 1.

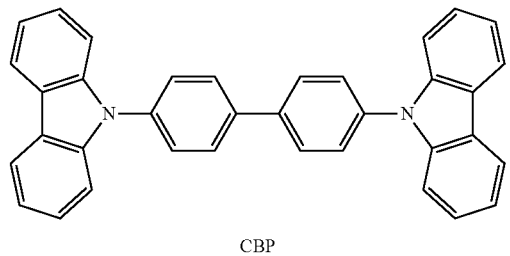 [SMILES: c1ccc2c(c1)c1ccccc1n2-c1ccc(-c2ccc(-n3c4ccccc4c4ccccc43)cc2)cc1 ; "CBP"]

CBP

Comparative Example 2: Fabrication of Green Organic Electroluminescent Element A green organic electroluminescent element was fabricated in the same manner as in Example 1, with the exception of using the following Compound A instead of Compound 1 synthesized in Synthesis Example 1.

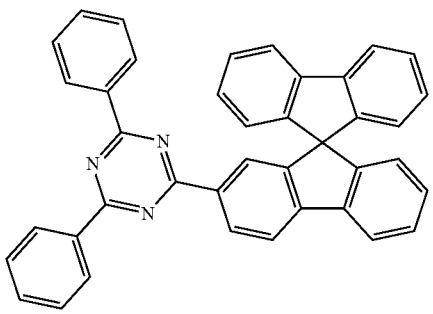

A

Comparative Example 3: Fabrication of Green Organic Electroluminescent Element A green organic electroluminescent element was fabricated in the same manner as in Example 1, with the exception of using the following Compound B instead of Compound 1 synthesized in Synthesis Example 1.

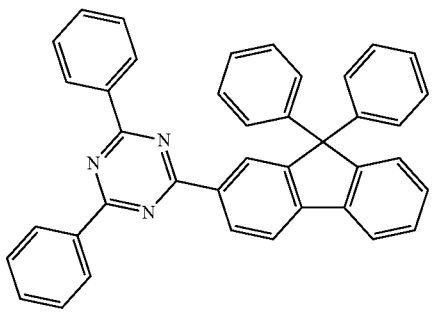

B

Evaluation Example 1

The green organic electroluminescent elements fabricated in Examples 1 to 41 and Comparative Examples 1 to 3 were measured for driving voltage at a current density of 10 mA/cm$^2$, current efficiency, and emitting peak, and the results are summarized in Table 1, below.

TABLE 1

| | Light-Emitting Material | Driving Volt. (V) | Emitting Peak (nm) | Current Efficiency (cd/A) |
|---|---|---|---|---|
| Example 1 | Compound 1 | 4.50 | 517 | 53.5 |
| Example 2 | Compound 3 | 4.61 | 515 | 51.5 |
| Example 3 | Compound 69 | 4.45 | 518 | 49.8 |
| Example 4 | Compound 129 | 4.57 | 518 | 51.7 |
| Example 5 | Compound 6 | 4.60 | 518 | 49.6 |
| Example 6 | Compound 74 | 4.59 | 517 | 51.7 |
| Example 7 | Compound 134 | 4.56 | 515 | 52.7 |
| Example 8 | Compound 7 | 5.10 | 518 | 49.8 |
| Example 9 | Compound 75 | 4.65 | 518 | 50.5 |
| Example 10 | Compound 135 | 4.35 | 517 | 52.5 |
| Example 11 | Compound 21 | 4.10 | 515 | 63.4 |
| Example 12 | Compound 23 | 4.05 | 518 | 65.4 |
| Example 13 | Compound 89 | 4.15 | 518 | 61.5 |
| Example 14 | Compound 91 | 4.05 | 517 | 63.3 |
| Example 15 | Compound 149 | 4.15 | 518 | 63.5 |
| Example 16 | Compound 151 | 4.11 | 517 | 64.2 |

TABLE 1-continued

| | Light-Emitting Material | Driving Volt. (V) | Emitting Peak (nm) | Current Efficiency (cd/A) |
|---|---|---|---|---|
| Example 17 | Compound 31 | 4.28 | 515 | 58.3 |
| Example 18 | Compound 35 | 4.15 | 518 | 60.5 |
| Example 19 | Compound 99 | 4.40 | 518 | 55.5 |
| Example 20 | Compound 159 | 4.33 | 518 | 56.6 |
| Example 21 | Compound 45 | 4.30 | 517 | 57.5 |
| Example 22 | Compound 53 | 4.20 | 515 | 56.5 |
| Example 23 | Compound 113 | 4.33 | 518 | 51.5 |
| Example 24 | Compound 173 | 4.30 | 518 | 52.7 |
| Example 25 | Compound 61 | 4.15 | 517 | 59.3 |
| Example 26 | Compound 62 | 4.10 | 518 | 62.7 |
| Example 27 | Compound 63 | 4.20 | 517 | 54.5 |
| Example 28 | Compound 64 | 4.23 | 515 | 56.5 |
| Example 29 | Compound 200 | 4.65 | 516 | 46.9 |
| Example 30 | Compound 206 | 4.23 | 517 | 47.2 |
| Example 31 | Compound 217 | 4.15 | 517 | 61.8 |
| Example 32 | Compound 218 | 4.26 | 518 | 62.5 |
| Example 33 | Compound 220 | 4.32 | 518 | 59.8 |
| Example 34 | Compound 21 | 4.10 | 516 | 63.4 |
| Example 35 | Compound 189 | 4.15 | 517 | 62.3 |
| Example 36 | Compound 193 | 4.35 | 518 | 57.8 |
| Example 37 | Compound 65 | 4.52 | 518 | 52.3 |
| Example 38 | Compound 231 | 4.41 | 518 | 51.3 |
| Example 39 | Compound 234 | 4.50 | 518 | 52.6 |
| Example 40 | Compound 250 | 4.35 | 518 | 57.6 |
| Example 41 | Compound 252 | 4.48 | 518 | 54.6 |
| C. Example 1 | CBP | 6.93 | 516 | 38.2 |
| C. Example 2 | Compound A | 4.98 | 517 | 39.6 |
| C. Example 3 | Compound B | 5.03 | 516 | 37.3 |

As understood from Table 1, the organic electroluminescent elements employing the compounds of the present invention in the light-emitting layer thereof (Examples 1 to 41) are far superior in terms of current efficiency and driving voltage compared to that employing the conventional material CBP in the light-emitting layer thereof (Comparative Example 1).

In addition, when used in the light-emitting layer of an organic electroluminescent element, the compounds having the linker (Examples 1 to 41) decrease the driving voltage and increases current efficiency in the organic electroluminescent element, compared to those lacking the linker (Comparative Examples 2 and 3).

Examples 42 TO 98: Fabrication of Blue Organic Electroluminescent Element

The compounds synthesized in the Synthesis Examples were purified by sublimation to a high degree of purity using a conventional method known in the art before being applied to the fabrication of blue organic electroluminescent elements having the structures listed in Table 2, below.

TABLE 2

| | Hole Injection Layer | Hole Transport Layer | Light-emitting Layer | Aux. Electron Transport Layer | Electron Transport Layer | Electron Injection Layer | Cathode |
|---|---|---|---|---|---|---|---|
| Material | DS-205 (Doosan Corporation) | NPB | ADN + 5% DS-405 (Doosan Corporation) | Individual Cpd. Synthesized in Synthesis Examples 1 to 57 | $Alq_3$ | LiF | Al |
| Thick. | 80 nm | 15 nm | 30 nm | 5 nm | 25 nm | 1 nm | 200 nm |

The structures of NPB, ADN, and $Alq_3$ listed in Table 2 are as follows.

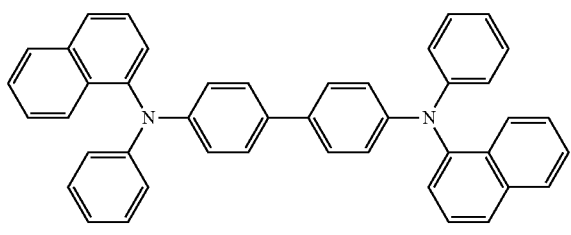

NPB

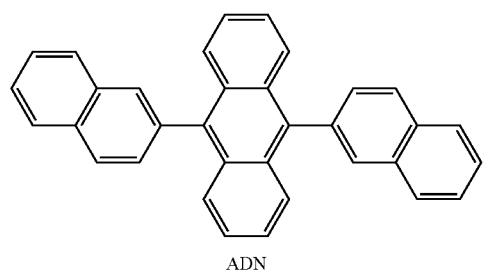

ADN

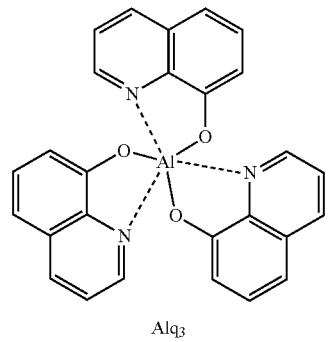

$Alq_3$

Comparative Example 5: Fabrication of Blue Organic Electroluminescent Element

A blue organic electroluminescent element was fabricated in the same manner as in Example 42, with the exception of using the following BCP instead of Compound 1 synthesized in Synthesis Example 1.

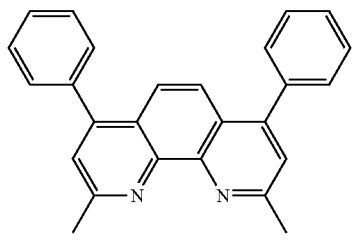

BCP

Evaluation Example 2

The blue organic electroluminescent elements fabricated in Examples 42 to 98 and Comparative Examples 4 and 5 were measured for driving voltage at a current density of 10 $mA/cm^2$, current efficiency, and emitting peak, and the results are summarized in Table 3, below.

TABLE 3

| | Material of Aux. Electron Transport Layer | Driving Volt. (V) | Current Efficiency (cd/A) | Emitting Peak (nm) |
|---|---|---|---|---|
| Example 42 | Compound 1 | 4.7 | 6.6 | 458 |
| Example 43 | Compound 3 | 4.5 | 6.3 | 458 |
| Example 44 | Compound 69 | 4.2 | 6.6 | 457 |
| Example 45 | Compound 129 | 4.1 | 6.0 | 458 |
| Example 46 | Compound 6 | 4.5 | 6.2 | 458 |
| Example 47 | Compound 74 | 4.2 | 6.6 | 458 |
| Example 48 | Compound 134 | 4.1 | 6.3 | 457 |
| Example 49 | Compound 7 | 4.4 | 6.2 | 458 |
| Example 50 | Compound 75 | 4.3 | 6.1 | 457 |
| Example 51 | Compound 135 | 4.4 | 6.2 | 458 |
| Example 52 | Compound 21 | 3.8 | 8.2 | 458 |
| Example 53 | Compound 23 | 4.1 | 7.2 | 458 |
| Example 54 | Compound 89 | 4.0 | 8.1 | 458 |
| Example 55 | Compound 91 | 4.1 | 8.1 | 457 |
| Example 56 | Compound 149 | 4.0 | 8.0 | 458 |
| Example 57 | Compound 151 | 4.2 | 7.8 | 458 |
| Example 58 | Compound 31 | 4.1 | 8.0 | 458 |
| Example 59 | Compound 35 | 4.1 | 7.5 | 457 |
| Example 60 | Compound 99 | 4.5 | 8.1 | 458 |
| Example 61 | Compound 159 | 4.2 | 7.6 | 458 |
| Example 62 | Compound 45 | 4.5 | 6.1 | 458 |
| Example 63 | Compound 53 | 4.6 | 6.2 | 458 |
| Example 64 | Compound 113 | 4.5 | 6.0 | 458 |
| Example 65 | Compound 173 | 4.2 | 6.1 | 458 |
| Example 66 | Compound 61 | 4.1 | 6.8 | 458 |
| Example 67 | Compound 62 | 4.1 | 6.9 | 458 |
| Example 68 | Compound 63 | 4.5 | 7.3 | 457 |
| Example 69 | Compound 64 | 4.2 | 7.6 | 458 |
| Example 70 | Compound 200 | 4.1 | 7.0 | 458 |
| Example 71 | Compound 206 | 4.3 | 7.7 | 458 |
| Example 72 | Compound 217 | 4.0 | 8.0 | 458 |
| Example 73 | Compound 218 | 4.1 | 8.1 | 458 |
| Example 74 | Compound 220 | 3.9 | 8.0 | 457 |

TABLE 3-continued

| | Material of Aux. Electron Transport Layer | Driving Volt. (V) | Current Efficiency (cd/A) | Emitting Peak (nm) |
|---|---|---|---|---|
| Example 75 | Compound 21 | 3.8 | 8.2 | 458 |
| Example 76 | Compound 189 | 4.0 | 8.2 | 458 |
| Example 77 | Compound 193 | 4.2 | 7.9 | 458 |
| Example 78 | Compound 65 | 4.3 | 7.6 | 457 |
| Example 79 | Compound 231 | 4.4 | 7.2 | 458 |
| Example 80 | Compound 234 | 4.3 | 7.6 | 458 |
| Example 81 | Compound 250 | 4.1 | 7.6 | 457 |
| Example 82 | Compound 252 | 4.3 | 7.7 | 458 |
| Example 83 | Compound 5 | 4.7 | 6.7 | 458 |
| Example 84 | Compound 13 | 4.6 | 6.5 | 458 |
| Example 85 | Compound 73 | 4.4 | 6.1 | 457 |
| Example 86 | Compound 133 | 4.6 | 6.9 | 458 |
| Example 87 | Compound 134 | 4.1 | 6.7 | 457 |
| Example 88 | Compound 29 | 4.4 | 7.2 | 458 |
| Example 89 | Compound 33 | 4.3 | 7.1 | 457 |
| Example 90 | Compound 97 | 4.4 | 7.5 | 458 |
| Example 91 | Compound 101 | 4.3 | 7.6 | 458 |
| Example 92 | Compound 157 | 4.1 | 7.5 | 458 |
| Example 93 | Compound 161 | 4.2 | 7.3 | 458 |
| Example 94 | Compound 282 | 4.5 | 7.9 | 458 |
| Example 95 | Compound 159 | 4.1 | 8.3 | 458 |
| Example 96 | Compound 205 | 4.5 | 8.0 | 457 |
| Example 97 | Compound 206 | 4.6 | 7.7 | 458 |
| Example 98 | Compound 336 | 4.5 | 7.9 | 458 |
| C. Example 4 | — | 4.7 | 5.6 | 457 |
| C. Example 5 | BCP | 5.3 | 5.9 | 458 |

As shown in Table 3, the compounds according to the present invention, when used in auxiliary electron transport layer of blue organic electroluminescent elements (Examples 42 to 98), impart excellent current efficiency and driving voltages to the blue organic electroluminescent elements.

The invention claimed is:

1. An organic electroluminescent element comprising, in the order,
   an anode;
   a hole injection layer;
   a hole transport layer;
   a light emitting layer;
   an auxiliary electron transport layer;
   an electron transport layer;
   an electron injection layer; and
   a cathode, wherein at least one of the auxiliary electron transport layer and the electron transport layer comprises the compound represented by the following Formula 1:

Formula 1

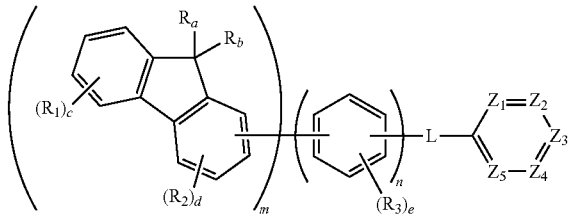

wherein,
$R_a$ and $R_b$ are the same or different from each other and are each independently a $C_1$-$C_{40}$ alkyl group or a $C_6$-$C_{60}$ aryl group,
$R_1$ to $R_3$ are the same or different from each other and are each independently selected from the group consisting of a hydrogen, a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, or adjacent ones of $R_1$ to $R_3$ are taken together to form a fused ring, L is selected from the group consisting of a single bond, phenylene, biphenylene, and a heteroarylene group having 5 to 18 nuclear atoms, $Z_1$ to $Z_5$ are the same or different from each other and are each independently N or $C(R_4)$, and provided that $Z_1$ to $Z_5$ include one or two N, and when $C(R_4)$ is present in a plural number, plural substituents are the same as or different from each other, c and e are each an integer of 0 to 4, d is an integer of 0 to 3, m and n are each an integer of 1 to 3, and $R_4$ is selected from the group consisting of a hydrogen, a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, or bonded to an adjacent substituent to form a fused ring, with the proviso that the compound, in which n is 1, L is a single bond, c is 1, and R1 is a C6-C60 aryl group, is excluded, wherein the alkyl and aryl groups of $R_a$ and $R_b$ and the alkyl, alkenyl, alkynyl, cycloalkyl, heterocycloalkyl, aryl, heteroaryl, alkyloxy, aryloxy, alkylsilyl, arylsilyl, alkylboron, arylboron, phosphine, phosphine oxide, and arylamine groups of $R_1$ to $R_4$; and the arylene and heteroarylene groups of L are optionally each independently unsubstituted or substituted with at least one selected from the group consisting of a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, provided that when the substituent is present in a plural number, plural substituents are the same or different from each other.

2. The organic electroluminescent element of claim 1, wherein the compound is selected from the group consisting of the compounds of the following Formula 2 to 4:

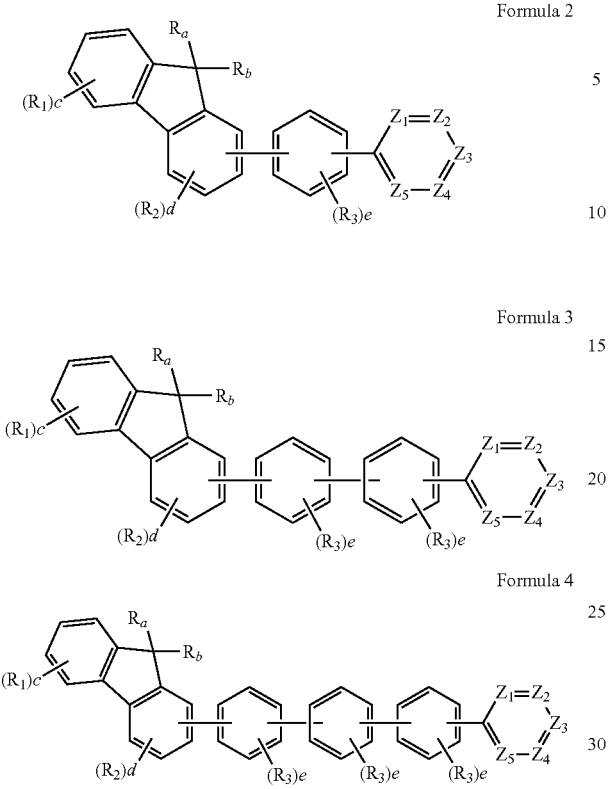
Formula 2
Formula 3
Formula 4
wherein,
$R_a$, $R_b$, $R_1$ to $R_3$, $Z_1$ to $Z_5$, c, d, and e are the same as defined in claim 1.
3. The organic electroluminescent element of claim 1, wherein the structure represented by
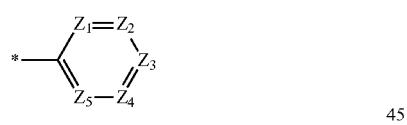
wherein * is a site where to bond with L, in Formula 1 is selected from the group consisting of the structures of the following C-1 to C-8, and C-10 to C-15:
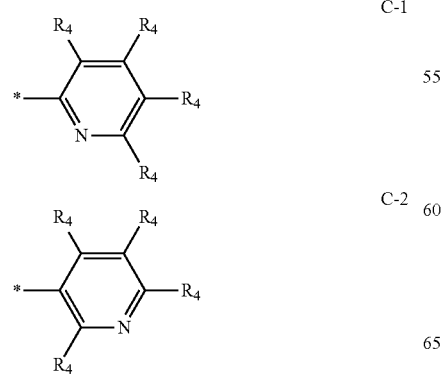
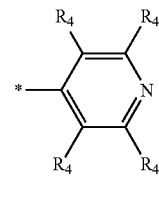
C-3
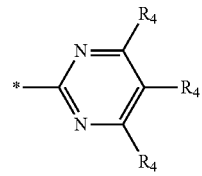
C-4
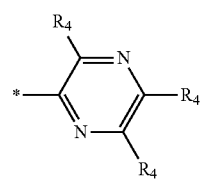
C-5
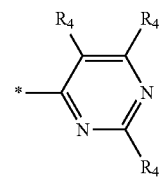
C-6
C-7
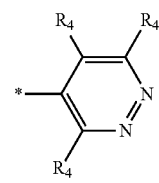
C-8
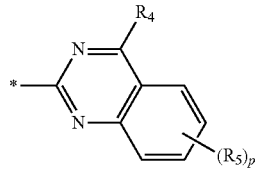
C-10
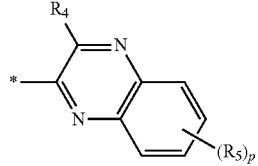
C-11
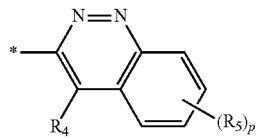
C-12

-continued

C-13
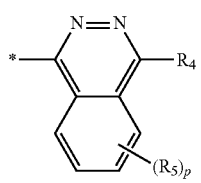

C-14
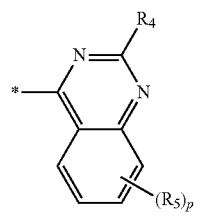

C-15
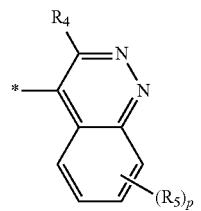

wherein,

R₄ is the same as defined in claim 1,

R₅ is selected from the group consisting of a hydrogen, a deuterium, a halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_6$-$C_{60}$ aryloxy group, a $C_1$-$C_{40}$ alkyloxy group, a $C_6$-$C_{60}$ arylamine group, a $C_1$-$C_{40}$ alkylsilyl group, a $C_1$-$C_{40}$ alkylboron group, a $C_6$-$C_{60}$ arylboron group, a $C_6$-$C_{60}$ arylphosphine group, a $C_6$-$C_{60}$ arylphosphine oxide group, and a $C_6$-$C_{60}$ arylsilyl group, or combines with an adjacent substituent to form a fused ring, p is an integer of 1 to 4, and the alkyl, alkenyl, alkynyl, cycloalkyl, heterocycloalkyl, aryl, heteroaryl, aryloxy, alkyloxy, arylamine, alkylsilyl, alkylboron, arylboron, arylphosphine, arylphosphine oxide and arylsilyl groups of R₅ are optionally each independently unsubstituted or substituted with at least one selected from the group consisting of a deuterium, a halogen, a cyano group, a nitro group, a $C_1$-$C_{40}$ alkyl group, a $C_2$-$C_{40}$ alkenyl group, a $C_2$-$C_{40}$ alkynyl group, a $C_6$-$C_{60}$ aryl group, a heteroaryl group having 5 to 60 nuclear atoms, a $C_6$-$C_{60}$ aryloxy group, a $C_1$-$C_{40}$ alkyloxy group, a $C_6$-$C_{60}$ arylamine group, a $C_3$-$C_{40}$ cycloalkyl group, a heterocycloalkyl group having 3 to 40 nuclear atoms, a $C_1$-$C_{40}$ alkylsilyl group, a $C_1$-$C_{40}$ alkylboron group, a $C_6$-$C_{60}$ arylboron group, a $C_6$-$C_{60}$ arylphosphine group, a $C_6$-$C_{60}$, arylphosphine oxide group and a $C_6$-$C_{60}$ arylsilyl group, and provided that when the substituent is present in a plural number, plural substituents are the same or different from each other.

4. The organic electroluminescent element of claim 1, wherein $R_a$ and $R_b$ are each independently a methyl or a phenyl.

5. The organic electroluminescent element of claim 1, wherein L is selected from the group consisting of the structures of the following L-1 to L-7:

L-1
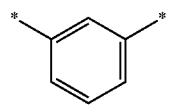

L-2
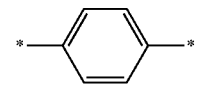

L-3
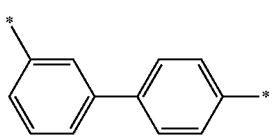

L-4
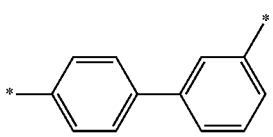

L-5
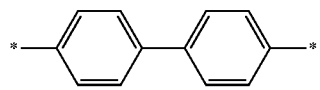

L-6
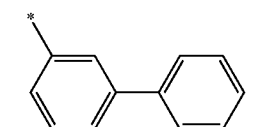

L-7
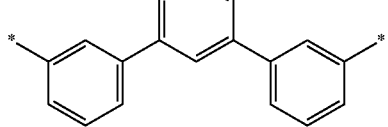

wherein * is a site where to bond.

6. The organic electroluminescent element of claim 2, wherein the compound of Formula 2 is selected from the group consisting of the following Compounds 5 to 20, 73 to 88, 253 to 260, 285 to 291, 294 to 299:

5
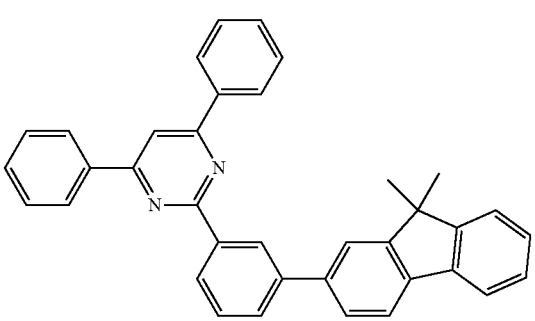

199
-continued
6
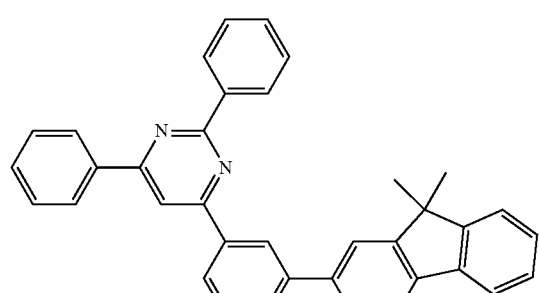
7
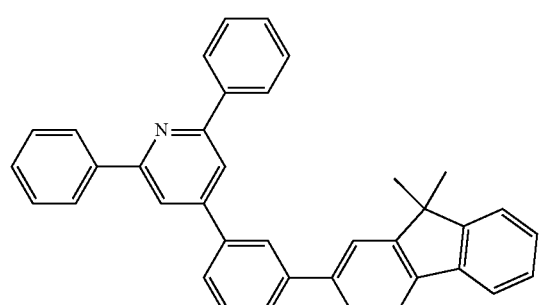
8
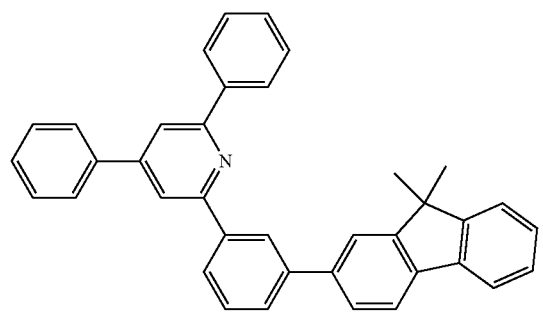
9
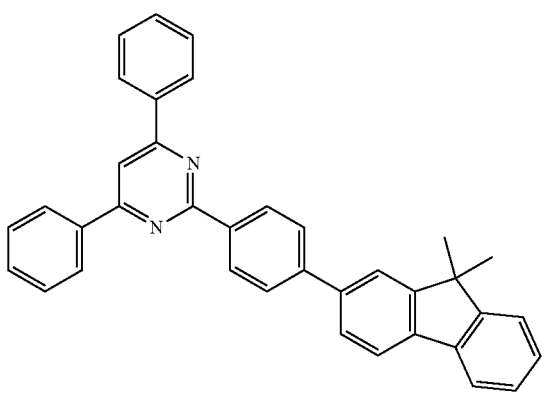
200
-continued
5
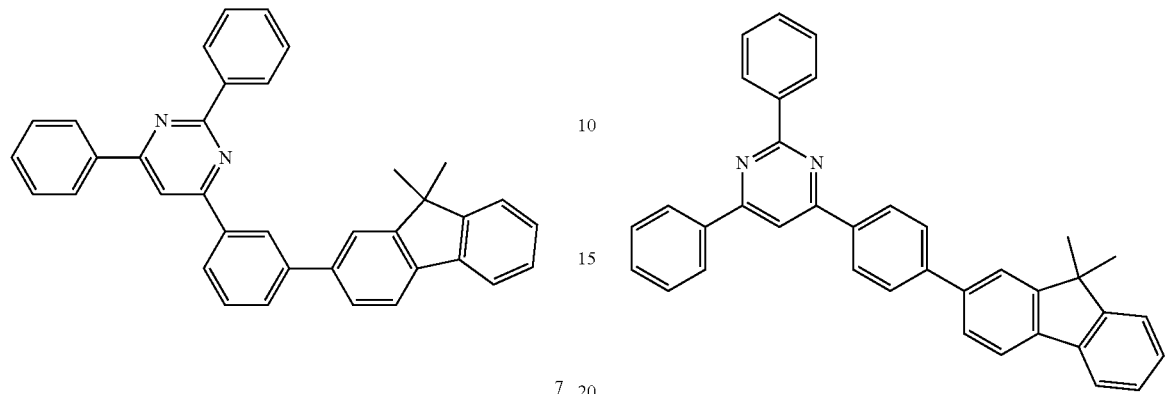
11
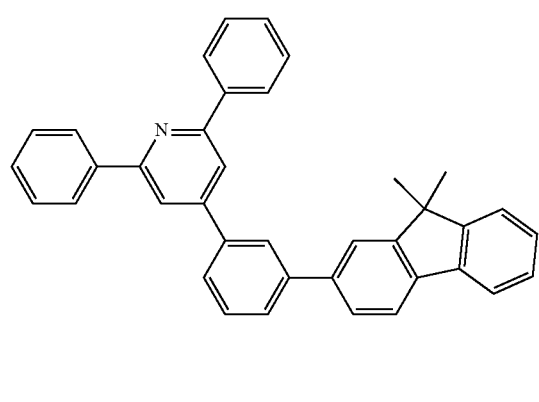
12
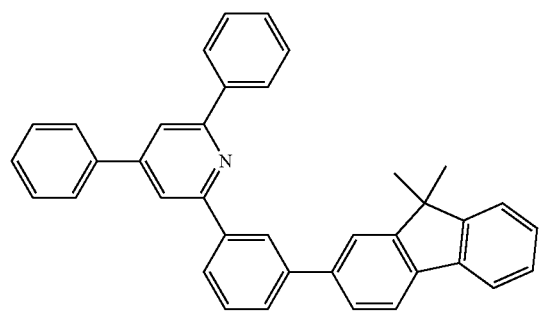
13
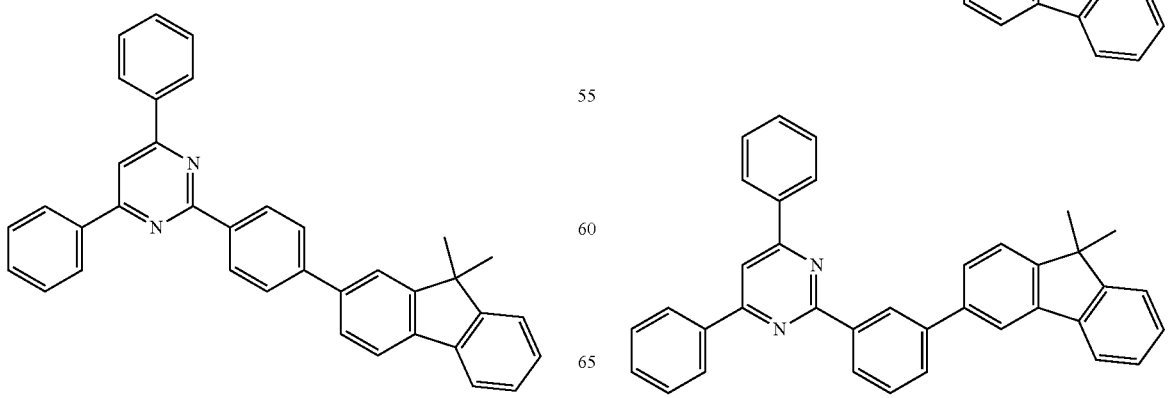

14
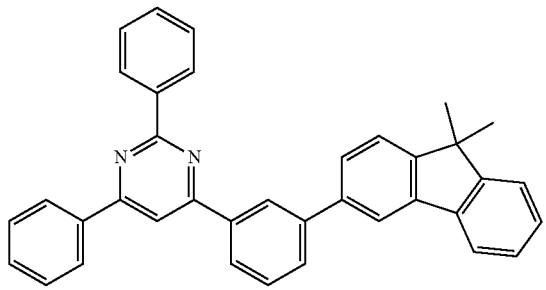
15
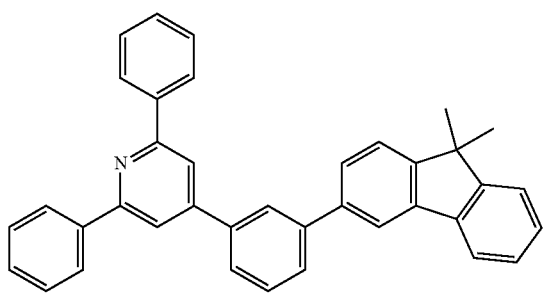
16
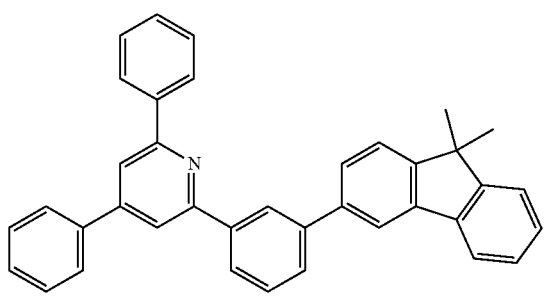
17
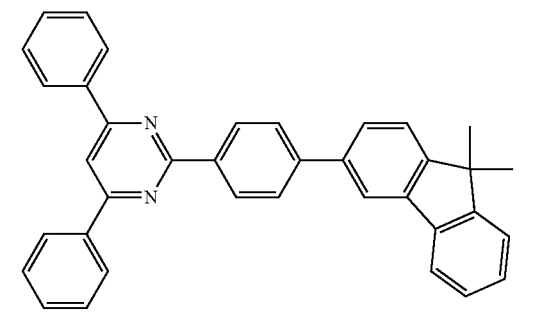
18
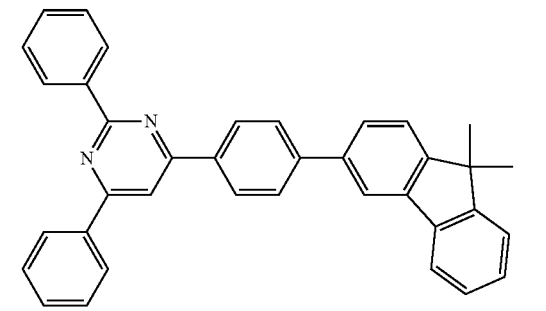
19
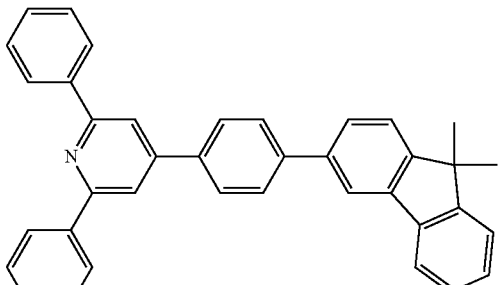
20
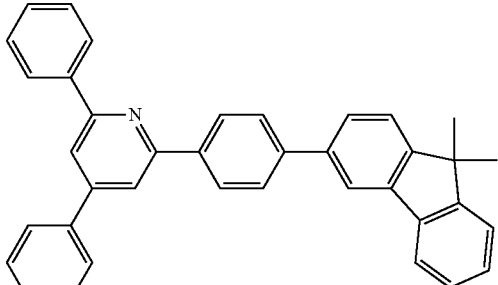
73
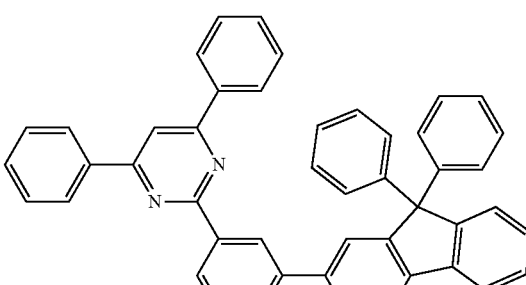
74
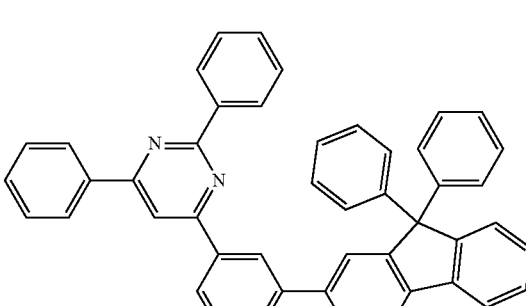
75
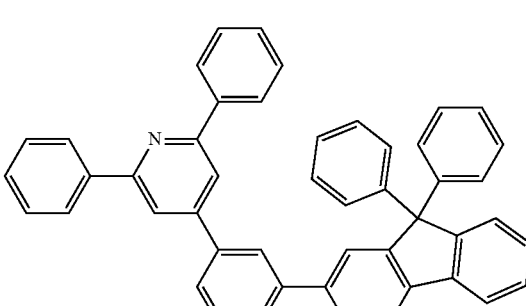

76
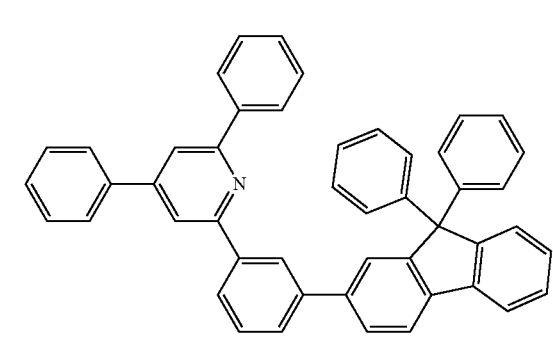
77
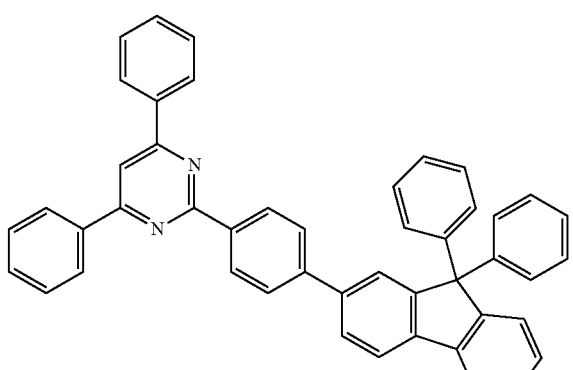
78
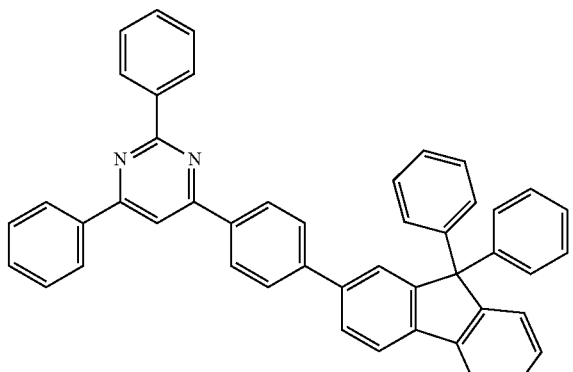
79
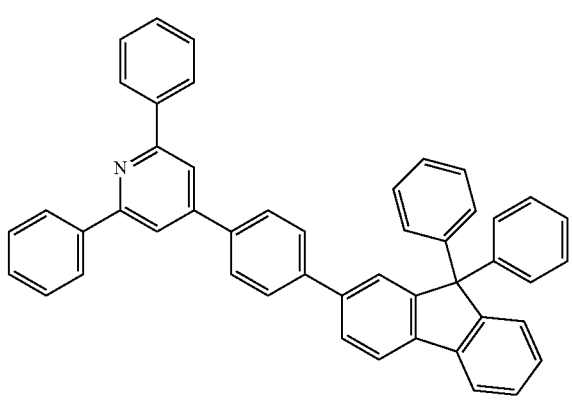
80
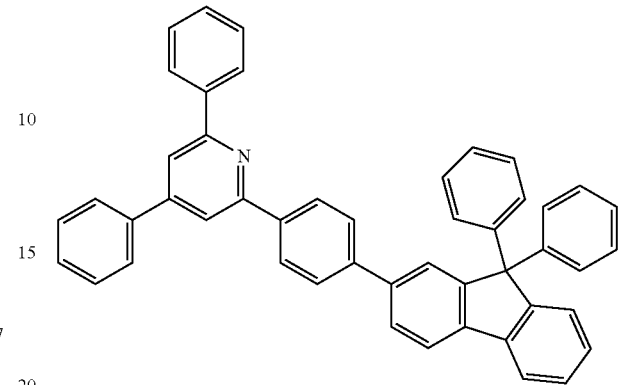
81
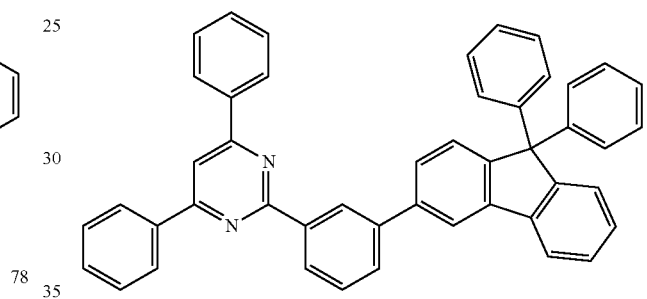
82
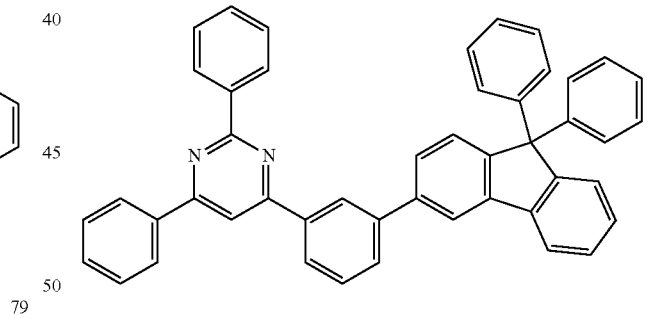
83
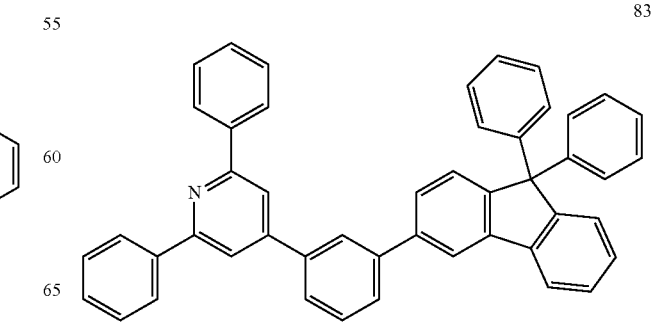

84
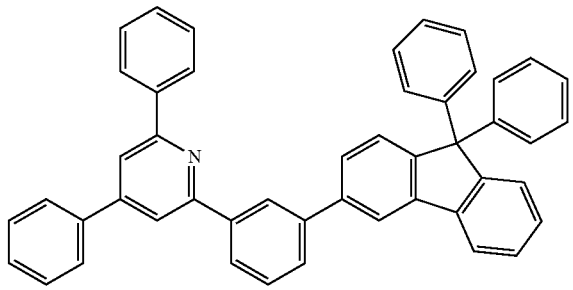
85
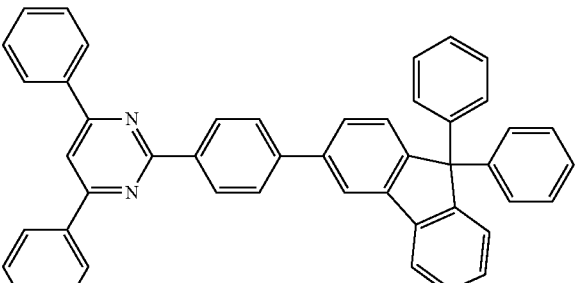
86
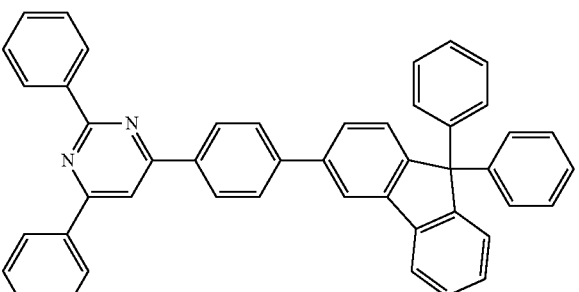
87
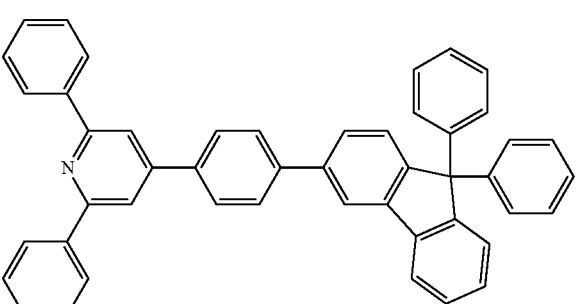
88
253
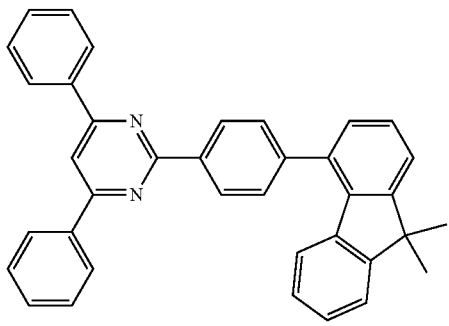
254
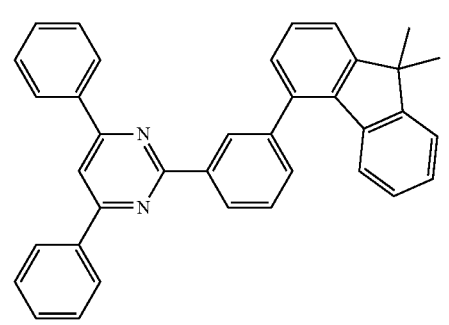
255
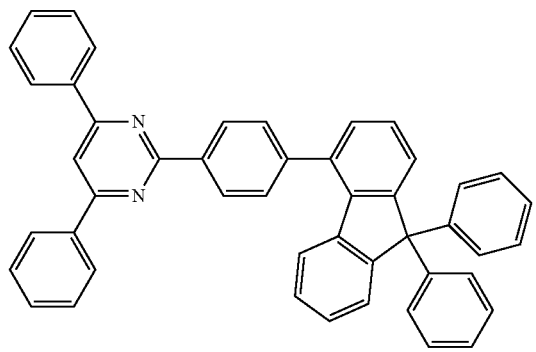
256
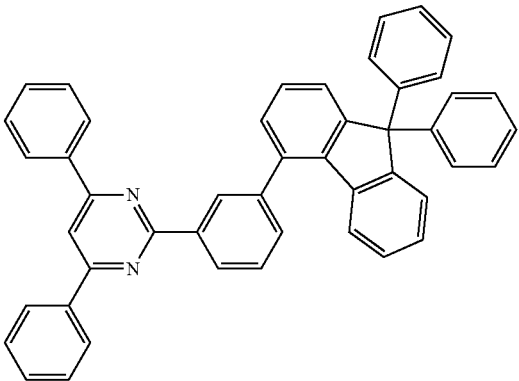

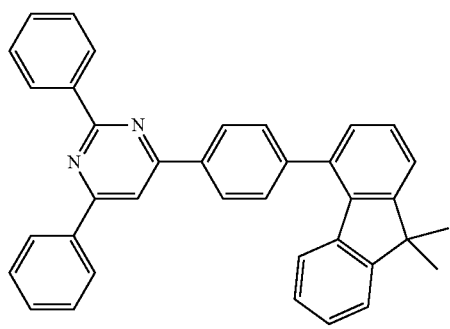
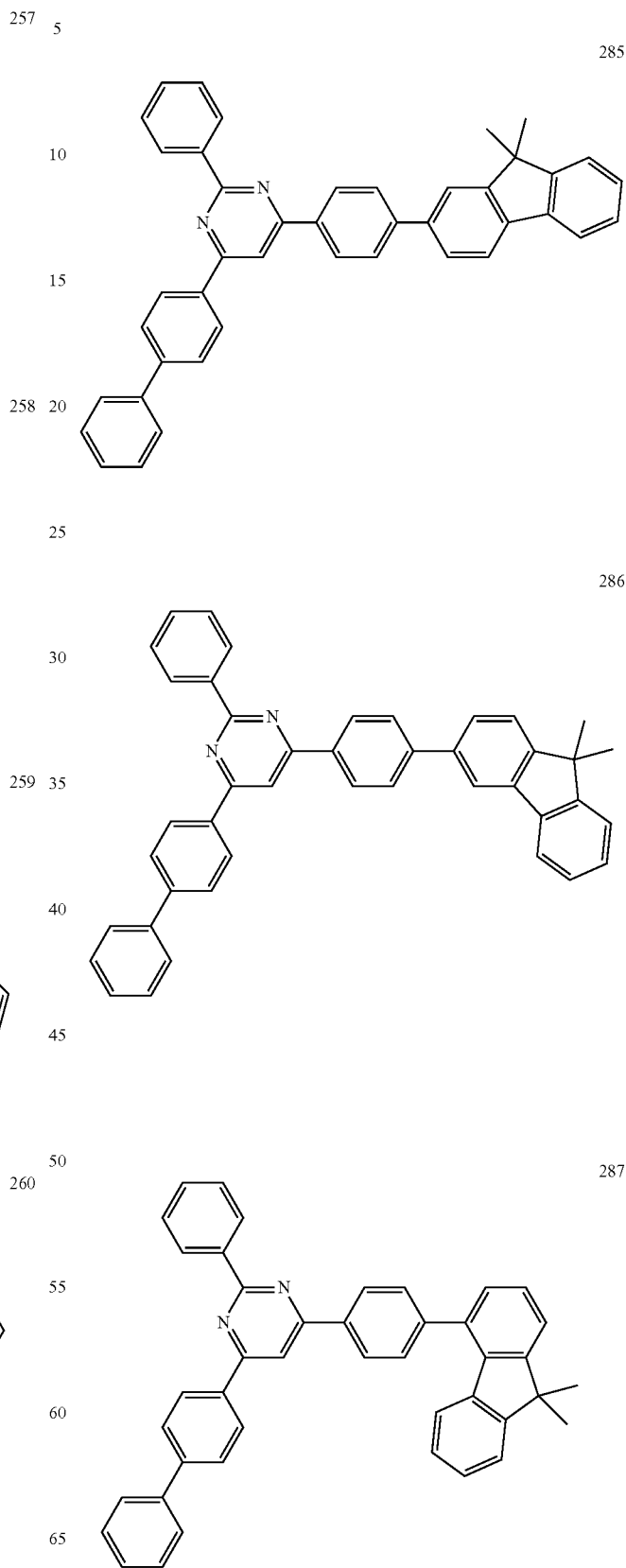

-continued
288
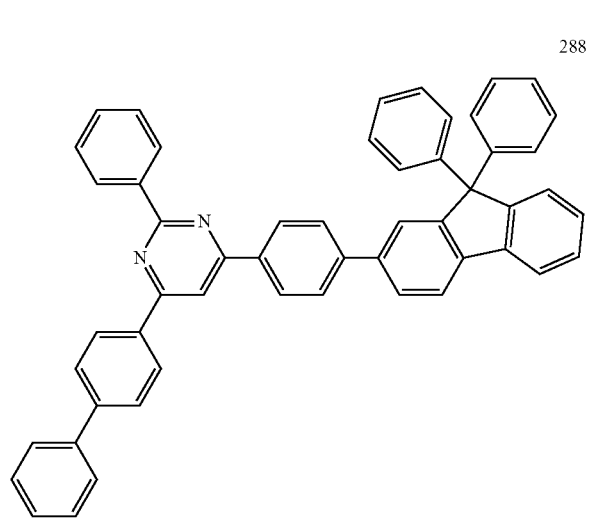
289
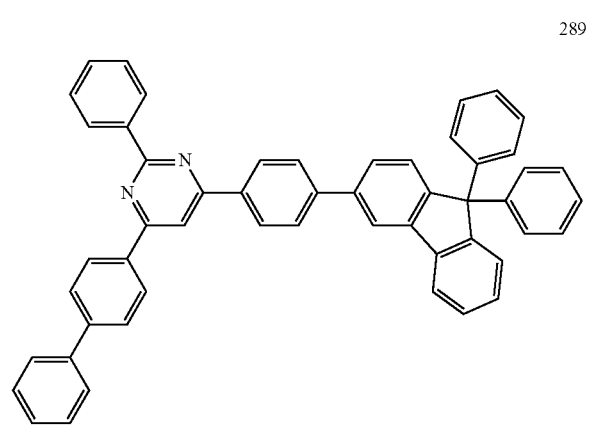
290
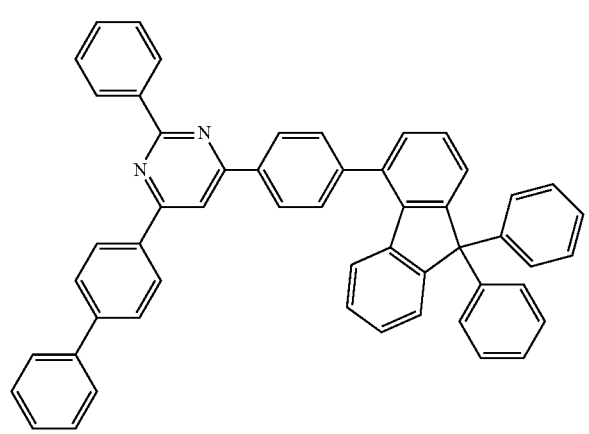
-continued
291
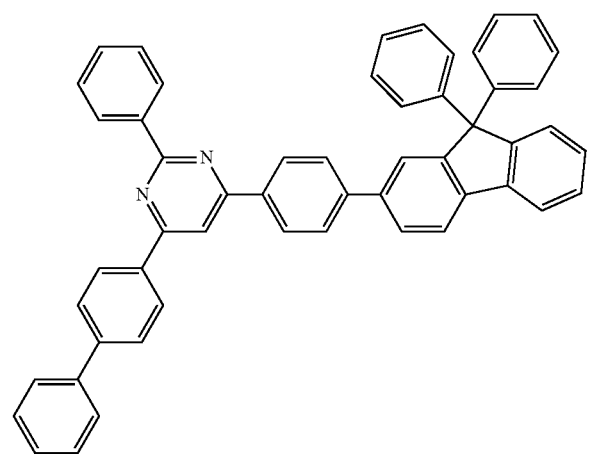
294
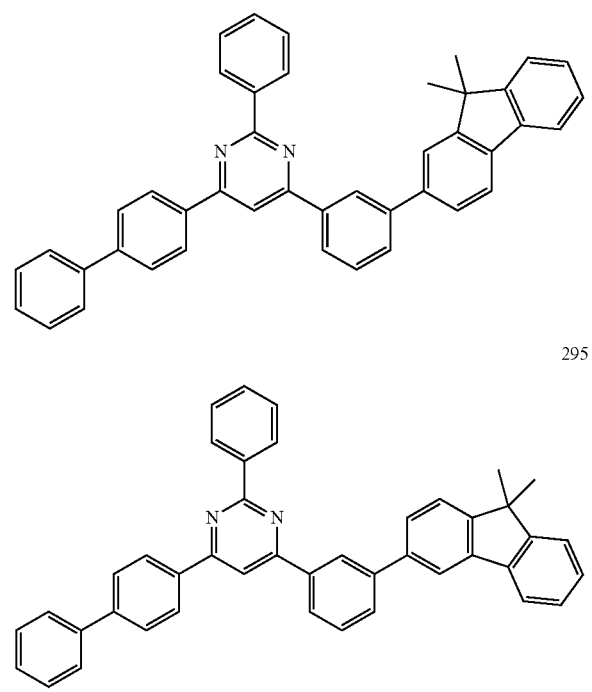
295
296

297
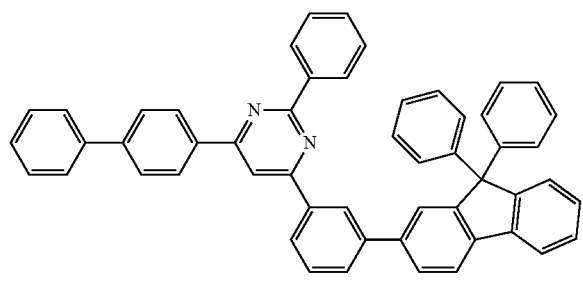
298
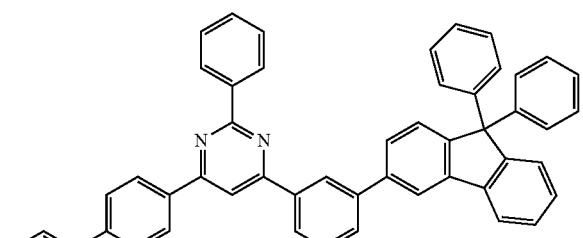
299
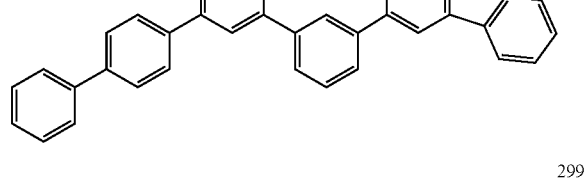
7. The organic electroluminescent element of claim 2, wherein the compound of Formula 3 is selected from the group consisting of the following Compounds 29 to 60, 66, 68, 97 to 128, 205, 206, 208, 209, 211 to 216, 261, 262, 264, 265, 267, 268, 270, 271, 273, 274, 276, 277, 279 to 283, 303 to 308, 312 to 317, 321 to 326, 330 to 331, 354 to 366:
29
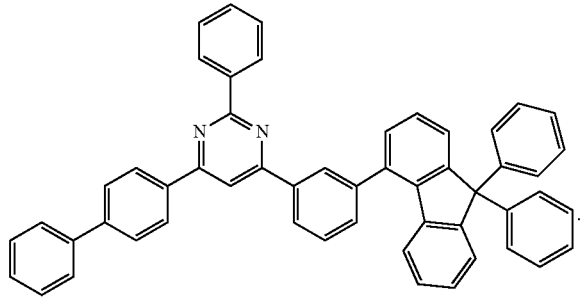
30
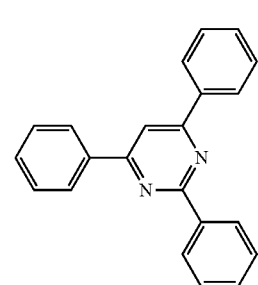
31
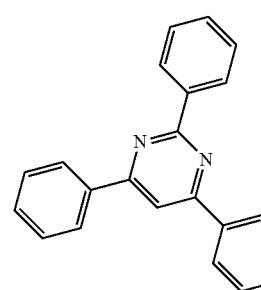
32
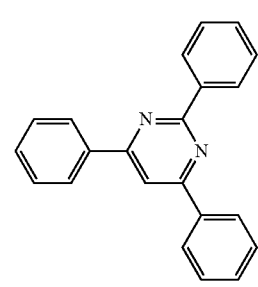
33
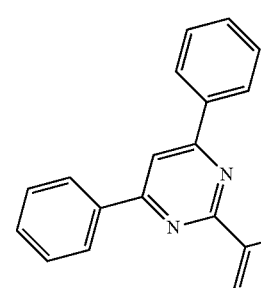

34
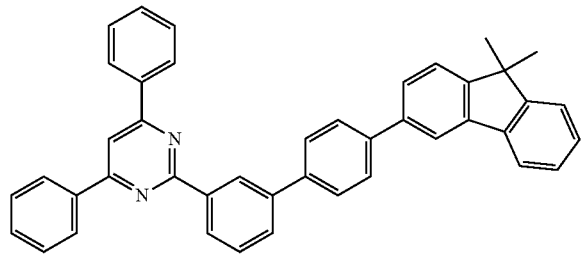
35
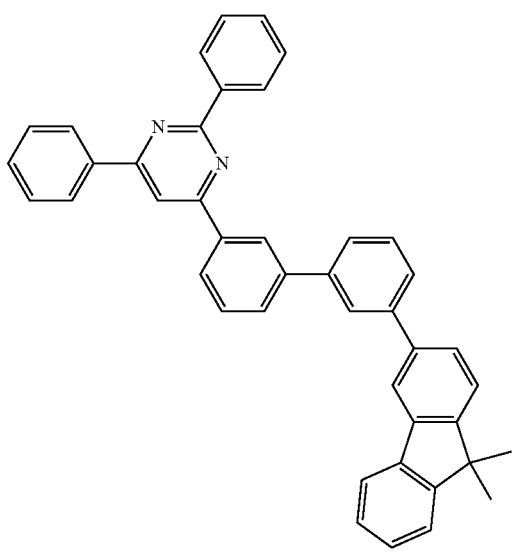
36
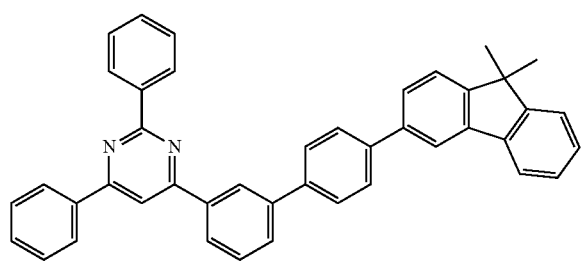
37
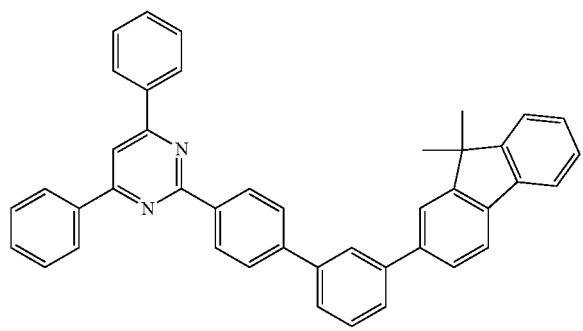
38
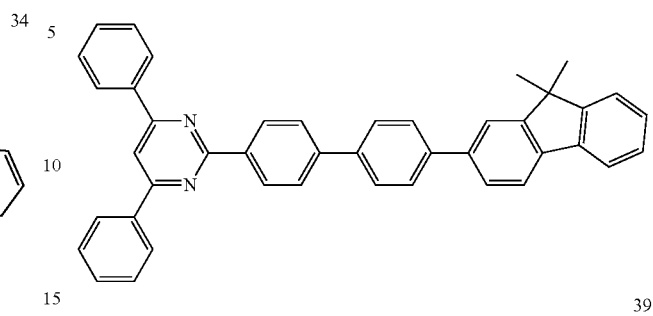
39
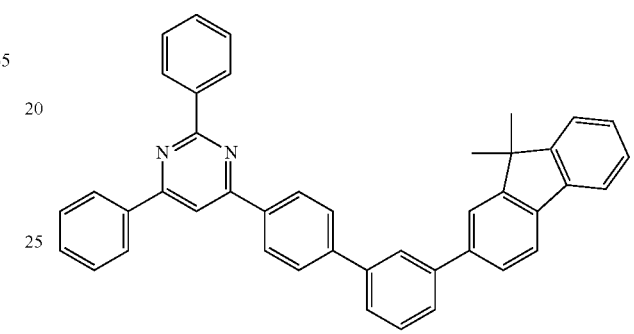
40
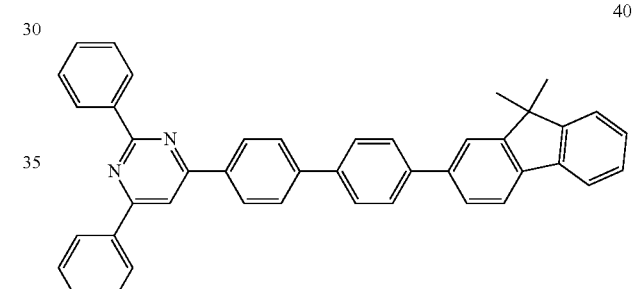
41
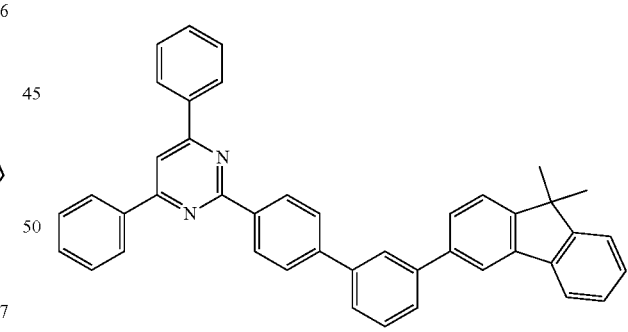
42
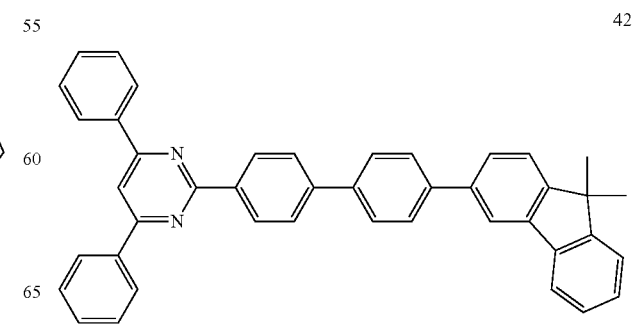

43
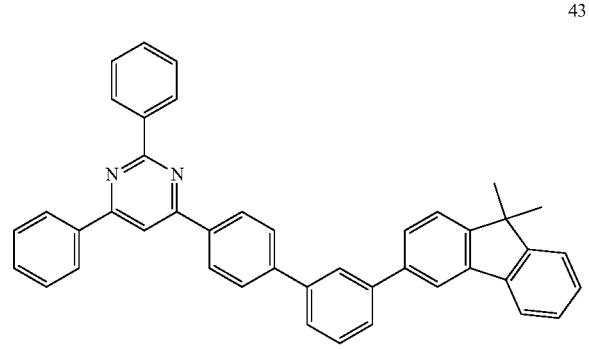
44
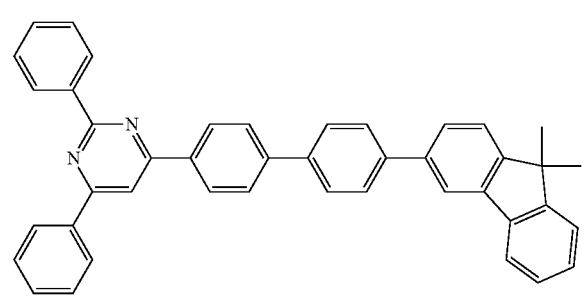
45
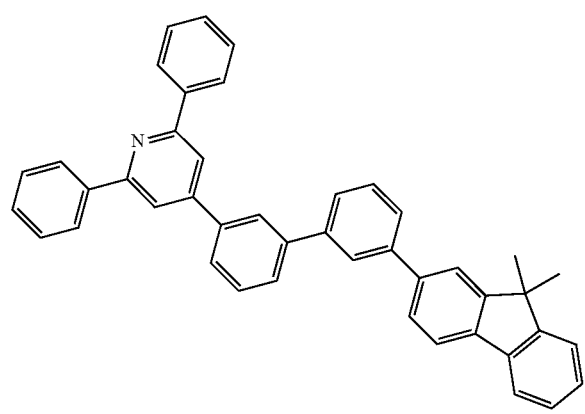
46
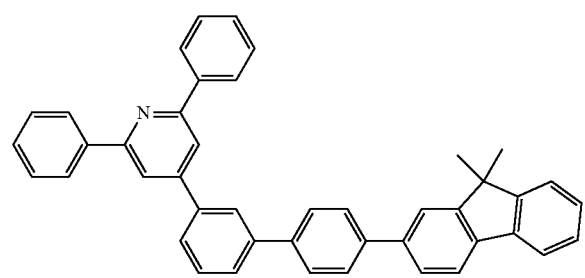
47
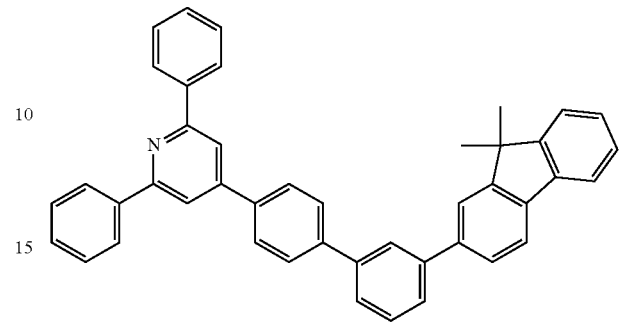
48
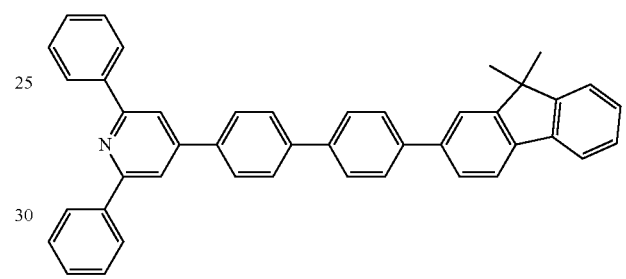
49
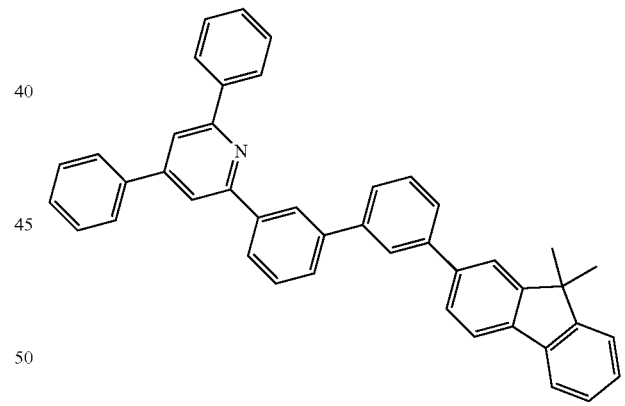
50
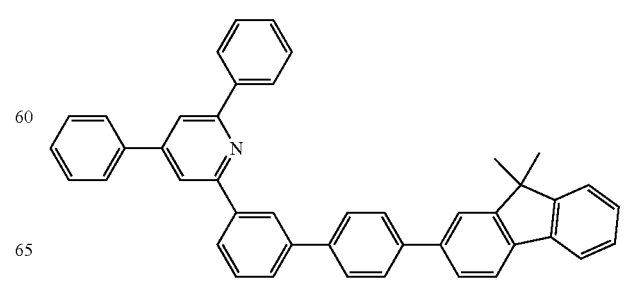

217
-continued
51
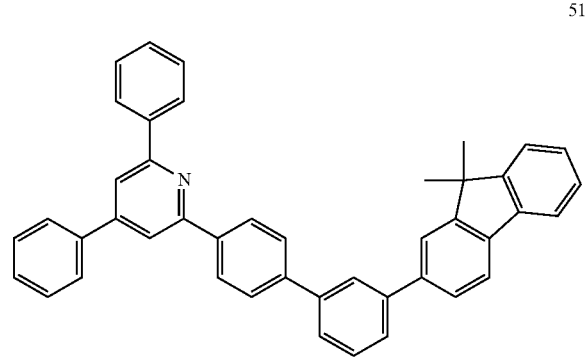
52
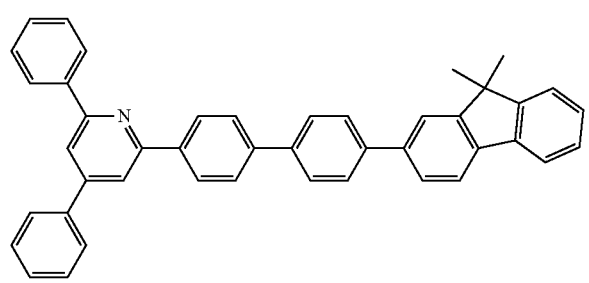
53
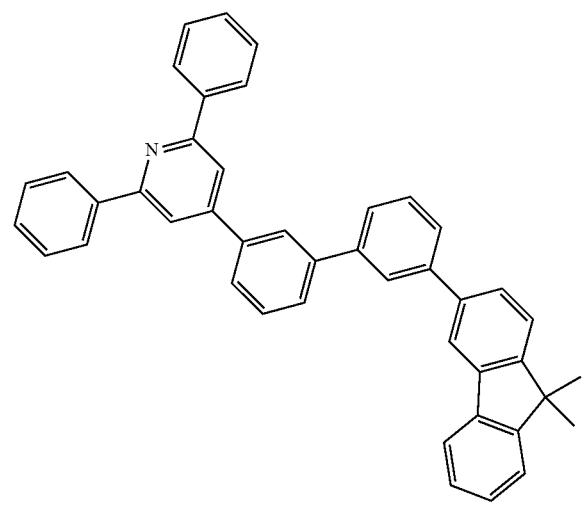
54
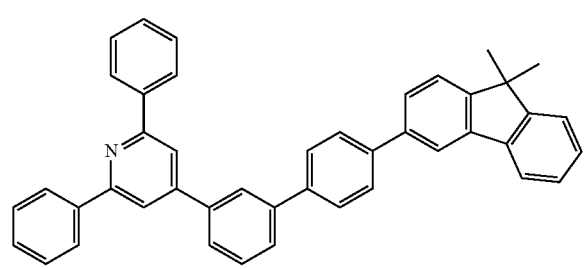
218
-continued
55
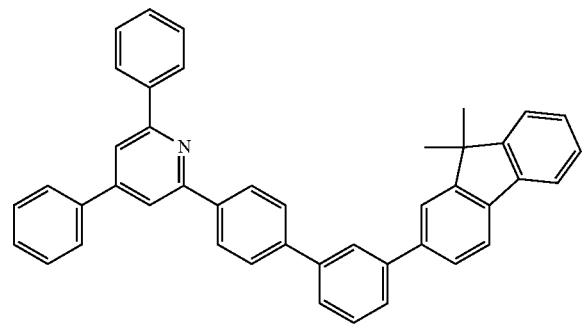
56
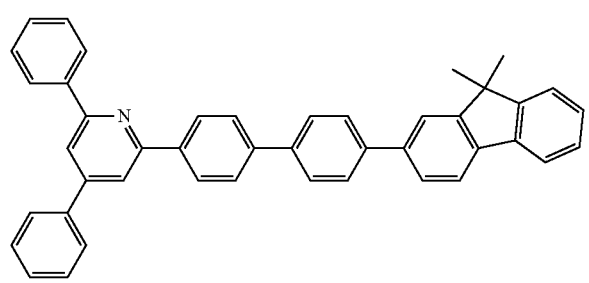
57
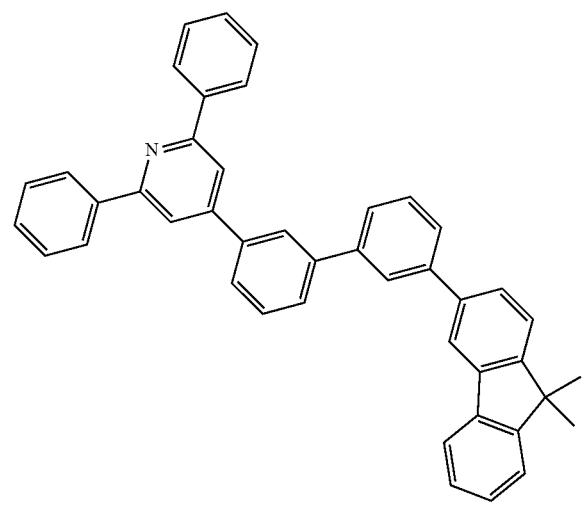
58
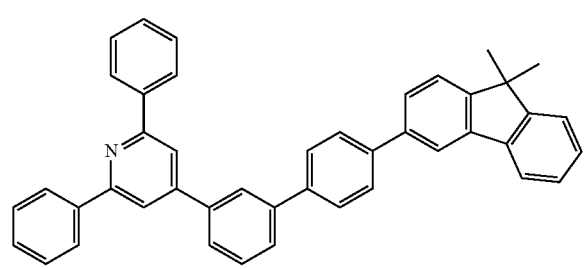

59
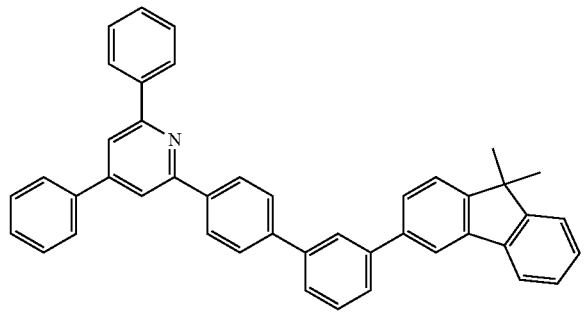
60
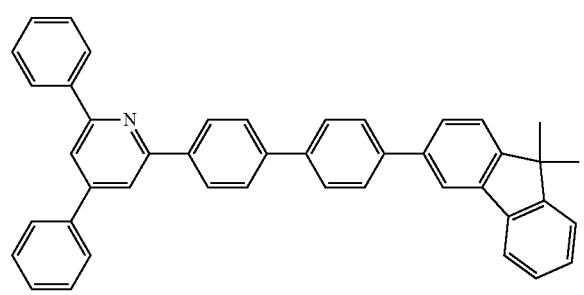
66
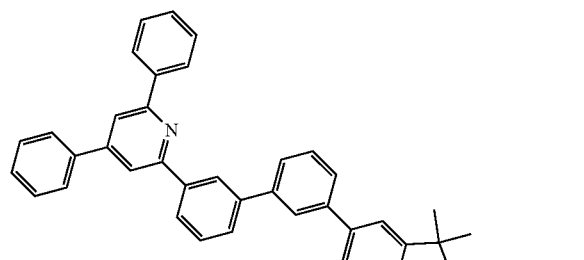
68
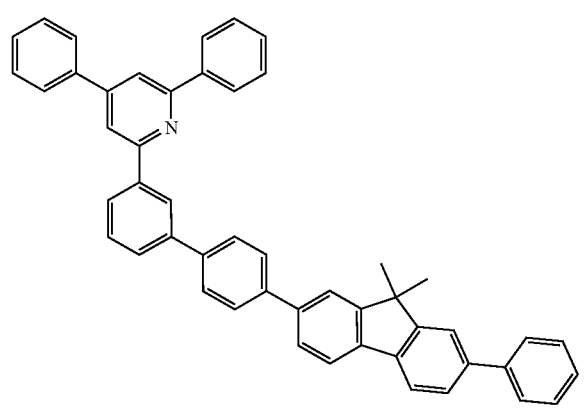
97
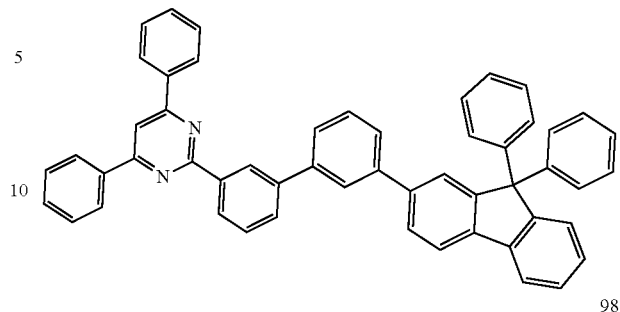
98
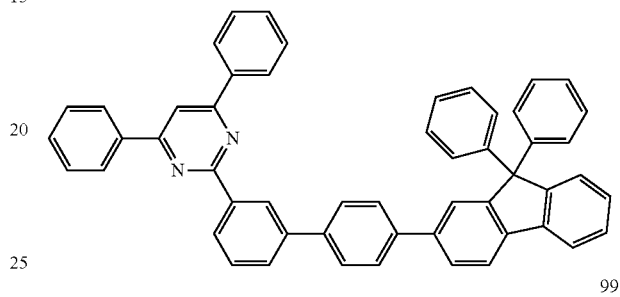
99
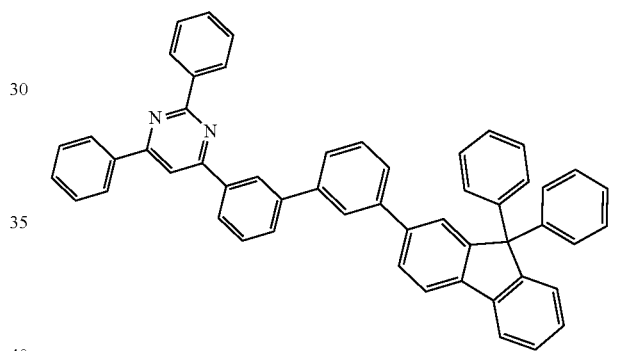
100
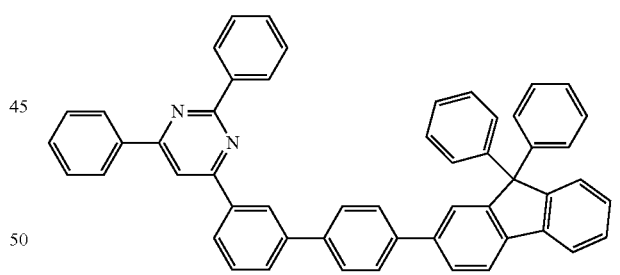
101
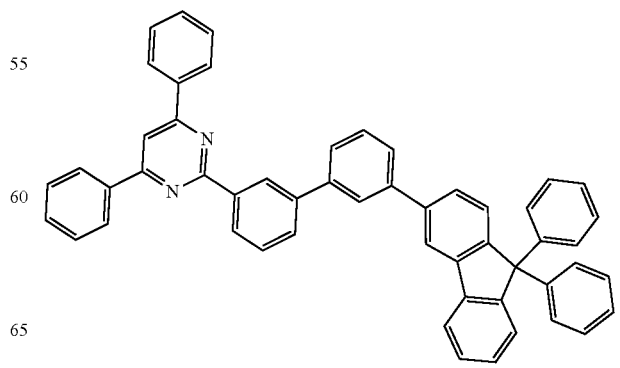

102
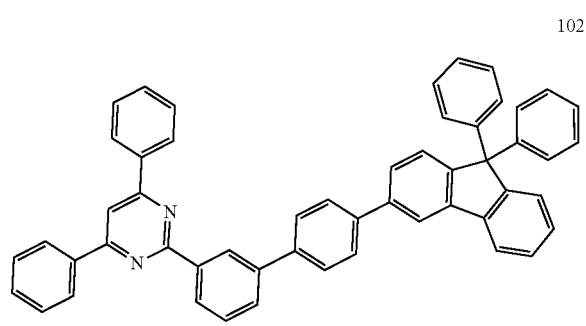
103
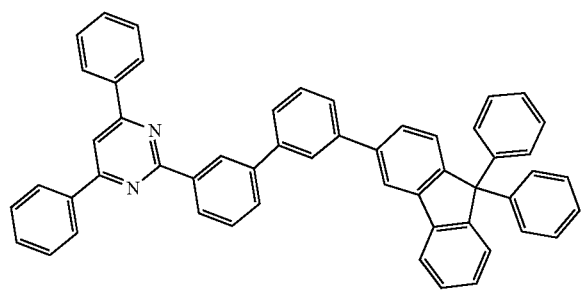
104
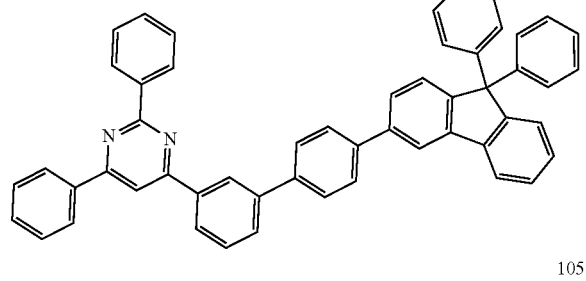
105
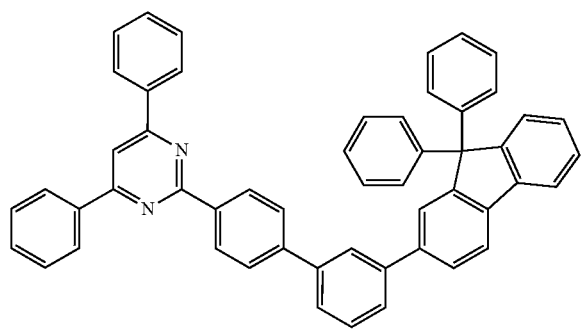
106
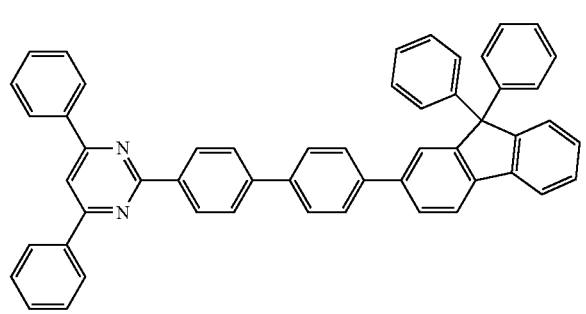
107
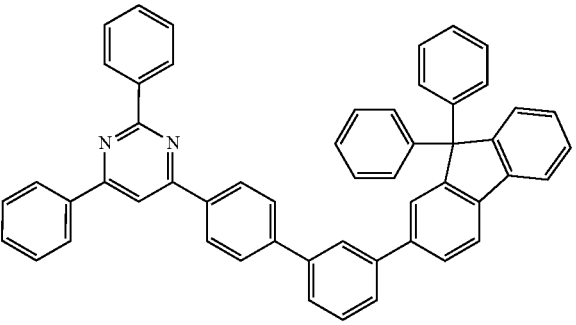
108
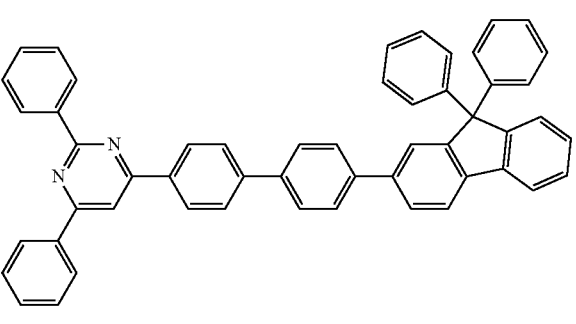
109
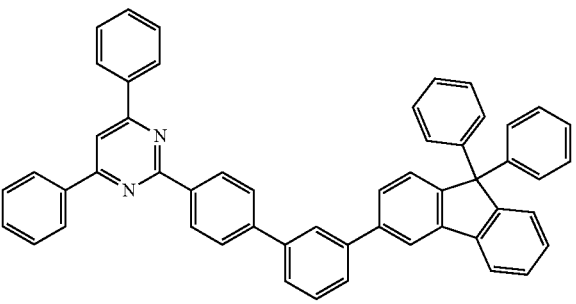
110
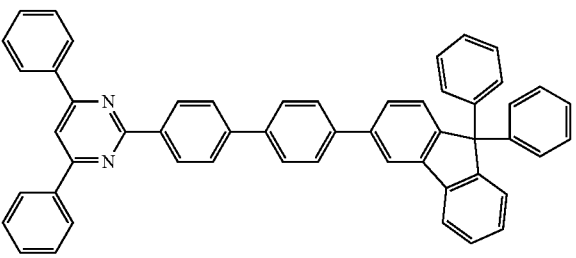
111
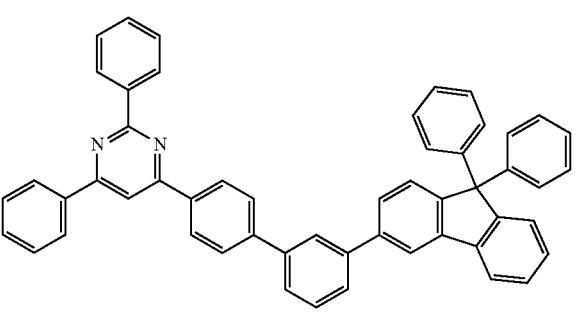

223
-continued

112

113

114

115

116

224
-continued

117

118

119

120

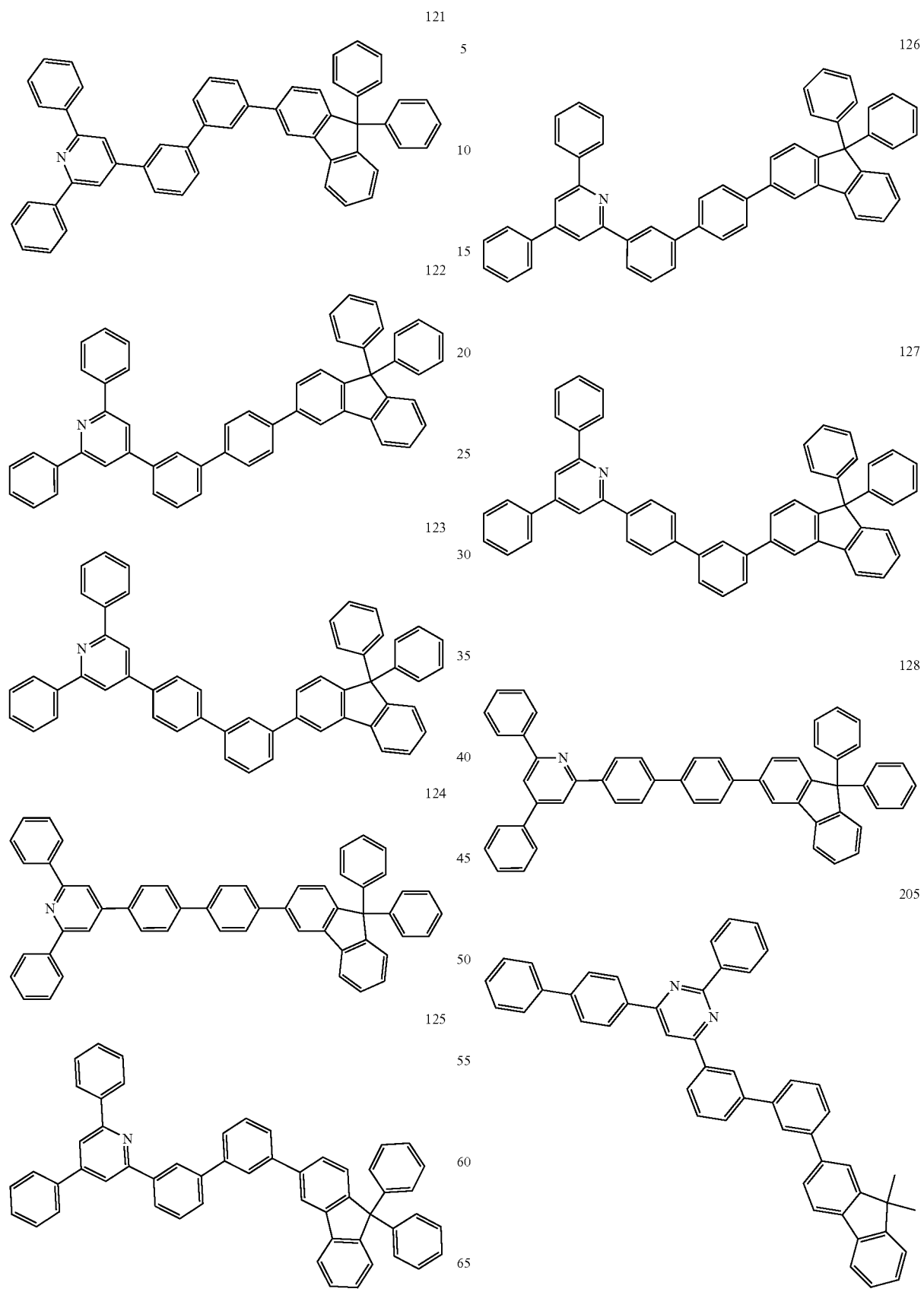

227
-continued
206
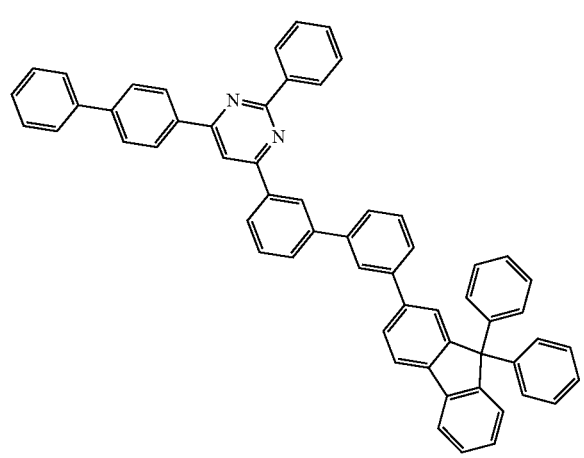
208
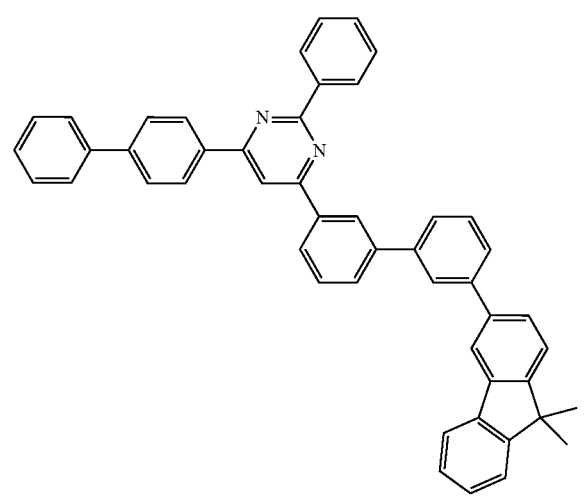
209
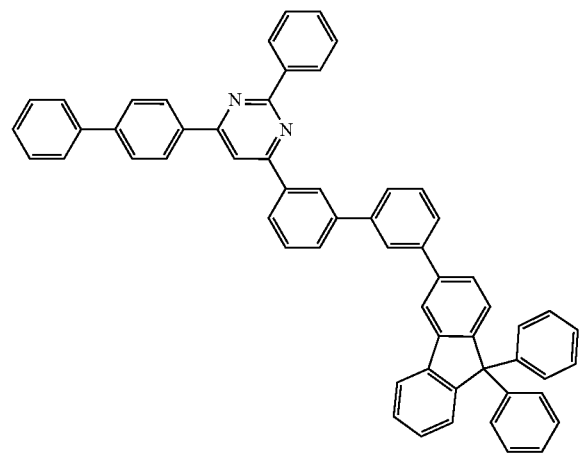
228
-continued
211
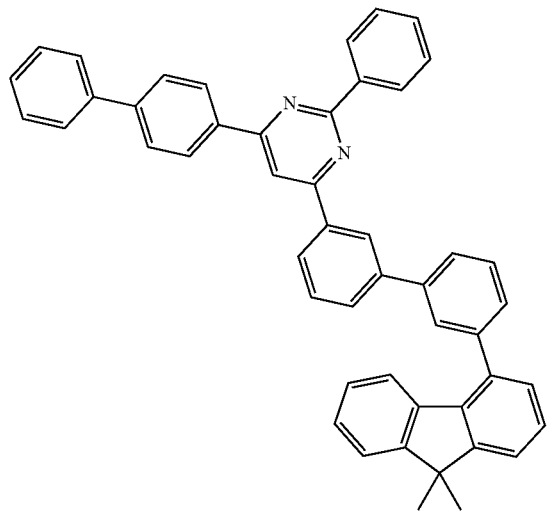
212
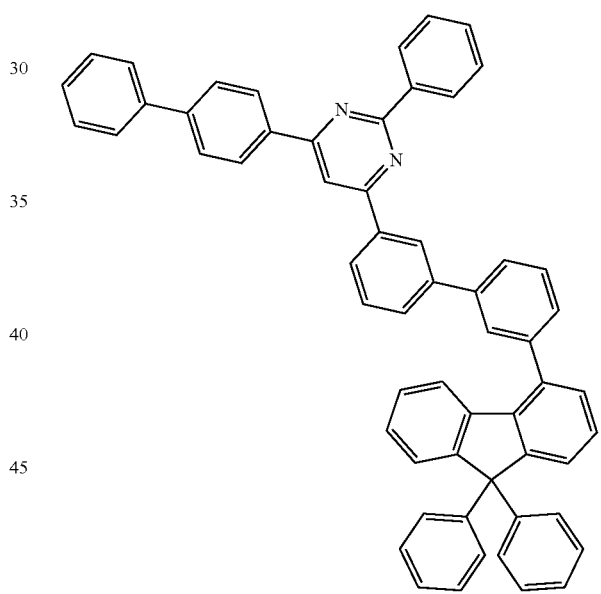
213
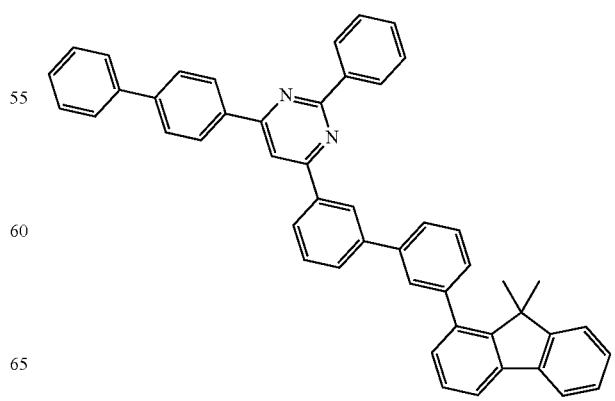

229
-continued
214
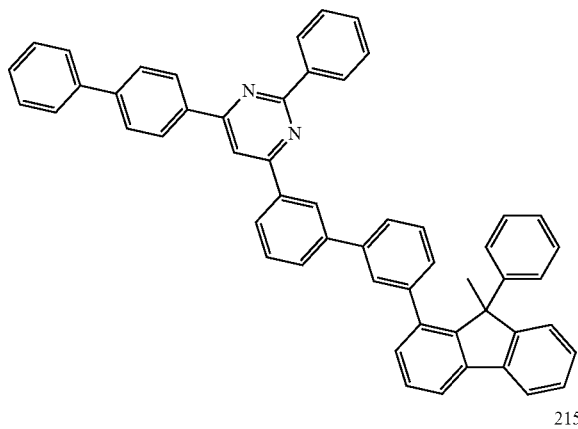
215
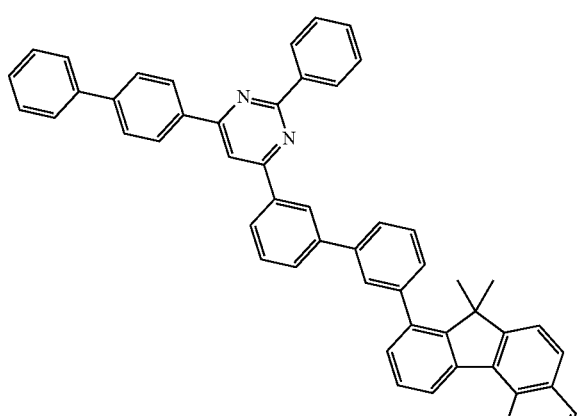
216
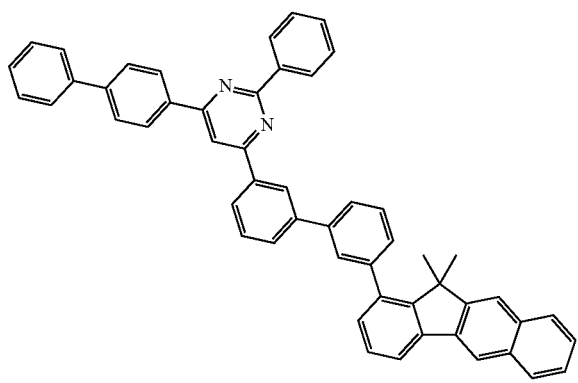
261
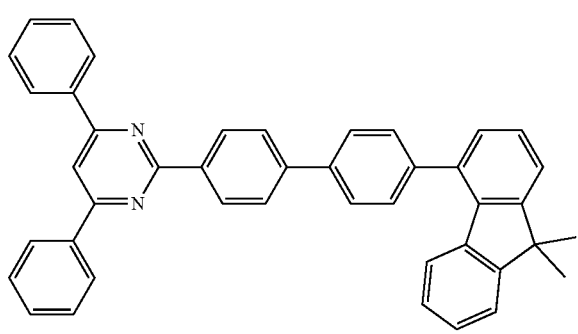
230
-continued
262
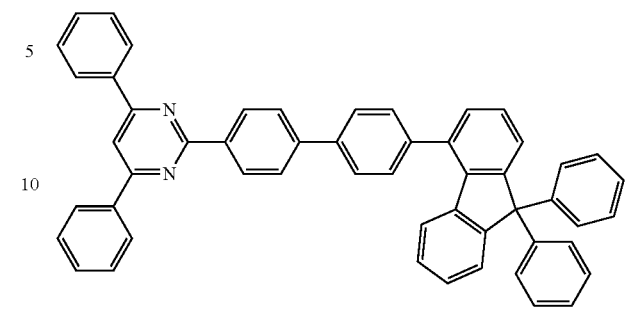
264
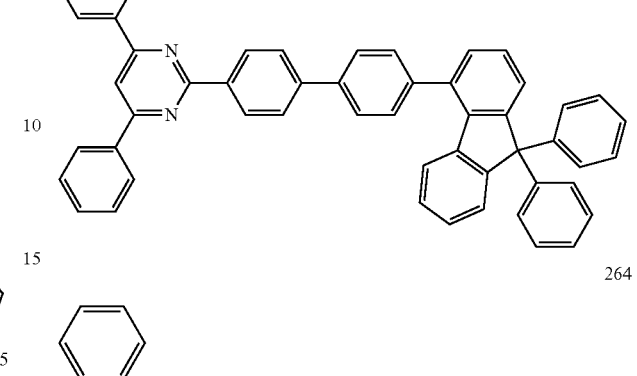
265
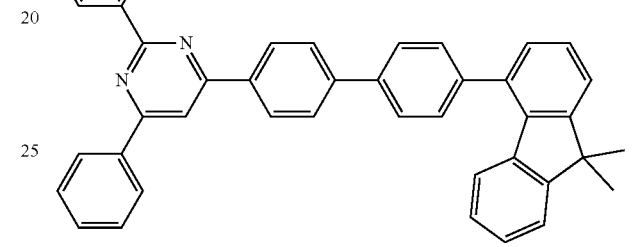
267
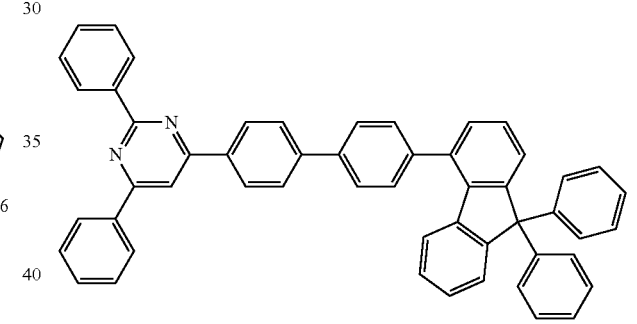
268
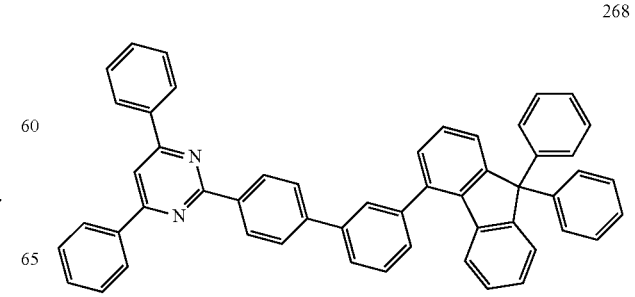

270
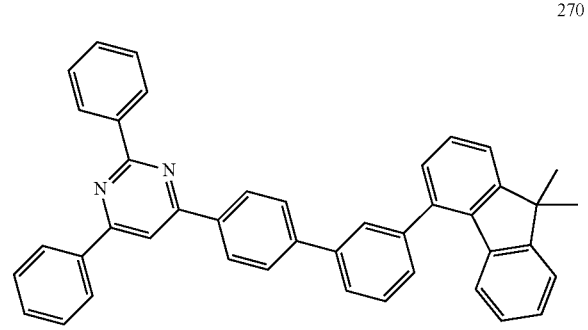
271
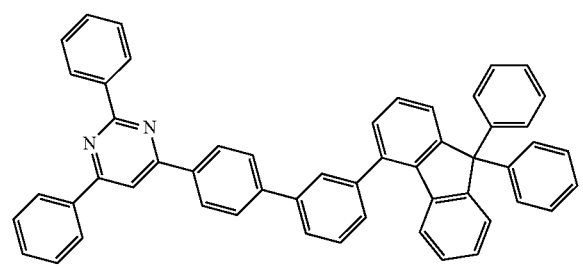
273
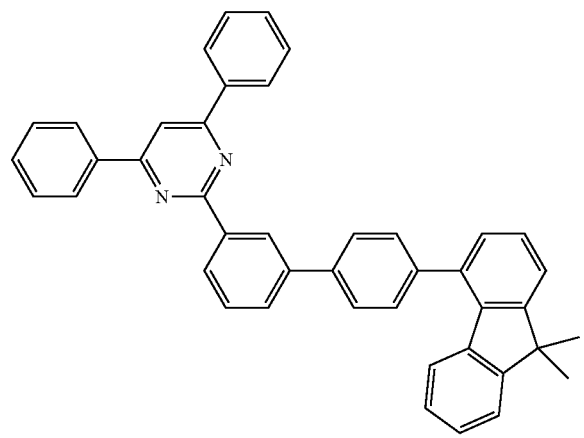
274
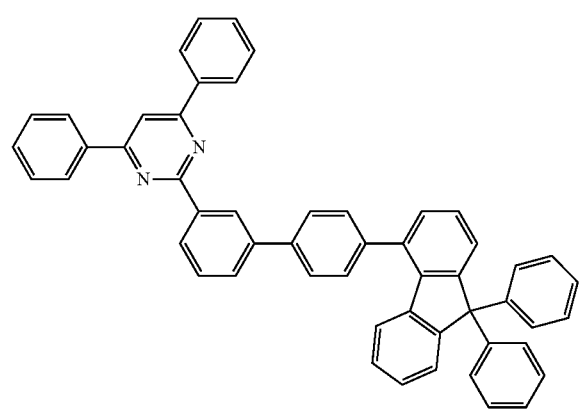
276
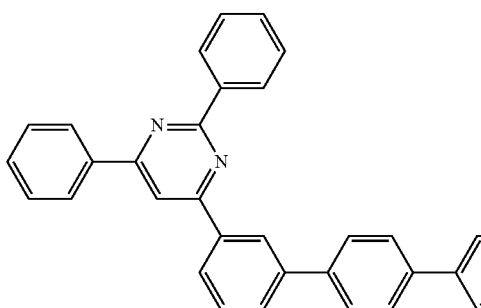
277
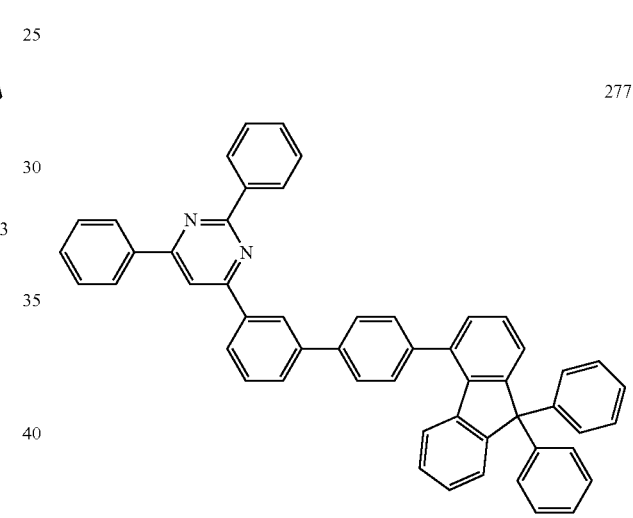
279
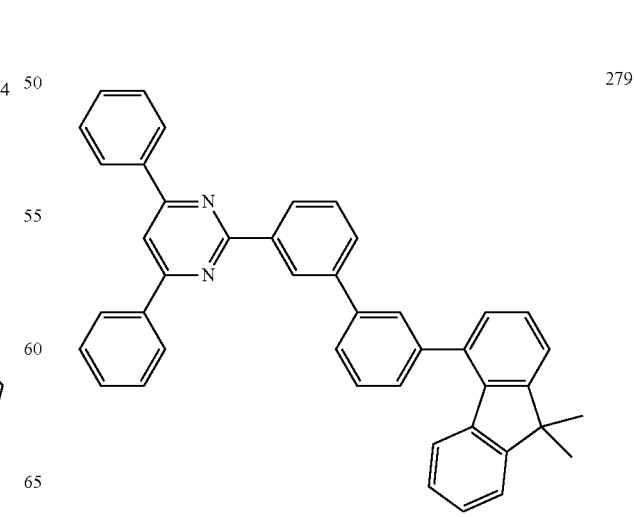

233
-continued
280
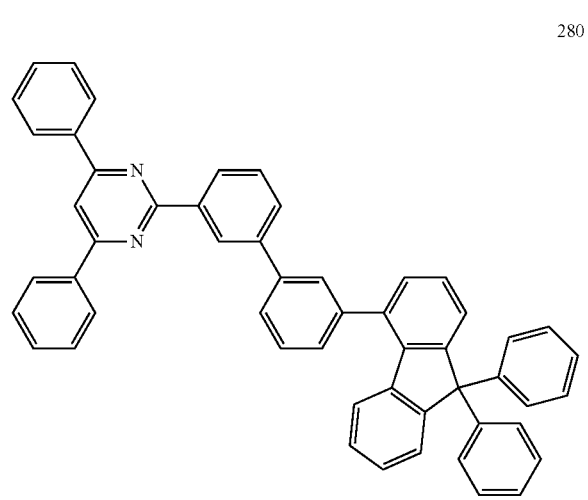
281
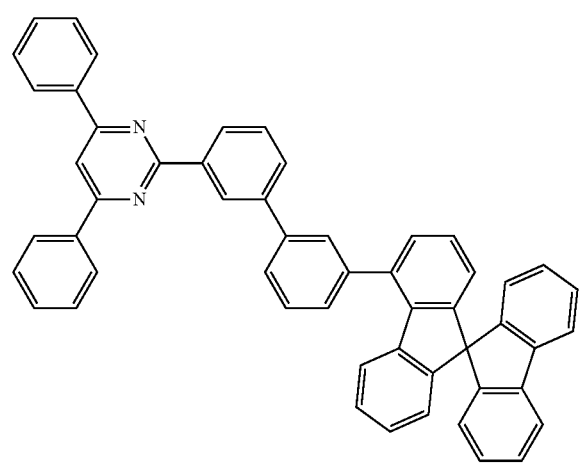
282
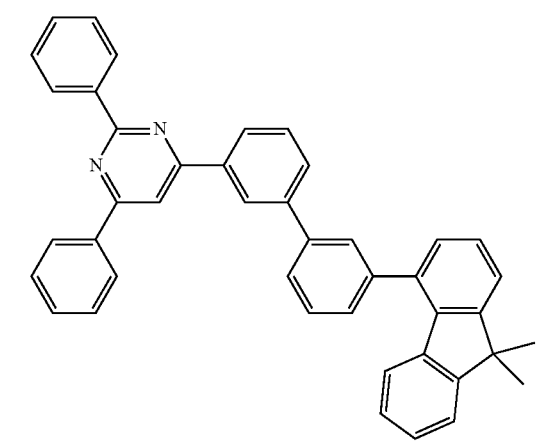
234
-continued
283
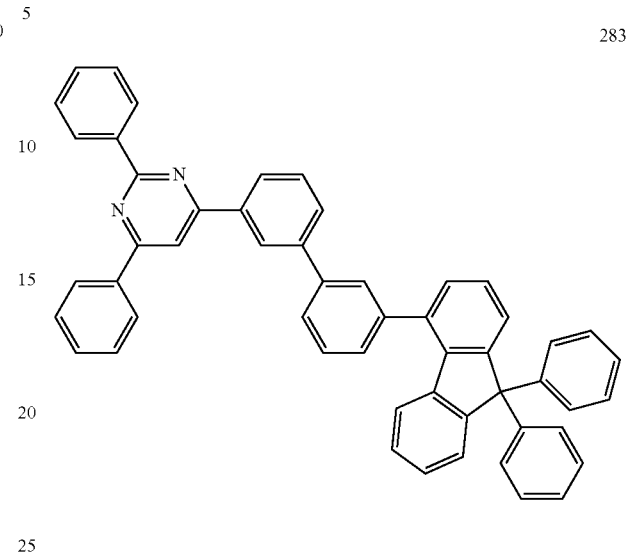
303
304
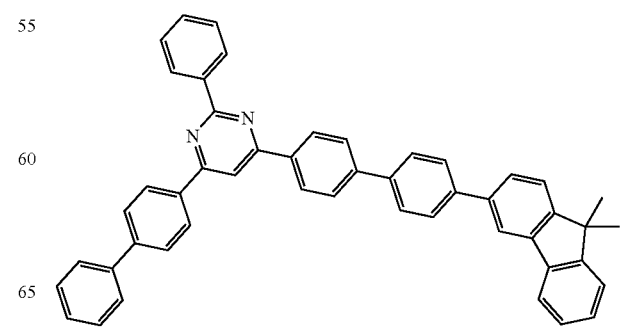

305
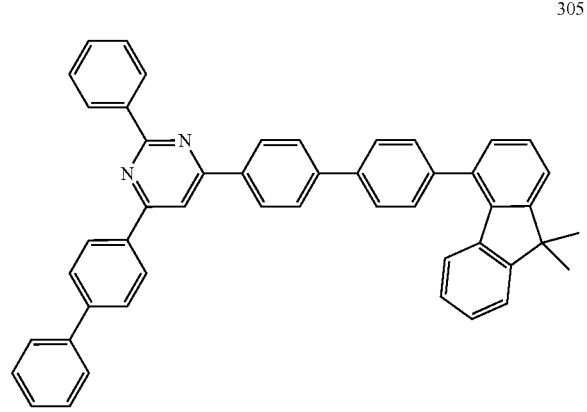
306
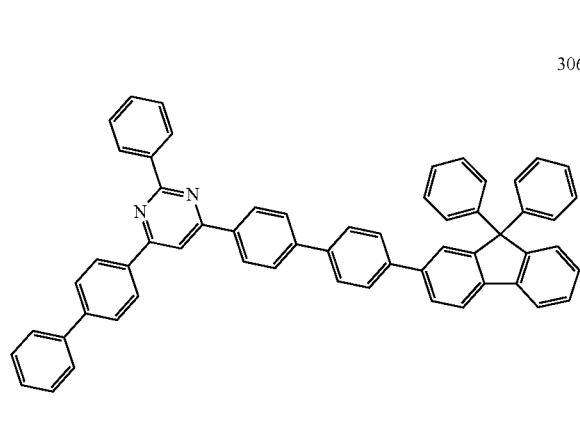
307
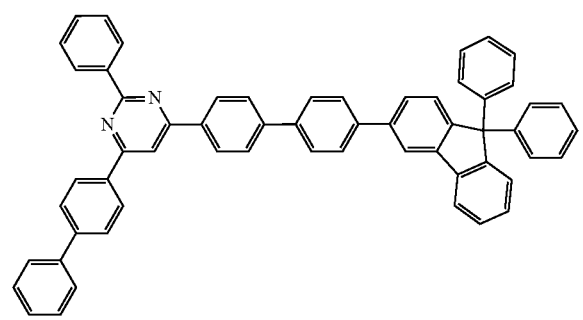
308
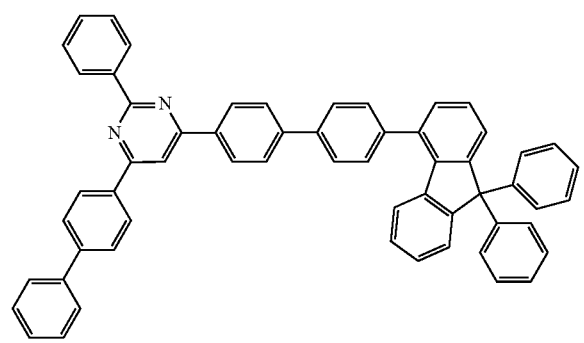
312
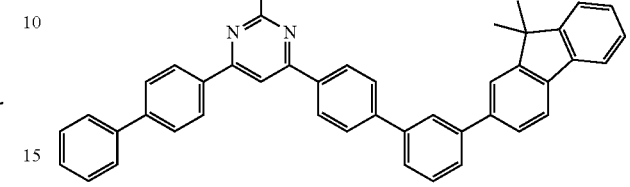
313
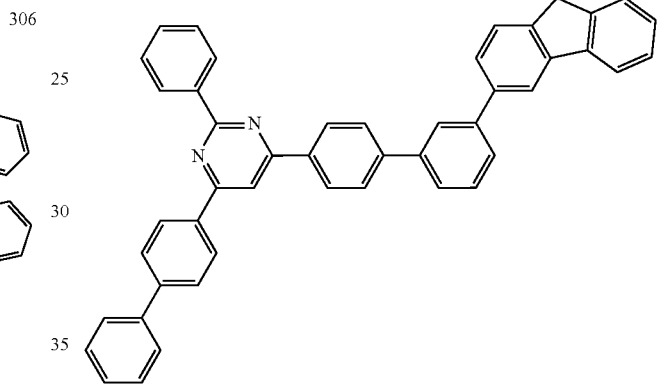
314
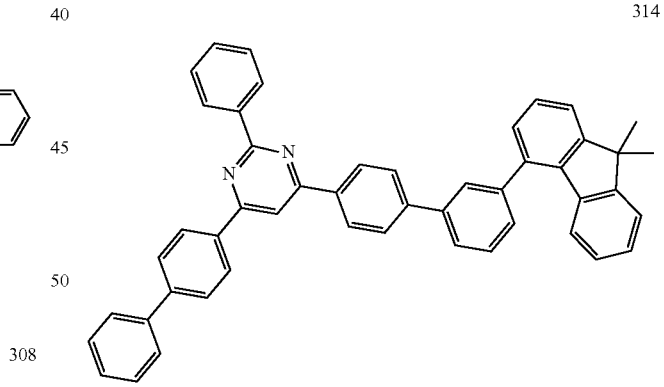
315
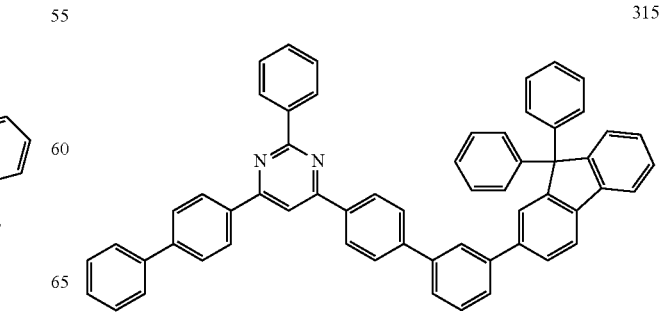

237
-continued
316
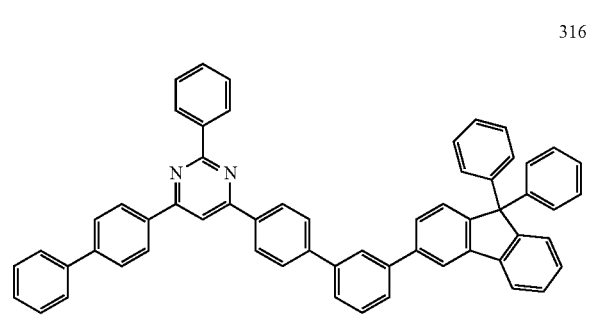
322
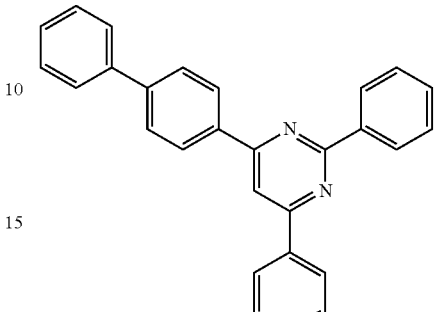
317
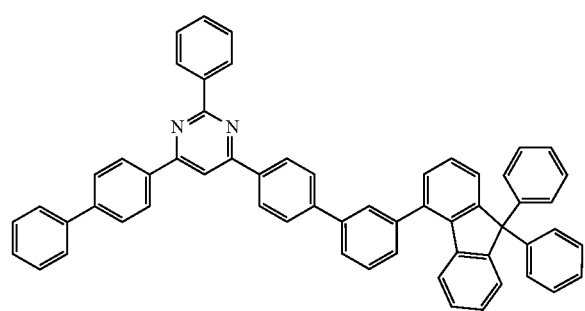
323
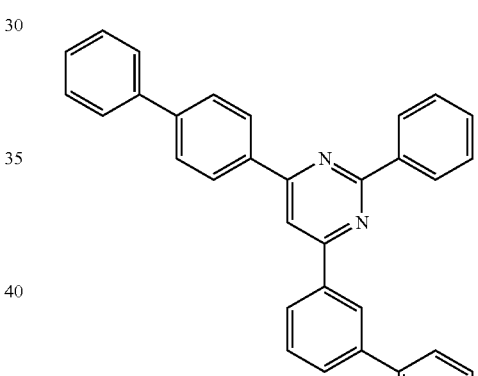
321
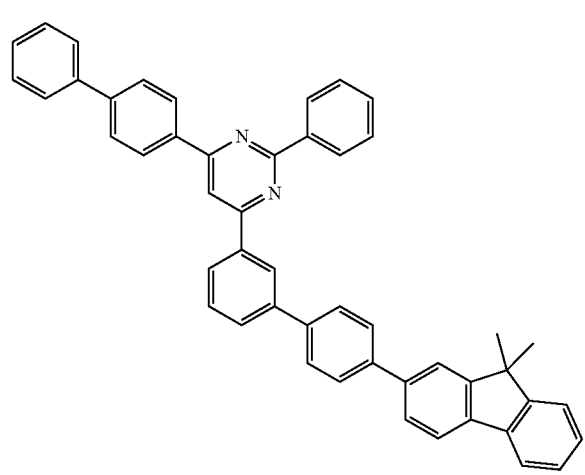
324
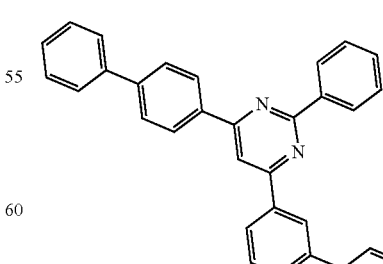
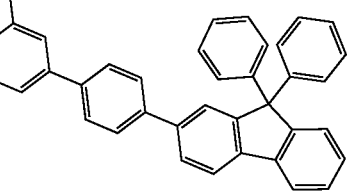
238
-continued 325
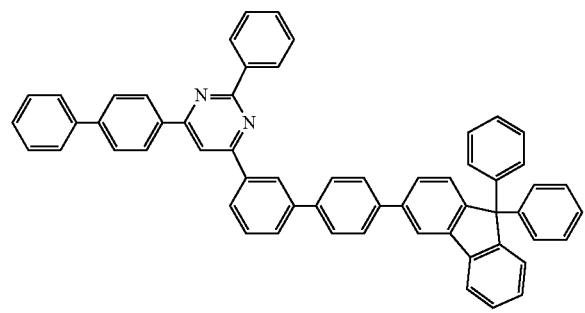
326
331
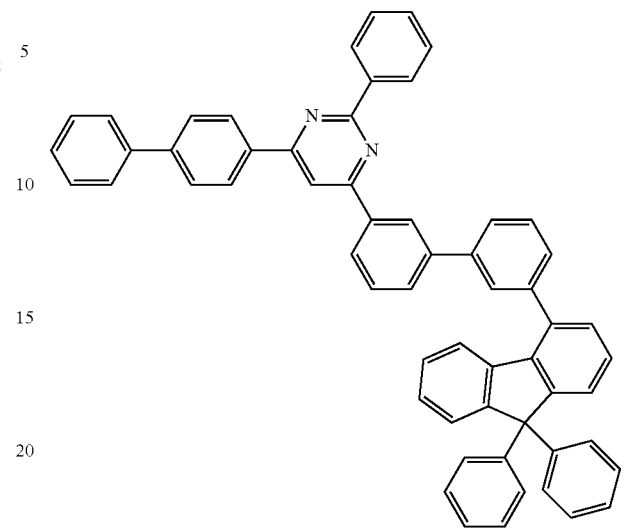
354
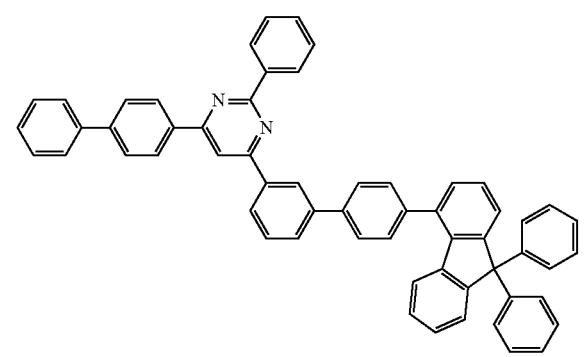
330
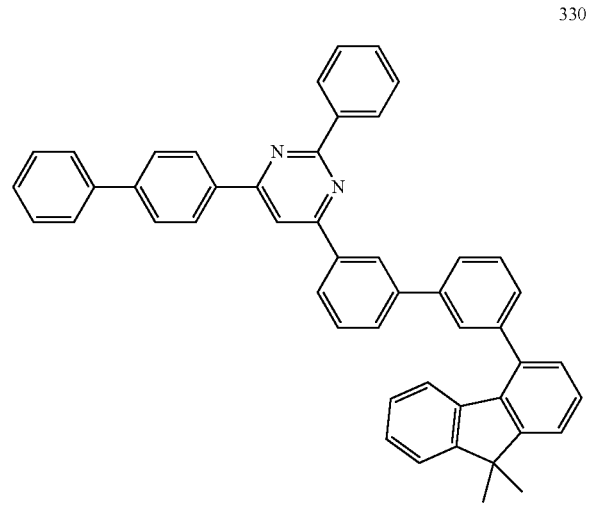
355
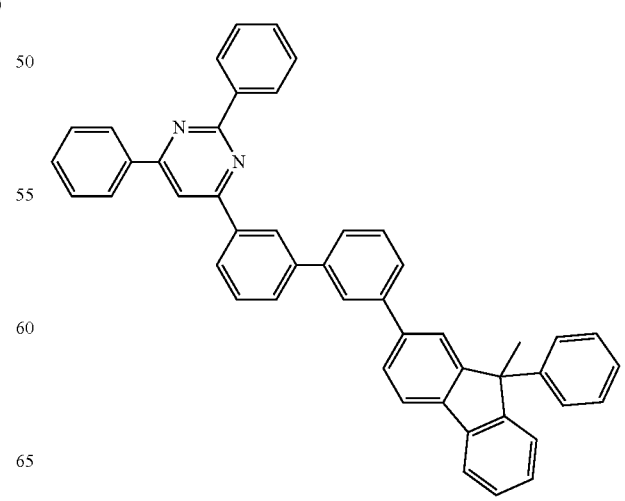

241
-continued
242
-continued
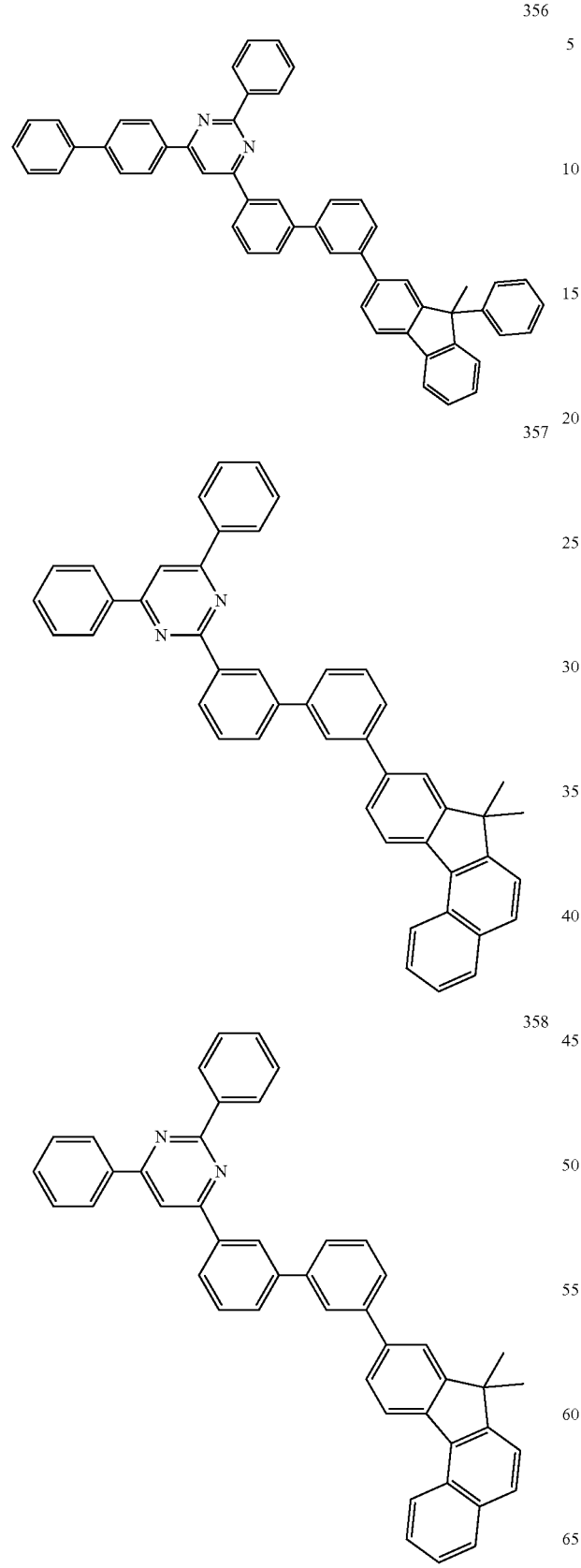
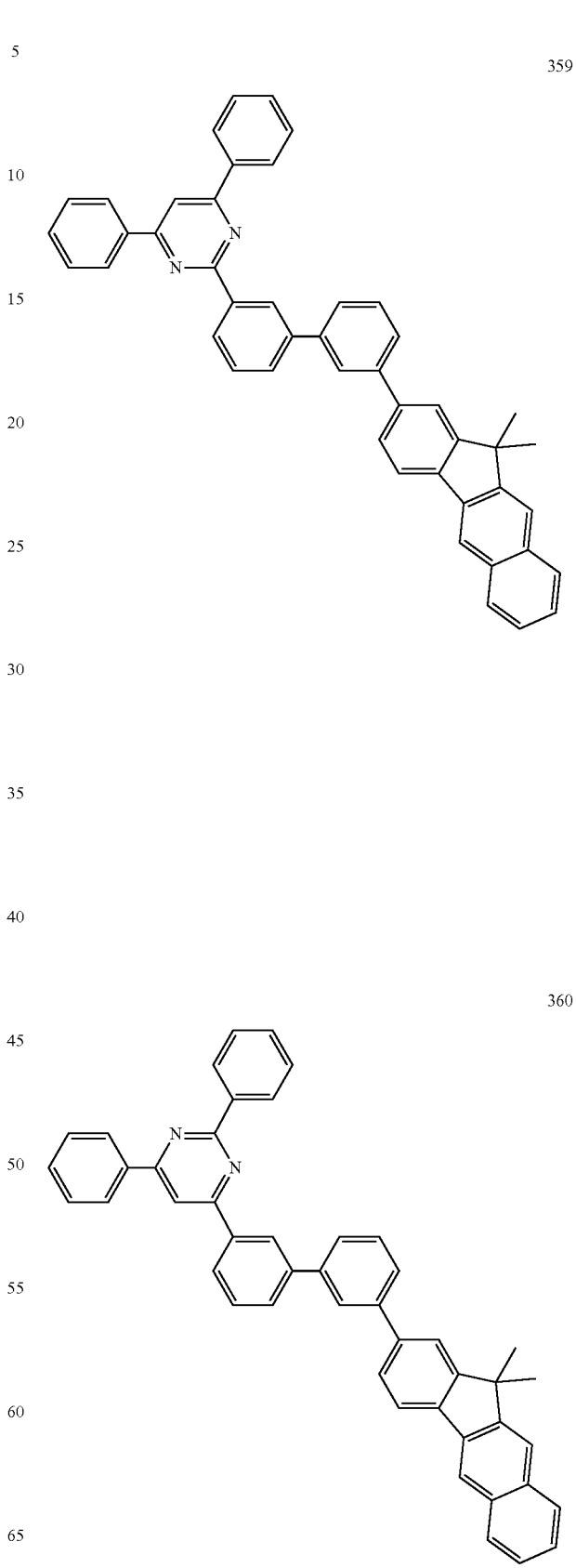

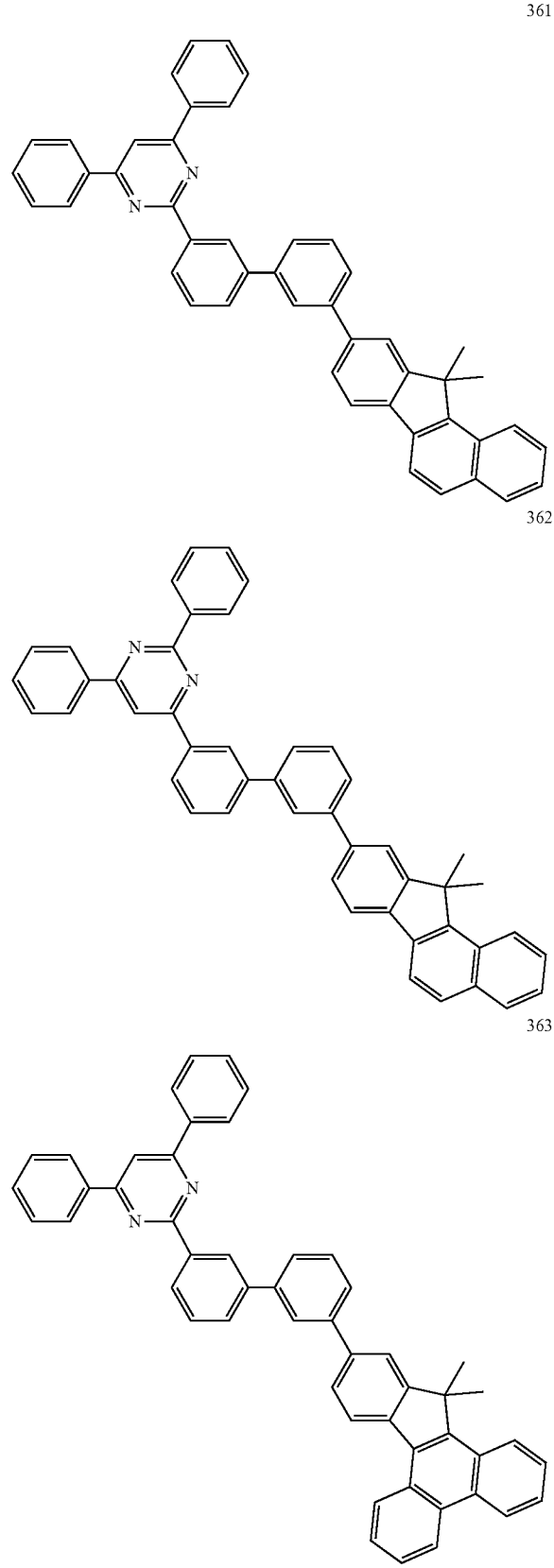 [SMILES: CC1(C)c2cc(-c3cccc(-c4cccc(-c5nc(-c6ccccc6)cc(-c6ccccc6)n5)c4)c3)ccc2-c2ccc3ccccc3c21 ; CC1(C)c2cc(-c3cccc(-c4cccc(-c5cc(-c6ccccc6)nc(-c6ccccc6)n5)c4)c3)ccc2-c2ccc3ccccc3c21 ; CC1(C)c2cc(-c3cccc(-c4cccc(-c5nc(-c6ccccc6)cc(-c6ccccc6)n5)c4)c3)ccc2-c2c1c1ccccc1c1ccccc21]
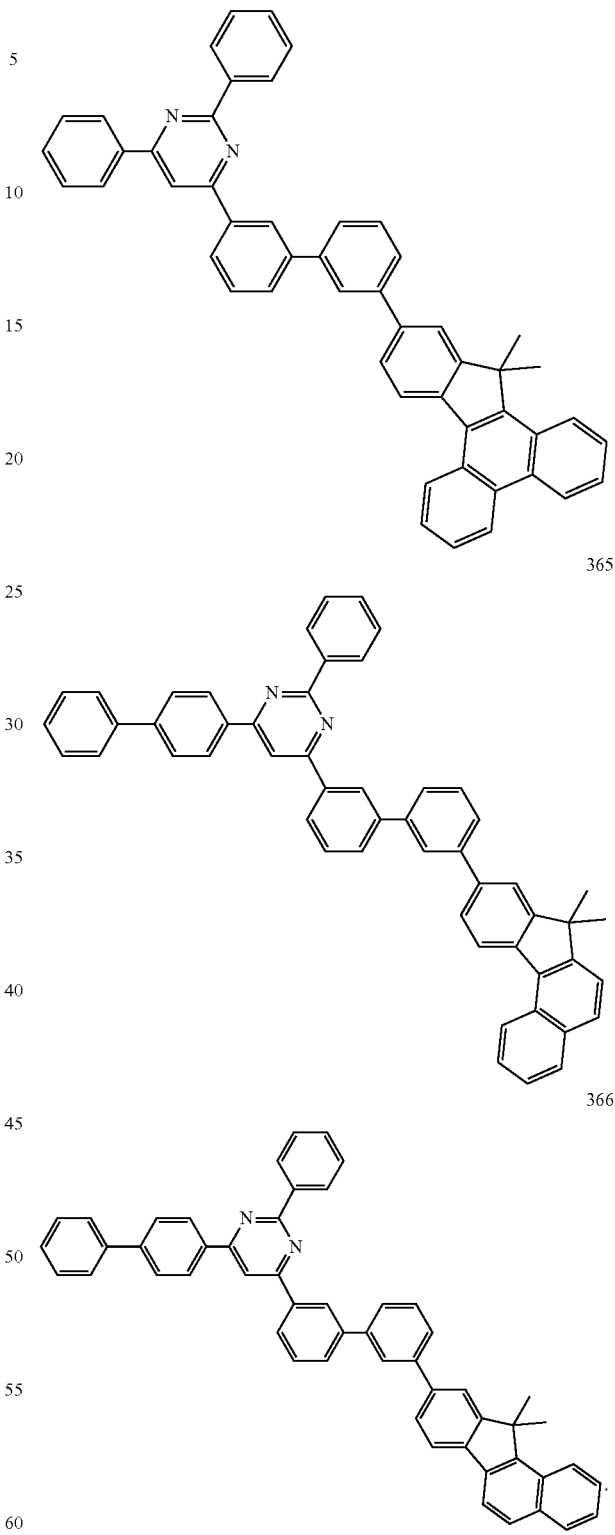
8. The organic electroluminescent element of claim 2, wherein the compound represented by Formula 4 is selected from the group consisting of the following Compounds 63, 64, 333, 334, 336, 337, 339 to 340, 342 to 343, 345 to 346, 348 to 349, 351 to 353:

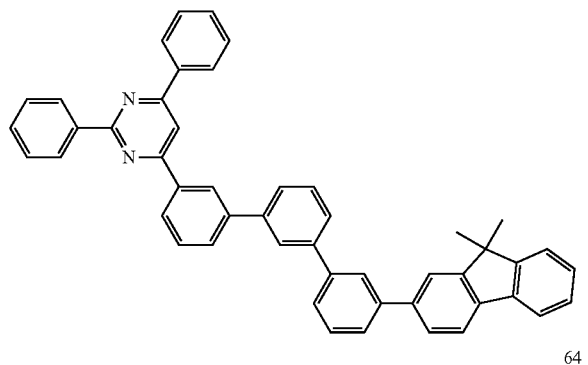
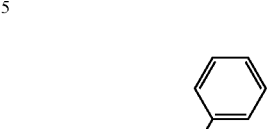
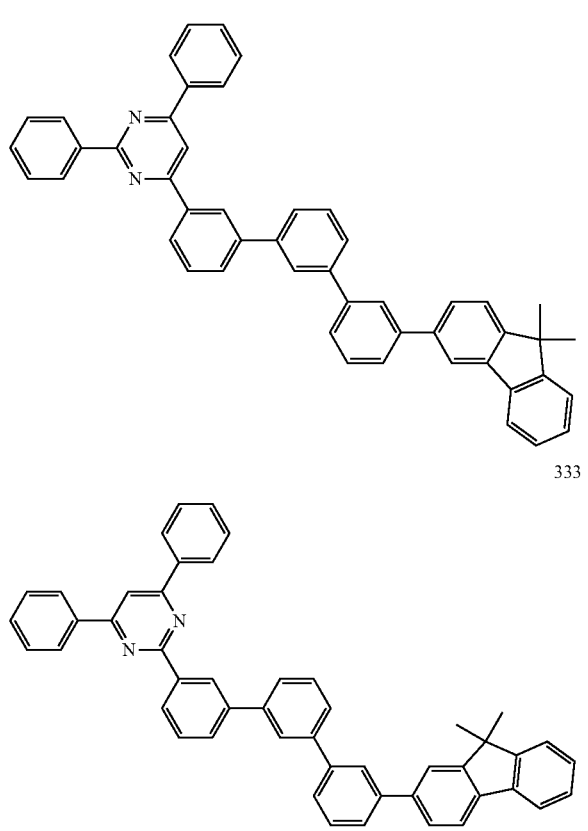
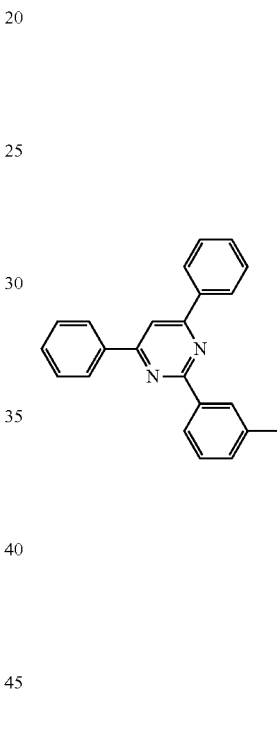
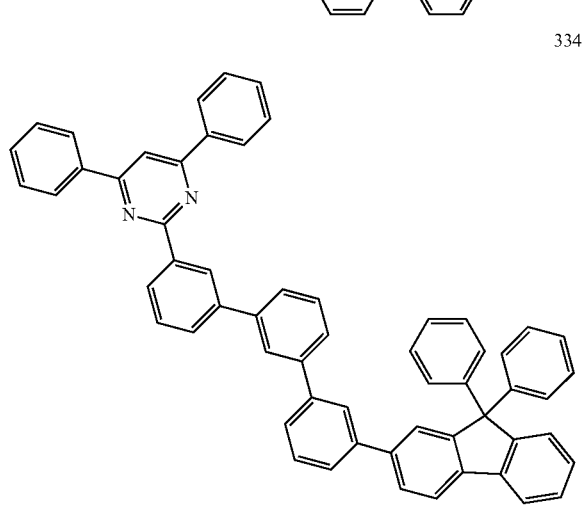

340
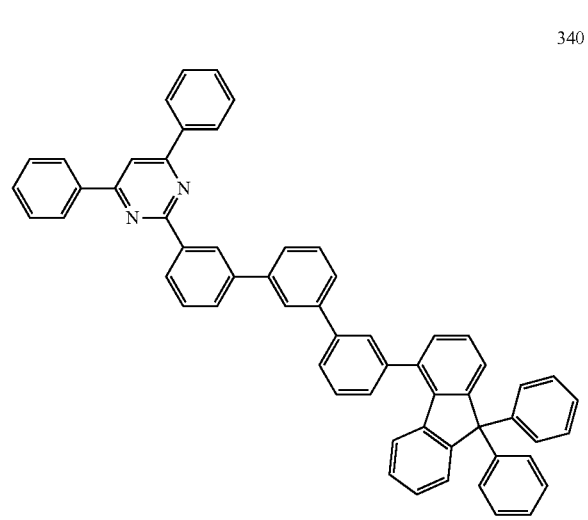
345
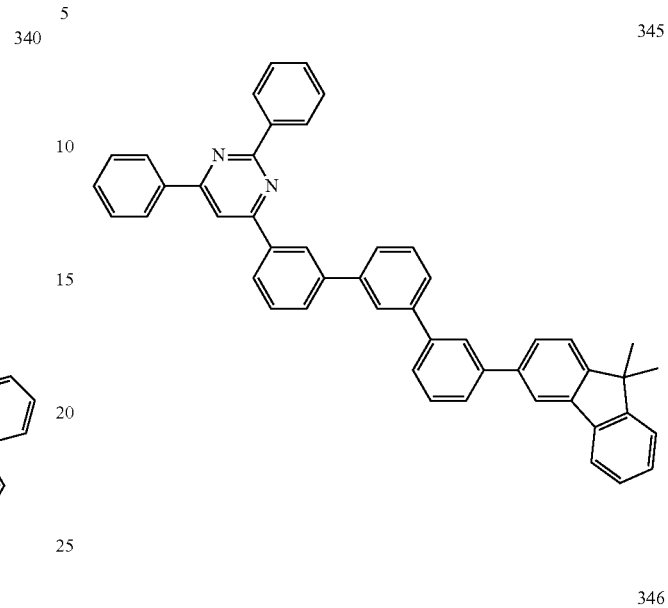
342
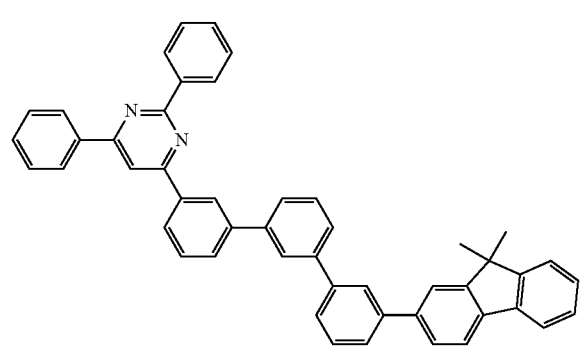
346
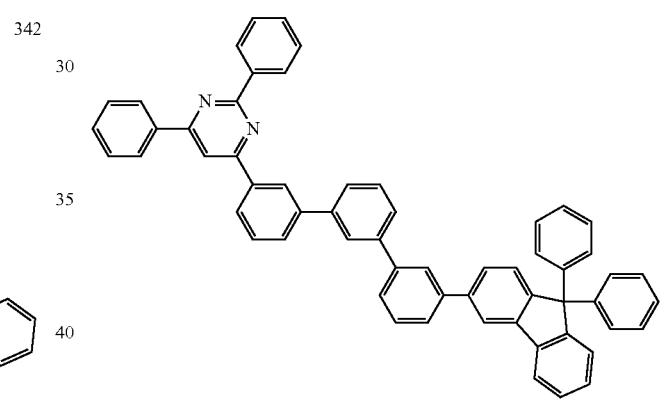
343
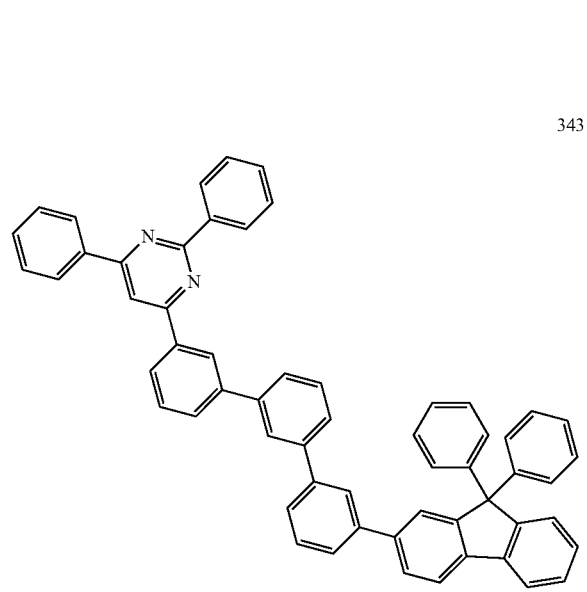
348
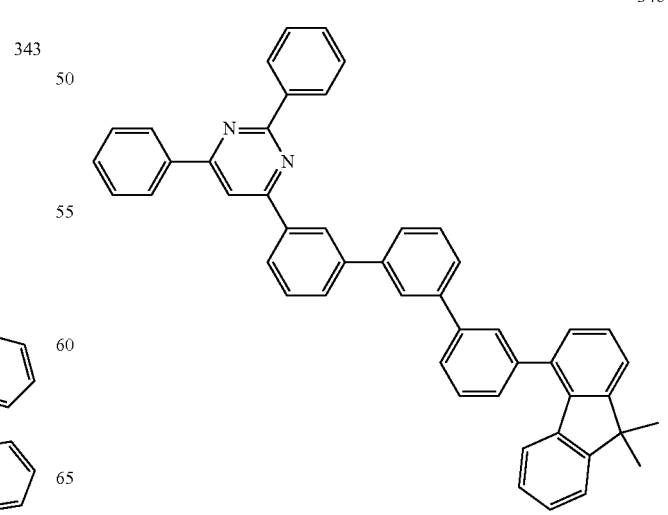

249
-continued
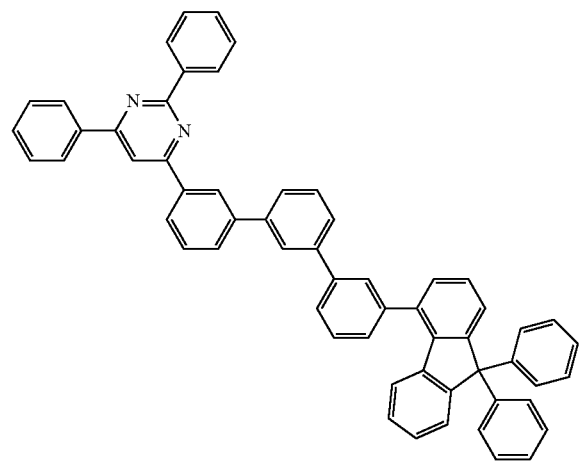
250
-continued
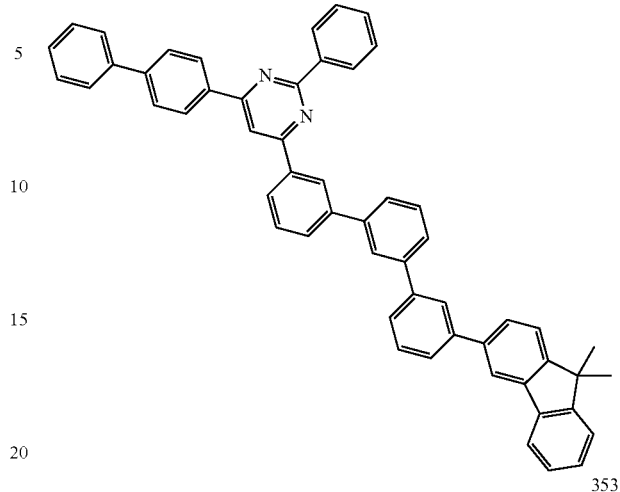
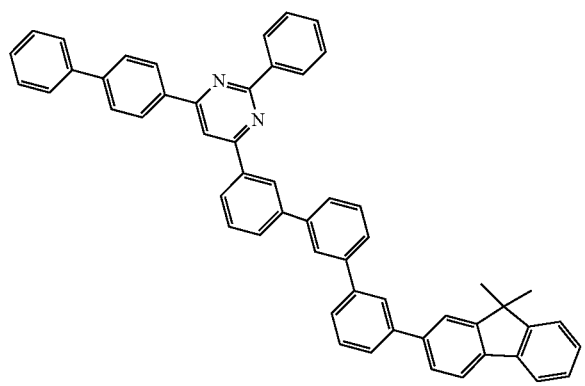
* * * * *